(12) United States Patent
Lee et al.

(10) Patent No.: US 8,597,926 B2
(45) Date of Patent: Dec. 3, 2013

(54) **HYDROGENASES ISOLATED FROM *THERMOCOCCUS* SPP., GENES ENCODING THE SAME, AND METHODS FOR PRODUCING HYDROGEN USING MICROORGANISMS HAVING THE GENES**

(75) Inventors: Jung Hyun Lee, Seongnam-si (KR); Sung Gyun Kang, Ansan-si (KR); Hyun Sook Lee, Ansan-si (KR); Sang Jin Kim, Ansan-si (KR); Kae Kyoung Kwon, Ansan-si (KR); Sun Shin Cha, Ansan-si (KR); Jung Ho Jeon, Ansan-si (KR); Yona Cho, Yongin-si (KR); Yun Jae Kim, Ansan-si (KR); Seung Seop Bae, Ansan-si (KR); Jae Kyu Lim, Siheung-si (KR); In Soon Jeong, Changwon-si (KR)

(73) Assignee: Korea Ocean Research & Development Institute, Ansan-si (KR)

( * ) Notice: Subject to any disclaimer, the term of this patent is extended or adjusted under 35 U.S.C. 154(b) by 255 days.

(21) Appl. No.: 12/746,090

(22) PCT Filed: Sep. 7, 2009

(86) PCT No.: PCT/KR2009/005060
§ 371 (c)(1),
(2), (4) Date: Jul. 8, 2010

(87) PCT Pub. No.: WO2010/027233
PCT Pub. Date: Mar. 11, 2010

(65) Prior Publication Data

US 2010/0311142 A1    Dec. 9, 2010

(30) Foreign Application Priority Data

Sep. 5, 2008  (KR) .......................... 10-2008-0087794
Sep. 5, 2008  (KR) .......................... 10-2008-0087806

(51) Int. Cl.
*C12N 9/02*  (2006.01)

(52) U.S. Cl.
USPC ........................................................ 435/189

(58) Field of Classification Search
USPC ........................................................ 435/189
See application file for complete search history.

(56) References Cited

PUBLICATIONS

Written Opinion—International Preliminary Exam Report (Jun. 28, 2010).*

* cited by examiner

*Primary Examiner* — Tekchand Saidha
(74) *Attorney, Agent, or Firm* — Clark Elbing LLP

(57) ABSTRACT

The present invention relates to novel hydrogenases isolated from novel hyperthermophilic strains belonging to *Thermococcus* spp., genes encoding the hydrogenases, and methods of producing hydrogen using strains having the genes. According to the hydrogen production methods of the invention, a large amount of hydrogen can be produced merely by culturing the strains in specific culture conditions. Thus, the methods of the invention have advantages in that they are more economic and efficient than existing hydrogen production methods and can produce hydrogen even at high temperature.

1 Claim, 18 Drawing Sheets

Fig. 1 B

INFORMATION STORAGE AND PROCESSING
- [J] Translation, ribosomal structure and biogenesis
- [A] RNA processing and modification
- [K] Transcription
- [L] Replication, recombination and repair
- [B] Chromatin structure and dynamics CELLULAR PROCESSES AND SIGNALING
- [D] Cell cycle control, cell division, chromosome partitioning
- [Y] Nuclear structure
- [V] Defense mechanisms
- [T] Signal transduction mechanisms
- [M] Cell wall/membrane/envelope biogenesis
- [N] Cell motility
- [Z] Cytoskeleton
- [W] Extracellular structures
- [U] Intracellular trafficking, secretion, and vesicular transport

- [O] Posttranslational modification, protein turnover, chaperones

METABOLISM
- [C] Energy production and conversion
- [G] Carbohydrate transport and metabolism
- [E] Amino acid transport and metabolism
- [F] Nucleotide transport and metabolism
- [H] Coenzyme transport and metabolism
- [I] Lipid transport and metabolism
- [P] Inorganic ion transport and metabolism
- [Q] Secondary metabolites biosynthesis, transport and catabolism POORLY CHARACTERIZED
- [R] General function prediction only
- [S] Function unknown

SEQUENCE LISTING

<160> NUMBER OF SEQ ID NOS: 60

<210> SEQ ID NO 1
<211> LENGTH: 1393
<212> TYPE: PRT

<213> ORGANISM: Thermococcus onnurineus NA1

<400> SEQUENCE: 1

```
Met Gly Phe Leu Ser Arg Leu Phe Gly Gly Lys Lys Glu Thr Asp Thr
1               5                   10                  15
Glu Glu Ile Gln Ile Val Ser Arg Lys Pro Val Gly Lys Phe His Val
                20                  25                  30
Glu Lys Val Phe His Ile Met Gly Arg Glu Thr Leu Val Gly Thr Val
            35                  40                  45
Glu Arg Gly Val Ile Tyr Pro Gly Tyr Lys Val Lys Gly Lys Lys Ala
        50                  55                  60
Ala Val Ile Tyr Arg Ile Glu Lys Gly Arg Lys Ala Val Asp Phe Val
65                  70                  75                  80
Val Asp Gly Asp Lys Ala Leu Ile Leu Glu Gly Ile Thr Lys Ala
                85                  90                  95
Glu Glu Gly Asp Thr Leu Glu Val Tyr Gln Ser Met Ile Ile Glu Leu
            100                 105                 110
Arg Glu Phe Thr Arg Val Glu Gly Asn Gly Lys Ala Glu Ile Val Val
        115                 120                 125
Glu Asn Gly Glu Val Lys Asp Val Arg Leu Lys Ile Val Glu Gly Pro
130                 135                 140
Arg Phe Phe Glu Leu Leu Thr Leu Gly Arg His Tyr Tyr Asp Val Pro
145                 150                 155                 160
Asp Leu Glu Ala Arg Ile Cys Ala Ile Cys Tyr Leu Ser His Ser Val
                165                 170                 175
Ala Ser Val Leu Gly Ile Glu Lys Ala Phe Gly Val Glu Val Ser Glu
            180                 185                 190
Glu Ile Gln Leu Leu Arg Glu Leu Gly Leu Ile Gly Glu Leu Leu Glu
        195                 200                 205
Ser His Ala Leu His Leu Tyr Leu Leu Val Ala Pro Asp Val Phe Gly
    210                 215                 220
Tyr Pro Asp Ala Ile Arg Met Ala Thr Lys His Gly Glu Leu Val Lys
225                 230                 235                 240
Glu Gly Leu Ala Leu Lys Ala Phe Gly Asn Ser Ile Arg Glu Leu Ile
                245                 250                 255
Gly Gly Arg Glu Ile His Gly Ile Asn Val Lys Pro Gly Gly Phe Gly
            260                 265                 270
Arg Tyr Pro Thr Val Glu Glu Leu Glu Asn Ile Glu Arg Glu Ser Gly
        275                 280                 285
Ala Leu Leu Arg Leu Ala Arg Arg Ala Val Arg Leu Phe Ala Ser Leu
290                 295                 300
Glu Pro Tyr Gly Glu Lys Ala Gly His Phe Val Ala Thr Asp Gly Tyr
305                 310                 315                 320
Leu Trp Gly Asp Lys Leu Ile Ser Asp Glu Asp Gly Ser Phe His Tyr
                325                 330                 335
Thr Glu Arg Ile Glu Glu Arg Ser Leu Val Tyr Ser Phe Ala Lys Gln
            340                 345                 350
Ser Arg Tyr Lys Gly Glu Pro Phe Phe Val Gly Ala Leu Pro Arg Leu
        355                 360                 365
Leu Leu Lys Ala Glu Met Leu Thr Pro Thr Ala Lys Arg Leu Phe Glu
370                 375                 380
Glu His Arg Glu Lys Leu Ala Thr Gly Tyr Val Ser Tyr Asn Asn Leu
385                 390                 395                 400
Ala Gln Ala Ile Glu Leu Val Tyr Ala Leu Glu Arg Ala Gly Glu Ile
```

```
                       405                 410                 415
Ala Lys Lys Leu Leu Asp Lys Gly Ile Lys Gly Glu Asn Val Pro Val
                420                 425                 430
Glu Val Lys Glu Gly Glu Gly Ile Gly Tyr Val Glu Ala Pro Arg Gly
            435                 440                 445
Val Leu Ile His His Tyr Arg Ile Asp Ser Gly Gly Lys Ile Ala Tyr
        450                 455                 460
Ser Asn Ile Ile Thr Pro Thr Ala Leu Asn His Ala Met Met Glu Ala
465                 470                 475                 480
Ser Leu Phe Lys Glu Ala Arg Lys Leu Tyr Gly Glu Thr Asp Glu Thr
                485                 490                 495
Val Leu Val Gln Arg Leu Glu Glu Thr Val Arg Ala Phe Asp Pro Cys
            500                 505                 510
Ile Ser Cys Ser Val His Ile Val Lys Leu Met Met Asp Lys Leu Lys
        515                 520                 525
Leu Ala Val Phe Glu Leu Thr Asp Cys Gly Gly Cys Ala Leu Asn Ile
        530                 535                 540
Leu Phe Leu Tyr Glu Lys Leu Phe Asp Leu Leu Glu Phe Tyr Glu Ile
545                 550                 555                 560
Thr Glu Phe His Met Ala Thr Ser Leu Ser Glu Gly Ser His Tyr Asp
                565                 570                 575
Val Ala Leu Val Thr Gly Thr Val Ser Ser Gln Arg Asp Leu Ala Leu
            580                 585                 590
Leu Lys Glu Ala Arg Asn His Ser Asp Tyr Leu Ile Ala Leu Gly Thr
        595                 600                 605
Cys Ala Thr His Gly Ser Val Gln Ala Ser Val Glu Gly Ser Ile Arg
        610                 615                 620
Glu Lys Leu Lys Arg Val Tyr Gly Asp Glu Gly Asn Pro Met Arg Ala
625                 630                 635                 640
Leu Asp Ser Lys Pro Val Val Glu Tyr Val Ala Val Asp Phe Ala Leu
                645                 650                 655
Pro Gly Cys Pro Tyr Asp Lys Asn Glu Val Tyr Gln Val Leu Met Asp
            660                 665                 670
Ile Ala Lys Gly Ile Glu Pro Val Lys Asp Tyr Pro Val Cys Val
        675                 680                 685
Glu Cys Lys Leu Asn Glu Tyr Glu Cys Val Leu Val Lys Lys Gly Leu
        690                 695                 700
Pro Cys Leu Gly Pro Ile Thr Tyr Gly Gly Cys Asn Ala Ala Cys Ile
705                 710                 715                 720
Arg Ser Gly Leu Gly Cys Ile Gly Cys Arg Gly Pro Leu Pro Gly Glu
                725                 730                 735
Val Asn Pro Ala Ser Glu Tyr Glu Ile Leu Lys Asp Leu Gly Tyr Asp
            740                 745                 750
Asp Asp Tyr Ile Leu Arg Lys Phe Lys Thr Phe Ala Arg Trp Glu Pro
        755                 760                 765
Met Ser Glu Asn Pro His Gln Thr Tyr Asp Ala Arg Ile Leu Glu Val
770                 775                 780
Lys Asp Leu Thr Pro Arg Glu Lys Leu Phe Thr Leu Arg Phe Leu Asp
                790                 795                 800
Pro Glu Ile Gly Glu His Phe Thr Phe Lys Pro Gly Gln Phe Val Ile
            805                 810                 815
Val Asp Ile Arg Gly Phe Gly Glu Phe Pro Ile Ser Leu Cys Ser Ser
        820                 825                 830
```

Pro Thr Arg Lys Gly Tyr Ile Gln Leu Cys Ile Arg Lys Ala Gly Arg
    835                 840                 845

Met Thr Lys Phe Ile His Gln Met Lys Glu Gly Glu Val Val Gly Ile
    850                 855                 860

Arg Gly Pro Tyr Gly Asn Gly Phe Pro Met Glu Lys Met Glu Gly Ser
865                 870                 875                 880

Asn Leu Leu Leu Val Ala Gly Leu Gly Met Ala Pro Leu Arg Ser
            885                 890                 895

Val Leu Trp Tyr Ala Ile Asp Thr Gly Lys Tyr Glu His Val Trp Leu
            900                 905                 910

Leu Tyr Gly Thr Lys Ala Tyr Glu Asp Ile Leu Phe Arg Asp Glu Ile
        915                 920                 925

Ile His Leu Leu Lys His Gly Asp Ala Val Gly Cys Ser Val Lys Leu
        930                 935                 940

Ala Tyr Glu Val Glu Ser Pro Ser Cys Ile Tyr Leu Glu Arg Gly Phe
945                 950                 955                 960

Phe Asp Arg Val Cys Lys Gly Val Val Thr Asp Leu Phe Arg Gly Glu
            965                 970                 975

Glu Phe Asp Val Asp Lys Ala Tyr Ala Leu Ile Cys Gly Pro Pro Val
            980                 985                 990

Met Tyr Arg Phe Val Ile Lys Glu  Leu Leu Asp Arg Lys  Leu Ser Pro
            995                 1000                 1005

Gly Arg  Ile Tyr Met Thr Leu  Glu Arg Arg Met Arg  Cys Gly Ile
    1010                 1015                 1020

Gly Lys  Cys Gly His Cys Ile  Val Gly Thr Ser Thr  Ser Ile Lys
    1025                 1030                 1035

Tyr Val  Cys Lys Asp Gly Pro  Val Phe Thr Tyr Trp  Asp Ala Leu
    1040                 1045                 1050

Ser Thr  Arg Gly Leu Ile Leu  Arg Tyr Val Lys Leu  Ser Ser Glu
    1055                 1060                 1065

Asn Phe  Ser Ser Phe Phe Glu  Ser Leu Arg Asn Trp  Gly Lys Val
    1070                 1075                 1080

Tyr Ala  Pro Ile Lys Arg Gly  Ser Ile Tyr Thr Phe  Gln Glu Val
    1085                 1090                 1095

His Glu  Leu Gly Glu Ile Glu  Leu Asn Tyr Thr Arg  Thr Met Leu
    1100                 1105                 1110

Pro Pro  Lys Lys Phe Phe Val  Arg Pro Arg Asp Glu  Ile Leu Arg
    1115                 1120                 1125

Leu Lys  Asn Gly Arg Trp Glu  Asn Gly Thr Asp Ala  Glu Pro Ile
    1130                 1135                 1140

Val Leu  Phe Gly Leu His Ser  Cys Asp Met His Gly  Leu Lys Ile
    1145                 1150                 1155

Leu Asp  Lys Val Tyr Leu Asp  Glu Pro Ala Asp Pro  Tyr Tyr Lys
    1160                 1165                 1170

Ala Arg  Arg Glu Lys Thr Phe  Ile Val Gly Ile Ser  Cys Met Pro
    1175                 1180                 1185

Asp Glu  Tyr Cys Phe Cys Lys  Ser Leu Gly Thr His  Phe Ala Met
    1190                 1195                 1200

Asp Gly  Phe Asp Leu Phe Leu  His Glu Leu Pro Asp  Gly Trp Leu
    1205                 1210                 1215

Val Arg  Ile Gly Ser Val Arg  Gly His Glu Val Val  Trp Glu Asn
    1220                 1225                 1230

Gly Glu  Leu Phe Glu Glu Val  Thr Asp Glu Asp Leu  Lys His Phe
    1235                 1240                 1245

```
Lys Glu Phe Glu Glu Arg Arg Ala Asn Ala Phe Gln Lys Glu Ile
    1250                1255                1260

Pro Gln Glu Gly Leu Ala Asp Met Leu Asp Leu Ala Tyr Asn Ser
    1265                1270                1275

Pro Val Trp Lys Glu Tyr Ala Glu Ile Cys Leu Ala Cys Gly Asn
    1280                1285                1290

Cys Asn Met Val Cys Pro Thr Cys Arg Cys Tyr Glu Val Cys Asp
    1295                1300                1305

Asn Trp Ile Ser Ala Tyr Asp Ala Val Arg Glu Arg Arg Tyr Asp
    1310                1315                1320

Ser Cys Phe Met Glu Asn His Gly Leu Val Ala Gly Gly His Asn
    1325                1330                1335

Phe Arg Pro Thr Arg Leu Asp Arg Phe Arg His Arg Tyr Tyr Cys
    1340                1345                1350

Lys Ser Tyr Phe Asp Pro Ser Ser Gly Tyr Asn Cys Val Gly Cys
    1355                1360                1365

Gly Arg Cys Asp Glu Phe Cys Pro Ala Lys Ile Glu His Val Lys
    1370                1375                1380

Val Leu Glu Glu Val Arg Gly Ser Leu Arg
    1385                1390

<210> SEQ ID NO 2
<211> LENGTH: 2496
<212> TYPE: PRT
<213> ORGANISM: Thermococcus onnurineus NA1

<400> SEQUENCE: 2

Met Asn Ala Ser Pro Phe Ile Ile Ser Phe Leu Ile Pro Leu Leu
1               5                   10                  15

Gly Pro Leu Leu Phe Lys Leu Asp Gly Arg Lys Ala Asp Val Phe Met
                20                  25                  30

Leu Ile Ala Val Val Ser Ser Phe Leu Ala Asn Leu Val Gly Val Leu
            35                  40                  45

Glu Tyr Leu Lys Val Gly Gly Ala His His Ile Val Tyr Leu Glu Thr
        50                  55                  60

Ser Ser Leu Gly Glu Val Tyr Gly Val Ile Ile Asp Pro Met Ser Val
65                  70                  75                  80

Leu Val Gly Phe Val Val Ser Leu Ala Gly Val Leu Phe Leu Leu Tyr
                85                  90                  95

Ala Val Asp Tyr Met Ser Glu Arg Asn Lys Gln His Pro Val Tyr Ser
                100                 105                 110

Asp Lys Gly Arg Phe Tyr Ala Trp Met Val Ile Phe Val Gly Ala Thr
            115                 120                 125

Leu Ala Phe Ile Tyr Ser Ser Thr Thr Leu Gln Leu Leu Ile Phe Phe
        130                 135                 140

Glu Ile Met Gly Leu Ala Cys Trp Gly Val Val Gly Tyr Tyr Lys Gly
145                 150                 155                 160

Pro Lys Ala Glu Arg Ala Ala Tyr Lys Ala Leu Leu Val Pro Asn Phe
                165                 170                 175

Gly Ala Met Val Gly Leu Tyr Thr Thr Val Gly Ile Gly Ile Leu Lys
            180                 185                 190

Leu His Asp Leu Ser Ile Tyr Ala Leu Gln Asn Leu Asn Asp Glu Leu
        195                 200                 205

Lys Leu Leu Val Phe Leu Gly Val Met Val Ala Ala Phe Thr Lys Ser
    210                 215                 220
```

```
Ala Gln Phe Pro Leu Tyr Ser Trp Leu Pro Asp Ala Met Ala Pro
225                 230                 235                 240

Thr Pro Ala Ser Ala Phe Leu His Gly Ala Ala Met Val Glu Met Gly
            245                 250                 255

Val Tyr Leu Leu Ala Arg Val Thr Gln Phe Met Gln Pro Ile Pro Glu
                260                 265                 270

Thr Ala Phe Tyr Val Met Leu Val Phe Val Ser Leu Thr Leu Leu Ile
            275                 280                 285

Ala Ile Leu Tyr Tyr Pro Leu Gln Lys Asp Ala Lys Arg Leu Leu Ala
        290                 295                 300

Tyr Ser Thr Ile Ala Glu Ala Gly Val Met Tyr Val Gly Val Leu Tyr
305                 310                 315                 320

Ala Val Leu Gly Ser Val Tyr Gly Leu Gln Ala Ala Met Phe Gln Leu
                325                 330                 335

Ala Asn His Ala Phe Val Lys Gly Leu Ala Phe Leu Thr Ala Gly Thr
            340                 345                 350

Phe Ser Tyr Ala Phe Gly Thr Leu Asp Met Glu Lys Ile Arg Gly Leu
        355                 360                 365

Gly Lys Leu Val Pro Val Gly Ala Ser Trp Phe Leu Ala Leu Leu
370                 375                 380

Gly Leu Ala Gly Val Pro Pro Leu Gly Leu Phe Phe Ser Lys Ala Tyr
385                 390                 395                 400

Leu Phe Met Asn Ala Ser Ser Ile Thr Ser Trp Val Gly Trp Ile Pro
                405                 410                 415

Leu Phe Leu Val Leu Ala Asp Ala Thr Val Phe Leu Ala Val Ser Leu
                420                 425                 430

Gly Trp Ile Lys Arg Met Val Phe Ser Glu Pro Leu Gln Glu Ser Ala
            435                 440                 445

Glu Val Ser Pro Leu Met Arg Phe Val Leu Val Leu Ile Val Leu
450                 455                 460

Ser Ile Val Ala Pro Phe Leu Ser Val Lys Leu Val Thr Gln Ile Gly
465                 470                 475                 480

Phe Met Gly Met Met Glu Ile Pro Ile Ala Leu Tyr Ser Leu Ser Ala
                485                 490                 495

Ile Ser Gly Leu Ile Gly Asp Phe Lys Arg Ser Ile Lys Ile Ser Ser
            500                 505                 510

Val Leu Ser Ala Ile Ala Ser Leu Ser Leu Gly Ile Ala Ala His
        515                 520                 525

Ala Leu Ser Arg Gly Leu Pro Val Gln Glu Ser Phe Leu Gly Ile Pro
            530                 535                 540

Leu Ile Ile Asp Ser Leu Ser Leu Pro Phe Leu Phe Ile Ala Leu
545                 550                 555                 560

Leu Ser Leu Val Val Ser Val Tyr Ser Ile Ser Tyr Met Glu Val His
                565                 570                 575

Arg Asp Thr Gly Arg Pro Leu Ala Tyr Thr Ile Leu Tyr Gly Thr Phe
            580                 585                 590

Val Leu Ser Ile Val Phe Val Ala Leu Thr Ser Asn Leu Leu Trp Phe
        595                 600                 605

Val Phe Phe Trp Glu Leu Met Thr Leu Thr Ser Phe Ile Phe Val Ser
            610                 615                 620

Trp Arg Glu Gln Asp Ala Gly Ile Lys Tyr Leu Leu Thr Met Gln Leu
625                 630                 635                 640

Ala Asn Thr Val Pro Leu Phe Val Ala Leu Gly Ile Ile Tyr Ser Ala
```

```
                645                 650                 655
Thr Gly Ser Phe Ser Val Asp Tyr Ala Thr Leu Arg Glu Val Ala Ser
                660                 665                 670

Ser Leu Ser Pro Val Gln Leu Lys Leu Leu Tyr Ala Met Phe Leu Val
                675                 680                 685

Thr Phe Leu Ala Lys Ser Gly Ser Val Pro Phe Gln Phe Trp Val Pro
690                 695                 700

Asp Ala Tyr Glu Ala Ala Pro Ser Asn Ile Ala Ser Leu Met Ala Gly
705                 710                 715                 720

Val Met Glu Lys Met Ala Val Tyr Gly Leu Ile Arg Leu Leu Cys Asn
                725                 730                 735

Ala Leu Pro Cys Ser Glu Gly Ile Gly Tyr Val Leu Val Ile Val Gly
                740                 745                 750

Ile Leu Thr Met Thr Phe Gly Thr Leu Tyr Ala Leu Arg Glu Thr His
                755                 760                 765

Ala Lys Arg Leu Leu Ala Tyr Ser Ser Val Gly Gln Met Gly Tyr Ile
                770                 775                 780

Trp Phe Ala Val Gly Met Gly Met Ile Phe Leu Thr Met Gly Met Glu
785                 790                 795                 800

Ser Leu Ala Tyr Leu Ala Phe Leu Ala Gly Val Phe His Ser Phe Asn
                805                 810                 815

His Thr Leu Phe Lys Gly Leu Leu Phe Leu Ile Ser Gly Asn Phe Glu
                820                 825                 830

Tyr Ser Ala Gly Thr Ala Asp Leu Asn Glu Leu Gly Gly Leu Arg Arg
                835                 840                 845

Ala Met Pro Tyr Ser Ser Leu Phe Thr Val Ile Gly Ala Leu Ser Leu
850                 855                 860

Ala Gly Val Pro Leu Phe Ser Gly Phe Leu Ser Lys Trp Met Ile Tyr
865                 870                 875                 880

Gln Ala Gly Tyr Tyr Ser Gly Ile Gly Leu Phe Val Phe Gly Ser Val
                885                 890                 895

Met Ala Val Phe Met Ser Ala Val Thr Leu Ala Tyr Ser Leu Lys Leu
                900                 905                 910

Tyr Thr Ser Ala Phe Gly Gly Glu Pro Asn Glu Arg Thr Glu Asn Ala
                915                 920                 925

Arg Glu Val Pro Ser Gly Met Leu Leu Gly Glu Gly Ile Ile Ala Leu
                930                 935                 940

Thr Ser Leu Ala Val Gly Ile Leu Pro Ala Ile Ala Tyr Pro Ile Leu
945                 950                 955                 960

Thr Ile Ser Leu Asn Gly Gly Asp Val Thr Val Thr Met Gly Ser Ile
                965                 970                 975

Ser Thr Asp Phe Glu Tyr Phe Ser Pro Ile Ala Leu Leu Leu Ala Val
                980                 985                 990

Ser Phe Ile Ala Val Ala Ser Tyr Phe Val Phe Arg Pro Lys Thr Thr
                995                 1000                1005

Asn Val Lys Pro Trp Asn Thr Gly Ala Leu Phe Leu Pro Glu Glu
    1010                1015                1020

Arg Tyr Gly Ala Lys Ala Arg Asp Tyr Tyr Arg Gln Tyr Phe Thr
    1025                1030                1035

Glu Met Glu Gly Leu Tyr Lys Leu Gly Ser Ala Ala Gly Lys Val
    1040                1045                1050

Gly Arg Val Leu Leu Ser Ala Leu Met Ser Val Tyr Leu Val Leu
    1055                1060                1065
```

-continued

```
Ala Arg Gly Leu Val Tyr Thr Gly Arg Glu Lys Lys Arg Ser Phe
    1070                1075                1080

Thr Leu Asp Glu Leu Arg His Arg Thr Val Arg Tyr Leu Asp Glu
    1085                1090                1095

Ala Phe Phe Ala Pro Met Met Asp Leu Leu Lys Asn Ile Ala Val
    1100                1105                1110

Leu Ala Ala Gly Ile Ser Val Ser Met Asp Glu Leu Phe Leu Ala
    1115                1120                1125

Ser Met Leu Thr Thr Val Ile Ile Leu Ala Leu Leu Val Leu Met
    1130                1135                1140

Asp Tyr Val Ser Ile Ile Ala Ala Pro Ile Val Leu Phe Leu Leu
    1145                1150                1155

Pro Pro Phe Leu Asp Gly Ile Gly Arg Arg Ile Lys Ala Arg Ile
    1160                1165                1170

Gln Tyr Arg Arg Gly Pro Pro Ile Met Gln Thr Phe Tyr Asp Leu
    1175                1180                1185

Glu Lys Leu Leu Lys Leu Pro Ser Val Leu Pro Thr Glu Gly Pro
    1190                1195                1200

Ile Phe Arg Leu Ala Pro Tyr Ile Ala Leu Ala Ser Ala Ile Ala
    1205                1210                1215

Gly Gly Leu Met Leu Pro Phe Gly Ser Glu Pro Val Leu Ala Phe
    1220                1225                1230

Gly Lys Ser Leu Ile Val Phe Phe Tyr Val Met Ala Met Val Ser
    1235                1240                1245

Val Val Met Ile Leu Ala Ala Phe Ser Val Gln Asn Ala Phe Ser
    1250                1255                1260

His Ile Gly Gly His Arg Glu Val Met Leu Ile Leu Ser Ile Glu
    1265                1270                1275

Pro Val Leu Ala Val Val Phe Gly Val Leu Ala Phe Lys Leu Gly
    1280                1285                1290

Thr Leu Asn Val Ala Glu Met Pro Phe Ser Ala Asn Leu Ser Leu
    1295                1300                1305

Ser Val Ala Leu Ala Tyr Ile Leu Leu Ala Tyr Ala Val Tyr Val
    1310                1315                1320

Glu Gly Gly Phe Val Pro Phe Asp Ile Ala Glu Ala Glu Thr Glu
    1325                1330                1335

Val Ile Gly Gly Pro Leu Thr Glu Tyr Ser Gly Arg Leu Leu Gly
    1340                1345                1350

Val Phe Lys Tyr Ala Leu Leu Val Lys Arg Val Val Leu Leu Trp
    1355                1360                1365

Leu Leu Ala Ser Met Ile Val Ile Pro Ala Met Arg Ser Leu Gly
    1370                1375                1380

Ile Thr Ser Ser Met Ala Leu Leu Val Ala Gln Leu Val Val Thr
    1385                1390                1395

Phe Leu Leu Tyr Ser Leu Ala Val Ala Val Glu Ala Ala Asn Ala
    1400                1405                1410

Arg Leu Arg Ile Asp Gln Ala Val Ser Leu Asn Lys Lys Val Phe
    1415                1420                1425

Leu Met Ser Leu Ala Val Leu Ile Ile Ala Leu Val Gly Trp Met
    1430                1435                1440

Glu Cys Ser Val Cys Ala Gly Gly Cys Arg Ser Ala Glu Val Glu
    1445                1450                1455

Asp Val Leu Glu Asp Gly His Leu Lys Glu Phe Val Glu Lys Phe
    1460                1465                1470
```

-continued

Arg Gly Ala Ile Phe Glu Cys Lys Lys Leu Thr Arg Asn Gln Tyr
1475                1480                    1485

Leu Phe Ile Val Asp Arg Glu Ala Leu Pro Glu Met Val Leu His
    1490                1495                1500

Trp His Asn His Ser Glu Leu Lys Glu Thr His Phe Ser Met Gly
1505                1510                    1515

Thr Gly Thr Asp Glu Arg Asn Ile Ala Gly Lys Phe Thr Tyr Ala
1520                1525                    1530

Pro Val Ile Asn Val Ala Val Glu Pro Gly Asn Gly Glu Arg Asn
1535                1540                    1545

Tyr Trp Val Ile Leu Lys Ala Tyr Leu Asp Glu Asp Asn Pro Glu
1550                1555                    1560

Phe Pro Ser Ile Ala Ala Lys Leu Pro Ala Ala Leu Trp Ala Glu
1565                1570                    1575

Arg Glu Val Tyr Asp Leu Leu Gly Phe Asn Pro Lys Gly His Pro
1580                1585                    1590

Asp Leu Arg Arg Leu Val Leu Pro Glu Asp Trp Pro Glu Gly Val
1595                1600                    1605

Tyr Pro Leu Arg Lys Asp His Asp Tyr Lys Ala Ser Pro Met Asp
1610                1615                    1620

Thr Pro Lys Cys Tyr Tyr Lys Pro Gly Pro Pro Asp Thr Met Thr
1625                1630                    1635

Val Pro Ile Gly Pro Tyr His Leu Ala Leu Asp Glu Pro Ala His
1640                1645                    1650

Phe Arg Ile Phe Val Lys Gly Glu Thr Val Val Asp Val Asp Tyr
1655                1660                    1665

Arg Gly Phe Tyr Ser His Arg Gly Ile Glu Lys Ile Gly Glu Gly
1670                1675                    1680

Arg Leu Thr Tyr Asn Gln Val Leu Phe Ile Ala Glu Arg Ile Cys
1685                1690                    1695

Gly Ile Cys Gly Phe Gln His Ser Thr Ser Tyr Ala Gln Ala Val
1700                1705                    1710

Glu Asn Ile Ala Gly Val Glu Ile Pro Glu Arg Ala Met Tyr Ile
1715                1720                    1725

Arg Thr Ile Met Leu Glu Ile Glu Arg Ile His Ser His Met Leu
1730                1735                    1740

Trp Ala Gly Val Ala Ala His Leu Thr Gly Phe Asp Thr Gly Phe
1745                1750                    1755

Met His Ala Trp Arg Val Arg Glu Pro Val Met Trp Leu Ala Glu
1760                1765                    1770

Arg Leu Thr Gly Asn Arg Lys Thr Tyr Gly Ile Asn Ile Val Gly
1775                1780                    1785

Gly Val Arg Arg Asp Phe Leu Asp Tyr Arg Lys Glu Met Ile Met
1790                1795                    1800

Glu Lys Ile Lys Glu Leu Arg Arg Gln Val Glu Glu Phe Ile Glu
1805                1810                    1815

Ile Ala Thr Gly Thr Ala Thr Phe Val Lys Arg Ala Glu Gly Val
1820                1825                    1830

Gly Ile Leu Pro Tyr Lys Val Ala Lys Ala Tyr Ser Val Leu Gly
1835                1840                    1845

Pro Asn Gly Arg Ala Ser Gly Arg Asn Ile Asp Ile Arg Arg Asp
1850                1855                    1860

Gln Pro Phe Ala Ala Tyr Lys Asp Leu Asp Phe Lys Val Pro Val

|  |  |  |  |  |  |  |  |  |  |  |
|---|---|---|---|---|---|---|---|---|---|---|
| 1865 | | | | 1870 | | | | 1875 | | |
| Tyr | Lys | Glu | Gly | Asp | Val | Leu | Ala | Arg | Phe | Leu | Ile | Arg | Met | Asp |
| 1880 | | | | | 1885 | | | | 1890 | | |
| Glu | Val | Leu | Glu | Ser | Ile | Trp | Ile | Ile | Glu | Gln | Ala | Ile | Asp | Gln |
| 1895 | | | | | 1900 | | | | 1905 | | |
| Met | Pro | Gly | Gly | Asp | Val | Phe | Val | Pro | Ile | Gly | Glu | Leu | Pro | Glu |
| 1910 | | | | | 1915 | | | | 1920 | | |
| Tyr | Glu | Glu | Ala | Leu | Gly | Tyr | Ser | Glu | Ala | Pro | Arg | Gly | Glu | Val |
| 1925 | | | | | 1930 | | | | 1935 | | |
| Ile | His | Tyr | Val | Met | Thr | Asp | Lys | Lys | Asn | Lys | Val | Tyr | Arg | Trp |
| 1940 | | | | | 1945 | | | | 1950 | | |
| Lys | Val | Arg | Ala | Pro | Thr | Tyr | Asn | Asn | Leu | Pro | Ala | Val | Pro | Glu |
| 1955 | | | | | 1960 | | | | 1965 | | |
| Met | Leu | Lys | Gly | Tyr | Ser | Val | Ala | Asp | Ala | Pro | Leu | Ile | Ile | Ala |
| 1970 | | | | | 1975 | | | | 1980 | | |
| Ser | Ile | Asp | Pro | Cys | Tyr | Ser | Cys | Thr | Glu | Arg | Val | Gln | Ile | Val |
| 1985 | | | | | 1990 | | | | 1995 | | |
| Asp | Val | Glu | Thr | Gly | Lys | Ala | Gln | Thr | Leu | Asn | Glu | Gln | Gln | Phe |
| 2000 | | | | | 2005 | | | | 2010 | | |
| Asn | Met | Leu | Ser | Ile | Gln | Lys | Gly | Lys | Gly | Val | Ala | Met | Ala | Gln |
| 2015 | | | | | 2020 | | | | 2025 | | |
| Ala | Ile | Ser | Phe | Thr | Asp | Arg | Leu | Lys | Phe | Trp | Lys | Arg | Pro | Glu |
| 2030 | | | | | 2035 | | | | 2040 | | |
| Glu | Asp | Val | Lys | Lys | Ala | Pro | Val | Thr | Thr | Ser | Tyr | Pro | Phe | Val |
| 2045 | | | | | 2050 | | | | 2055 | | |
| Asp | Ile | Glu | Lys | Pro | Pro | Glu | Tyr | Arg | Gly | Ile | Pro | Arg | Ile | Asp |
| 2060 | | | | | 2065 | | | | 2070 | | |
| Pro | His | Leu | Cys | Ile | Gly | Cys | Gly | Ala | Cys | Val | Arg | Ala | Cys | Pro |
| 2075 | | | | | 2080 | | | | 2085 | | |
| Pro | Asp | Ala | Leu | Thr | Ile | Glu | Trp | Asp | Phe | Glu | Asn | Gly | Arg | Lys |
| 2090 | | | | | 2095 | | | | 2100 | | |
| Arg | Ile | Val | Phe | Asn | Ala | Ala | Arg | Cys | Ile | Arg | Cys | His | Arg | Cys |
| 2105 | | | | | 2110 | | | | 2115 | | |
| Val | Glu | Val | Cys | Pro | Thr | Gly | Ala | Met | Gln | Gly | Thr | Thr | Arg | Phe |
| 2120 | | | | | 2125 | | | | 2130 | | |
| Glu | Ile | Ala | Thr | Pro | Asn | Lys | Glu | Asp | Leu | Ile | Glu | Val | Val | Asp |
| 2135 | | | | | 2140 | | | | 2145 | | |
| His | Lys | Leu | Tyr | Arg | Cys | Pro | Arg | Cys | Gly | Arg | Tyr | Glu | Glu | Phe |
| 2150 | | | | | 2155 | | | | 2160 | | |
| Thr | Glu | Arg | Gln | Ile | Gly | Lys | Met | Phe | Gln | Ile | Leu | Pro | Glu | Glu |
| 2165 | | | | | 2170 | | | | 2175 | | |
| Val | Ile | Asp | Gln | His | Gly | Ile | Ala | Glu | Arg | Ala | Phe | Leu | Cys | Arg |
| 2180 | | | | | 2185 | | | | 2190 | | |
| Glu | Cys | Arg | Met | Glu | Glu | Ser | Ala | Lys | Thr | Leu | Ala | Val | Gln | Gly |
| 2195 | | | | | 2200 | | | | 2205 | | |
| Pro | Tyr | Ala | Asp | Ser | Leu | Leu | Leu | Ser | Leu | Tyr | Pro | Arg | Gly | Ser |
| 2210 | | | | | 2215 | | | | 2220 | | |
| Lys | Val | Met | Gly | Glu | Arg | Arg | Met | Ser | Gly | Leu | Lys | Ser | Val | Trp |
| 2225 | | | | | 2230 | | | | 2235 | | |
| Val | Phe | His | Val | Asp | Ser | Gly | Ser | Cys | Asn | Gly | Cys | Asp | Ile | Glu |
| 2240 | | | | | 2245 | | | | 2250 | | |
| Ile | Leu | Asp | Val | Leu | Thr | Pro | Tyr | Tyr | Asp | Ala | Glu | Arg | Leu | Gly |
| 2255 | | | | | 2260 | | | | 2265 | | |

```
Ile Lys Leu Val Pro Ser Pro Arg His Ala Asp Ala Leu Leu Val
    2270            2275            2280

Ser Gly Pro Leu Thr Arg Gln Thr Tyr Tyr Ala Val Lys Ala Ala
    2285            2290            2295

Tyr Glu Ala Met Pro Pro Lys Pro Arg Ile Val Val Ala Ile Gly
    2300            2305            2310

Thr Cys Ala Ser Ser Gly Gly Ile Phe Tyr Asn Gly Tyr Pro Ile
    2315            2320            2325

Tyr Asn Pro Asn Pro Glu Arg Gly Ser Asp Arg Leu Arg Thr Gly
    2330            2335            2340

Gly Ile Glu Val Leu Leu Ala Glu Tyr Gly Lys Lys Pro Asp Met
    2345            2350            2355

Tyr Ile Pro Gly Cys Pro Pro Ser Pro Glu Glu Ile Leu Tyr Gly
    2360            2365            2370

Leu Ala Gln Leu Leu Gly Leu Lys Glu Lys Lys Met Lys Gly Glu
    2375            2380            2385

Tyr Tyr Tyr Ala Asp Glu Ile Glu Phe Val Leu Pro Glu Arg Pro
    2390            2395            2400

Ile Glu Glu Arg Ile Tyr Leu Thr Leu Arg Glu Ser Leu Arg Arg
    2405            2410            2415

Val Val Gly Tyr Phe Asp Arg Glu Lys Val Leu Glu Asp Phe Met
    2420            2425            2430

Ala Leu Val Glu Lys Ala Gln Glu Ser Glu Asn Pro Arg Glu Arg
    2435            2440            2445

Leu His Glu Leu Val Ile Gly Tyr Phe Leu Arg Glu Lys Asp Ser
    2450            2455            2460

Arg Val Lys Phe Ala Ile Arg Phe Leu Glu Asn Glu Tyr Trp Arg
    2465            2470            2475

Leu Lys Asp Ala Tyr Glu Lys Arg His Leu Ala Leu Val Lys Ala
    2480            2485            2490

Gly Val Arg
    2495

<210> SEQ ID NO 3
<211> LENGTH: 990
<212> TYPE: PRT
<213> ORGANISM: Thermococcus onnurineus NA1

<400> SEQUENCE: 3

Met Val Asp Trp Arg Leu Phe Glu Pro Leu Phe Asn Tyr Ala Arg Lys
1               5                   10                  15

Lys Ser Leu Trp Ile Val Ser Phe Cys Thr Gly Cys Gly Gly Ile Glu
                20                  25                  30

Met Pro Pro Leu Met Thr Ser Arg Tyr Asp Leu Glu Arg Phe Gly Met
            35                  40                  45

Ile Pro Asp Pro Ser Pro Arg Gln Tyr Asp Leu Phe Leu Ile Thr Gly
        50                  55                  60

Tyr Val Thr Pro Lys Thr Leu Lys Arg Ile Ile Thr Tyr Glu Met
65                  70                  75                  80

Ala Pro Asp Pro Lys Tyr Val Leu Ala His Gly Ser Cys Pro Leu Asn
                85                  90                  95

Gly Gly Ile Tyr Trp Asp Ala Tyr Asn Ala Ile Lys His Leu Asp Lys
            100                 105                 110

Tyr Ile Pro Val Asp Val Val Ile Ala Gly Cys Met Pro Arg Pro Glu
        115                 120                 125
```

-continued

```
Ala Val Met Asp Gly Ile Gln Lys Ile Met Glu Met Ile Glu Asn Gly
    130                 135                 140

Thr Ala Asp Gly Trp Lys Arg Tyr Lys Glu Asn Tyr Glu Trp Tyr Lys
145                 150                 155                 160

Lys Asn Gln Asp Glu Leu Phe Gly Glu Gly Trp Arg Glu Arg Glu Ala
                165                 170                 175

Arg Arg Trp Ile Pro Trp Leu Val Asp Lys Lys Glu Met Gly
            180                 185                 190

Glu Val Lys Trp Glu Arg Glu Gln Met Leu Val Asp Lys Ile Leu Glu
    195                 200                 205

Lys Ala Pro Tyr Ala Glu Gly Lys Val Arg Arg Glu Arg Ile Glu
    210                 215                 220

Phe Ser Ile Pro Ala Asp Arg Ile Arg Asp Phe Leu Met Leu Leu Arg
225                 230                 235                 240

Asp Asn Asp Phe Glu Leu Met Leu Gln Ile Thr Thr Val Asp Trp Pro
                245                 250                 255

Asn Asp Gly Glu Leu Glu Leu Ile Tyr Gln Met Trp Ser Val Thr His
                260                 265                 270

Arg Thr His Ala Met Val Arg Thr Arg Ile Pro Arg Asp Leu Asp Lys
    275                 280                 285

Ala Arg Met Pro Thr Val Lys Asp Ile Tyr Pro Val Ala Glu Thr Tyr
    290                 295                 300

Glu Arg Asp Ala His Asp Phe Phe Gly Val Tyr Phe Glu Gly Asn Glu
305                 310                 315                 320

Lys Met Glu Met Pro Trp Ile Leu Asp Asp Thr Glu Gln Gly Leu Phe
                325                 330                 335

Pro His Arg Lys Asp Phe Asp Met Leu Thr Tyr Val Lys Lys Lys Tyr
                340                 345                 350

Lys Leu Leu Asp Arg Phe Asp Glu Asp Lys Asp Asn Tyr Val Ile Met
                355                 360                 365

Val Ser Gln Asn Glu Leu Ile Arg Glu Ala Arg Glu Asn Gly Met Asp
    370                 375                 380

Leu Leu Pro Ile Asp Lys Asp Thr Tyr Glu Leu Phe Phe Gly Pro Gln
385                 390                 395                 400

His Met Ala Thr Glu Asn Phe Ser Ile Ile Leu Lys Met Asp Gly His
                405                 410                 415

Arg Val Val Lys Ala Ile Ala Asn Pro Gly Phe Leu His Arg Gly Phe
                420                 425                 430

Glu Lys Leu Ala Glu Tyr Arg Pro Trp His Thr Asn Ile Ala Leu Leu
    435                 440                 445

Leu Arg Ile Cys Val Pro Glu Pro Asp Val Pro Glu Ala Ile Tyr Ser
    450                 455                 460

Met Ala Val Asp Glu Ile Ile Gly Trp Glu Val Pro Glu Arg Ala Gln
465                 470                 475                 480

Trp Ile Arg Thr Thr Val Leu Glu Met Ala Arg Val Ser Ala Tyr Leu
                485                 490                 495

Phe Trp Ile Met Gly Leu Ser Phe Lys Leu Gly Val Tyr Thr Ala Gly
                500                 505                 510

Gln Trp Ala Ala Ala Tyr Arg Glu Arg Leu Met Ala Leu Phe Glu Gln
                515                 520                 525

Leu Thr Gly Ala Arg Val Tyr His Ile Tyr Thr Ile Pro Gly Gly Val
    530                 535                 540

Arg Arg Asp Ile Pro Gly Asp Lys Trp Leu Arg Gln Leu Lys Asp Thr
545                 550                 555                 560
```

```
Val Glu Tyr Ile Arg Ser Lys Leu Ser Asp Phe Asp Asn Leu Val Phe
                565                 570                 575

Glu Asn Tyr Val Ala His Arg Arg Leu Glu Gly Ile Gly Val Met Asp
            580                 585                 590

Lys Lys Phe Ala Leu Ala Glu Gly Val Thr Gly Pro Asn Leu Arg Ala
        595                 600                 605

Thr Gly Val Pro Tyr Asp Val Arg Arg Ala Asp Pro Tyr Leu Leu Tyr
    610                 615                 620

Pro Glu Leu Asp Phe Glu Val Pro Val Leu Lys Glu Gly Asp Ala Leu
625                 630                 635                 640

Ala Arg Ala Leu Ile Arg Arg Phe Glu Leu Glu Gln Asp Leu Tyr Ile
                645                 650                 655

Leu Asp Gln Leu Leu Glu Met Gly Pro Pro Ser Gly Pro Tyr Lys Val
            660                 665                 670

Glu Asp Pro Lys Leu Lys Asn Leu Pro Arg Phe Lys Val Pro Ala Gly
        675                 680                 685

Asp Ala Phe Ala His Val Glu Ser Thr Lys Gly Asp Phe Gly Ala Tyr
    690                 695                 700

Val Val Ser Asp Gly Lys His Lys Pro Tyr Arg Val Gln Ile Arg Gly
705                 710                 715                 720

Pro Ser Ile Ala His Gly Val Arg Val Leu Glu Gln Leu Leu Val Gly
                725                 730                 735

Ala Arg Ile Ala Asp Val Pro Val Ile Leu Met Ser Leu Asp Asn Cys
            740                 745                 750

Pro Pro Asp Ile Asp Arg Met Glu Val Asp Phe Lys Val Ala Pro Glu
        755                 760                 765

Glu Lys Val Arg Lys Pro Ser Phe Ile Lys Pro Trp Met Gly Leu
    770                 775                 780

Lys Tyr Leu Phe Lys Lys Pro Val Thr Ile Lys Ile Pro Tyr Glu Arg
785                 790                 795                 800

Val Gln Ile Ala Lys Asp Tyr Arg Gly Phe His Thr Leu Asp Trp Lys
                805                 810                 815

Lys Cys Val Gly Cys Asn Phe Cys Gly Gln Ile Cys Pro Ala Arg Ala
            820                 825                 830

Ile Glu Met Thr Trp Ile Glu Val Asp Gly Lys Met Glu Lys Arg Pro
        835                 840                 845

His Pro Lys Ile Asp Tyr Gly Arg Cys Thr Phe Cys Glu Phe Cys Val
    850                 855                 860

Asp Val Cys Pro Pro Gly Ala Leu Gly Phe Ile Glu Asn Tyr Ile Leu
865                 870                 875                 880

Thr Thr Glu Trp Lys Asp Glu Glu Leu Glu Leu Phe Asp Trp Val Pro
                885                 890                 895

Ile His Pro Asp Lys Phe Arg Glu Ile Asn Glu Lys Phe Pro Asp Tyr
            900                 905                 910

Arg Phe Pro Val Glu Lys Ile Glu Phe Asn Lys Glu Thr Lys Glu Val
        915                 920                 925

Thr Tyr Tyr Leu Arg Asp Gly Glu Val Met Lys Phe Lys Ile Leu Gly
    930                 935                 940

Tyr Gly Ile Arg Pro Pro Lys Pro Pro Thr Lys Pro Ala Gln Lys Ala
945                 950                 955                 960

Ala Ala Lys Ala Ala Glu Lys Asn Asp Thr Lys Pro Val Glu Lys Pro
                965                 970                 975

Thr Glu Lys Lys Glu Ala Gly Lys Ile Glu Glu Lys Lys Glu
```

```
              980             985             990
```

<210> SEQ ID NO 4
<211> LENGTH: 3724
<212> TYPE: PRT
<213> ORGANISM: Thermococcus onnurineus NA1

<400> SEQUENCE: 4

```
Met Glu Thr Leu Ile Leu Ala Leu Gly Asn Glu Leu Met Lys Asp Asp
1               5                  10                  15

Gly Val Gly Leu Lys Val Gly Arg Leu Leu Ala Glu Lys Gly Tyr Asn
            20                  25                  30

Val Leu Glu Val Gly Thr Asp Ile Phe Met Leu Gln Ser His Tyr Ser
        35                  40                  45

Gly Glu Glu Arg Leu Ile Ile Ile Asp Ala Ile Leu Ser Glu Lys Phe
    50                  55                  60

Lys Pro Gly Glu Ile Ile His Val Ser Gly Gly Glu Val Phe Glu Lys
65                  70                  75                  80

Leu Lys Ala Glu Ile Arg Ser Ala His Phe Met Gly Ala Ile Asp Gly
                85                  90                  95

Leu Lys Leu Leu Met Ala Leu Asp Glu Arg Leu Ala Asn Val Glu Ile
            100                 105                 110

His Phe Ile Gly Ile Val Ala Lys Glu Ile Asn Leu Gly Met Glu Leu
        115                 120                 125

Thr Glu Glu Val Arg Glu Ala Leu Pro Lys Ala Val Glu Leu Val Glu
    130                 135                 140

Glu Leu Val Lys Lys Met Lys Asn Leu Tyr Leu Pro Ile Thr Val Asp
145                 150                 155                 160

His Ile Ala Arg Val Glu Gly Lys Gly Gly Val Glu Ile Val Val Gly
                165                 170                 175

Asp Asp Gly Val Lys Glu Val Lys Leu Asn Ile Ile Glu Gly Pro Arg
            180                 185                 190

Phe Phe Glu Ala Ile Thr Ile Gly Lys Lys Leu Asp Glu Ala Leu Ala
        195                 200                 205

Val Tyr Pro Arg Ile Cys Ser Phe Cys Ser Ala Ala His Lys Leu Thr
    210                 215                 220

Ala Val Glu Ala Ala Glu Lys Ala Val Gly Phe Glu Val Arg Glu Glu
225                 230                 235                 240

Ile Gln Ala Leu Arg Glu Val Leu Tyr Ile Gly Asp Met Ile Glu Ser
                245                 250                 255

His Ala Leu His Leu Tyr Leu Leu Val Leu Pro Asp Tyr Met Gly Tyr
            260                 265                 270

Ser Asn Pro Leu Lys Met Leu Asp Lys Tyr Lys Glu Ile Asn Ile
        275                 280                 285

Ala Leu Asp Leu Lys Asn Leu Gly Ser Trp Met Met Asp Glu Leu Gly
    290                 295                 300

Ala Arg Ala Ile His Gln Glu Asn Val Val Met Gly Gly Phe Gly Lys
305                 310                 315                 320

Leu Pro Asp Lys Thr Thr Leu Glu Lys Met Lys Lys Arg Leu Gln Glu
                325                 330                 335

Ala Leu Pro Leu Ala Glu Tyr Thr Phe Glu Leu Phe Ser Lys Leu Glu
            340                 345                 350

Gln Tyr Glu Glu Val Glu Gly Pro Ile Ile His Met Ala Val Arg Pro
        355                 360                 365

Arg Gly Asp Val Tyr Gly Ile Tyr Gly Asp Ala Ile Ser Val Ser Asp
```

```
            370                 375                 380
Gly Phe Glu Phe Pro Ser Glu Gly Tyr Lys Lys His Met Val Glu Arg
385                 390                 395                 400

Val Val Glu His Ser Phe Ala Lys His Ser Phe Tyr Asn Gly Glu Lys
                405                 410                 415

Pro Phe Met Thr Gly Ala Ile Ser Arg Val Val Asn His Ala Asp Lys
                420                 425                 430

Leu Tyr Gly Arg Ala Lys Glu Leu Tyr Glu Ser His Lys Asp Leu Leu
                435                 440                 445

Arg Pro Thr Asn Pro Phe Ala Asn Asn Leu Ala Gln Ala Leu Glu Leu
            450                 455                 460

Val Tyr Phe Met Glu Arg Gly Ile Asp Leu Ile Asp Glu Ala Leu Ala
465                 470                 475                 480

Lys Trp Pro Ile Arg Pro Arg Asp Glu Val Asp Val Lys Asp Gly Phe
                485                 490                 495

Gly Val Ser Thr Thr Glu Ala Pro Arg Gly Ile Leu Val Tyr Ala Leu
                500                 505                 510

Glu Val Lys Asp Gly Arg Val Ala Tyr Ala Asp Ile Ile Thr Pro Thr
                515                 520                 525

Ala Phe Asn Leu Ala Met Met Glu Val His Val Arg Met Met Ala Glu
            530                 535                 540

Lys His Tyr Asn Asp Asp Pro Glu Arg Leu Lys Leu Leu Ala Glu Met
545                 550                 555                 560

Val Val Arg Ala Tyr Asp Pro Cys Ile Ser Cys Ser Val His Val Ala
                565                 570                 575

Arg Leu Met Glu Gly Lys Val Arg Ile Gly Phe Tyr Ala Leu Thr Ser
                580                 585                 590

Cys Tyr Gly Cys Gln Leu Arg Phe Ala Met Met Asp Glu Ile Leu Gln
            595                 600                 605

Leu Leu Pro Asn Ala Glu Ile Val Cys Trp Tyr Met Leu Asp Arg Asp
610                 615                 620

Ser Ser Glu Asp Glu Pro Val Asp Ile Ala Phe Ile Glu Gly Ser Val
625                 630                 635                 640

Ser Thr Glu Glu Glu Val Glu Leu Val Lys Lys Ile Arg Glu Asn Ala
                645                 650                 655

Lys Ile Val Val Ala Val Gly Ala Cys Ala Thr Gln Gly Gly Val Gln
                660                 665                 670

Ser Trp Glu Lys Asp Lys Ser Leu Glu Glu Leu Trp Lys Ala Val Tyr
            675                 680                 685

Gly Asp Gly Lys Val Lys Phe Glu Pro Lys Met Ala Glu Pro Leu Glu
            690                 695                 700

Asn Tyr Ile Lys Val Asp Tyr Arg Ile Tyr Gly Cys Pro Pro Glu Lys
705                 710                 715                 720

Lys Asp Phe Ile Tyr Ala Ile Gly Thr Phe Leu Val Gly Ser Trp Pro
                725                 730                 735

Glu Asp Ile Asp Tyr Pro Val Cys Leu Glu Cys Arg Leu Lys Gly Asn
            740                 745                 750

Thr Cys Ile Leu Ile Glu Lys Gly Glu Pro Cys Leu Gly Pro Ile Thr
            755                 760                 765

Arg Ala Gly Cys Asp Ala Arg Cys Pro Ser Tyr Gly Ile Ala Cys Ile
            770                 775                 780

Gly Cys Arg Gly Ala Ile Gly Tyr Asp Val Ala Trp Phe Asp Ser Leu
785                 790                 795                 800
```

-continued

Ala Arg Thr Phe Lys Glu Lys Gly Leu Thr Lys Glu Ile Leu Glu
            805                 810                 815

Arg Met Lys Ile Phe Asn Ala His Asn Pro Lys Leu Glu Glu Met Val
            820                 825                 830

Asp Lys Val Phe Gln Phe Gln Gly Val Lys Glu Met Asn Glu Ala His
            835                 840                 845

Val Cys Met Cys His Asp Asn Pro Tyr Ala Leu Asp Arg Val Lys Val
            850                 855                 860

Leu Arg Val Tyr Arg Leu Thr Glu Thr Glu Lys Leu Phe Leu Phe Arg
865                 870                 875                 880

Phe Glu Asp Gln Glu Ile Ala Glu Asn Trp Thr Phe Lys Pro Gly Gln
                    885                 890                 895

Phe Val Gln Leu Thr Ile Pro Gly Val Gly Glu Val Pro Ile Ser Ile
                    900                 905                 910

Cys Ser Ser Pro Met Lys Arg Gly Phe Phe Glu Leu Cys Ile Arg Lys
                    915                 920                 925

Ala Gly Arg Val Thr Thr Val Val His Lys Leu Lys Pro Gly Asp Thr
            930                 935                 940

Val Leu Val Arg Gly Pro Tyr Gly Asn Gly Phe Pro Val Asp Glu Trp
945                 950                 955                 960

Glu Gly Met Asp Leu Leu Leu Ile Ala Ala Gly Leu Gly Thr Ala Pro
                    965                 970                 975

Leu Arg Ser Val Phe Leu Tyr Ala Met Asp Asn Arg Trp Lys Tyr Gly
                    980                 985                 990

Asn Ile Thr Phe Ile Asn Thr Ala Arg Tyr Gly Lys Asp Leu Leu Phe
            995                 1000                1005

Tyr Lys Glu Leu Glu Ala Met Lys Asp Leu Ala Glu Ala Glu Asn
    1010                1015                1020

Val Gln Ile Ile Gln Ser Val Thr Arg Asp Pro Asp Trp Pro Gly
    1025                1030                1035

Arg His Gly Arg Pro Gln Lys Phe Ile Val Glu Ala Asn Thr Asn
    1040                1045                1050

Pro Lys Asn Thr Ala Ile Ala Ile Cys Gly Pro Pro Arg Met Tyr
    1055                1060                1065

Lys Ala Val Phe Glu Ala Leu Ile Asn Tyr Gly Tyr Arg Pro Glu
    1070                1075                1080

Asn Ile Tyr Val Thr Leu Glu Arg Lys Met Lys Cys Gly Ile Gly
    1085                1090                1095

Lys Cys Gly His Cys Asn Val Gly Thr Ser Thr Ser Trp Lys Tyr
    1100                1105                1110

Val Cys Arg Asp Gly Pro Val Phe Thr Tyr Phe Asp Ile Val Ser
    1115                1120                1125

Thr Pro Gly Leu Leu Asp Met Arg Tyr Val Lys Leu Pro Lys Glu
    1130                1135                1140

Asn Thr Tyr Glu Phe Leu Glu Arg Leu Lys Asn Leu Gly Lys Leu
    1145                1150                1155

Tyr Ala Pro Val Lys Ile Ser Asp Gln Phe Tyr Asp Phe Arg Glu
    1160                1165                1170

Ile Asp Asp Val Arg Lys Ile Glu Phe Asn Tyr Thr Arg Thr Leu
    1175                1180                1185

Met Pro Pro Lys Lys Phe Phe Ala Pro Arg Glu Lys Met Phe
    1190                1195                1200

Glu Phe Ser Ile Ser Lys Ala Glu Tyr Arg Glu Val Ile Pro Glu
    1205                1210                1215

```
Val Glu Pro Phe Val Leu Phe Gly Leu His Ala Cys Asp Ile Tyr
    1220            1225                1230

Gly Leu Lys Ile Leu Asp Ser Val Tyr Leu Asp Glu Tyr Pro Asp
    1235            1240                1245

Lys Tyr Tyr Lys Val Arg Arg Glu Lys Gly Ile Ile Ile Gly Ile
    1250            1255                1260

Ser Cys Met Pro Asp Glu Tyr Cys Phe Cys Asn Leu Leu Arg Thr
    1265            1270                1275

Asp Phe Glu His Asp Gly Phe Asp Leu Phe Phe His Glu Leu Pro
    1280            1285                1290

Asp Gly Trp Leu Ile Arg Ile Gly Thr Pro Thr Gly His Arg Ile
    1295            1300                1305

Val Asp Lys Asn Ile Lys Leu Phe Thr Glu Val Ala Gln Glu Asp
    1310            1315                1320

Ile Cys Asn Phe Arg Glu Phe Glu Arg Lys Arg Ala Gln Ala Phe
    1325            1330                1335

Arg Tyr His Glu Glu Trp Asp Asn Ile His Tyr Leu Leu Glu Leu
    1340            1345                1350

Glu Met Glu His Pro Leu Trp Glu Lys Glu Ala Glu Lys Cys Phe
    1355            1360                1365

Ala Cys Gly Asn Cys Ser Thr Val Cys Pro Thr Cys Arg Cys Tyr
    1370            1375                1380

Glu Val Gln Asp Ile Val Asn Leu Asp Gly Asp Thr Gly Tyr Arg
    1385            1390                1395

Glu Arg Arg Trp Asp Ser Cys Lys Phe Arg Ser His Gly Leu Val
    1400            1405                1410

Ala Gly Gly His Asn Phe Arg Pro Thr Lys Lys Asp Arg Phe Ile
    1415            1420                1425

Asn Arg Tyr Leu Cys Lys Met Ser Phe His Trp Thr Leu Gly Ile
    1430            1435                1440

Asn Phe Cys Val Gly Cys Gly Arg Cys Thr Ala Phe Cys Pro Ala
    1445            1450                1455

Gly Ile Asp Phe Val Lys Asn Leu Arg Ile Ile Ala Gly Leu Glu
    1460            1465                1470

Asp Ala Ser Cys Pro Ser Lys Leu Ser Glu Glu Ile Pro Lys Lys
    1475            1480                1485

Gly Phe Ala Tyr Ala Asn Asn Ile Arg Gly Glu Asp Ile Met Ala
    1490            1495                1500

Gln Asn Asn Ser Leu Val Leu Tyr Asp Val His Glu Thr Val Asp
    1505            1510                1515

Val Cys Ser Asn Val Gly Cys Val Lys Thr Lys Ala Thr Pro Ser
    1520            1525                1530

Arg Leu Leu Phe Ala Gly Phe Met Ala Gly Ala Tyr Ile Ala Phe
    1535            1540                1545

Gly Phe Ile Phe Ala Ile Val Ala Ser Ala Ser Phe His Pro Lys
    1550            1555                1560

Leu Gly Thr Phe Pro Asn Leu Ser Leu Phe Lys Leu Leu Leu Gly
    1565            1570                1575

Ala Val Phe Pro Val Gly Leu Ile Ala Val Leu Leu Gly Gly Ala
    1580            1585                1590

Asp Leu Trp Thr Gly Asn Ala His Ile Val Thr Leu Ser Lys Met
    1595            1600                1605

Thr Gly Arg Ala Ser Val Lys Asp Val Leu Tyr Asn Trp Ile Gly
```

```
                    1610                1615                1620

Ser Tyr Thr Gly Asn Phe Val Gly Ser Val Phe Leu Ala Phe Leu
1625                    1630                1635

Ala Val Tyr Gly Thr Gly Leu Met Ala Gly Gly Leu Phe Lys Asp
1640                    1645                1650

Val Leu Ile Gly Ile Gly Asn Tyr Lys Val Ala Leu Thr Pro Trp
1655                    1660                1665

Lys Ala Leu Trp Leu Gly Ile Gly Cys Asn Trp Leu Val Asn Val
1670                    1675                1680

Ala Ile Trp Leu Tyr Ile Arg Ala Lys Asp Thr Ala Gly Lys Val
1685                    1690                1695

Ile Val Thr Trp Phe Pro Ile Phe Ala Phe Val Ala Ile Gly Phe
1700                    1705                1710

Glu His Ser Ile Ala Asn Met Trp Ala Ile Ser Ala Ser Ile Phe
1715                    1720                1725

Ala Ser Asp Gly Ala Ile Ser Trp Val Gln Phe Phe His Asn Ile
1730                    1735                1740

Ile Pro Val Thr Ile Gly Asn Ala Ile Gly Gly Phe Leu Phe Val
1745                    1750                1755

Gly Phe Tyr His Trp Tyr Leu Ala Asp Gly Arg Asn Ala Ile Lys
1760                    1765                1770

Glu Leu Ile Asp Phe Val Glu Val Leu Ala Leu Phe Val Phe Ile
1775                    1780                1785

Met Val Leu Ile Pro Ala Gly Ile Ala Tyr Ala Leu Ser Gly Leu
1790                    1795                1800

Gly Asn Ile Ala Thr Trp Leu Val Pro Leu Ile Ile Ser Val Tyr
1805                    1810                1815

Gly Val Val Met Thr Tyr Leu Val Arg Arg Ala Leu Met Glu Glu
1820                    1825                1830

Phe Lys Ile Gly Leu Cys Pro Tyr Cys Gly Met Gly Cys Arg Phe
1835                    1840                1845

Tyr Ile Lys Thr Leu Asn Gly Gln Pro Ile Gly Ile Glu Pro Tyr
1850                    1855                1860

Pro Gly Gly Val Asn Glu Gly Lys Leu Cys Pro Lys Gly Val Ala
1865                    1870                1875

Ala Val Asp Phe Leu Arg His Lys Asp Arg Leu Lys Lys Pro Leu
1880                    1885                1890

Lys Arg Thr Glu Asn Gly Phe Val Glu Ile Ser Trp Glu Gln Ala
1895                    1900                1905

Ile Lys Glu Ile Ala Glu Lys Leu Leu Glu Ile Arg Glu Lys Tyr
1910                    1915                1920

Gly Pro Asp Thr Leu Gly Phe Phe Ser Ser Ala Arg Cys Ser Asn
1925                    1930                1935

Glu Glu Asn Tyr Leu Leu Gln Lys Ile Ala Arg Leu Leu Gly Thr
1940                    1945                1950

Asn Asn Val Asp His Cys Ala Arg Leu Cys His Ala Ser Thr Val
1955                    1960                1965

Val Gly Leu Ala Gln Thr Val Gly Ala Ala Ala Gln Ser Gly Ser
1970                    1975                1980

Tyr Thr Asp Ile Pro Lys Ala Lys Val Leu Leu Ile Trp Gly Tyr
1985                    1990                1995

Asn Pro Ser Glu Thr His Pro Val Leu Met Arg Tyr Ile Leu Arg
2000                    2005                2010
```

```
Ala Arg Asp Asn Gly Ala Lys Ile Ile Val Val Asp Pro Arg Lys
    2015                2020                2025

Thr Arg Thr Val Trp Phe Ala Asp Met His Leu Gln Leu Lys Pro
    2030                2035                2040

Gly Thr Asp Ile Val Leu Ala Asn Ala Met Met His Val Ile Ile
    2045                2050                2055

Glu Glu Arg Leu Tyr Asp Arg Glu Phe Ile Met Asn Arg Thr Lys
    2060                2065                2070

Gly Phe Glu Lys Leu Ile Ala Ala Val Gln Lys Tyr Thr Pro Glu
    2075                2080                2085

Tyr Ala Glu Glu Ile Thr Gly Val Pro Ala Lys Leu Ile Arg Glu
    2090                2095                2100

Ala Ala Ile Thr Phe Ala Thr Ala Gly Arg Gly Ile Val Met Trp
    2105                2110                2115

Ala Met Gly Leu Thr Gln His Val Thr Gly Ala Ala Asn Val Lys
    2120                2125                2130

Ala Leu Ala Asp Leu Ala Leu Ile Cys Gly Tyr Val Gly Arg Glu
    2135                2140                2145

Gly Thr Gly Leu Phe Pro Met Arg Gly Gln Asn Asn Val Gln Gly
    2150                2155                2160

Ala Cys Asp Met Ala Ala Leu Pro Asn Val Phe Pro Gly Tyr Gln
    2165                2170                2175

Lys Val Thr Asp Asp Glu Lys Arg Lys His Val Ala Glu Ile Trp
    2180                2185                2190

Gly Val Glu Asp Leu Pro Ser Lys Pro Gly Leu Thr Ile Pro Glu
    2195                2200                2205

Met Ile Asp Ala Ala Lys Gly Glu Leu Lys Ala Leu Tyr Ile
    2210                2215                2220

Met Gly Glu Asn Pro Val Met Ser Asp Pro Asn Thr Lys His Val
    2225                2230                2235

Ile Glu Ala Leu Lys Asn Leu Glu Leu Leu Val Val Gln Asp Ile
    2240                2245                2250

Phe Leu Thr Glu Thr Ala Glu Leu Ala His Tyr Val Leu Pro Ala
    2255                2260                2265

Ala Ala Tyr Ala Glu Lys Glu Gly Ser Phe Thr Ala Ser Glu Arg
    2270                2275                2280

Arg Val Gln Trp Asn Phe Lys Ala Ile Glu Pro Pro Gly Glu Ala
    2285                2290                2295

Lys Pro Asp Trp Glu Ile Leu Thr Met Leu Gly Lys Ala Leu Gly
    2300                2305                2310

Leu Pro Lys Phe Asp Tyr Ser Asp Val Glu Asp Ile Thr Arg Glu
    2315                2320                2325

Ile Thr Leu Val Ala Pro Gln Tyr Arg Gly Ile Thr Pro Glu Arg
    2330                2335                2340

Leu Lys Arg Glu Val Met Gly Val Gln Trp Pro Cys Pro Ser Glu
    2345                2350                2355

Asp His Pro Gly Thr Pro Arg Leu His Val Glu Arg Phe Ala Thr
    2360                2365                2370

Pro Asp Gly Lys Ala Asn Ile Ile Pro Val Glu Phe Lys Pro Pro
    2375                2380                2385

Ala Glu Glu Pro Asp Glu Glu Tyr Pro Phe Ile Leu Thr Thr Phe
    2390                2395                2400

Arg Ile Val Gly Gln Tyr His Thr Leu Thr Met Ser Asn Arg Ser
    2405                2410                2415
```

```
Glu Ser Leu Lys Lys Arg Trp Ser Ser Pro Tyr Ala Gln Ile Ser
    2420            2425            2430

Pro Glu Asp Ala Lys Lys Leu Gly Ile Gln Asp Gly Glu Met Ile
    2435            2440            2445

Arg Ile Val Thr Arg Arg Gly Ser Tyr Thr Cys Arg Ala Val Val
    2450            2455            2460

Thr Glu Asp Val Ser Glu Gly Val Ile Ala Val Pro Trp His Trp
    2465            2470            2475

Gly Ala Asn Ile Leu Thr Asn Asp Val Leu Asp Pro Glu Ala Lys
    2480            2485            2490

Ile Pro Glu Leu Lys Val Ala Ala Cys Arg Val Glu Lys Ile Gly
    2495            2500            2505

Gly Cys Met Glu Lys Lys Leu Phe Ile Asn Leu Gly Arg Cys Ile
    2510            2515            2520

Ala Cys Arg Ala Cys Glu Val Ala Cys Glu Lys Glu His Gly Ile
    2525            2530            2535

Ser Phe Ile Thr Val Tyr Glu Phe Arg Asp Ile Ala Val Pro Leu
    2540            2545            2550

Asn Cys Arg His Cys Glu Lys Ala Pro Cys Ile Glu Val Cys Pro
    2555            2560            2565

Thr Lys Ala Ile Tyr Arg Asp Glu Asp Gly Ala Val Val Ile Asp
    2570            2575            2580

Glu Ser Lys Cys Ile Gly Cys Tyr Met Cys Ser Ala Val Cys Pro
    2585            2590            2595

Tyr Ala Ile Pro Ile Val Asp Pro Ile Lys Glu Leu Ala Val Lys
    2600            2605            2610

Cys Asp Leu Cys Ala Glu Arg Arg Lys Glu Gly Arg Asp Pro Leu
    2615            2620            2625

Cys Ala Ala Val Cys Pro Thr Asp Ala Ile Ile Tyr Ala Asp Leu
    2630            2635            2640

Asn Glu Leu Met Glu Glu Lys Arg Arg Arg Lys Ala Glu Arg Ile
    2645            2650            2655

Val Glu Ala Gln Arg Lys Ala Val Glu Thr Leu Ala Tyr Phe Gly
    2660            2665            2670

Val Leu Lys Val Glu Leu Cys Val Gly Cys Gly Val Cys Ala Lys
    2675            2680            2685

Ala Cys Pro His Ser Ala Ile Ser Val Phe Glu Asp Ser Val Arg
    2690            2695            2700

Arg Ile Val Phe Asp Pro Lys Lys Cys Glu Glu Cys Ser Phe Glu
    2705            2710            2715

Cys Asn Glu Ala Cys Pro Thr Gly Ala Leu Glu Gly Lys Ser Asp
    2720            2725            2730

Lys Arg Glu Leu Val Phe Glu Phe Ala Tyr Cys Ala Ile Cys Gly
    2735            2740            2745

Lys Arg Leu Asn Ile Val Lys Glu Glu Ala Glu Tyr Leu Ala Lys
    2750            2755            2760

Lys Leu Ile Glu Leu Gly Glu Asn Pro Glu Ile Ala Phe Leu Cys
    2765            2770            2775

Asp Asp Cys Lys Arg Lys Arg Leu Phe Gly Val Ala Asn Lys Tyr
    2780            2785            2790

Glu Ala Tyr Leu Gly Met Ser Gly Met Arg Phe Ala Phe Leu Cys
    2795            2800            2805

Arg Glu Arg Pro Glu Pro Thr Gly Lys Lys Ile Ala Val Ile Gly
```

-continued

```
            2810                2815                2820

Ala Gly Pro Ala Gly Leu Ala Thr Gly Tyr Leu Val Cys Gln
    2825                2830                2835

Gly His Glu Val His Val Tyr Asp Lys Leu Pro Glu Pro Gly Gly
    2840                2845                2850

Leu Met Leu Phe Gly Ile Pro Glu Phe Arg Ile Pro Ile Tyr Arg
    2855                2860                2865

Val Arg Glu Gly Tyr Glu Glu Leu Glu Arg Val Tyr Asn Val Lys
    2870                2875                2880

Phe Phe Thr Arg Thr Lys Val Tyr Phe Gly Asn Leu Glu Gly Glu
    2885                2890                2895

Ser Gly Asp Glu Phe Val Glu Asn Arg Val Asp Phe Lys Glu Leu
    2900                2905                2910

Val Glu Lys Tyr Asp Ala Val Leu Ile Ala Thr Gly Thr Trp Lys
    2915                2920                2925

Cys Trp Ile Pro Asn Ile Glu Gly Ala Glu Leu Glu Gly Val Phe
    2930                2935                2940

Pro Ala Leu Glu Tyr Leu Phe Arg Ile Lys Ser Ala Lys Leu Gly
    2945                2950                2955

His Met Asp Trp Gly Lys Val Thr Pro Val Glu Gly Lys Lys Val
    2960                2965                2970

Leu Val Val Gly Ala Gly His Thr Ala Val Asp Ala Ala Leu Glu
    2975                2980                2985

Ser Val Leu Leu Gly Ala Asp Lys Val Tyr Leu Ser Tyr Arg Arg
    2990                2995                3000

Thr Ile Arg Glu Ala Pro Ala Gly Ala Tyr Glu Ile Asn Leu Leu
    3005                3010                3015

Gln Gln Arg Gly Val Lys Trp Leu Glu Arg Thr Met Pro Val Arg
    3020                3025                3030

Ile Ile Gly Glu Asn Gly Lys Val Arg Ala Val Glu Leu Val Lys
    3035                3040                3045

Thr Lys Leu Ser Glu Pro Asp Glu Ser Gly Arg Arg Arg Pro Val
    3050                3055                3060

Pro Ile Glu Gly Ser Asn Phe Gln Ile Asp Val Asp Tyr Val Ile
    3065                3070                3075

Phe Ala Val Gly Gln Ser Pro Thr Pro Pro Phe Ala Glu Glu Ile
    3080                3085                3090

Asp Ile Ala Val Asp Lys Lys Gly Arg Ile Val Val Asp Asn Arg
    3095                3100                3105

His Met Thr Ser Arg Glu Gly Val Phe Ala Ala Gly Asp Val Val
    3110                3115                3120

Leu Gly Pro Ser Lys Val Gly Lys Ala Val Lys Asp Gly Leu Tyr
    3125                3130                3135

Ala Ala Glu Ala Met His Met Trp Leu Met Gly Arg Met Thr Arg
    3140                3145                3150

Arg Ile Leu His Val Asp Tyr Ser Leu Cys Ile Gly Cys Glu Thr
    3155                3160                3165

Cys Glu Ala Val Cys Asp Phe Leu His Gly Gly Lys Pro Asn Ile
    3170                3175                3180

Arg Ile Tyr Tyr Thr Val Thr Gly Leu Pro Ile Pro Ile Asn Cys
    3185                3190                3195

Arg His Cys Glu Arg Ala Pro Cys Met Asp Val Cys Pro Ala Gly
    3200                3205                3210
```

-continued

Ala Ile Tyr Arg Asp Ser Asp Gly Ala Ile Ile Ile Asn Pro Asp
3215                3220                3225

Lys Cys Ile Gly Cys Tyr Met Cys Leu Ala Val Cys Pro Phe Gly
3230                3235                3240

Val Pro Ser Phe Asp Val Lys Thr Lys Ala Val Thr Lys Cys Asp
3245                3250                3255

Met Cys Ala Asp Arg Arg Arg Leu Gly Met Glu Pro Ala Cys Ala
3260                3265                3270

Glu Met Cys Pro Ala Glu Ala Ile Phe Phe Gly Lys Pro Glu Glu
3275                3280                3285

Val Glu Asp Arg Ile Arg Arg Arg Thr Ala Glu Arg Ile Ala Arg
3290                3295                3300

Glu Arg Ile Ala Ala Val Asp Met Glu Gly Val Gly Arg Met Leu
3305                3310                3315

Met Leu Trp Glu Ser Gln Ile Pro Ile Asn Gln Val Phe Glu Leu
3320                3325                3330

Arg Cys Arg Ser Met Thr Tyr Phe Gly Val Gly Ala Ile Asn Lys
3335                3340                3345

Phe Tyr Asp Ile Ala Lys Asp Leu Lys Glu Asn Arg Gly Ile Thr
3350                3355                3360

Lys Val Ile Leu Val Thr Gly Lys Ser Ser Tyr Lys Lys Cys Gly
3365                3370                3375

Ala Trp Asp Val Val Lys Pro Ala Leu Glu Glu Tyr Gly Ile Glu
3380                3385                3390

Tyr Val His Tyr Asp Lys Val Gly Pro Asn Pro Thr Val Asp Met
3395                3400                3405

Ile Asp Glu Ala Thr Gln Leu Gly Lys Glu Phe Gly Ala Gln Ala
3410                3415                3420

Val Ile Gly Ile Gly Gly Gly Ser Pro Ile Asp Ser Ala Lys Ser
3425                3430                3435

Val Ala Ile Leu Leu Glu Tyr Thr Asp Lys Thr Ala Arg Asp Leu
3440                3445                3450

Tyr Glu Leu Lys Phe Thr Pro Thr Lys Ala Lys Pro Ile Ile Ala
3455                3460                3465

Val Asn Thr Thr His Gly Thr Gly Thr Glu Val Asp Arg Phe Ala
3470                3475                3480

Val Ala Ser Ile Pro Glu Lys Glu Tyr Lys Pro Ala Ile Ala Tyr
3485                3490                3495

Asp Cys Ile Tyr Pro Leu Tyr Ser Ile Asp Asp Pro Ala Leu Met
3500                3505                3510

Thr Lys Leu Pro Ala Asp Gln Thr Arg Tyr Val Thr Ile Asp Ala
3515                3520                3525

Leu Asn His Ile Thr Glu Ala Ala Thr Thr Lys Phe Ala Ser Pro
3530                3535                3540

Tyr Ser Ile Leu Leu Ala Gln Glu Thr Ala Arg Leu Ile Phe Asp
3545                3550                3555

Tyr Leu Pro Glu Ala Leu Ala His Pro Asp Asn Leu Gln Ala Arg
3560                3565                3570

Tyr Tyr Leu Leu Tyr Ala Ser Ala Ile Ala Gly Ile Ser Phe Asp
3575                3580                3585

Asn Gly Leu Leu His Phe Thr His Ala Leu Glu His Pro Leu Ser
3590                3595                3600

Ala Val Lys Pro Asp Leu Pro His Gly Leu Gly Leu Ala Met Leu
3605                3610                3615

Leu Pro Ala Val Ile Lys His Ile Tyr Pro Ala Thr Ala Arg Ile
    3620                3625                3630

Leu Ala Glu Val Tyr Arg Pro Leu Val Pro Glu Ala Lys Gly Val
    3635                3640                3645

Pro Gly Glu Ala Glu Leu Val Ala Lys Lys Val Glu Glu Trp Leu
    3650                3655                3660

Phe Asn Ile Gly Ile Thr Gln Lys Leu Ile Asp Val Gly Phe Thr
    3665                3670                3675

Glu Glu Asp Val Asp Lys Leu Ala Glu Leu Ala Met Thr Thr Pro
    3680                3685                3690

Ser Leu Asp Leu Leu Ser Leu Ala Pro Ile Glu Ala Thr Lys
    3695                3700                3705

Glu Thr Val Ala Ala Ile Tyr Arg Asp Ser Leu Tyr Pro Leu Asn
    3710                3715                3720

Lys

<210> SEQ ID NO 5
<211> LENGTH: 1658
<212> TYPE: PRT
<213> ORGANISM: Thermococcus onnurineus NA1

<400> SEQUENCE: 5

Met Glu Val Ile Phe Leu Phe Ile Val Ile Leu Ser Val Ala Ser
1               5                   10                  15

Phe Ile Gly Val Phe Ser Arg Ser Ala Ile Leu Thr Lys Leu Val Asn
                20                  25                  30

Ala Leu Ser Ala Leu Gly Ser Leu Thr Ile Ala Tyr Ala Gly Ile Val
            35                  40                  45

Gly Leu Lys Glu Ser Val Glu Leu Asn Ile Thr Leu Leu His Leu Lys
        50                  55                  60

Ser Asp Ser Ile Ile Asn Ala Phe Ser Thr Leu Thr Leu Lys Val Asp
65                  70                  75                  80

Pro Leu Ser Gly Phe Phe Met Ile Ile Leu Gly Ile Leu Gly Phe Cys
                85                  90                  95

Thr Ser Val Tyr Gly Ile Ala Tyr Leu Asp Met Tyr Lys Gly Asp Lys
                100                 105                 110

Arg Leu Tyr Ala Phe Asn Tyr Pro Leu Phe Leu Leu Phe Met Phe Leu
            115                 120                 125

Val Leu Val Ser Trp Asn Leu Leu Trp Phe Val Val Phe Trp Glu Leu
        130                 135                 140

Met Thr Leu Phe Ser Gln Phe Leu Val Ala Phe Glu Arg Asn Glu Lys
145                 150                 155                 160

Thr Leu Ile Ala Thr Leu Lys Tyr Phe Cys Met Thr Lys Ala Ala Ala
                165                 170                 175

Asp Phe Met Leu Ile Ala Ile Val Leu Val Leu Ile Thr Ile Ser Gly
            180                 185                 190

Gly Gly Asp Tyr Asp Ile Leu Ser Ser Gln Leu Val Asn Tyr Phe Arg
        195                 200                 205

Ser His Pro Leu Glu Met Tyr Leu Val Ser Ala Gly Phe Met Ile Gly
    210                 215                 220

Leu Gly Val Lys Ala Ala Leu Val Pro Phe His Val Trp Leu Pro Asp
225                 230                 235                 240

Ala Tyr Val Glu Ala Pro Ser Asn Val Ser Ser Leu Leu Ser Gly Ala
                245                 250                 255

```
Met Glu Lys Met Pro Val Tyr Met Met Phe Arg Phe Phe Leu Ser Phe
            260                 265                 270

Thr Pro Leu Thr Pro Asn Ile Gly Leu Leu Ile Ala Leu Phe Gly Thr
            275                 280                 285

Leu Thr Leu Phe Phe Gly Thr Met Tyr Ala Leu Lys Gln Thr Asp Ser
    290                 295                 300

Lys Arg Leu Leu Ala Tyr His Ser Val Gly Gln Ile Gly Tyr Val Val
305                 310                 315                 320

Phe Ala Leu Gly Ala Gly Ile Tyr Leu Leu Ser Lys Gly Tyr Thr Thr
                    325                 330                 335

Phe Gly Ala Leu Ala Leu Met Ala Ser Leu Phe His Ala Leu Asn His
                340                 345                 350

Ala Phe Phe Lys Gly Leu Leu Phe Leu Thr Ala Gly Ser Ile Leu Tyr
            355                 360                 365

Arg Thr Gly Ser Arg Asp Leu Asp His Leu Gly Gly Leu Ala Arg Phe
    370                 375                 380

Met Pro Ile Thr Ala Phe Ala Ala Leu Ile Gly Ser Leu Ser Ile Ala
385                 390                 395                 400

Gly Met Pro Pro Phe Asn Gly Phe Val Ser Lys Trp Met Ile Tyr Val
                    405                 410                 415

Ser Thr Leu Pro Thr Pro Thr Leu Val Ser Leu Phe Gly Ala Leu Ala
                420                 425                 430

Leu Phe Ile Ser Ala Val Thr Ala Ser Phe Val Lys Tyr Phe Thr
            435                 440                 445

Ser Ile Phe Val Arg Pro Ala Lys Glu Ile Thr Val Lys Glu Val
    450                 455                 460

Pro Val Ser Met Trp Ala Ser Gln Leu Ile Leu Ala Val Leu Cys Val
465                 470                 475                 480

Ile Phe Gly Val Tyr Pro Ala Leu Pro Leu Glu Ala Ile Ser Lys Ala
                    485                 490                 495

Val Asp Ser Val Gly Val Thr Thr Pro Ser Ile Thr Val Phe Pro Gly
                500                 505                 510

Leu Ile Val Ser Asp Gly Ile Gly Asn Ile Ala Pro Leu Ala Leu Leu
            515                 520                 525

Val Phe Ser Gly Ala Leu Thr Ala Val Leu Ala Ile Phe Pro Tyr
    530                 535                 540

Lys Ile Ser Leu Pro Val Trp Thr Thr Gly Thr Arg Arg Ser Leu Ala
545                 550                 555                 560

Met Arg Leu Pro Ala Ser Ser Tyr Tyr Ala Ser Phe Glu Glu Phe
                    565                 570                 575

Glu Asp Val Tyr Ser Trp Gly Glu Trp Cys Val Cys Thr Thr Lys Arg
                580                 585                 590

Leu Trp Asp Ala Thr Lys Ala Val Leu Ser Asn Phe Glu Glu Val Ser
            595                 600                 605

Phe Asp Leu Asp Lys Met Met Thr Gly Ala Trp Leu Met Leu Ile
    610                 615                 620

Leu Leu Thr Ile Leu Gly Gly Val Leu Met Asn Ala Val Tyr Ala
625                 630                 635                 640

Ala Leu Asn Leu Ile Phe Ile Val Leu Phe Ala Pro Leu Leu Asp Gly
                    645                 650                 655

Ile Glu Arg Lys Val Lys Ala Arg Leu Gln Ser Arg Gln Gly Pro Pro
                660                 665                 670

Leu Ile Gln Thr Trp Leu Asp Leu Leu Lys Leu Phe Arg Arg Pro Asn
            675                 680                 685
```

```
Val Arg Pro Arg Glu Ser Val Arg Trp Leu Phe Glu Pro Ala Pro Ala
    690             695                 700
Ile Ala Leu Val Ser Val Leu Ala Ala Ser Leu Phe Ile Pro Ser Leu
705             710                 715                 720
Leu Pro Gly Ser Leu Asp Thr Trp Gly Asp Ile Ile Ala Phe Ile Tyr
                725                 730                 735
Leu Ser Thr Leu Ser Ala Val Ala Ile Ala Leu Gly Ala Phe Ser Thr
            740                 745                 750
Gly Ser Pro Tyr Ala Gln Ile Gly Ser His Arg Glu Val Ser Ile Ile
        755                 760                 765
Met Ala Glu Glu Phe Ser Leu Ala Phe Ile Val Ala Ala Leu Ala Ala
    770                 775                 780
Ser Ser Gly Gly Leu Ser Phe Ser Arg Leu Phe Pro Leu Gln Leu Lys
785             790                 795                 800
Val Ser Thr Ile Thr Gly Ala Leu Ala Phe Ala Val Met Ala Tyr Val
            805                 810                 815
Ala Gly Ala Arg Ile Pro Phe Asp Val Ala Glu Ala Glu Pro Glu Ile
                820                 825                 830
Val Glu Gly Pro Phe Ile Glu Phe Ser Gly Lys Gly Leu Gly Met Leu
            835                 840                 845
Lys Leu Ser Ile Tyr Val Lys Arg Leu Leu Leu Thr Thr Ile Leu Leu
850                 855                 860
Asn Phe Phe Leu Pro Gln Asp Gly Thr Val Arg Val Leu Val Tyr Val
865                 870                 875                 880
Ile Gly Leu Val Ile Ile Ser Val Val Tyr Ala Ser Ile Glu Ala His
                885                 890                 895
Tyr Gly Arg Phe Arg Thr Lys Asp Ala Ala Arg Phe Leu Lys Arg Phe
                900                 905                 910
Ala Ile Val Gly Ile Leu Ser Trp Ile Leu Gly Val Val Gly Trp Met
            915                 920                 925
Val Phe Asp Ile Leu Lys Gly Cys Lys Ile Leu Glu His Asn Asp Lys
    930                 935                 940
Met Thr Val Ala Glu Val Gly Ala Ser Asn Ile Arg Glu Ile Ala Arg
945                 950                 955                 960
Ala Leu Phe Glu Arg Gly Tyr Tyr Ser Ser Gly Met Gly Val Asp
                965                 970                 975
Glu Arg Pro Ile Asn Gly Arg Phe Ala Met Tyr His Ile Phe Asn Cys
            980                 985                 990
Asp Thr Glu Gly Arg Tyr Val Val Leu Lys Ile Thr Ser Pro Glu Gly
        995                 1000                1005
Ser Pro Glu Val Pro Ser Ile Thr Pro Val Ile Lys Gly Ala Glu
    1010                1015                1020
Trp Ser Glu Arg Glu Ala Met Asp Met Leu Gly Ile Val Phe Ser
    1025                1030                1035
Gly His Pro Lys Pro Glu Arg Leu Ile Leu Pro Asp Asp Trp Pro
    1040                1045                1050
Glu Gly Val Tyr Pro Leu Arg Lys Asp Phe Pro Tyr Asn Lys Lys
    1055                1060                1065
Leu Pro Pro Ser Lys Pro Ile Glu Lys Glu Arg Glu His Lys Lys
    1070                1075                1080
Asp Val Met Glu Ile Pro Leu Gly Pro Tyr His Pro Ser Leu His
    1085                1090                1095
Glu Pro Glu Tyr Phe Glu Leu Tyr Val Lys Gly Asp Lys Val Val
```

```
                      1100                1105                1110

Asp  Ala  Glu  Tyr  Arg  Gly  Phe  His  Ile  His  Arg  Gly  Met  Glu  Lys
          1115                1120                1125

Leu  Ala  Glu  Ser  Arg  Met  Thr  Ile  Asn  Gln  Ile  Pro  Phe  Leu  Ala
          1130                1135                1140

Glu  Arg  Ile  Cys  Gly  Ile  Cys  Gly  Cys  Thr  His  Ser  Ala  Ala  Tyr
          1145                1150                1155

Cys  Gln  Ala  Val  Glu  Asp  Ala  Ala  Gly  Ile  Tyr  Val  Pro  Glu  Arg
          1160                1165                1170

Ala  Gln  Tyr  Ile  Arg  Thr  Ile  Met  Leu  Glu  Val  Glu  Arg  Ile  His
          1175                1180                1185

Ser  His  Leu  Leu  Trp  Phe  Gly  Val  Val  Cys  His  Leu  Leu  Gly  Phe
          1190                1195                1200

Asp  Ser  Gly  Phe  Met  His  Ile  Trp  Arg  Ala  Arg  Glu  Tyr  Ile  Met
          1205                1210                1215

Asp  Ile  Ala  Glu  Leu  Ile  Thr  Gly  Asn  Arg  Lys  Thr  Tyr  Gly  Ile
          1220                1225                1230

Asn  Ile  Val  Gly  Gly  Val  Arg  Arg  Asp  Ile  Thr  Glu  Asp  Lys  Lys
          1235                1240                1245

Glu  Lys  Thr  Leu  Lys  Leu  Leu  Asp  Met  Val  Glu  Lys  Glu  Ser  Arg
          1250                1255                1260

Glu  Val  Leu  Asp  Asn  Ile  Ala  Glu  Met  Lys  Glu  Leu  Arg  Glu  Arg
          1265                1270                1275

Met  Glu  Gly  Val  Gly  Val  Leu  Pro  Lys  Lys  Glu  Ala  Arg  Glu  Ile
          1280                1285                1290

Gly  Val  Val  Gly  Pro  Met  Ala  Arg  Ser  Ser  Gly  Ile  Asp  Thr  Asp
          1295                1300                1305

Val  Arg  Arg  Asp  His  Pro  Tyr  Ala  Ala  Tyr  Lys  Asp  Leu  Asp  Phe
          1310                1315                1320

Lys  Val  Pro  Val  Tyr  Lys  Glu  Gly  Asp  Val  Phe  Ala  Arg  Phe  Leu
          1325                1330                1335

Val  Arg  Tyr  Glu  Glu  Ile  Phe  Glu  Ser  Phe  Asn  Met  Ile  Arg  Gln
          1340                1345                1350

Ala  Leu  Glu  Asn  Met  Pro  Pro  Gly  Glu  Leu  Ile  Asn  Asp  Glu  Tyr
          1355                1360                1365

Glu  Ile  Pro  Pro  Phe  Lys  Leu  Gly  Ile  Gly  Val  Thr  Glu  Ala  Pro
          1370                1375                1380

Arg  Gly  Glu  Asn  Ile  His  Ala  Val  Ile  Thr  Trp  Gly  Glu  Asn  Met
          1385                1390                1395

Ile  Tyr  Arg  Trp  His  Pro  Arg  Ala  Ala  Thr  Tyr  Asn  Asn  Leu  Pro
          1400                1405                1410

Ala  Val  Pro  Ile  Met  Leu  Arg  Gly  Asn  Asp  Val  Ala  Asp  Ala  Pro
          1415                1420                1425

Leu  Ile  Ile  Ala  Ser  Ile  Asp  Pro  Cys  Phe  Ser  Cys  Thr  Asp  His
          1430                1435                1440

Val  Ser  Ile  Ile  Asp  Ser  Glu  Ser  Gly  Lys  Ile  Leu  Trp  Arg  Gly
          1445                1450                1455

Pro  Leu  Lys  Glu  Gly  Val  Arg  Val  Met  Val  Lys  Asn  Ser  Leu
          1460                1465                1470

Trp  Val  Phe  His  Leu  Asn  Ser  Gly  Ser  Cys  Asn  Gly  Cys  Asp  Ile
          1475                1480                1485

Glu  Ile  Leu  Asn  Ile  Phe  Ala  Pro  Arg  Asn  Asp  Val  Glu  Arg  Leu
          1490                1495                1500
```

-continued

Gly Ile Lys Leu Val Gly Ser Pro Arg His Ala Asp Ala Ile Ala
1505                1510                1515

Phe Thr Gly Pro Ile Thr Arg Glu Cys Leu Pro Lys Val Ile Asp
1520                1525                1530

Ala Leu Lys Ala Val Pro Glu Pro Lys Val Val Leu Ala Ile Gly
    1535                1540                1545

Ala Cys Ala Cys Gly Gly Gly Ile Trp Tyr Asp Thr Tyr Ser Val
    1550                1555                1560

Ile Gly Gly Val Lys Glu Leu Tyr Arg Ile Leu Lys Glu Glu Tyr
    1565                1570                1575

Asn Met Glu Pro Pro Ala Thr Val Phe Ile Pro Gly Cys Pro Pro
    1580                1585                1590

Lys Pro Glu Ala Ile Ile Tyr Gly Val Ala Val Ala Ser Gly Met
    1595                1600                1605

Leu Glu Ser Lys Gln Lys Lys Thr Val Tyr Val Glu Pro Glu Glu
    1610                1615                1620

Ser Val Ala Asn Glu Lys Leu Met Ile Ala Glu Leu Ile Ser Glu
    1625                1630                1635

Thr Glu Lys Thr Arg His Phe Met Pro Gly Ile Val Ile Arg Gly
    1640                1645                1650

Val Glu Asp Glu Pro
    1655

<210> SEQ ID NO 6
<211> LENGTH: 1145
<212> TYPE: PRT
<213> ORGANISM: Thermococcus onnurineus NA1

<400> SEQUENCE: 6

Leu Ser Glu Ile Thr Leu Asn Lys Val Cys Arg Ile Ala Gly Glu Ala
1               5                   10                  15

Lys Leu Val Leu Tyr Glu Glu Asn Gly Thr Val Gln Asp Ala Leu Phe
            20                  25                  30

Ile Ala Thr Ala Pro Ile Arg Gly Phe Glu Lys Leu Val Val Gly Lys
        35                  40                  45

Asn Pro Leu Phe Ala Val Glu Ala Val Met Arg Ile Cys Gly Leu Cys
    50                  55                  60

His Ala Ser His Gly Ile Ala Met Ser Glu Ala Ile Glu Asn Ala Ile
65                  70                  75                  80

Gly Ile Ile Pro Pro Arg Asn Gly Ile Leu Met Arg Glu Ala Leu Gly
                85                  90                  95

Leu Val Asn Arg Ile Gln Ser His Met Leu Glu Phe Leu Met Val Ala
            100                 105                 110

Gly Asp Leu Leu Ile Glu Glu Lys Arg Glu Glu Val Leu Phe Gln Leu
        115                 120                 125

Met Asp Phe His Ala Lys Ile Ser Asp Tyr Leu Leu Lys Met Gly Gly
    130                 135                 140

Ala Ala Thr His Pro Pro Asn Leu Thr Val Gly Gly Met Phe Ser Val
145                 150                 155                 160

Pro Lys Trp Ser Val Phe Asn Asn Leu Lys Ala Arg Leu Pro Lys Leu
                165                 170                 175

Thr Gly Gln Trp Glu Glu Ile Ala His Leu Leu Thr Asp Glu Asp Ile
            180                 185                 190

Gln Thr Glu Val Ala Asp Glu Leu Arg Glu Lys Lys Ala Glu Asn Asn
        195                 200                 205

```
Tyr Leu Val Ser Ser Leu Phe Tyr Gly Asp Arg Phe Asn Ile Asn Ala
    210                 215                 220

Glu Arg Ile Glu Thr Met Pro Tyr Tyr Glu Tyr Arg Lys Asp Asn Pro
225                 230                 235                 240

His Ser Lys Glu Ser Thr Thr Leu Ile Ala Phe Tyr Gly Gly Glu Lys
                245                 250                 255

Val Glu Ala Gly Pro Arg Ala Arg Met Lys Val Tyr Arg Glu Phe Thr
                260                 265                 270

Asp Ser Ser Leu Tyr Gly Leu His Thr Ala Arg Val Gln Asp Thr Thr
            275                 280                 285

Leu Ala Leu Ile Arg Leu Glu Glu Ile Leu Asp Ser Ile Lys Met Asp
290                 295                 300

Glu Pro Phe Arg Thr Lys Asn Ile Val Phe Gly Pro Gly Lys Gly Val
305                 310                 315                 320

Gly Val Tyr Glu Ala Pro Arg Gly Thr Leu Ile His Leu Ile Glu Leu
                325                 330                 335

Gly Asp Glu Gly Arg Val Val Ser Ser Lys Ile Ile Val Pro Thr Met
                340                 345                 350

Phe Asn Ile Pro Val Met Glu Glu Met Ala Lys Gly Leu Ser Val Lys
            355                 360                 365

Ala Ala Glu Ala Val Met Arg Leu Tyr Asp Pro Cys Ile Pro Cys Thr
370                 375                 380

Thr His Val Val Arg Leu Gly Gly Met Glu Lys Leu Lys Val Leu His
385                 390                 395                 400

Val Asp Val Gly Gly Cys Glu Gly Cys Asn Val Ser Ile Ile Arg Ala
                405                 410                 415

Tyr Pro Lys Leu Met Asp Leu Ile Glu Leu Asp Ile Ser Tyr Leu Arg
                420                 425                 430

Lys Asp Glu Cys Lys Leu Asp Glu Tyr Asp Val Ala Ile Ile Thr Gly
            435                 440                 445

Gly Ala Cys Met Asn Glu Pro Arg Ile Leu Glu Glu Leu Lys Glu Ile
450                 455                 460

Arg Glu Lys Ala His Thr Val Ala Phe Gly Ser Cys Ala Thr Phe
465                 470                 475                 480

Ser Gly Ile Leu Arg Phe Cys Arg Gly Gly Gln Glu Pro Arg Pro Asp
                485                 490                 495

His Arg Asn Phe Gln Pro Ile Asn Ser Val Ile Lys Val Asp Tyr Ser
                500                 505                 510

Ile Pro Gly Cys Pro Pro Thr Pro Gln Met Leu Gln Ser Phe Lys
            515                 520                 525

Phe Tyr Ile Asn Gly Asp Glu Arg Arg Leu Arg Leu Phe Lys Val Ser
530                 535                 540

Ala Asp Ile Lys Lys Leu Ser Gly Phe Asp Leu Ile Asp Ile Val
545                 550                 555                 560

Leu Thr Gly Leu Cys Ile Gly Cys Gly Ala Cys Glu Leu Ser Cys Pro
                565                 570                 575

Thr Asn Ala Ile Lys Leu Ile Asp Lys Arg Pro Asn Leu Val Gln Glu
                580                 585                 590

Lys Cys Ile Arg Cys Gly Thr Cys Tyr Ile Arg Cys Pro Arg Ala Ser
            595                 600                 605

Gln Ile Leu Ser Met Gly Gly Ala Arg Met Met Ser Val Ser Glu Asn
610                 615                 620

Leu Leu Gly Asn Val Phe Gly Ile Tyr Leu Ala Arg Ala Thr Asp Glu
625                 630                 635                 640
```

```
Glu Ile Leu Lys Arg Lys Val Ala Ser Gly Gly Ala Val Thr Ala Leu
            645                 650                 655

Leu Ala Tyr Ala Leu Glu Lys Gly Leu Ile Asp Gly Val Val Thr Ala
            660                 665                 670

Lys Arg Thr Glu Gly Leu Glu Gly Gln Ala Val Val Ala Arg Thr Arg
            675                 680                 685

Glu Glu Leu Leu Glu Thr Ala Gly Asn Lys Trp Ser Ile Val Pro Phe
        690                 695                 700

Ala Ser Arg Met Lys Ala Lys Ile Glu Glu Asp Leu Lys Asn Val
705                 710                 715                 720

Ala Val Val Cys Leu Pro Cys Gln Ala Gln Phe Phe Gly Gln Met Arg
                725                 730                 735

Asp Phe Pro Leu Leu Glu Ser Asp Phe Gly Arg Ile Lys Tyr Ile
                740                 745                 750

Val Ser Leu Phe Cys Ile Gly Thr Phe Ala Phe Glu Ala Phe Leu Asn
            755                 760                 765

Tyr Leu Arg Met Lys His Gly Ile Met Ala Gln Asp Ile Lys Asp Ile
770                 775                 780

Val Leu Lys Gly Asp Phe Leu Glu Ile Tyr His Gly Asp Ser Val Leu
785                 790                 795                 800

Ser Leu Pro Ile Lys Glu Val Tyr Ser Tyr Leu Gln Ala Gly Cys Leu
                805                 810                 815

Val Cys Thr Asp Tyr Thr Gly Thr Trp Ser Asp Ile Ser Ala Gly Phe
                820                 825                 830

Val Glu Ser Glu Arg Gly Trp Thr Val Leu Ile Thr Arg Asn Leu Lys
            835                 840                 845

Ala Glu Glu Leu Val Lys Ser Ala Glu Lys Asp Gly Tyr Ile Glu Leu
        850                 855                 860

Arg Asp Gly Ser His Val Met Gly Glu Val Leu Lys Ala Ala Arg Glu
865                 870                 875                 880

Lys Leu Ala Arg Ala Gln Lys Asn Met Met Tyr Leu Leu Ile Lys
            885                 890                 895

Lys Val Lys Ile Leu Lys Trp Gln Asp Gly Leu Val Pro Thr Glu Asp
            900                 905                 910

Tyr Ile Cys Val Glu Glu Thr Phe Glu Ile Phe Ala Val His Glu Lys
            915                 920                 925

Asp Glu Glu Phe Leu Ala Glu Leu Pro Ala Ser Pro Asn Gln Leu Lys
        930                 935                 940

Glu Leu Gly Ala Gly Phe Val Val Cys Gly Gly Tyr Glu Arg Pro Glu
945                 950                 955                 960

Asp Ile Val Asp Val Trp Val Glu Gly Lys Glu Ile Tyr Val Lys Leu
                965                 970                 975

Lys Asp Thr Pro Ala Thr Gly Val Leu Val Val Lys His Thr Pro Cys
        980                 985                 990

Gly Asp Pro Tyr Arg Met Lys Glu Gly Arg Ile Leu Ser Arg Lys Gly
            995                 1000                1005

Glu Glu Val Lys Ile Thr Pro Gly Leu Val Leu Lys Ile Ser Ser
        1010                1015                1020

Thr Met Thr Thr Leu Ala Glu Thr Trp Arg Lys Thr Gly Gly Thr
        1025                1030                1035

His Trp Ala Ala Leu Phe Asp Leu Asn Ala Asn Val Val Ala Phe
        1040                1045                1050

Ser Glu Asp Ile Gly Arg His Asn Ala Val Asp Lys Val Val Gly
```

```
                1055                1060                1065

Tyr Ala  Val Leu Asn Gly Leu  Asp Leu Glu Arg Leu  Ile Leu Ala
         1070                1075                1080

Ser Ser  Gly Arg Met Pro Tyr  Gly Met Val Arg Lys  Ala Val Asn
         1085                1090                1095

Ala Gly  Ile Pro Val Val Val  Thr Lys Ser Pro Pro  Thr Asp Lys
         1100                1105                1110

Gly Val  Glu Leu Ala Arg Glu  His Gly Val Thr Leu  Ile Gly Phe
         1115                1120                1125

Ala Arg  Gly Arg Arg Phe Asn  Val Tyr Ser Gly Glu  His Arg Leu
         1130                1135                1140

Leu Phe
    1145

<210> SEQ ID NO 7
<211> LENGTH: 2903
<212> TYPE: PRT
<213> ORGANISM: Thermococcus onnurineus NA1

<400> SEQUENCE: 7

Met Glu Glu Leu Phe Ile Leu Ser Phe Ser Ile Pro Leu Val Gly Gly
1               5                   10                  15

Leu Leu Leu Phe Lys Leu Asp Gly Lys Arg Ala Asp Tyr Phe Met Leu
            20                  25                  30

Ile Thr Val Ile Leu Ala Thr Ile Leu Asn Leu Ala Gly Val Tyr Glu
        35                  40                  45

Phe Tyr Ser Ser Gly Met Pro Thr Ile His Lys Thr Leu Val Ser Ser
    50                  55                  60

Thr Thr Leu Gly Glu Val Tyr Gly Leu Leu Ile Asp Pro Met Ser Val
65                  70                  75                  80

Cys Val Gly Leu Val Val Ile Thr Ala Gly Leu Leu Phe Met Ile Tyr
                85                  90                  95

Ala Lys Asp Tyr Met Ser Pro Glu Asn Lys Glu His Pro Val Tyr Glu
            100                 105                 110

Asp Lys Gly Arg Phe Tyr Ala Trp Met Val Leu Phe Ile Gly Ala Thr
        115                 120                 125

Leu Ala Phe Ile Tyr Ser Ser Val Leu Gln Leu Leu Ile Phe Phe
    130                 135                 140

Glu Ile Met Ser Leu Ala Cys Trp Gly Val Ala Gly Tyr Tyr Gly Ser
145                 150                 155                 160

Lys Lys Ala Lys Arg Ala Ala Tyr Lys Ala Leu Leu Val Thr Asn Phe
                165                 170                 175

Gly Ala Val Ile Gly Leu Tyr Thr Ala Val Gly Ile Gly Ile Thr His
            180                 185                 190

Leu His Asp Leu Ser Ile Phe Ala Tyr Ser Gly Leu Asn Asp Ser Leu
        195                 200                 205

Lys Leu Val Val Phe Ile Gly Val Met Ile Ala Ala Phe Thr Lys Ser
    210                 215                 220

Ala Gln Phe Pro Leu Tyr Ser Trp Leu Pro Asp Ala Met Val Ala Pro
225                 230                 235                 240

Thr Pro Ala Ser Ala Phe Leu His Gly Ala Ala Met Val Glu Met Gly
                245                 250                 255

Val Tyr Leu Leu Ala Arg Phe Ile Gln Phe Met Asn Pro Ile Pro Lys
            260                 265                 270

Glu Gly Phe Tyr Val Met Ala Ala Leu Ile Ile Ala Thr Gln Ile Ile
```

```
                275                 280                 285
Cys Ile Leu Met Tyr Pro Leu Gln Lys Ser Ala Lys Arg Leu Leu Ala
290                 295                 300

Tyr Ser Thr Ile Ala Glu Ser Gly Leu Met Tyr Val Ala Leu Ala Thr
305                 310                 315                 320

Ala Val Leu Gly Leu Gln Gly Gly Leu Gln Ala Ser Met Phe Gln Leu
                325                 330                 335

Phe Asn His Ala Tyr Ile Lys Gly Leu Ala Phe Leu Thr Ala Gly Thr
                340                 345                 350

Phe Ser Tyr Ala Leu Gly Thr Leu Glu Met Asp Arg Ile Lys Gly Leu
                355                 360                 365

Ile Lys Ser Pro Val Val Gly Tyr Ser Trp Thr Phe Ala Leu Leu Gly
                370                 375                 380

Leu Ala Gly Val Pro Pro Phe Gly Val Phe Phe Gly Lys Leu Gly Ile
385                 390                 395                 400

Leu Ser Asn Ala Lys Ala Met Glu Glu Ser Val Leu Ile Ile Ala Met
                405                 410                 415

Phe Val Leu Leu Leu Asp Ser Ala Val Phe Leu Met Val Ser Leu
                420                 425                 430

Lys Arg Ile His Gly Met Val Phe Ser Glu Gly Gly Glu Glu Val Glu
                435                 440                 445

Ile Thr Pro Leu Met Lys Ala Val Met Val Ile Leu Leu Val Leu Ala
                450                 455                 460

Met Leu Ala Pro Tyr Ile Ala Tyr Pro Leu Ile Val Lys Val Gly Trp
465                 470                 475                 480

Met Phe Asp Val Thr Leu Thr Leu Ser Leu Asp Arg Thr Ala Val Phe
                485                 490                 495

Phe Val Leu Asn Val Ala Ile Leu Gly Ile Ala Ala Leu Val Ala Ser
                500                 505                 510

Phe Arg Tyr Met Arg Ile Tyr Glu Phe Lys Pro Lys Ile Pro Tyr Tyr
                515                 520                 525

Pro Thr Leu Ala Ile Phe Ile Val Ser Met Leu Leu Ile Pro Met Val
530                 535                 540

Gln Asp Trp Leu Ser Phe Leu Phe Leu Trp Glu Ile Met Thr Leu Ala
545                 550                 555                 560

Ser Tyr Phe Leu Ile Ile Tyr Asp Trp Pro Glu Glu Ser Val Lys Lys
                565                 570                 575

Ala Gly Trp Lys Tyr Phe Val Thr Met His Leu Phe Asp Thr Ser Pro
                580                 585                 590

Leu Met Leu Ala Val Thr Met Tyr Tyr Ala Phe His Gly Thr Phe Asn
                595                 600                 605

Phe Gly Ala Ile Thr Glu Tyr Ser Asn Ala Ile Val Ala Leu Phe Leu
610                 615                 620

Leu Gly Phe Ala Ala Lys Ala Gly Leu Phe Pro Leu His Phe Trp Leu
625                 630                 635                 640

Pro Asp Ala His Pro Ala Ala Pro Ser Pro Val Ser Ala Leu Met Ser
                645                 650                 655

Gly Ala Met Val Glu Leu Gly Leu Tyr Gly Thr Ile Arg Val Leu Asn
                660                 665                 670

Ala Val Gly Trp Ser Val Ala Thr Trp Ile Val Tyr Leu Ile Gly Ala
                675                 680                 685

Met Ala Val Leu Ser Met Leu Ala Ala Ile Phe Ser Tyr Ala Leu Gln
690                 695                 700
```

-continued

```
Asp Asp Val Lys Arg Leu Phe Ala Trp Ser Thr Ile Asp Asn Met Gly
705                 710                 715                 720

Trp Met Tyr Leu Leu Ile Leu Ala Gly Leu Gly Val Ser Gly Val
            725                 730                 735

Glu Lys Gly Val Asp Tyr Tyr Val Ala His Gly Leu Ala Lys Ala
        740                 745                 750

Ala Ala Phe Ile Ser Thr Gly Ala Leu Leu Tyr Val Phe Gly Thr Arg
        755                 760                 765

Ser Leu Lys Lys Ala Lys Gly Met Met Asn Thr Asp Ser Leu Thr Ala
770                 775                 780

Gly Leu Met Met Ala Ser Ile Phe Ala Leu Glu Gly Val Pro Pro Phe
785                 790                 795                 800

Asn Leu Phe Met Asn Lys Leu Asn Val Ile Lys Thr Leu Leu Thr Val
                805                 810                 815

Ser Pro Ala Leu Ala Tyr Phe Thr Ala Leu Glu Trp Val Ile Ala Phe
            820                 825                 830

Ile Leu Phe Leu Arg Val Val His Ala Tyr Ile Leu Ser Glu Gly Glu
                835                 840                 845

Pro Glu Ala Lys Arg Lys Leu Ala Gly Ser Ile Ala Leu Ser Val Ile
    850                 855                 860

Val Leu Leu Ile Leu Ser Met Val Ser Gln Phe Val Cys Asp Tyr Ile
865                 870                 875                 880

Trp Val Arg Trp Met Glu Gly Leu Phe Thr Leu Ala Val Ile Leu Tyr
                885                 890                 895

Phe Leu Ser Ile Pro Ala Ala Leu Ala Leu Lys Arg Ser Phe Lys Ala
            900                 905                 910

Ser Ile Ser Ile Gly His Ile Leu Thr Ala Leu Ala Ser Ile Ala Leu
        915                 920                 925

Leu Ala Phe Thr Phe Val Ser Ile Pro Asp Ile Leu Ser Gly Lys Ala
    930                 935                 940

Ile Glu Phe Thr Tyr Asp Leu Gly Val Ala Gln Ile Pro Phe Gln Ile
945                 950                 955                 960

Asp Gly Leu Ser Leu Ile Met Cys Phe Ile Phe Gly Ala Leu Gly Leu
                965                 970                 975

Ala Ala Ser Ile Tyr Ser Pro Arg Tyr Met Ala Ile Tyr Glu Lys Ser
            980                 985                 990

Gly Arg Gly Trp Met Tyr Ile Thr Ile Tyr Ser Val Phe Met Leu Ser
        995                 1000                1005

Met Ile Leu Ile Val Thr Ile Ala Asn Met Phe Trp Phe Ile Phe
    1010                1015                1020

Leu Trp Glu Val Met Thr Phe Thr Ser Tyr Leu Leu Thr Ile Trp
    1025                1030                1035

Glu Ser Asp Lys Glu Asp Val Arg Lys Ala Gly Trp Lys Tyr Phe
    1040                1045                1050

Val Thr Met His Ile Val Ser Thr Leu Pro Leu Ile Ile Ala Leu
    1055                1060                1065

Ala Leu Leu Tyr Ala Asp Val Ser Ser Ile Glu Gly Leu Asn Phe
    1070                1075                1080

Glu Ser Leu Ala Ala Leu Lys Leu Ser Pro Val Phe Tyr Ala Leu
    1085                1090                1095

Phe Leu Ile Gly Phe Gly Ser Lys Ser Gly Val Val Pro Leu His
    1100                1105                1110

Phe Trp Ala Pro Glu Ala Tyr Thr Val Ala Pro Ser Asn Val Ser
    1115                1120                1125
```

```
Ala Leu Met Ala Gly Ala Leu Glu Lys Val Ala Val Tyr Ala Leu
    1130            1135                1140

Ile Arg Thr Thr Cys Phe Ile Met Lys Pro Asn Glu Thr Phe Gly
    1145            1150                1155

Tyr Ala Val Ala Leu Leu Gly Thr Val Thr Leu Thr Val Gly Thr
    1160            1165                1170

Leu Tyr Ala Leu Lys Gln Thr Asp Ala Lys Arg Leu Leu Ala Tyr
    1175            1180                1185

His Ser Ile Gly Gln Ile Gly Tyr Ile Trp Leu Gly Met Gly Val
    1190            1195                1200

Gly Ile Val Phe Ile Ala Arg Gly Asp Met Tyr Ser Ala Phe Gly
    1205            1210                1215

Ala Ile Ala Leu Ala Ser Ser Leu Tyr His Leu Val Asn His Thr
    1220            1225                1230

Phe Phe Lys Gly Leu Leu Phe Leu Ser Thr Gly Ser Ile Phe Tyr
    1235            1240                1245

Arg Thr Arg Ser Arg Asp Leu Asn Gln Leu Arg Gly Leu Ala Lys
    1250            1255                1260

Leu Met Pro Phe Thr Ala Leu Phe Thr Phe Ile Ala Ala Met Ser
    1265            1270                1275

Ile Ala Gly Thr Pro Pro Phe Asn Gly Phe Met Ser Lys Trp Met
    1280            1285                1290

Ile Tyr Gln Ser Thr Phe Leu Ser Gly Asn Gly Leu Ile Val Phe
    1295            1300                1305

Phe Gly Val Met Ala Leu Phe Ile Ser Ala Ala Thr Leu Ala Ser
    1310            1315                1320

Phe Ile Lys Phe Tyr Thr Thr Ala Phe Gly Gly Glu Pro Thr Glu
    1325            1330                1335

Phe Thr Lys Asp Ala Glu Glu Val Pro Ser Pro Met Leu Ile Ala
    1340            1345                1350

Lys Gly Phe Leu Ala Ser Leu Cys Ile Leu Leu Gly Leu Val Pro
    1355            1360                1365

Ser Leu Ile Leu Pro Ile Leu Leu Ser Pro Gly Ala Ala Leu Ala
    1370            1375                1380

Gly Ile Asp Val Ser Gly Leu Met Asp Thr Asn Tyr Trp Leu Val
    1385            1390                1395

Thr Ile Lys Ala Pro Leu Met Pro Thr Gly Ala Glu Ser Tyr Phe
    1400            1405                1410

Lys Pro Leu Leu Phe Ala Thr Leu Phe Gly Val Ile Phe Leu Gly
    1415            1420                1425

Met Tyr Leu Leu Phe Pro Ile Ser Lys Lys Thr Tyr Arg Pro Trp
    1430            1435                1440

Thr Leu Gly Glu Pro Val Ala Met Glu His Tyr Lys Phe Lys Ala
    1445            1450                1455

Ile Asn Tyr Tyr Glu Pro Phe Glu Glu Tyr Ile His Pro Leu Tyr
    1460            1465                1470

His Thr Gly His Val Leu Ser Glu Phe Gly Ser Ala Leu Ile Gly
    1475            1480                1485

Ala Val Ala Asn Ala Tyr Val Ser Thr Thr Arg Ala Leu His Arg
    1490            1495                1500

Val Cys Asp Ser Ile Ser Lys Ser Val Ala Gly Ile Gly Lys Glu
    1505            1510                1515

Tyr Glu Lys Lys Cys Pro Glu Val Tyr Leu Asp Glu Tyr Phe Leu
```

-continued

```
            1520                1525                1530

Ala Pro Leu Val Lys Ile Val Arg Val Ser Gly Val Leu Leu Asp
    1535                1540                1545

Glu Gly Phe Met Arg Pro Asn Ala Ala Phe Thr Ile Ala Leu Val
    1550                1555                1560

Thr Leu Ala Val Ile Leu Ala Leu Met Val Leu Met Thr Leu Glu
    1565                1570                1575

Lys Ile Ala Phe Ala Ala Leu Ser Leu Met Ile Ile Ile Leu Leu
    1580                1585                1590

Pro Pro Leu Leu Asp Gly Ile Ser Arg Lys Ile Lys Ala Thr Val
    1595                1600                1605

Gln Glu Arg Gln Gly Pro Pro Val Phe Gln Thr Tyr Tyr Asp Leu
    1610                1615                1620

Ser Ser Leu Leu Ser Met Glu Pro Ile Leu Pro Thr Asp Arg Leu
    1625                1630                1635

Gly Phe Leu Ile Ala Pro Tyr Val Ala Phe Ala Ser Ala Val Ser
    1640                1645                1650

Ala Ala Leu Leu Leu Pro Phe Gly Asn Phe Val Pro Val Ala Phe
    1655                1660                1665

Thr Gly Asp Ile Phe Val Phe Leu Tyr Val Leu Ala Ile Phe Ser
    1670                1675                1680

Ile Ser Met Met Met Ala Gly Phe Leu Val Asn Asn Thr Tyr Ser
    1685                1690                1695

Asn Ala Gly Ala Asn Arg Glu Met Met Leu Ile Leu Ser Val Glu
    1700                1705                1710

Pro Ile Leu Gly Ile Ala Ile Gly Ile Leu Ala Leu Lys Thr His
    1715                1720                1725

Ser Leu Ser Val Ser Gly Ile Pro Leu Asn Leu Ser Leu Thr Pro
    1730                1735                1740

Ser Val Val Leu Ala Phe Ile Phe Leu Ala Tyr Ala Val Tyr Thr
    1745                1750                1755

Glu Cys Ala Phe Ile Pro Phe Asp Ile Ala Glu Ala Glu Thr Glu
    1760                1765                1770

Ile Leu Glu Gly Pro Leu Val Glu Tyr Ser Gly Lys Leu Leu Gly
    1775                1780                1785

Ile Phe Lys Trp Ala Met Leu Ile Lys Arg Val Ala Leu Ile Trp
    1790                1795                1800

Leu Phe Ala Ser Phe Ile Val Ile Pro Val Met Lys Gly Phe Val
    1805                1810                1815

Asp Ile Thr Thr Pro Tyr Gly Gly Ala Val Thr Leu Ala Ala Gln
    1820                1825                1830

Leu Val Leu Leu Val Val Phe Tyr Val Met Ser Ala Ile Ile Glu
    1835                1840                1845

Ser Thr Thr Ala Arg Met Lys Val Ile Gln Ala Ile Arg Gln Asn
    1850                1855                1860

Thr Val Ile Phe Leu Ala Gly Ile Val Ala Leu Val Ile Ala Ser
    1865                1870                1875

Leu Gly Trp Met Ser Glu Val Ile Lys Phe Asn Glu Ala Leu Lys
    1880                1885                1890

Lys Lys Arg Val His Arg Gly Asp Glu Lys Ala Lys Val Thr Arg
    1895                1900                1905

Glu Tyr Leu Asp Glu Ile Ile Glu Lys Phe Gly Glu Lys Ile Arg
    1910                1915                1920
```

-continued

Asp Val Lys Gln Ala Ala Tyr Asn Gln Trp Ile Ile Thr Val Glu
1925                1930                1935

Arg Glu Asp Leu Pro Glu Ile Val Leu Tyr Phe Leu Asn His Pro
1940                1945                1950

Glu Trp Lys Glu Thr Gln Leu Ser Ser Met Val Ala Thr Asp Glu
1955                1960                1965

Arg Pro Leu Asn Gly Lys Phe Ser Ile Thr Tyr Trp Leu Ser Val
1970                1975                1980

Asn Gly Lys Ala Gly Asp Phe Tyr Leu Gly Val Arg Ala Tyr Leu
1985                1990                1995

Pro Glu Asp Asp Pro Arg Phe Thr Ser Ile Ala Ala Lys His Arg
2000                2005                2010

Gly Ala Asn Trp Tyr Glu Arg Glu Ala Met Glu Met Leu Gly Leu
2015                2020                2025

Thr Ala Glu Gly His Pro Asp Pro Arg Arg Leu Val Leu Pro Asp
2030                2035                2040

Asp Trp Pro Ser Cys Val Tyr Pro Leu Arg Lys Asp Phe His Tyr
2045                2050                2055

Ser Asn Ser Pro Pro Gly Glu Lys Phe Tyr Pro Tyr Lys Glu Pro
2060                2065                2070

Lys Lys Asp Glu Ile Val Val Pro Tyr Gly Pro Tyr His Val Ala
2075                2080                2085

Leu Glu Glu Ala Ala His Phe Arg Leu Tyr Val Lys Gly Glu Thr
2090                2095                2100

Ile Thr Asp Val Asp Tyr Arg Gly Phe Tyr Ala His Arg Gly Ile
2105                2110                2115

Glu Lys Ile Ser Glu Gly Arg Leu Thr Tyr Asp Gln Val Cys Phe
2120                2125                2130

Ile Ala Glu Arg Ile Cys Gly Ile Cys Gly Cys Thr His Ser Thr
2135                2140                2145

Ala Tyr Cys Gln Ala Val Glu Asn Ala Gly Gly Ile Glu Val Pro
2150                2155                2160

Glu Arg Ala Glu Tyr Ile Arg Thr Ile Val Leu Glu Ile Glu Arg
2165                2170                2175

Leu His Ser His Leu Leu Asn Phe Gly Ile Val Ser His Leu Val
2180                2185                2190

Gly Tyr Asp Tyr Gly Phe Met Lys Ala Trp Arg Ile Arg Glu His
2195                2200                2205

Val Met Trp Leu Ala Glu Arg Leu Thr Gly Asn Arg Lys Thr Tyr
2210                2215                2220

Gly Met Leu Leu Val Gly Gly Val Arg Arg Asp Leu Leu Glu Tyr
2225                2230                2235

Arg Lys Ser Leu Ile Glu Asp Val Leu Lys Lys Ile Lys Thr Glu
2240                2245                2250

Phe Ser Glu Leu Val Asp Glu Ala Ile Ser Thr Ser Thr Phe Val
2255                2260                2265

Lys Arg Leu Glu Gly Val Gly Val Leu Pro Tyr Lys Val Ala Lys
2270                2275                2280

Glu Trp Asp Val Asp Gly Pro Leu Gly Arg Gly Ser Gly Arg Asp
2285                2290                2295

Phe Asp Val Arg Arg Asp His Pro Tyr Ala Ala Tyr Lys Tyr Leu
2300                2305                2310

Asp Phe Lys Val Pro Val Tyr Lys Glu Gly Asp Val Leu Ala Arg
2315                2320                2325

```
Ala Leu Val Arg Ile Glu Glu Val Phe Glu Ser Ile Trp Ile Ile
    2330                2335                2340

Glu Gln Ala Leu Asp Gln Met Pro Gly Gly Asp Ile Leu Ala Glu
    2345                2350                2355

Tyr Lys Glu Ile Pro Pro Tyr Ser Glu Ala Ile Gly Met Thr Glu
    2360                2365                2370

Ala Pro Arg Gly Glu Asn Ile His Tyr Val Met Thr Gly Glu Asn
    2375                2380                2385

Asn Lys Val Tyr Arg Tyr Arg Ala Arg Ala Ala Thr Tyr Asn Asn
    2390                2395                2400

Leu Pro Ala Val Pro Asp Met Met Arg Gly Tyr Thr Ile Ala Asp
    2405                2410                2415

Ala Pro Leu Ile Val Ala Ser Ile Asp Pro Cys Tyr Ser Cys Thr
    2420                2425                2430

Glu Arg Val Gln Val Val Asp Val Glu Ser Gly Lys Val Arg Val
    2435                2440                2445

Leu Ser Glu Thr Glu Phe Asn Lys Leu Ser Ile Lys Ala Ser Arg
    2450                2455                2460

Arg Val Met Ala Val Thr Leu Lys Tyr Pro Phe Val Lys Leu Glu
    2465                2470                2475

Ala Pro Pro Glu Tyr Arg Gly Ile Pro Gln Ile Asp Ala Thr Leu
    2480                2485                2490

Cys Ile Gly Cys Gly Ala Cys Val Asn Ala Cys Pro Pro Asp Ala
    2495                2500                2505

Leu Leu Arg Ile Asp Asp Tyr Asn Arg Gly Val Arg Glu Ile Val
    2510                2515                2520

Leu Asp Val Gly Arg Cys Ile Arg Cys Ala Arg Cys Glu Glu Val
    2525                2530                2535

Cys Pro Thr Gly Ala Ile Lys Leu Thr Asn Leu Phe Glu Ala Ala
    2540                2545                2550

Ser Pro Asp Arg Met Asp His Val Glu Val Val Arg Leu Arg Leu
    2555                2560                2565

Val Lys Cys Lys Asn Cys Gly Arg Tyr Ala Asp Phe Thr Glu Arg
    2570                2575                2580

Gln Val Arg Lys Ala Leu Gln Ile Leu Pro Glu Glu Ile Ile Glu
    2585                2590                2595

Arg Glu Ala Leu Glu Glu Lys Val Trp Ile Cys Arg Asp Cys Arg
    2600                2605                2610

Arg Lys Gly Thr Val Asp Gly Thr Ile Glu Ala Ser Lys Glu Val
    2615                2620                2625

Val Leu Met Ser Gly Lys Pro Lys Leu Arg Ser Ile Trp Val Phe
    2630                2635                2640

His Leu Asn Thr Gly Ser Cys Asn Gly Cys Asp Ile Glu Ile Ile
    2645                2650                2655

Asp Val Leu Thr Pro Phe Tyr Asp Val Glu Arg Phe Gly Ile Lys
    2660                2665                2670

Leu Val Gly Ser Pro Arg His Ala His Ala Leu Leu Val Ser Gly
    2675                2680                2685

Pro Leu Thr Arg Gln Ala Tyr Tyr Gly Ala Lys Glu Thr Ile Lys
    2690                2695                2700

Ala Met Pro Pro Glu Pro Arg Val Ile Val Ala Ile Gly Thr Cys
    2705                2710                2715

Thr Cys Ser Gly Gly Ile Phe Tyr Asn Gly Tyr Pro Val Tyr Arg
```

```
                    2720                2725                2730

Arg Pro Glu Ser Gly Arg Glu Gly Ser Glu Tyr Pro Arg Arg Gly
    2735                2740                2745

Gly Ile Ala Glu Leu Ile Ala Asp Leu Arg Asp Glu Gly Glu Lys
    2750                2755                2760

Val Gly Pro Val Ile Tyr Ile Pro Gly Cys Pro Pro Arg Pro Glu
    2765                2770                2775

Glu Ile Ile Tyr Gly Ile Ala Gln Leu Val Gly Leu Val Glu Lys
    2780                2785                2790

Lys Leu Ser Tyr Gln Glu Tyr Ser Asp Glu Leu Val Pro Phe Lys
    2795                2800                2805

Leu Pro Glu Gly Pro Leu Glu Glu Arg Ile Arg Leu Thr Leu Met
    2810                2815                2820

Glu Arg Leu Arg His Leu Val Gly Tyr Leu Asp Arg Glu Lys Ile
    2825                2830                2835

Leu Glu Asp Phe Met Gly Leu Val Lys Glu Ala Glu Lys Ser Glu
    2840                2845                2850

Asn Pro Arg Glu Glu Leu Ala Arg Leu Val Lys Asp Tyr Ala Ala
    2855                2860                2865

Lys Cys Gly Asp Val Arg Leu Gly Phe Cys Met Met Leu Leu Glu
    2870                2875                2880

Arg Glu Tyr Trp Arg Val Lys Asp Ala Leu Asp Ala Gly Lys Glu
    2885                2890                2895

Phe Val Tyr Trp Val
    2900

<210> SEQ ID NO 8
<211> LENGTH: 1387
<212> TYPE: PRT
<213> ORGANISM: Thermococcus onnurineus NA1

<400> SEQUENCE: 8

Met Phe Gly Tyr Trp Asp Ala Leu Tyr Phe Val Phe Ile Phe Ile Ile
1               5                   10                  15

Gly Leu Ile Ile Ala Trp Met Leu Asn Glu Trp Ala Lys Lys Ser Gly
                20                  25                  30

Met Gly Thr Arg Glu Ala Gly Asp Gly Thr Lys Val Phe Ile Ser Gly
            35                  40                  45

Glu Asp Pro Asp Lys Val Ile Pro Gly Phe Glu His Tyr Glu Gly Tyr
        50                  55                  60

Tyr Thr Gly Lys Asn Val Met Trp Gly Leu Thr Tyr Ala Leu Lys Arg
65                  70                  75                  80

Phe Phe Ala Leu Leu Arg Asn Glu His Thr Gly Leu Leu Thr Asp Tyr
                85                  90                  95

Val Ser Tyr Leu Leu Ile Thr Thr Ala Phe Val Leu Gly Val Ile Leu
                100                 105                 110

Ile Trp Gly Met Ser Ile Lys Val Pro Ala Asp Gln Asn Arg Thr Asn
            115                 120                 125

Gly Thr Thr Ser Glu Arg Glu Met Leu Glu Lys Arg Ile Ala Gln Leu
        130                 135                 140

Cys Arg Phe Ile Gly Arg Ser Pro Trp Val Phe His Val Asn Ser Gly
145                 150                 155                 160

Ser Cys Asn Gly Cys Asp Ile Glu Ile Ile Ala Ala Leu Thr Pro Arg
                165                 170                 175

Tyr Asp Ala Glu Arg Phe Gly Val Lys Leu Val Gly Ser Pro Arg His
```

```
                180                 185                 190
Ala Asp Val Leu Leu Val Thr Gly Pro Val Thr Asp Gln Ser Leu Glu
            195                 200                 205
Arg Val Lys Leu Val Tyr Glu Gln Thr Pro Asp Pro Lys Ile Val Ile
        210                 215                 220
Ala Val Gly Ser Cys Pro Thr Gly Gly Ser Val Phe Tyr Glu Ser Pro
225                 230                 235                 240
Phe Thr Asn Ala Pro Leu Ser Asn Ile Ile Pro Val Asp Val Tyr Val
                245                 250                 255
Pro Gly Cys Pro Pro Arg Pro Glu Ala Ile Leu Tyr Gly Val Val Leu
            260                 265                 270
Ala Leu Glu Lys Leu Ala Lys Ile Leu Lys Gly Glu Val Pro Glu Gly
        275                 280                 285
Glu Glu Met Ala Asp Asp Asn Arg Ile Met Glu Asn Val Asp Asn Val
    290                 295                 300
Arg Glu Pro Thr Lys Glu Asp Thr Val Ala Glu Thr Ile Lys Ser Arg
305                 310                 315                 320
Phe Pro Asn Ala His Val Glu Ile Arg Glu Asn Lys Trp Gly Arg Lys
                325                 330                 335
Arg Val Trp Val Ile Val Pro Arg Glu Asp Tyr Lys Ala Leu Met Lys
            340                 345                 350
Phe Leu Leu Glu Leu Asp Pro Glu Ala His Tyr Ser Ile Gly Ile Glu
        355                 360                 365
Gln Asp Tyr Gly Glu Glu Ile Gly Tyr Met Ser His Ile Leu Leu His
    370                 375                 380
Tyr Asp Asn Ala Pro Ala Val Ser Leu Leu Val Asp Val Arg Val Pro
385                 390                 395                 400
Lys Asp Asp Pro Val Ile Pro Asp Ile Ser Asp Ile Phe Pro Ile Ala
                405                 410                 415
Leu Gln Tyr Glu Arg Glu Ala Ala Glu Met Met Gly Ile Val Phe Glu
            420                 425                 430
Gly Ile Pro Asp Ser Arg Arg Leu Phe Leu Pro Asp Asp Phe Pro Glu
        435                 440                 445
Gly Ile Tyr Pro Leu Arg Leu Asp Glu Lys Gly Ile Pro Glu Glu Ile
    450                 455                 460
Val Lys Asn Ala Gly His Pro Tyr Tyr Leu Lys Gly Gly Asp Lys Met
465                 470                 475                 480
Thr Lys Lys Val Glu Tyr Trp Ile Lys Ile Pro Phe Gly Pro Ile His
                485                 490                 495
Pro Gly Leu Glu Glu Pro Glu Lys Phe Ile Leu Thr Leu Asp Gly Glu
            500                 505                 510
Arg Ile Val Asn Val Asp Val Lys Leu Gly Tyr Asn Leu Arg Gly Leu
        515                 520                 525
Gln Trp Ile Ala Tyr Arg Arg Asn Tyr Val Gln Ile Met Tyr Leu Ala
    530                 535                 540
Glu Arg Ile Cys Gly Ile Cys Ser Phe Ser His Asn His Thr Tyr Thr
545                 550                 555                 560
Arg Ala Val Glu Glu Ala Ala Gly Ile Glu Val Pro Glu Arg Ala Glu
                565                 570                 575
Tyr Ile Arg Ala Ile Ile Gly Glu Leu Glu Arg Val His Ser His Leu
            580                 585                 590
Leu Asn Leu Gly Val Leu Gly His Asp Ile Gly Tyr Asp Thr Val Leu
        595                 600                 605
```

-continued

His Leu Thr Trp Leu Ala Arg Glu Arg Val Met Asp Val Leu Glu Ala
610                615                620

Ile Ser Gly Asn Arg Val Asn Tyr Ser Met Val Thr Ile Gly Gly Val
625                630                635                640

Arg Arg Asp Ile Asp Glu Lys Gly Lys Arg Leu Ile Leu Asp Met Ile
                    645                650                655

Lys Tyr Tyr Arg Ser Ile Met Pro Gln Ile Glu Glu Val Phe Leu His
                660                665                670

Asp Pro Thr Ile Glu Ala Arg Leu Arg Asp Cys Ala Val Ile Ser Lys
            675                680                685

Arg Val Ala Leu Glu Gln Gly Ala Val Gly Pro Thr Ala Arg Ala Ser
690                695                700

Gly Leu Lys Val Asp Ala Arg Trp Ser Glu Arg Leu Gly Val Tyr Pro
705                710                715                720

Asp Leu Gly Val Lys Pro Val Met Pro Gln Asp Val Thr Gly Glu Lys
                    725                730                735

Pro His Gly Asp Val Phe Asp Arg Ala Ala Val Arg Ile Gly Glu Ile
                740                745                750

Tyr Gln Ser Leu Asp Met Leu Glu His Ala Leu Asp Gln Met Pro Glu
            755                760                765

Gly Lys Ile Lys Thr Phe Pro Lys Asp Asn Ile Leu Val Ala Lys Leu
770                775                780

Lys Ile Met Val Asp Gly Glu Gly Ile Gly Arg Tyr Glu Ala Pro Arg
785                790                795                800

Gly Glu Leu Val His Tyr Val Arg Gly Lys Lys Gly Ser Asp Lys Pro
                    805                810                815

Leu Arg Trp Lys Pro Arg Glu Pro Thr Phe Pro Asn Leu Phe Ala Val
                820                825                830

Ala Lys Gly Val Thr Gly Asp Gln Val Ala Asp Phe Val Leu Ala Val
            835                840                845

Ala Ser Ile Asp Pro Cys Leu Ser Cys Thr Asp Arg Val Ala Val Val
850                855                860

Gln Asp Gly Lys Lys Arg Ile Leu Thr Glu Thr Asp Leu Leu Arg Leu
865                870                875                880

Ser Ile Lys Lys Thr Arg Glu Ile Asn Pro Glu Val Lys Gly Asp Pro
                    885                890                895

Thr Pro Val Gly Phe Gly Cys Ser Arg Met Asp Val Met Ala Asn Ile
                900                905                910

Ile Tyr Pro Val Ala Gly Leu Ile Gly Leu Tyr Ala Phe Val Ser Leu
            915                920                925

Ala Ser Leu Val Trp Glu Gly Ile Asp Arg Lys Leu Val Ala Arg Met
930                935                940

Gln Arg Arg Val Gly Pro Pro Leu Leu Gln Pro Leu Tyr Asp Phe Phe
945                950                955                960

Lys Leu Ala Ser Lys Glu Thr Ile Ile Pro Asn Thr Ala Asn Phe Met
                    965                970                975

Phe Arg Ala Ala Pro Val Leu Ala Leu Ala Thr Ala Ile Ala Leu Leu
                980                985                990

Ala Tyr Thr Pro Met Gly Phe Ala Pro Leu Leu Ala Ser Lys Gly Asp
            995                1000                1005

Val Ile Val Phe Ile Tyr Leu Leu Thr Leu Ile Gly Phe Phe Lys
    1010                1015                1020

Ile Leu Gly Gly Ile Ser Ser Gly Ser Pro Tyr Ala Lys Ile Gly
1025                1030                1035

Ala Ala Arg Glu Ala Ala Ile Met Val Ser Arg Glu Pro Ala Met
            1040                1045                1050

Met Leu Ala Leu Phe Ala Ile Ile Trp Arg Leu Gly Lys Leu Gly
            1055                1060                1065

Val Asn Lys Pro Phe Ser Met Glu Val Phe Tyr Gln Tyr Asn Ile
            1070                1075                1080

Trp Glu Ile Gly Thr Pro Leu Ser Leu Ile Gly Ala Val Ile Leu
        1085                1090                1095

Leu Tyr Val Phe Val Ile Trp Leu Ala Ser Glu Ile Glu Val Gly
        1100                1105                1110

Tyr Phe Asn Ile Pro Asp Ala Glu Glu Ile Ala Glu Gly Leu
        1115                1120                1125

Leu Ala Glu Tyr Ser Gly Arg Tyr Leu Ala Leu Leu Lys Leu Thr
        1130                1135                1140

Lys Ala Leu Lys Thr Tyr Ile Ala Ala Ser Leu Val Val Ala Ile
        1145                1150                1155

Phe Phe Pro Trp Gly Ile Ala Asp Tyr Phe Asn Leu Thr Gly Leu
        1160                1165                1170

Pro Ala Asn Val Val Asn Leu Leu Phe His Thr Leu Lys Val Phe
        1175                1180                1185

Ile Leu Leu Phe Ala Val Gln Ser Val Phe Arg Ala Thr Thr Gly
        1190                1195                1200

Arg Leu Lys Ile Thr Gln Ala Val Asp Phe Leu Trp Lys Asn Val
        1205                1210                1215

Phe Leu Ala Ser Leu Ile Gly Thr Leu Leu Ile Ala Met Glu Val
        1220                1225                1230

Ile Met Val Arg Leu Ser Pro Leu Ile Pro Thr Val Leu Arg Asn
        1235                1240                1245

Met Phe Lys Lys Pro Ala Thr Asn Leu Phe Pro Ala Thr Glu Pro
        1250                1255                1260

Val Pro Val Pro Asp Asn Phe Arg Gly Gln Leu Lys Tyr Asn Val
        1265                1270                1275

Asp Lys Cys Val Gly Cys Arg Met Cys Val Thr Val Cys Pro Ala
        1280                1285                1290

Gly Val Phe Val Phe Leu Pro Glu Ile Arg Lys Val Ala Leu Trp
        1295                1300                1305

Thr Ala Arg Cys Val Tyr Cys Ser Gln Cys Val Asp Val Cys Pro
        1310                1315                1320

Thr Ala Ala Leu Gln Met Ser Asp Glu Phe Leu Leu Ala Ser Tyr
        1325                1330                1335

Asn Asn Tyr Asp Asp Lys Phe Ile Pro Leu Lys Pro Glu Lys Val
        1340                1345                1350

Glu Glu Ile Lys Lys Lys Leu Glu Glu Gln Lys Lys Ala Lys Ala
        1355                1360                1365

Ala Ala Ala Ala Lys Lys Ala Met Glu Lys Lys Glu Ala Gly Lys
        1370                1375                1380

Glu Ala Lys Lys
        1385

<210> SEQ ID NO 9
<211> LENGTH: 854
<212> TYPE: PRT
<213> ORGANISM: Thermococcus onnurineus NA1

<400> SEQUENCE: 9

```
Met Gly Met Ala Glu Lys Arg Ile Ser Val Val Cys Pro Trp Cys Ser
1               5                   10                  15

Val Gly Cys Arg Phe Tyr Ile Val Asn Val Asn Gly Tyr Pro Lys Lys
            20                  25                  30

Ile Glu Phe Asp Tyr Asp His Asp Ile Arg Asn His Gly Lys Leu Cys
                35                  40                  45

Pro Lys Gly Val Ala Ala Phe Gln His Leu Arg His Pro Asp Arg Leu
        50                  55                  60

Lys Lys Pro Leu Lys Arg Val Gly Glu Arg Gly Gly Lys Phe Lys
65                  70                  75                  80

Glu Ile Ser Trp Glu Glu Ala Ile Lys Glu Ile Ala Gln Lys Leu Ser
                85                  90                  95

Glu Ile Lys Glu Lys Tyr Gly Ser Glu Ala Leu Ala Phe Leu Gly Ser
            100                 105                 110

Glu Arg Cys Ser Ile Glu Glu Asn Tyr Val Leu Gln Lys Leu Ala Arg
            115                 120                 125

Ala Leu Gly Thr Asn Asn Ile Glu Tyr Val Cys Arg Met Cys Gln Ser
        130                 135                 140

Thr Ala Val Ala Gly Lys Gly Met Val Leu Gly His Pro Gly Leu Thr
145                 150                 155                 160

Asn Pro Phe Glu Asp Ile Leu Lys Ala Lys Val Ile Val Leu Trp Gly
                165                 170                 175

Tyr Asn Pro Ala Ala Thr Asn Pro Val Phe Phe Gly Gln Tyr Ile Glu
            180                 185                 190

Lys Ala Ile Leu Asp Asn Asn Ala Thr Leu Ile Val Val Asp Pro Arg
        195                 200                 205

Lys Thr Lys Thr Ala Lys Tyr Ala Asp Ile His Leu Gln Pro Tyr Pro
210                 215                 220

Gly Thr Asp Leu Ala Ile Ala Leu Ala Met Leu Asn Val Ile Ile Thr
225                 230                 235                 240

Glu Glu Leu Tyr Asp Lys Asp Phe Val Ala Glu Arg Ala Glu Gly Leu
            245                 250                 255

Glu Glu Leu Ala Lys Thr Val Glu Lys Tyr Thr Pro Glu Trp Ala Glu
            260                 265                 270

Lys Val Ser Gly Val Pro Ala Glu Leu Ile Arg Lys Ala Ala Ile Thr
        275                 280                 285

Phe Ala Thr Ala Gly Thr Ala Ala Leu Leu Thr Asn Glu Gly Val Asn
290                 295                 300

Gln His Ala Asn Gly Thr Arg Thr Val Met Ala Ile Thr Glu Met Met
305                 310                 315                 320

Val Leu Cys Gly Tyr Phe Gly Lys Glu Gly Val Met Ser Gly Ala Ile
            325                 330                 335

Pro Gly Ala His Asn Gly Met Gly Ala Gly Leu Met Gly Ile Gly Pro
            340                 345                 350

His Glu Leu Pro Gly Arg Phe Pro Leu His Ala Glu His Lys Arg
            355                 360                 365

Arg Ile Glu Glu Ala Trp Gly Phe Lys Ile Pro Glu Lys Pro Gly Ile
370                 375                 380

Thr Tyr Val Glu Met Ile Asp Ala Ile Leu Glu Gly Lys Leu Lys Ala
385                 390                 395                 400

Leu Tyr Val Met Gly Thr Asn Pro Ala Lys Ala Leu Pro Asn Leu Lys
            405                 410                 415

Lys Ala Glu Glu Ala Phe Lys Asn Ile Glu Phe Leu Val Val Gln Asp
```

```
                420             425             430
Ile Phe Leu Thr Glu Thr Ala Lys Tyr Ala Asp Ile Val Leu Pro Ala
            435             440             445

Ala Ala Trp Phe Glu Lys Asp Gly Thr Ala Ile Ser Phe Glu Arg Arg
    450             455             460

Val Gln Arg Ser Phe Lys Ala Asp Ala Pro Gly Glu Ala Lys Pro
465             470             475             480

Asp Trp Glu Ile Leu Val Met Leu Ala Lys Glu Leu Gly Phe Gly Glu
                485             490             495

Tyr Phe Asn Tyr Ser Asp Ala Asp Ile Leu Arg Glu Ile Asn Arg
            500             505             510

Ile Ile Pro Pro Leu Ala Gly Ala Thr Pro Glu Arg Leu Lys Lys Asn
            515             520             525

Leu Lys Gly Cys Met Ile Pro Cys Pro Asp Glu Asn Thr Glu Val Pro
    530             535             540

Arg Leu Phe Val Gln Gly Phe Leu Thr Pro Asn Gly Lys Ala Gln Leu
545             550             555             560

Ile Pro Val Glu Tyr Lys Glu Pro Gly Glu Val Pro Asp Glu Tyr
            565             570             575

Pro Phe Trp Leu Thr Asn Tyr Arg Phe Val Gly His Phe His Thr Gly
            580             585             590

Thr Met Ser His Arg Ser Lys Ser Leu Ser Lys Arg Trp Pro Glu Glu
            595             600             605

Tyr Ile Glu Ile Asn Glu Asn Asp Ala Lys Arg Leu Gly Ile Lys Asp
            610             615             620

Gly Asp Leu Val Arg Val Glu Thr Arg Arg Ala Ala Leu Val Leu Arg
625             630             635             640

Ala Lys Val Thr Pro His Ile Arg Glu Gly Val Val Ala Ala Pro Trp
                645             650             655

His Trp Asp Phe Asn Tyr Leu Thr Thr Asp Val Leu Asp Glu Tyr Ala
            660             665             670

Lys Met Pro Glu Leu Lys Thr Ala Ala Cys Arg Ile Ser Lys Val Glu
            675             680             685

Gly Met Ser Lys Lys Ile Phe Ile Asp Phe Lys Arg Cys Ile Ala Cys
    690             695             700

Lys Ala Cys Glu Val Ala Cys Glu Met Glu His Gly Glu Ala Arg Ile
705             710             715             720

Arg Val Phe Glu Phe Pro Asp Leu Thr Ser Val Ala Phe Asn Cys Arg
                725             730             735

His Cys Glu Lys Ala Pro Cys Met Glu Val Cys Pro Val Asn Ala Leu
            740             745             750

Ser Lys Asp Asp Asp Gly Ala Val Val Leu Asp Pro Leu Lys Cys Ile
            755             760             765

Gly Cys Leu Met Cys Gly Leu Ala Cys Pro Phe Gly Ile Pro Lys Ile
    770             775             780

Asp Glu Tyr Asn Lys Ile Met Asp Lys Cys Asp Leu Cys Ala His Arg
785             790             795             800

Arg Ala Glu Gly Lys Leu Pro Ala Cys Val Ser Ala Cys Pro Thr Glu
            805             810             815

Ala Leu Lys Tyr Gly Asp Ile Asn Asp Val Leu Trp Ala Arg Glu Gly
            820             825             830

Lys Ile Val Ala Glu Leu Lys Asp Ile Gly Asp Arg Thr Asn Val Leu
    835             840             845
```

Glu Ala Tyr Leu Ile Arg
                850

<210> SEQ ID NO 10
<211> LENGTH: 630
<212> TYPE: PRT
<213> ORGANISM: Thermococcus onnurineus NA1

<400> SEQUENCE: 10

Met Ala Gly Lys Lys Val Pro Ser Lys Gln Val Ser Ile Thr Pro Gly
1               5                   10                  15

Val Gly Lys Leu Ile Glu Lys Ala Glu Glu Asp Gly Val Lys Thr Ala
            20                  25                  30

Trp His Arg Phe Leu Glu Gln Gln Pro Gln Cys Gly Phe Gly Leu Leu
        35                  40                  45

Gly Val Cys Cys Lys Asn Cys Thr Met Gly Pro Cys Arg Ile Asp Pro
    50                  55                  60

Phe Gly Val Gly Pro Thr Lys Gly Val Cys Gly Ala Asp Ala Asp Thr
65                  70                  75                  80

Ile Val Ala Arg Asn Ile Val Arg Met Ile Ala Ala Gly Thr Ala Gly
                85                  90                  95

His Ser Asp His Ser Arg Asp Val Val His Val Phe Lys Gly Ile Ala
            100                 105                 110

Glu Gly Lys Phe Lys Asp Tyr Lys Leu Thr Asp Val Glu Lys Leu Lys
        115                 120                 125

Glu Leu Ala Lys Ile Leu Gly Val Glu Thr Glu Gly Lys Ser Glu Asn
    130                 135                 140

Glu Ile Ala Leu Glu Val Ala His Ile Leu Glu Met Glu Phe Gly Lys
145                 150                 155                 160

Gln Asp Glu Glu Pro Val Arg Leu Leu Ala Ala Thr Ala Pro Lys Lys
                165                 170                 175

Arg Ile Lys Val Trp Glu Lys Leu Gly Val Leu Pro Arg Ala Ile Asp
            180                 185                 190

Arg Glu Ile Cys Leu Ser Met His Arg Thr His Ile Gly Cys Asp Ala
        195                 200                 205

Asp Pro Ala Ser Leu Leu Leu His Gly Val Arg Thr Ala Leu Ala Asp
    210                 215                 220

Gly Trp Cys Gly Ser Met Met Ala Thr Tyr Leu Ser Asp Ile Leu Phe
225                 230                 235                 240

Gly Thr Pro Lys Pro Ile Lys Ser Leu Ala Asn Leu Gly Val Leu Lys
                245                 250                 255

Glu Asp Met Val Asn Ile Ile Val His Gly His Asn Pro Ile Leu Ser
            260                 265                 270

Met Lys Ile Ala Glu Ile Ala Gln Ser Glu Glu Met Gln Lys Leu Ala
        275                 280                 285

Glu Gln Tyr Gly Ala Lys Gly Ile Asn Val Ala Gly Met Cys Cys Thr
    290                 295                 300

Gly Asn Glu Val Leu Ser Arg Met Gly Val Gln Val Ala Gly Asn Phe
305                 310                 315                 320

Leu Met Gln Glu Leu Ala Ile Ile Thr Gly Ala Val Glu Ala Val Ile
                325                 330                 335

Val Asp Tyr Gln Cys Leu Met Pro Ser Leu Val Asp Val Ala Ser Cys
            340                 345                 350

Tyr His Thr Lys Ile Ile Thr Thr Glu Pro Lys Ala Arg Ile Pro Gly
        355                 360                 365

```
Ala Ile His Val Glu Phe Glu Pro Glu Lys Ala Asp Glu Ile Ala Lys
        370                 375                 380

Glu Ile Ile Lys Ile Ala Ile Glu Asn Tyr Lys Asn Arg Val Pro Ala
385                 390                 395                 400

Lys Val Tyr Ile Pro Glu His Lys Met Glu Leu Val Ala Gly Phe Ser
                405                 410                 415

Val Glu Ala Ile Leu Glu Ala Leu Gly Gly Thr Leu Glu Pro Leu Ile
            420                 425                 430

Lys Ala Leu Gln Asp Gly Thr Ile Lys Gly Ile Val Gly Ile Val Gly
            435                 440                 445

Cys Asn Asn Pro Arg Val Lys Gln Asn Tyr Gly His Val Thr Leu Ala
    450                 455                 460

Lys Glu Leu Ile Lys Arg Asp Ile Leu Val Val Gly Thr Gly Cys Trp
465                 470                 475                 480

Gly Ile Ala Ala Ala Met His Gly Leu Leu Thr Pro Glu Ala Ala Glu
                485                 490                 495

Met Ala Gly Pro Gly Leu Lys Ala Val Cys Glu Ala Leu Gly Ile Pro
                500                 505                 510

Pro Cys Leu His Met Gly Ser Cys Val Asp Cys Ser Arg Ile Leu Leu
        515                 520                 525

Val Leu Ser Ala Leu Ala Asn Ala Leu Asn Val Asp Ile Ser Asp Leu
    530                 535                 540

Pro Val Ala Gly Ser Ala Pro Glu Trp Met Ser Glu Lys Ala Val Ala
545                 550                 555                 560

Ile Gly Thr Tyr Phe Val Ala Ser Gly Val Phe Thr His Leu Gly Val
                565                 570                 575

Ile Pro Pro Val Leu Gly Ser Gln Lys Val Thr Lys Leu Leu Thr Asp
                580                 585                 590

Asp Ile Glu Asp Leu Leu Gly Gly Lys Phe Tyr Val Glu Thr Asp Pro
            595                 600                 605

Val Lys Ala Ala Glu Thr Ile Tyr Asn Val Ile Ile Glu Lys Arg Lys
            610                 615                 620

Lys Leu Gly Trp Pro Ile
625                 630

<210> SEQ ID NO 11
<211> LENGTH: 877
<212> TYPE: PRT
<213> ORGANISM: Thermococcus onnurineus NA1

<400> SEQUENCE: 11

Met Ser Glu Arg Leu Val Pro Val Val Cys Pro Tyr Cys Gly Val Gly
1               5                   10                  15

Cys Arg Leu Tyr Ile Arg Ser Val Asp Gly Tyr Pro Val Gly Ile Glu
                20                  25                  30

Tyr Ala Lys Asp Ile Pro Asn Ile Ser Asn Glu Leu Gly Lys Leu Cys
            35                  40                  45

Pro Lys Gly Asn Ala Val Val Glu Tyr Leu Leu Ala Lys Asp Arg Leu
        50                  55                  60

Lys Arg Pro Leu Lys Ala Lys Glu Gln Gly Lys Phe Val Glu Ile Ser
65                  70                  75                  80

Trp Ser Glu Ala Ile Lys Glu Val Ala Glu Arg Leu Lys Ala Tyr Ala
                85                  90                  95

Lys Asp Asp Pro Asn Gln Leu Met Phe Phe Gly Ser Ala Arg Thr Phe
            100                 105                 110
```

-continued

Asn Glu Pro Asn Tyr Leu Val Gln Lys Leu Ala Arg Met Leu Gly Thr
            115                 120                 125

Asn Asn Val Asp His Cys Ala Arg Leu Cys His Ala Pro Thr Val Thr
130                 135                 140

Gly Leu Lys Ala Val Phe Gly Ala Gly Ala Met Thr Asn Thr Tyr Lys
145                 150                 155                 160

Asp Ile Glu Glu Ala Asn Val Ile Phe Ile Ile Gly His Asn Tyr Ala
                165                 170                 175

Glu Thr His Pro Val Gly Phe Arg Tyr Val Leu Lys Ala Lys Glu Arg
            180                 185                 190

Gly Ala Lys Val Ile Val Ala Asp Pro Arg Phe Thr Arg Thr Ala Trp
            195                 200                 205

Phe Ala Asp Ile Phe Leu Gln His Tyr Pro Gly Ser Asp Ile Ala Leu
210                 215                 220

Ile Asn Gly Leu Ile His Val Ile Ile Lys Glu Arg Leu Tyr Asp Glu
225                 230                 235                 240

Lys Phe Val Arg Glu Arg Cys Val Gly Phe Asp Glu Val Val Ala Ala
                245                 250                 255

Val Glu Lys Phe Thr Pro Glu Phe Val Glu Lys Val Thr Gly Val Pro
            260                 265                 270

Ala Glu Leu Ile Ile Glu Ala Ala Arg Thr Phe Ala Thr Ala Gly Lys
            275                 280                 285

Gly Val Ile Thr Trp Ala Met Gly Leu Thr Gln His Thr His Gly Thr
290                 295                 300

Glu Asn Val Lys Leu Leu Gly Thr Leu Ala Ala Ile Cys Gly Tyr Gln
305                 310                 315                 320

Gly Lys Glu Gly Ala Gly Cys Ser Pro Met Arg Gly Gln Asn Asn Val
                325                 330                 335

Gln Gly Ala Cys Asp Met Ala Ala Leu Pro Asn Val Phe Pro Gly Tyr
            340                 345                 350

Gln Ala Val Thr Asp Pro Glu Lys Arg Lys Phe Phe Glu Glu Phe Trp
            355                 360                 365

Gly Val Glu Leu Ser Gly Glu Val Gly Leu Thr Thr Val Glu Ala Ala
370                 375                 380

Tyr Ala Ala Asp Lys Gly Lys Val Lys Ala Tyr Tyr Val Met Gly Glu
385                 390                 395                 400

Asn Pro Val Ile Ser Glu Ala Asn Ala Asn His Val Met His Thr Leu
                405                 410                 415

Glu Lys Leu Glu Phe Met Val Val Gln Asp Ile Val Pro Thr Pro Thr
            420                 425                 430

Met Glu Tyr Ala Asp Ile Val Leu Pro Ala Ala Ala Met Leu Glu Asn
            435                 440                 445

Glu Gly Ser Leu Thr Asn Thr Glu Arg Arg Val Gln Trp Ser Phe Gln
450                 455                 460

Ala Val Lys Pro Pro Gly Glu Ala Arg Pro Asp Trp Trp Ile Leu Ser
465                 470                 475                 480

Glu Val Gly Lys Ala Ile Gly Phe Asp Lys Thr Gly Ser Gly Gly Phe
                485                 490                 495

Val Tyr Asn Asp Ala Ala Asp Val Leu Arg Glu Ile Asn Ala Cys Thr
            500                 505                 510

Pro Gln Tyr Arg Gly Ile Thr Pro Glu Arg Leu Lys Glu Asn Leu Ala
            515                 520                 525

Gly Leu His Trp Pro Cys Pro Ser Glu Asp His Pro Gly Thr Arg Val
530                 535                 540

Leu Tyr Lys Glu Lys Phe Leu Thr Pro Ser Gly Lys Ala Asn Leu Ala
545                 550                 555                 560

Ala Val Pro Glu Tyr Lys Gly Pro Val Glu Met Pro Asp Glu Tyr
            565                 570                 575

Pro Phe Leu Leu Thr Thr His Arg Tyr Val Gly Met Tyr His Thr Ala
        580                 585                 590

Thr Met Thr Met Arg Ser Cys Ala Leu Lys Lys Arg Trp Pro Glu Pro
        595                 600                 605

Leu Ala Glu Ile His Pro Asp Asp Ala Val Lys Leu Gly Ile Lys Ser
    610                 615                 620

Gly Asp Trp Val Lys Val Val Thr Arg Arg Gly Ala Tyr Pro Ile Lys
625                 630                 635                 640

Ala Lys Val Thr Arg Ala Val Lys Lys Gly Val Ile Ala Val Pro Trp
                645                 650                 655

His Trp Gly Ala Asn Val Leu Thr Asn Asp Ala Leu Asp Pro Val Ala
                660                 665                 670

Lys Ile Pro Glu Thr Lys Ala Cys Ala Cys Asn Val Ala Lys Ile Thr
            675                 680                 685

Glu Glu Glu Ala Arg Lys Leu Met Glu Lys Leu Pro Pro Leu Ile Pro
    690                 695                 700

Lys Ile Glu Val Val Arg Gly Met Ala Arg Lys Thr Val Phe Ile Asp
705                 710                 715                 720

Phe Ser Lys Cys Ile Glu Cys Arg Ala Cys Glu Val Ala Cys Glu Arg
                725                 730                 735

Glu His Ser Gly Met Ser Phe Ile Ser Val Phe Glu Trp Gln Glu Met
                740                 745                 750

Ala Ala Met Ala Leu Asn Cys Arg His Cys Glu Lys Ala Pro Cys Val
                755                 760                 765

Glu Val Cys Pro Thr Asn Ala Leu Tyr Arg Asp Lys Asp Gly Ala Val
            770                 775                 780

Leu Leu Ala Pro Gln Lys Cys Ile Gly Cys Leu Met Cys Gly Ile Val
785                 790                 795                 800

Cys Pro Phe Gly Ile Pro Glu Leu Asp Leu Ile Asn Lys Ile Met Gly
                805                 810                 815

Lys Cys Asp Leu Cys Ala His Arg Arg Ala Glu Gly Lys Leu Pro Ala
                820                 825                 830

Cys Val Glu Thr Cys Pro Thr Asp Ala Leu Ile Tyr Gly Asp Phe Asn
            835                 840                 845

Glu Ile Val Lys Lys Arg Arg Glu Lys Phe Thr Lys Thr Ile Glu
    850                 855                 860

Leu Ala Lys Thr Ala Glu Arg Ile Pro Leu Thr Gly Val
865                 870                 875

<210> SEQ ID NO 12
<211> LENGTH: 4194
<212> TYPE: DNA
<213> ORGANISM: Thermococcus onnurineus NA1

<400> SEQUENCE: 12
atgggattcc taagcagact gttcggtggg aagaaggaaa ccgacactga ggaaattcag      60
atagtctcga ggaagccagt tggaaagttc cacgttgaga aggtcttcca catcatggga     120
cgcgaaaccc tcgtggggac cgtggagaga ggagtaatct atccaggcta caaggttaag     180
ggaaagaaag ccgcagtgat ctacaggata gagaaggta gaaggctgt ggattttgtc       240

```
gtcgacggag acaaggctgc actcattctc gagggaatta ctaaagcgga agagggagat    300
acccttgaag tctatcagtc gtgaatgata atcgagttga gggagttcac gagagttgaa    360
ggcaacggca aagccgagat agttgtcgag aacggtgaag ttaaggacgt caggctcaaa    420
atcgttgaag ggccgcgctt cttcgagctg ctgactttgg gaaggcatta ctatgacgtt    480
ccagacttgg aagcgaggat atgcgccata tgctacctct cacacagcgt cgcctcggtt    540
ctgggcatag agaaggcctt cggagttgaa gtttcggagg agatccagct cctaagagag    600
ctcggcctca tcggtgaatt actggagagc cacgcactcc acctgtacct gctcgttgct    660
ccagacgttt tcggttatcc tgacgcgata agaatggcta cgaagcacgg ggagctcgtc    720 aaggagggc ttgcactgaa ggccttcggc aacagtataa gggaactcat tggaggaagg    780
gagatccacg gcataaacgt taaacccggt ggatttggca ggtatccgac ggttgaggaa    840
cttgaaaaca tcgagaggga gagtgggggcc ctcctgagac tcgcaaggag agcggtgagg    900
ctattcgctt cgcttgagcc ctacggcgaa aaggcgggac acttcgtcgc gacggacggc    960
tacctatggg gcgacaagct gatttccgat gaggatggct ctttccacta caccgagaga   1020
atagaggaac gctcactggt ttacagcttc gcaaagcaga gccgctataa gggtgagccc   1080
ttcttcgttg gcgcactgcc gaggctcctg ctcaaagcag atgctgac acccacagcg    1140 aagaggctct tcgaggagca gggaaaaag ctcgccaccg gttacgtcag ctacaacaac   1200
ctcgctcagg ccatagagct cgtctacgcg cttgaaaggg cggagagat agcaaagaaa   1260 ctcctcgaca agggcataaa gggtgaaaac gttcccgttg aagtcaaaga aggcgagggc   1320
atagggtacg tggaagcgcc tagggggtgtc ctaatacatc actaccgcat tgactctggg   1380
ggcaaaatcg cctactcgaa catcataacg cccacggctt taaaccacgc tatgatggag   1440
gcaagcctgt tcaaggaagc gagaaaactc tacgagaga cggacgagac ggtactcgtc   1500
cagaggctgg aggaaacggt tagagccttt gatccgtgca tttcctgttc agtgcacatc   1560
gtgaagcttt agatgatgga caagctcaag ttggccgtct tcgagcttac cgactgcggc   1620
ggctgtgcgc tgaatattct cttcctctac gagaagctgt ttgacctgct cgagttctac   1680
gagataacgg agttccacat ggcgaccagc ctaagcgagg ggagccacta cgacgtggcc   1740
ctcgtaaccg gaacggtctc aagccagcgc gacctagcgc tcctcaagga ggcaagaaac   1800
cactccgact acctcatagc cctcggaacc tgcgcaacgc acggctcggt tcaggctagc   1860
gtcgagggga gcataaggga gaagctgaag agggtctatg gagatgaggg caacccgatg   1920
agggcgctga ctcgaagcc cgtcgttgag tacgtcgccg ttgatttcgc cctcccaggc   1980
tgtccctacg acaaaaacga ggtatatcag gttctgatgg acattgccaa aggcattgag   2040
ccggtaaaga aagactaccc cgtctgcgtc gagtgcaagc tcaacgaata cgaatgtgtt   2100
ctcgtgaaga agggcctccc ctgcctcggt ccaataacct acggcggctg caacgctgct   2160
tgtatacgct ccgggctggg atgcataggc tgtcgcgggc cgttgcccgg cgaggtgaat   2220
cctgcaagtg agtacgagat actcaaggat ctgggctacg atgatgacta catcctcagg   2280
aagttcaaga ccttcgcgag gtgggagcca tgaatgagcg agaatccaca tcaaacttac   2340
gatgcgcgca ttctggaagt gaaggaccta acacccaggg agaagctctt cacgctccgc   2400
ttcttagacc cggaaattgg cgaacacttc acattcaagc ccggccagtt cgtcatcgtc   2460
gatatacggg gcttcggtga gttccccata agcctctgct cctcaccaac gagaaaagga   2520
tacattcagc tctgcatcag aaaagccgga aggatgacca agttcatcca tcagatgaaa   2580
gagggagaag tggtgggcat ccgcgggccc tacggcaacg gcttcccgat ggagaaaatg   2640
```

-continued

```
gagggctcga atctactcct ggtcgccggt ggactcggta tggcacccct ccgctcggtt    2700
ctctggtacg cgatagacac cggaaagtac gagcacgtct ggctcctcta cggcaccaaa    2760
gcctacgagg acatactctt ccgcgacgag ataatccacc tgctgaagca cggcgacgcg    2820
gttggctgca gcgtaaagct cgcctatgag gtcgaaagcc cctcgtgcat ctacctcgag    2880
cggggcttct tcgacagggt gtgcaagggt gtcgttaccg acctcttccg cggggaggag    2940
ttcgacgtcg acaaggctta cgccctcatc tgtgggccgc cggttatgta ccgcttcgtc    3000
atcaaggagc tcctagacag gaaactctcg ccgggcagga tatacatgac cctcgagagg    3060
cgcatgcgct gcggaatagg caagtgcggc cactgtatag tgggaacgag cacctccata    3120
aagtacgtct gcaaggacgg ccccgtcttc acatactggg atgctctctc cacgaggggg    3180
ttgatatgat tgagatatgt aaaactatca tctgagaact ttagctcatt ttttgaatct    3240
ctaaggaatt ggggcaaagt ctacgctccc atcaaaagag gaagcattta cacattccaa    3300
gaagttcacg agctaggaga gatagaactc aactatacaa ggacaatgct acctccaaaa    3360
aagttcttcg tgaggccaag ggacgaaatt cttcgcctga gaacggtcg ctgggaaaat    3420 ggaaccgacg cagagccgat agttctcttc ggcctccact cctgcgatat gcacgggctc    3480
aagattctcg ataaggtcta tctcgacgag cccgccgacc cgtactacaa ggcgaggcgc    3540
gagaaaacct tcatagttgg gataagctgc atgcccgacg agtattgctt ctgcaagagt    3600
ctcggcacgc actttgccat ggacggcttt gacctattcc tgcacgagct tcccgacgga    3660
tggctcgtca ggataggaag tgtgagggga cacgaggtag tctgggagaa cggtgagctc    3720
ttcgaggagg tgaccgacga ggacttgaag cacttcaagg agttcgagga gaggcgcgca    3780
aatgcgttcc agaaggagat cccgcaggaa ggactcgcag acatgctcga tttggcctac    3840
aacagcccgg tctggaagga gtacgccgag atatgcctgg cctgcggcaa ctgcaacatg    3900
gtctgtccta cctgccgctg ctacgaggtc tgcgataact ggatcagcgc ctacgacgcc    3960
gtcagagaga gacgctacga ctcctgcttt atggagaacc acggactggt tgccggaggc    4020
cacaacttca ggccaactag actcgacaga ttcaggcaca gatactactg caagagctac    4080
ttcgatccct cctcgggtta taactgcgta ggttgtggaa ggtgtgacga gttctgcccg    4140
gcgaagatag agcacgtcaa ggttcttgag gaggtcaggg ggtcgctgag atga          4194
```

<210> SEQ ID NO 13
<211> LENGTH: 7506
<212> TYPE: DNA
<213> ORGANISM: Thermococcus onnurineus NA1

<400> SEQUENCE: 13

```
atgaacgcct ctcccttcat tatatctttt ttgatccccc tgctcctcgg tccactcctg      60
ttcaaattag acggtagaaa ggccgatgta ttcatgctca tcgccgttgt gtcttccttc     120
ctggctaatc ttgtgggagt cctcgaatac ctgaaagtcg gtggcgctca tcatatcgtt     180
tacctcgaaa cttcttccct cggtgaggtc tacggcgtta taatcgaccc aatgagcgtt     240
ttggtcggtt ttgtcgtgag cttggctggc gtgctgttcc ttctctacgc ggtggactac     300
atgagcgaga gaaacaagca gcaccccgtc tactctgata aagggcaggtt ctatgcttgg     360 atggtcatct tcgttggagc tacgctgcca ttcatatact cctccacgac gcttcagctg     420
ctcatattct tcgagataat gggactcgcc tgctggggtg tcgttgggta ttataagggc     480
ccaaaagccg agagggctgc atacaaggcc ctgcttgtgc cgaacttcgg tgccatggtg     540
ggcctctaca ccaccgttgg cattggcatc ctcaagctcc atgatttgag catctatgcg     600
```

```
ctccagaacc tgaatgatga gctcaagctt ctcgtgttcc ttggcgtaat ggttgcggcc    660
tttaccaaga gcgcccagtt cccgctctat tcatggcttc cggatgcaat ggcggcgccg    720
acacctgctt ccgcttttct ccacggtgct gcaatggttg aaatgggcgt ttacctgctc    780
gccagggtca cccagttcat gcaaccgatt ccggagacag ctttctacgt tatgctcgtc    840
ttcgtgtcgc taactttact catagcaatt ctctactacc cgctccagaa ggacgccaag    900
agactccttg cttattcaac catagcagag gcaggagtga tgtacgttgg cgtgctctat    960
gccgtgcttg gctctgtcta tggtctccag gcggccatgt tccagctggc taaccacgct   1020
ttcgtcaagg gtcttgcctt cctcaccgcg ggaaccttca gttacgcttt tggaacgctc   1080
gacatggaga agattagggg cctcggaaag ctcgttccgg tcgttggtgc aagctggttc   1140
ttagcccttc tcggcctggc tggagttcct ccgctcggcc tgttcttcag caaggcgtat   1200
ctcttcatga acgcgtcttc aataaccagc tgggttggct ggattccgct cttcctagtg   1260
ttggccgatg ccacggtttt ccttgcggta tctctcggat ggattaagag gatggtattc   1320
agcgagcccc tccaggagag tgcagaagtt ccccgctga tgcgctttgt cctcgtagtc   1380
ctaatagtcc tgtccatcgt tgcgccgttc ctaagcgtga agctcgtgac tcagataggg   1440
ttcatggggt gaatgatgga aattccaatc gcgctctact cactctcagc gatttccggc   1500
ctgattggag actttaagcg gagcattaag atttcaagcg tcctctcagc catagcatcc   1560
ctatcccttc tgggcatagc tgcccacgcc ctgtccaggg ggcttcccgt tcaggagagc   1620
tttttgggca ttcccctaat catagacagc ctctccctcc cgttcctgtt catcatagcc   1680
ctgctcagcc ttgtggtttc agtgtattcc atttcatata tggaagtcca cagagatacc   1740
ggaagaccac tggcgtacac catcctctac ggcacgttcg tgctgtcgat tgtattcgtg   1800
gctctgacgt caaacctgct ctggttcgtc ttcttctggg agctgatgac cctaacttcc   1860
ttcatcttcg tgagctggag ggagcaggac gctggaatta aatacctcct cacgatgcag   1920
ctcgccaaca cggtgcccct cttcgtggcc ctcggcataa tctactccgc cactggaagc   1980
ttcagcgttg attacgccac gcttagggag gttgcatctt ccctttctcc agtccagctc   2040
aagctgctct acgcgatgtt cctcgtgacg ttccttgcaa aatctggaag cgtgcccttc   2100
cagttctggg tgcccgatgc atacgaagcc gctcccagca atatagcctc gctgatggcc   2160
ggcgtcatga gaagatggc ggtttacggt ctgataaggc tcctctgcaa cgccctgcca   2220
tgcagtgaag gcattggtta cgttctcgtt atcgtcggca tacttaccat gaccttcgga   2280
accctctacg ccctcagaga gactcacgca aagaggctcc tcgcttactc aagcgttgga   2340
caaatgggct acatctggtt cgcggtgggc atgggcatga tcttcctgac gatgggcatg   2400
gagagcctgg cttacctggc cttcctcgcc ggagtcttcc actccttcaa tcacacactc   2460
ttcaagggc tgctctttct catctcgggc aacttcgagt actccgccgg aaccgctgac   2520
ctcaacgagc ttggtggttt gaggagggca atgccgtact cgtcgctctt caccgtcata   2580
ggtgcgctct ccctcgctgg agtgcccctc ttcagcggtt tcctctccaa gtggatgatt   2640
taccaggccg gctactactc tggaatcggc tccttcgtct ttggctccgt aatgcggtg   2700
tttatgagcg ccgtaaccct tggcatattcg ctcaagctct acacctctgc ctttggggc   2760
gaaccgaacg agagaactga gaacgccagg gaagtcccgt cgggtatgct cctcggtgag   2820
ggaattattg ccttaacttc acttgccgtt ggaatacttc cggctattgc ttacccgata   2880
ttaacgattt cattgaatgg cggcgacgtc accgttacaa tgggctcgat atccactgac   2940
tttgagtact tctcgccaat agccctgctc cttgcggttt cattcattgc ggttgcttca   3000
```

```
tacttcgtct tcaggccaaa gacgaccaat gtcaaaccct ggaacactgg agcgcttttc    3060
ctgccggagg agaggtatgg agcgaaggcc agggactatt acaggcagta ctttaccgag    3120
atggagggcc tctacaagct tggaagcgcc gctggcaagg tcggaagggt ccttctctct    3180
gctctgatgt ccgtctacct cgttctcgcc aggggcctcg tctacaccgg cagggagaag    3240
aagcgctcct tcacccttga cgagcttcgc caccgcaccg tcaggtacct ggacgaggca    3300
ttcttcgcgc cgatgatgga tctactcaaa aacatcgccg tgctggcagc gggcatctcg    3360
gtgtccatgg acgagctctt cctggcttca atgctgacca cggtgataat actcgcactc    3420
cttgtgttgt gaatggacta cgtaagcatt atcgctgctc cgatcgtcct cttcctcctt    3480
ccaccgttcc ttgacggaat agggagaagg ataaaggcga ggattcagta caggagagga    3540
ccgcctataa tgcagacgtt ctacgacctc gaaaagcttc tcaagctgcc gtcagtgctt    3600
ccaactgagg gcccaatctt caggctggcc ccgtacatag ccctggcatc tgccattgcc    3660
ggcggcctaa tgcttccctt cggaagcgag ccggtgttgg cttttggaaa gagcctcata    3720
gtgttcttct acgtcatggc gatggtcagc gtagtgatga tacttgctgc tttctccgtc    3780
cagaacgcgt tctctcacat aggtggacac agagaggtca tgctgatact ctcgattgag    3840
ccagtgctgg ccgtcgtctt cggtgtcctg gcattcaagc ttggaacgct caacgtcgct    3900
gagatgcctt tcagtgctaa cctctcgctt tccgttgccc tagcttacat cttgctggct    3960
tacgcggtct acgttgaggg cggattcgtt ccatttgaca tagctgaggc agaaaccgaa    4020
gtaatcgggg gcccgctcac cgagtacagc ggaaggctcc tcggagtctt caagtacgcc    4080
ctgctcgtca gagggttgt cctgctctgg ctgctggcgt ctatgattgt gattcccgcc    4140
atgaggtctc tcggtataac aagctcaatg gcactgctcg tcgcccagct ggtcgttacg    4200
tttctgcttt attcgcttgc cgtggccgtt gaggctgcaa acgcccgcct gaggatcgac    4260
caggcggttt cccttaacaa gaaggtcttc ctgatgtccc ttgctgtcct gataatagcg    4320
ctggtggggt ggtgaatgga gtgcagcgtg tgtgcgggtg gatgcagatc ggctgaagtt    4380
gaggacgtcc ttgaggatgg tcatctaaag gaattcgtgg agaagtttag gggagcgatc    4440
ttcgagtgca agaagctgac gaggaaccag tacctgttca tcgttgatag ggaggcactt    4500
ccggagatgg tcctccactg gcacaaccat tccgagctaa aagaaaccca cttctcgatg    4560
ggaacaggaa ccgatgagag gaacatcgcc ggaaagttca cctacgctcc ggtaataaac    4620
gttgccgttg agcctggaaa cggggagagg aactactggg ttattctgaa ggcctacctc    4680
gacgaggaca acccggagtt cccctccata gccgcgaagc ttccagcagc cctctgggcg    4740
gagagggaag tctatgatct gcttggcttc aaccccaaag gccatcccga cctgaggagg    4800
ctcgtcctgc cggaggactg gccggagggt gtttacccgc tcaggaagga ccatgactac    4860
aaggcctcgc cgatggatac gccaaagtgc tactacaagc ccgggccgcc cgacacaatg    4920
acggttccga ttggtccgta ccacctggcg ctcgacgagc cggcccactt caggatattc    4980
gtcaaggggg aaacggtggt tgacgttgac taccgcggct tctactccca cagggaatc     5040
gagaagatag agagggaag actgacctac aatcaggtgc tcttcatagc cgagagaata    5100
tgtggaatct gtggcttcca gcactcgacg agctacgccc aggcggttga aaacatagcc    5160
ggcgttgaaa tccccgagag ggccatgtac ataaggacga taatgctgga gatagaaagg    5220
attcactccc acatgctctg gccggtgtt gcggctcacc tgacgggctt tgacacggga    5280
ttcatgcacg cttggcgcgt cagagagcct gttatgtggc tcgcagagag gctcacagga    5340
aacaggaaga cctacggaat caacatcgtc ggaggagtta ggagggactt cctcgactac    5400
```

-continued

```
cgcaaggaga tgataatgga gaagatcaag gagctcagga ggcaggtcga agagttcatc    5460
gaaatagcga ccggtacggc aaccttcgtc aagagggccg agggggttgg aattctgccg    5520
tacaaggtgg ccaaggctta ctcagtcctt ggtccgaacg gaagggccag tgggaggaac    5580
attgacatta gaagggatca gccgttcgca gcatacaagg attggactt caaggttcca    5640 gtctacaagg agggcgacgt cttggcaagg ttcctcatca ggatggacga ggtgctcgag    5700
agcatctgga taatagagca ggccattgac cagatgccgg gaggagacgt cttcgtgccg    5760 atagggagc ttccggagta tgaagaggcc ctaggctaca gtgaagctcc aagggggcgaa    5820 gtcatccact acgtcatgac tgacaagaag aacaaggtct accgctggaa ggttagagcc    5880
ccgacctaca acaaccttcc agctgttccg gagatgctca agggctacag cgttgccgat    5940
gccccgctca tcatagcgag catagatccg tgctactcct gtacgagag ggttcagata    6000 gtggacgttg agaccggaaa ggcccagacc ctgaacgagc agcagttcaa catgctctca    6060
atacagaagg gcaaggggt ggcctgaatg gcccaggcga tttccttcac cgacaggctc    6120
aagttctgga agcgaccaga ggaggacgtt aagaaggctc ccgtcacgac ttcttatcct    6180
tttgttgata tcgaaaagcc gccggaatat aggggcatac ctcgcataga tcctcacctc    6240
tgcattggtt gtggagcctg tgttagggcc tgtccaccgg acgcgctcac gatagagtgg    6300
gacttcgaga acgggaggaa gaggatagtc ttcaacgccg cgcgctgcat aaggtgccac    6360
cgctgcgtcg aggtttgtcc aaccggtgcg atgcagggca caacgaggtt cgagatagcg    6420
acgccgaaca aggaggacct catcgaggtc gttgaccaca agctctacag atgcccgcgc    6480
tgtgggcggt acgaggagtt caccgagagg cagatagga agatgttcca gattctgccg    6540
gaggaagtca ttgaccagca cggcatagct gagagggctt ttctctgcag ggagtgcagg    6600
atggaggaga gcgccaagac cttggcggtt caagggccct atgcggatag ccttctcctt    6660
tccctctatc cgagaggctc aaaggtgatg ggtgagagga gatgaatgag cgggttgaag    6720
tccgtttggg tcttccacgt tgacagtggg agctgcaacg gctgcgacat agagatactc    6780
gacgtgctca cgccctatta cgacgccgag aggcttggga taaagctcgt gccgagtcca    6840
agacatgccg atgccctcct cgtttcaggc ccactcacga ggcagactta ctacgctgtc    6900
aaagcagcct acgaggcgat gccgccgaag ccgaggatag ttgtggccat aggcacctgc    6960
gcgtccagtg gtggtatatt ctacaacggt tacccaatct acaacccgaa ccctgagagg    7020
ggaagcgaca ggctcaggac gggtggaata gaggtccttt tggcggagta cgggaaaaag    7080
cccgacatgt acattccagg atgtccaccg agtccgagg agatactata tgggctggcc    7140
cagctcctcg gcctgaagga gaagaagatg aagggcgagt actactatgc agacgagatt    7200
gagttcgttc ttccagagag acccatcgag gagaggattt acctgacgct cagagaatcc    7260
ctgaggcgcg tcgtggggta cttcgacagg gagaaggttc tcgaggactt catggccctc    7320
gtggaaaagg ctcaggagag cgagaacccg agggagaggc tccacgagct agtcatcgga    7380
tacttcctga gggagaagga ttcccgtgtg aagttcgcga taaggttcct cgaaaacgag    7440
tactggaggt tgaaggatgc ctacgaaaag aggcacctgg cacttgttaa agctggtgta    7500
cgttaa                                                               7506
```

<210> SEQ ID NO 14
<211> LENGTH: 2982
<212> TYPE: DNA
<213> ORGANISM: Thermococcus onnurineus NA1

<400> SEQUENCE: 14

```
atggtggact ggagactctt tgaacctctc tttaattatg cgagaaagaa gagcctttgg      60
attgtgtcgt tctgtaccgg atgcggcggt atagagatgc cgcccctcat gacgtcaagg     120
tatgacctag agcgattcgg tatgataccg gacccgagtc caagacagta cgacctcttc     180
ctcatcacgg gctacgttac gccaaagacc ctcaaaagaa tcataatcac ctacgaaatg     240
gcacctgatc caaagtacgt cctggcgcac ggctcctgcc cgctcaacgg tggaatctac     300
tgggacgcct acaacgctat caagcacctc gacaagtaca tcccggtcga tgtcgtcata     360
gccggatgca tgccgcggcc agaggcagtc atggacggaa tccagaagat aatggagatg     420
attgagaacg gaacagcaga cggatggaag aggtacaagg agaactacga gtggtacaag     480
aagaaccagg acgagctctt cggcgaagga tggcgtgaga gggaagccag aaggtggatc     540
ccatggctgg tggacaagaa aaaggaggag tgaatggggg aagttaagtg ggagagagag     600
cagatgctcg ttgacaaaat ccttgaaaaa gcccctacg ccgagggcaa ggtgcggcgc      660
gaacggagga ttgagttcag cattccggca gacaggataa gggacttcct catgctgctc     720
agggataacg acttcgagct catgctccag ataacgaccg tcgactggcc caacgacggt     780
gagcttgagc ttatctatca gatgtggagc gtgacccaca gaacccacgc catggtcaga     840
acacggattc cgagggatct cgataaggca aggatgccaa ccgtcaagga tatctaccct     900
gtggctgaga cctacgagag ggacgcccac gacttctttg gagtctactt cgagggcaat     960
gagaagatgg agatgccgtg gatcctcgac gataccgagc aggggctctt cccgcacaga    1020
aaggacttcg acatgctgac ctacgtgaag aagaagtaca agctgctcga caggttcgat    1080
gaggataagg acaactacgt gatttgaatg gtttcacaga atgagctcat tcgggaagcg    1140
agagaaaatg ggatggatct gctcccaatc gataaggaca cttacgagtt gttctttggc    1200
ccacagcaca tggctactga gaacttcagc ataatcctca agatggacgg tcacagggtt    1260
gtgaaggcta tagccaaccc cggcttcctc cacaggggct ttgagaagct cgccgagtac    1320
aggccgtggc acacgaacat agcgctcctc cttagaatct gtgttccaga gccagacgtc    1380
cccgaggcaa tatctcaat ggccgttgat gagataatcg gctgggaggt tccagagagg     1440
gctcagtgga ttagaacaac cgtcctcgaa atggcgaggg tttccgcata tctgttctgg    1500
ataatgggtc tcagcttcaa gctcggtgtc tacactgccg gtcagtgggc tgctgcctac    1560
agggagaggc tgatggccct cttcgagcaa ctgaccggtg ccagggtcta tcacatatac    1620
accatccccg gcggtgtcag gagggacatt ccgggcgaca agtggcttcg ccagctcaag    1680
gacaccgtcg agtacatcag gagcaagtta tcagacttcg acaaccttgt cttcgagaac    1740
tacgttgccc acaggaggct tgagggaatt ggagtgatgg acaagaagtt tgccctcgcc    1800
gaaggcgtca ctgggccaaa cctcagagcc accggcgttc cctacgacgt gaggagggca    1860
gatccatacc tgctctatcc agagctcgac ttcgaggttc ccgtcctgaa ggagggcgat    1920
gccctcgcga gggctttgat aaggcgcttc gagcttgagc aggatcttta catcctcgac    1980
cagctcctcg agatgggacc gccgagcgga ccgtataagg ttgaagatcc caagctcaag    2040
aatctcccga ggtttaaggt tccggctgga gatgcatttg cccacgtgga atcaacgaag    2100
ggcgactttg gtgcctatgt cgtcagtgat ggaaagcaca agccgtacag agtgcagata    2160
aggggcccaa gtatagccca cggagtcagg gttctcgagc agctcttggt tggagcaaga    2220
atagccgacg tccccgtgat attgatgagc cttgacaact gtccaccaga cattgacagg    2280
tgaatggagg ttgattttaa ggtcgcccca gaggagaaag tcaggaagaa gccatcattc    2340
atcaagccct ggatgggcct caagtacctc ttcaagaagc ccgttactat caagatacc     2400
```

| | |
|---|---|
| tacgagaggg tacagatagc taaggactac aggggattcc acaccctaga ctggaagaag | 2460 |
| tgtgtcggct gtaacttctg cggccagata tgtccggcga gggcaataga gatgacctgg | 2520 |
| atagaagtgg atggcaagat ggagaagagg ccacatccaa agatagacta tggcaggtgt | 2580 |
| accttctgtg agttctgtgt cgacgtctgt ccacctggag cgctgggctt catcgagaac | 2640 |
| tacatcctca ccaccgagtg aaggacgag gagctggagc tctttgactg ggttccaatc | 2700 |
| catccagaca agttcaggga gataaacgag aagttccccg actacagatt cccggtggag | 2760 |
| aagatagagt tcaacaagga aacgaaggag gtcacctact acctgagaga cggagaggtc | 2820 |
| atgaagttca agatactcgg ctacggcatc agaccgccga agccaccgac aaagcctgct | 2880 |
| cagaaggcag ccgcaaaagc agcggaaaag aatgatacca agcctgttga aaagcccact | 2940 |
| gagaagaagg aagctgggaa gatagaagaa aagaaagaat ga | 2982 |

<210> SEQ ID NO 15
<211> LENGTH: 11208
<212> TYPE: DNA
<213> ORGANISM: Thermococcus onnurineus NA1

<400> SEQUENCE: 15

| | |
|---|---|
| atggagaccc taatcctcgc cctcggcaac gaacttatga aggatgatgg tgtcggcctg | 60 |
| aaagtcggca ggcttttggc ggaaaaaggt tacaacgttc tagaagttgg cacagacata | 120 |
| ttcatgctcc agagccatta cagtggagag gaaaggctca taatcatcga cgccatactt | 180 |
| agcgaaaagt tcaagcccgg agaaataatc cacgtgagcg gcggtgaagt tttcgagaag | 240 |
| ctgaaagctg aaattaggag tgcgcacttc atggggcaa tagacgggct caaactcctc | 300 |
| atggcactcg atgaaaggct tgccaacgtt gaaatccact tcattggtat tgttgctaag | 360 |
| gaaatcaacc tgggtatgga actgaccgag gaagttaggg aagcccttcc gaaggctgtt | 420 |
| gagctcgttg aagaattagt caaaaaataa atgaagaacc tctaccttcc aatcaccgtt | 480 |
| gatcacatag cgcgtgtaga gggcaaggc ggcgttgaaa tagtcgttgg tgatgacggg | 540 |
| gtcaaggagg tcaagctcaa catcattgag ggtccgaggt tctttgaggc gataaccata | 600 |
| ggcaagaagc tcgacgaggc tttggccgtt tatcctagga tatgctcctt ctgttcagca | 660 |
| gcccacaagc tcactgccgt cgaggcggct gaaaaggcag ttggctttga ggtacgcgag | 720 |
| gagatacagg ccctcaggga ggttctctac attggagaca tgatagagag ccacgcgctc | 780 |
| cacctctacc tcctcgtcct gccagattac atgggctact ccaacccgct caaaatgctt | 840 |
| gacaagtaca agaaagagat caacattgcc cttgacctta agaacctcgg aagctggatg | 900 |
| atggacgagc ttggtgcaag ggccatccac caggaaaacg tcgtcatggg tggttttggc | 960 |
| aagctccccg acaagactac gctggagaag atgaagaaga ggctccagga ggcccttcca | 1020 |
| cttgcagaat acaccttcga gctgttctcc aagcttgagc agtacgagga agtcgagggg | 1080 |
| ccgataatcc atatggccgt caggccgagg ggagacgtct acggcatata cggcgacgcc | 1140 |
| ataagcgtca gcgacggttt cgagttcccg agcgagggct acaagaagca catggttgag | 1200 |
| cgcgttgtgg agcacagctt cgccaagcac agcttctaca acggggagaa gcccttcatg | 1260 |
| acgggagcca tatcgcgcgt tgtcaaccat gctgataagc tctacggaag gcaaaggag | 1320 |
| ctctacgaga gccacaagga cttactcagg ccaaccaacc ccttcgccaa caacctcgcc | 1380 |
| caggcgcttg agttagtgta cttcatggag aggggcatcg accttatcga cgaggccctc | 1440 |
| gctaaatggc cgataaggcc gagggacgag gtagatgtaa aggacggctt cggtgtcagc | 1500 |
| accaccgagg caccgcgtgg aatcctcgtc tacgccctag aagtcaagga cggaagagta | 1560 |

-continued

```
gcttacgcgg atatcataac gcccacagcc ttcaatctcg ccatgatgga ggttcatgta   1620
cgcatgatgg ctgagaagca ctacaacgac gatcctgaga ggctgaagct ccttgctgag   1680
atggtcgtca gggcctacga cccgtgcatc tcctgttcgg tgcacgtggc gaggctttag   1740
atggagggga aggttcgtat agggttttac gctctcacct catgctacgg ctgtcagctc   1800
cggttcgcca tgatggacga gatacttcag ctgctcccga acgctgaaat cgtctgctgg   1860
tacatgcttg accgtgacag cagtgaagat gagcccgtcg atatagcctt catcgaagga   1920
agcgtttcaa cagaggaaga ggttgaactc gtcaagaaga tacgcgagaa cgccaagata   1980
gtcgttgcag ttggggcgtg tgcaacccag ggtgggttc agagctggga gaaggataag    2040
agcctcgaag agctatggaa ggccgtttac ggcgatggga aggttaagtt cgagccgaag   2100
atggccgaac ccctcgaaaa ctacatcaaa gttgactacc gcatctacgg ttgcccacct   2160
gagaagaagg acttcatcta tgccataggt accttcctcg ttggttcttg gccagaggac   2220
atcgattacc cggtctgtct tgagtgcaga ctgaagggta acacatgcat tctcatcgag   2280
aagggcgagc cgtgccttgg cccgataacg agagcgggct gtgacgcaag atgcccgagc   2340
tacggaatag catgcatagg atgtagaggg gcgataggct acgacgttgc atggttcgac   2400
tcacttgcca ggacgttcaa ggaaaagggc ctcaccaagg aagaaatcct cgaaagaatg   2460
aagattttca acgcacacaa tccaaagctg gaggagatgg tcgataaggt ctttcagttt   2520 caggggggtga aagaatgaat gaacgaggct cacgtctgca tgtgtcacga caatccctac   2580
gcccttgaca gggtcaaggt tctcagagtg taccgtttaa cagaaacaga gaagctattt   2640
ctgttcaggt ttgaagatca agagatagcc gagaactgga cctttaagcc aggacagttc   2700
gttcagctta ccatacccgg tgttggcgaa gtcccgataa gcatctgctc gtctcccatg   2760
aagagaggat tctttgagct ctgtatcaga aaggcgggaa gagtcaccac agttgttcac   2820
aagctcaagc cgggcgacac tgtccttgtc cgcgggccgt acggaaacgg cttccctgtc   2880
gatgagtggg aagggatgga cctactcctc atcgccgcag gattaggaac agccccactc   2940
aggagcgtct tcctctacgc catggacaac cgctggaagt acggaaacat aaccttcatc   3000
aacaccgccc gttacggaaa ggacctcctc ttctacaagg aacttgaagc catgaaggat   3060
ctcgcagagg ccgagaacgt ccagataatt cagagcgtaa ccagagatcc tgactggccc   3120
ggcagacatg gaaggcctca gaagttcata gtcgaggcca ataccaaccc gaagaacacc   3180
gcgatagcta tctgcggtcc gccgaggatg tataaggcgg tcttcgaggc gctcatcaat   3240
tacggttacc gccctgagaa catctatgta acgctgaaaa ggaaaatgaa gtgtggaata   3300
ggcaagtgcg gccactgtaa cgtcggaacg agtactagct ggaagtacgt ctgcagagat   3360
ggaccggttt tcacgtactt cgacatagta tcaacgccgg gactgctgga ctgaatgaga   3420
tacgtcaagc ttccaaaaga aaatacatat gaatttttag aaagactaaa aaacctcgga   3480
aagctgtacg ccccagtgaa aatttccgat cagttctatg attttagaga aattgacgac   3540
gtcagaaaga ttgaattcaa ctacacgaga accctgatgc cgccgaagaa gttcttcttc   3600
gcaccaaggg agaagatgtt cgagttcagc atctcaaaag cagagtatag ggaagtaatc   3660
cccgaagtcg agcccttcgt cctcttcggt ctccacgcct gcgacatcta cggtctgaag   3720
atactcgaca gcgtatatct ggatgagtac ccagacaagt actacaaagt caggcgtgaa   3780
aaaggcataa tcatcggtat aagctgtatg cccgacgagt actgcttctg caacctgctc   3840
aggacggact cgagcacgga cggctttgat ctgttcttcc acgagctccc tgacggctgg   3900
ctgataagga tagggacccc caccggtcat aggatagtcg acaagaacat caagctcttc   3960
```

```
actgaagtcg cacaggagga catctgcaac ttcagagagt tcgagaggaa gcgcgcccag   4020
gcttttaggt atcatgagga gtgggacaac atccactacc tcctcgagct ggagatggag   4080
caccccctct gggagaaaga ggccgagaag tgcttcgcct gcggcaactg cagcacggtg   4140
tgtccgacct gccgctgcta tgaggttcag gacatcgtca acctcgacgg agacacggga   4200
tacagggaaa ggcgctggga ctcgtgtaag ttcaggagcc acggactggt cgcgggcggc   4260
cacaacttca ggccgacgaa gaaggaccgc ttcataaacc gctatctctg taagatgtcc   4320
ttccactgga cacttggaat taacttctgt gtgggctgtg aagatgtac tgccttctgt    4380 ccggcgggca ttgatttcgt gaagaacctc agaattatag ctggattgga ggatgcatcc   4440
tgcccgtcaa agctgagcga ggaaattcca agaaaggtt ttgcatatgc caacaacatt    4500
agaggtgaag acatatgaat ggcacagaat aattcactcg tgctgtatga tgttcatgag   4560
accgtggatg tgtgctcaaa cgttggctgt gttaagacca aggccactcc atcaaggctg   4620
ctctttgcgg gtttcatggc tggtgcatac atagcctttg gattcatttt tgccatagtc   4680
gctagtgcaa gcttccatcc aaagctgggc actttcccaa acctatctct cttcaagctg   4740
cttctgggtg cagttttccc agtcggtctc atagccgtcc ttcttggcgg tgcggacctc   4800
tggacgggca acgcccatat agtaacactt tcgaaaatga cgggcagggc gagcgttaag   4860
gatgtgctct acaactggat cggcagctac acaggcaatt tcgtaggctc ggtcttcttg   4920
gcattcttgg cagtttacgg aacggggctc atggcaggtg gtttgttcaa ggacgttctg   4980
ataggcattg gcaactacaa agtggcgctc accccatgga aggccctctg gctgggaata   5040
ggctgtaact ggcttgtgaa cgtggcgata tggctctaca ttcgcgccaa agacactgcc   5100
gggaaggtaa tcgtaacctg gttcccgatc ttcgccttcg ttgccatagg ttttgagcac   5160
agcatagcca atatgtgggc cataagcgcc agcatatttg cctcggacgg tgcgataagc   5220
tgggtccagt tcttccacaa cataatccca gtcacgatag gaaatgccat cggaggcttc   5280
ctctttgtgg gcttctacca ctggtacctc gctgacggta gaaatgccat taagagctg    5340 attgactttg tcgaggtgct ggcactcttc gtctttatca tggtgcttat cccagcggga   5400
atagcctacg ccctcagcgg tctcggaaac attgccacat ggcttgtgcc actcatcata   5460
agtgtctatg gagttgtgat gacgtattta gtaaggagag cgctgtgaat ggaggagttt   5520
aagattggcc tgtgcccata ctgtgggatg gggtgcaggt tttacataaa gactcttaac   5580
gggcagccca taggaataga gccgtatccc ggtggtgtta atgaaggaaa gctctgtcca   5640
aagggtgtcg ccgccgttga cttcctcaga cacaaagata ggctgaaaaa gccgctcaag   5700
agaactgaaa acggcttcgt cgagataagc tgggaacagg cgataaagga gattgctgaa   5760
aagcttctgg agatacgcga gaagtacggg ccggatacgt taggcttctt ctcaagtgcc   5820
cgttgttcca acgaggagaa ctacctcctg cagaaaatag cccgccttct gggcaccaac   5880
aacgtcgacc actgcgcgag gctctgtcac gcctcaacgg tcgtcggtct tgctcagacg   5940
gttggcgctg ccgctcagag cggctcctac acggacatac ccaaggctaa ggtactcctg   6000
atatggggat acaacccgtc agaaacccac ccggttctca tgcgctacat cctccgcgcg   6060
agggacaacg gggccaagat aatcgtcgta gatccgagga agacgaggac tgtctggttc   6120
gccgatatgc acctccagct taagcctgga acggacatag tcctagccaa cgccatgatg   6180
cacgtcatca ttgaagaaag gctctatgac agggagttca tcatgaaccg gacgaagggc   6240
tttgagaagc tcatagcagc tgtccagaag tacacgccag aatacgccga ggaaataacc   6300
ggtgttcccg ccaagctcat cagagaagcc gctataacct ttgctactgc cggacggggc   6360
```

```
atcgtgatgt gggcaatggg actgacgcag cacgtcactg gggcggccaa cgttaaggcc    6420
ctcgctgatc tggctctgat ctgtggctac gtcggaagag aaggaacagg tctcttcccg    6480
atgcgcggtc agaacaatgt tcagggagca tgtgacatgg cagccttgcc aaacgtcttt    6540
ccaggctatc agaaggtaac tgacgacgag aagaggaagc acgtggcgga aatttggggc    6600
gttgaagatc tgccctcgaa gccgggcctt actattccag agatgattga tgcggctgct    6660
aaaggcgagt tgaaggcact ctacataatg ggcgagaatc cggtcatgag cgatccgaac    6720
acgaagcacg ttatcgaggc tctcaagaac ctcgaacttc tcgttgttca ggatatattc    6780
ctcaccgaaa cggccgagct ggctcactac gtgctcccag cagccgcata cgccgagaag    6840
gaaggatcat tcaccgcgag cgagaggcgc gtccagtgga acttcaaggc gattgagccg    6900
ccaggagaag ccaaaccgga ctgggagata ctgacgatgc ttggaaaggc tctcggcctg    6960
ccaaagttcg actactcaga cgttgaagat attacgaggg agataaccct cgttgctccg    7020
cagtaccgtg gataaccccc cgagaggctc aagcgagagg ttatgggtgt gcagtggccg    7080
tgcccgagcg aggatcatcc tggaacgccg aggctgcacg tcgagcgctt cgccacccccc 7140 gacgaaaagg ccaacataat ccccgtagag ttcaagccac ctgcagaaga gcccgatgag    7200
gagtacccat tcatactgac gacattccgc atcgtcggcc agtaccacac actcacgatg    7260
agtaacagga gtgaaagctt gaagaagcgc tggtccagcc cgtacgccca gataagtccg    7320
gaagatgcaa agaagctggg tatacaggat ggtgaaatga taaggatagt tacgagacgt    7380
ggaagctaca cctgcaggggc ggtcgttact gaagatgtct cggaaggggt gatcgcagtt    7440
ccgtggcact ggggggccaa tatactcacg aacgatgtcc tcgatccaga agcaaagatt    7500
cccgagctga aggtggccgc atgtagggtg gagaagattg gggggtgctg aatggagaaa    7560
aagctgttca taaacctcgg cgcgtgcatt gcctgccgcg cctgcgaggt ggcctgtgag    7620
aaggagcacg gaatttcatt catcacggtc tatgagttca gggacatagc ggttcccctc    7680
aactgccgcc actgtgagaa ggctccgtgt atcgaagtct gcccgacgaa ggccatctat    7740
cgcgacgaag atggcgcagt tgtgatagac gagtccaagt gtatcggctg ctacatgtgt    7800
tcggccgtct gccoctacgc gattccgata gttgacccga taaggagct ggctgtgaag    7860 tgtgacctat gtgccgaaag aaggaaggag ggcagagatc cgctctgcgc tgcggtctgt    7920
cccaccgatg cgataatcta cgctgacctc aacgagctga tggaagagaa gaggaggcgc    7980
aaggccgagc gcatcgtcga agcccagagg aaggcggtcg aaacgctcgc ctacttcggg    8040
tgagtgctga aggtggagct ctgtgtgggg tgtggggttt gtgcaaaggc ctgccccac    8100 tcggccattt cagttttttga agatagtgtg aggaggatag tcttcgaccc gaagaaatgc    8160
gaagaatgct cctttgagtg caacgaagcc tgcccaacgg gggcgctgga agggaagtca    8220
gacaaaaggg agctggtctt tgagtttgcc tactgtgcca tctgcgggaa aaggctcaac    8280
atcgtgaagg aagaagccga atatcttgca aaaaagctga ttgagctggg tgaaaaccct    8340
gagattgcct ttctctgtga tgactgcaag aggaaaaggc tgtttggcgt tgccaacaaa    8400
tatgaggctt acctggggtg aatgagcggg atgaggtttg cgttcctgtg tagggaaaga    8460
ccagaaccaa ctgggaagaa gatagccgtt atcggagccg gaccggcagg cttggcggca    8520
actggctacc ttgtctgtca gggtcatgag gttcatgttt acgacaagtt gccggagcct    8580
ggaggattaa tgctatttgg cataccagag ttcaggattc caatataccg cgttagagaa    8640
ggctatgaag aattagaaag ggtctacaat gtcaagttct tcaccagaac caaagtgtac    8700
ttcgggaatc tggaaggaga atcaggagac gagttcgttg agaacagggt agacttcaag    8760
```

-continued

```
gaactcgtgg agaagtacga tgcggtacta atagcaacag gaacgtggaa gtgctggatt    8820
ccaaacattg agggagcgga gcttgagggt gtcttcccgg ccctcgagta tctctttagg    8880
ataaagagcg ccaagctcgg ccacatggat tggggcaagg tcacaccagt ggagggcaag    8940
aaagtgctgt tcgttggtgc cggccacaca gccgtcgatg ccgcattgga gagcgttctc    9000
ctcggagcgg ataaggtgta cctcagttac cgcaggacga taagggaggc tcctgcgggg    9060
gcctacgaga ttaacctcct ccagcagagg gtgtgaagt ggctggagag gacgatgccg      9120
gtcaggataa taggtgagaa cggaaaggtc agagctgtgg agctggtgaa gaccaagctc    9180
agtgaacccg acgagagcgg caggaggaga cctgttccaa tagaaggttc gaacttccag    9240
atagacgtgg attatgtcat cttcgccgtc ggtcagagcc ccactccacc cttcgcagaa    9300
gagatcgata tagccgtcga taagaagggc aggatcgtag ttgataacag gcacatgacg    9360
agcagggaag gtgttttcgc cgcaggagac gtcgttttag gcccgtcaaa ggttggtaag    9420
gctgttaagg atggcctgta tgctgctgag gccatgcaca tgtggctgat ggggaggtga    9480
atgacgagga gaatccttca cgttgattac agcctttgta ttggctgtga cgtgtgag     9540
gcagtctgtg acttcctcca cggtggcaag cccaacataa ggatttacta cactgtcacc    9600
ggacttccga ttccaataaa ctgccgccac tgcgagaggg caccctgtat ggacgtctgt    9660
cctgcaggtg caatttaccg cgacagcgac ggagccatca taataaaccc tgacaagtgc    9720
ataggctgct acatgtgtct tgccgtctgt ccatttggcg tgccgagctt tgacgtcaag    9780
actaaggcag tcacgaagtg cgatatgtgt gccgacagga gaaggcttgg catggaacct    9840
gcctgcgccg agatgtgtcc cgcagaggca atattctttg gaaagcccga agaggtcgag    9900
gacaggataa gacgcaggac tgccgagagg atagcacgcg agaggatagc tgccgtagac    9960
atggaaggtg ttgggaggat gctttaaatg ttgtgggagt cccagatccc cataaatcag   10020
gtgttcgaac ttcgctgcag atccatgaca tacttcggtg ttggagccat taacaagttc   10080
tacgacatag ccaaggatct taaggaaaac cgcggcataa ccaaggtcat tctcgtcact   10140
ggaaagagtt catacaagaa gtgtggcgcc tgggacgttg tcaagcccgc ccttgaggag   10200
tacggtattg agtacgtcca ctacgataag gtcggcccaa acccaaccgt tgatatgatc   10260
gatgaggcca cccagctcgg taaagagttt ggagcccagg ctgttattgg cattggtggt   10320
ggaagtccaa ttgacagcgc caagagcgtt gcgattctgc tggagtacac cgacaagact   10380
gccagggacc tttacgagct taagttcacc ccaacgaagg ccaagcccat catagccgtg   10440
aacacgactc acgaactgg aactgaagtc gacaggttcg cagtggcttc gattccggag    10500
aaggagtaca agccggccat agcctacgac tgtatctacc cactctactc catcgacgac   10560
ccggcgctta tgacaaagct tccggccgac cagactcgct acgtaaccat tgatgccctt   10620
aaccacatca cagaggccgc caccaccaag tttgctagcc cttactcaat acttctcgcc   10680
caggagaccg ccaggctgat attcgactac ctcccagagg ccctggctca cccggacaac   10740
ctgcaggcca ggtactacct gctctacgcc tccgcgatag cgggtatatc cttcgacaac   10800
ggcctgctcc acttcaccca cgctcttgag caccccgctca cgccgtaaa gccagacctt    10860
ccacacggac ttggcctcgc catgctcctg ccggcagtta tcaagcacat ctacccggcc   10920
accgccagga tactcgccga ggtctacagg ccactcgttc cagaagctaa gggagtcccg   10980
ggagaggctg aactcgtcgc aaagaaggtt gaggagtggc tcttcaacat cggaatcact   11040
cagaagctga ttgacgttgg cttcactgag gaggacgttg ataagctcgc cgaactcgcc   11100
atgaccaccc caagcctcga cctgttgctt tcacttgccc cgattgaggc taccaaggag   11160
```

| | |
|---|---|
| accgtcgcgg ccatctaccg cgactcactc tacccgctta acaagtga | 11208 |

<210> SEQ ID NO 16
<211> LENGTH: 4986
<212> TYPE: DNA
<213> ORGANISM: Thermococcus onnurineus NA1

<400> SEQUENCE: 16

| | |
|---|---|
| atggaggtaa tttttctttt tattgtcatt attctgtcag ttgcatcttt cattggagtc | 60 |
| ttttcgagga gcgcaatttt aacgaagtta gtaaatgctc tctccgctct tggctcattg | 120 |
| acaatagcct atgccgggat tgtaggtctt aaagagagcg ttgaattaaa tatcactctg | 180 |
| ttacatctga aatcggattc cattatcaat gcgttctcaa ctctaacact caaagtcgac | 240 |
| ccgctgtcag gcttttccat gataatactc ggaattctgg gcttctgtac atcggtttat | 300 |
| ggtattgcat acttagacat gtataaagga gacaagagac tatatgcctt caactatccc | 360 |
| ctcttcctgc tcttcatgtt ccttgttctc gtctcatgga atctcttgtg gttcgttgtg | 420 |
| ttttgggaac tgatgactct cttctcccag ttcctggtag cgtttgaaag gaacgagaag | 480 |
| actctcattg cgaccctcaa gtacttctgc atgactaaag ccgcagcaga ctttatgctg | 540 |
| atagccatag tattggtact cataacaatc tctggcggag gtgattacga tatcctctcg | 600 |
| tcccagctcg taaactattt ccgctctcat cctctggaga tgtatcttgt aagtgctgga | 660 |
| ttcatgatcg gacttggtgt caaggccgcc cttgtgccgt tccacgtatg gcttccagac | 720 |
| gcatacgtgg aggcaccaag taacgtctcg tcattgctca gtggggccat ggaaaaaatg | 780 |
| ccagtgtata tgatgttccg cttttttcctg agtttcaccc cactaacccc taatattggt | 840 |
| ctactcatag cactgttcgg aacattaacc ctgtttttg gtacgatgta cgcactaaag | 900 |
| caaacagact caaagcgcct actggcctac catagtgtcg gccagatagg ttacgttgtc | 960 |
| tttgcccttg gggcagggat atatctcctt tccaagggt acaccacatt cggagctctt | 1020 |
| gcccttatgg catccctatt ccacgctctc aaccatgcat tcttcaaggg actgctcttc | 1080 |
| ctaacagcag gctcgatcct ttatagaact ggaagcaggg atttggacca cttgggagga | 1140 |
| ctagcgagat ttatgccgat aacggcattt gctgcactga taggttctct ttccatagct | 1200 |
| gggatgccac cattcaacgg ctttgttagc aagtggatga tatacgtttc aacacttccg | 1260 |
| actccgactc tcgtttccct gtttggggcc ctagcactat tcataagcgc tgtaacaacc | 1320 |
| gcatctttcg ttaagtactt cacttccatc tttgtaagac cgcctgccaa ggagataacg | 1380 |
| gtcaaagaag tcccagtatc aatgtgggcg tcccagttga ttctcgcagt ctttgtgta | 1440 |
| atttttggtg tttatccagc attgccactg gaagcaatct caaaagcggt tgactcagta | 1500 |
| ggcgtgacca ctccatcaat cacggtcttt cccggtctca tagtgtccga cggtattgga | 1560 |
| aacatagctc ctctggctct cctggtattc tccggagctc tgaccgcagt gttactagcc | 1620 |
| attttcccat acaaaatcag tcttccggtg tggacaactg gcacgagacg gtccctggcc | 1680 |
| atgaggcttc cagcgagctc atactatgcc tcctttgagg aagaattcga ggatgtttat | 1740 |
| agctggggag aatggtgtgt atgtaccacg aaaagactat gggacgccac aaaagccgtc | 1800 |
| ttgtccaact tgaggaagt atccttcgac ttggacaaga tgatgactgg agcttggcta | 1860 |
| atgctcctta tactccttac aatactcggg gtgttctgt tatgaatgaa tgcagttttat | 1920 |
| gctgccctca atctaatctt catagtactc tttgctccgt tattagacgg aatcgagagg | 1980 |
| aaagtcaaag caagacttca gtcaagacaa gggccgccgt taatccagac gtggcttgat | 2040 |
| ttattaaagc tcttcagaag gccaaacgtc aggcctaggg agtccgtaag atggctgttc | 2100 |

```
gaaccagcac cagcaatagc gcttgtatct gtattggcgg cgtccctgtt catcccatca    2160
ctgcttcctg gctctttaga cacatggggg gatataatcg ccttcatata cctctcaacg    2220
ctctcagccg tcgccatagc tctcggagcg ttctcaactg gaagtccata tgcccaaata    2280
ggatcccaca gagaagtttc aatcataatg gcagaggaat tctccttggc ttttatagtg    2340
gccgcactcg cagcatccag tggaggtctc tcgttctcgc acttttccc cctccaacta     2400 aaagtatcta ccataacagg tgctctggca ttcgcagtta tggcatacgt cgcgggagcc    2460
agaatcccat ttgacgtcgc tgaagccgaa ccagagatag tcgagggtcc cttcatagag    2520
ttcagcggga aaggcctggg aatgttaaag ctctcaatct acgtgaaacg gctacttctc    2580
accacgatac tcctgaactt cttcctaccc caagatggca cagtgagagt actagtctac    2640
gtcattggac tagtcatcat atcagttgtt tacgcgtcaa ttgaagccca ctatggaaga    2700
ttcaggacta aagacgccgc cagattcctc aagcgttttg caatagttgg aatcctaagt    2760
tggattttgg gagtggtggg gtggtaaatg gtatttgata tcctcaaagg atgtaaaata    2820
ctggagcaca atgataagat gacagtcgcc gaggtcggcg ccagcaatat acgggagatt    2880
gcaagggcgt tattcgagag gggttattac tactctagtg gcatgggagt agacgaacgg    2940
cccataaacg ggaggtttgc aatgtaccac atattcaact gcgatacaga gggaagatat    3000
gtggttctca agataacatc ccccgaaggg agccctgagg taccgtcaat aaccctgtt     3060 atcaagggtg ctgaatggtc agagagagaa gccatggaca tgctcggcat agttttcagt    3120
gggcatccaa agcccgaaag gcttattcta ccggacgatt ggccagaagg agtctatccc    3180
ttgagaaaag actttcctta caacaaaaag cttccaccgt caaaacccat agaaaagaa     3240 agggagcaca aaaagacgt catggagata cccctgggac catatcatcc ctcccttcac     3300
gaaccagagt attttgagct ctatgttaaa ggagacaaag tcgtagatgc ggaatacagg    3360
ggatttcaca tccatagggg aatggagaag cttgctgaat cacgaatgac aataaaccaa    3420
atcccattcc tcgcggagag gatatgtgga atctgtggtt gcacccattc cgccgcatac    3480
tgtcaggcag ttgaggatgc tgctggcatc tacgttccgg agagagcaca gtatataagg    3540
acaataatgc ttgaggtaga gagaattcac agccacctcc tttggttcgg ggttgtatgc    3600
catcttctcg gctttgacag cggcttcatg cacatctgga gggctagaga atacataatg    3660
gacatagcag agctcataac cggcaacaga aagacctacg gaataaatat tgtcggaggg    3720
gtaagaagag acatcacgga ggataaaaag gaaaaaacgc tgaaacttct ggacatggtt    3780
gaaaagagaa gcagggaagt acttgataac atcgctgaga tgaaggagct cagagaaagg    3840
atggagggtg tcggagttct accgaagaaa gaggccaggg agataggtgt ggtcggtccc    3900
atggccagga gctctgggat tgatactgat gtaaggcgag accatcccta cgcggcttac    3960
aaggacttgg acttcaaagt cccggtttac aaagaagggg acgttttgc aaggttcctc     4020 gtaagatacg aagaaatttt tgagagcttc aatatgataa gacaggccct ggaaaatatg    4080
cctccaggag aactgataaa tgacgaatat gagattcctc cattcaaact cggtatcgga    4140
gtcactgaag ctccacgtgg ggagaacatc acgccgtga taacatgggg agagaacatg     4200
atttaccgct ggcatccaag agctgcaacc tataacaacc tcccggcggt tcctataatg    4260
ctcagaggga atgacgttgc agatgctccc ctaataatag ccagcataga cccatgcttc    4320
tcctgtacag accacgtctc aataattgat tctgaaagcg ggaagattct gtggagaggg    4380
ccgcttaagg agggcgtgag gagggtctga atggtaaaaa atagtctatg ggttttcat    4440 ctcaactccg gctcgtgtaa cggctgtgat atagagatcc taaatatctt tgcaccacga    4500
```

-continued

| | |
|---|---|
| aacgatgttg aaagactcgg gataaagctc gttggctctc ccagacatgc agacgccata | 4560 |
| gcatttaccg gaccaattac aagggagtgt ctgccaaagg ttattgacgc tctgaaagcg | 4620 |
| gttccggagc caaaagtggt tctggccata ggagcgtgcg cctgtggagg gggcatatgg | 4680 |
| tatgatactt actccgtaat aggtggtgtt aaagagctct acaggattct aaaagaagaa | 4740 |
| tacaacatgg agcctcccgc gacggttttt atacctggct gtcccccaaa gccagaggcc | 4800 |
| ataatctacg gtgtggctgt tgctagtggg atgctagagt caaaacagaa gaagactgtc | 4860 |
| tatgtcgagc cggaggaatc tgtggcaaat gagaagctaa tgatcgccga gctcataagt | 4920 |
| gaaacagaaa agacgaggca ctttatgccg ggaattgtca tcagggggt tgaggatgag | 4980 |
| ccttga | 4986 |

<210> SEQ ID NO 17
<211> LENGTH: 3447
<212> TYPE: DNA
<213> ORGANISM: Thermococcus onnurineus NA1

<400> SEQUENCE: 17

| | |
|---|---|
| ttgagtgaga ttaccctcaa caaagtgtgc cgaatcgccg gtgaggcgaa gctcgtgctg | 60 |
| tatgaggaaa acggaacagt tcaagatgca ctcttcatcg ccactgcccc aattagggga | 120 |
| tttgagaagc ttgtagtagg caaaaatcca cttttcgcgg tcgaagctgt catgagaatc | 180 |
| tgcggtctct gtcatgcgtc ccacggtata gcgatgagcg aggccataga aaatgccatt | 240 |
| ggaataatac caccaagaaa cggaatactg atgagagaag ccctcggcct cgtgaacagg | 300 |
| attcagagcc acatgctcga gttcctcatg gttgctgggg acctgctaat cgaggagaaa | 360 |
| agggaagaag ttctgttcca gctcatggac ttccacgcca agatcagcga ctaccttctc | 420 |
| aagatgggag gcgcagcaac acatccccca aacctcaccg tgggaggaat gttctctgtc | 480 |
| cccaagtgga gcgtcttcaa caaccctcaag gcacgccttc caaagctgac cgggcagtgg | 540 |
| gaagagatag cacatttgct gaccgatgag gacatccaga cagaagttgc tgatgaactc | 600 |
| agggagaaga aagcggaaaa caactacctg gtaagcagcc tgttctacgg ggacaggttc | 660 |
| aacataaacg ccgagagaat tgagacaatg ccctattatg aatacagaaa ggacaacccc | 720 |
| cactcaaagg agtccaccac actcatagcc ttctacggtg gggaaaaggt tgaagctggc | 780 |
| ccaagggcaa ggatgaaagt ttaccgggag tttacagatt cttccctcta tggccttcac | 840 |
| accgcgaggg ttcaggatac aacgctggca ctcattaggc ttgaagaaat ccttgacagc | 900 |
| ataaagatgc acgagccgtt cagaacgaag aacatagttt tcgggccagg caagggtgtt | 960 |
| ggagtctacg aggcaccaag gggaacactc atccacttga tcgaacttgg agacgagggc | 1020 |
| aggtggtttt cctccaagat aatcgtcccc acaatgttca acattcccgt gatggaggag | 1080 |
| atggcaaaag gtctgagcgt taaagcggcc gaggccgtta tgcgcctata tgacccatgt | 1140 |
| attccatgta cgacccacgt tgtgaggttg ggggatgaa tggagaagct taaggttctt | 1200 |
| catgttgatg taggggggttg tgagggatgc aacgtcagta tcattcgcgc atatccaaag | 1260 |
| ctcatggact tgatagagct cgacatatca tacctgcgga aggatgagtg taagctcgac | 1320 |
| gagtacgacg tggcgataat aaccggtgga gcatgtatga acgaaccaag gattcttgaa | 1380 |
| gagctaaagg agataaggga aaaagctcac actgtggtgg ccttcggttc gtgtgcaacc | 1440 |
| ttcagcggga tattgcgctt ctgccgcggc gggcaggagc caaggcccga ccacaggaac | 1500 |
| ttccagccca taaacagcgt gattaaagtt gattactcca tcccgggctg cccgccaaca | 1560 |
| ccacagatgc tccagtcctt cttcaagttc tacatcaacg gtgacgagag aaggctgagg | 1620 |

```
ctcttcaagg tgagtgccga cataaagaag ctgagcggct ttgacctgat agacgatata   1680
gtgcttacgg gcctctgcat aggttgtggt gcctgtgagc tgtcgtgccc gaccaacgca   1740
atcaagctga tagacaagag gcctaacctc gttcaggaga agtgtatccg ctgcggcacc   1800
tgctatataa ggtgtccgcg cgcctcacag attctgtcca tgggtggtgc gagatgaatg   1860
atgagcgttt cagaaaatct tttgggaaac gtctttggaa tttatcttgc gcgggcaacc   1920
gatgaggaaa tactcaaaag aaaggttgcc agcggcggtg cggttacagc cctcttagcc   1980
tacgccctgg agaagggcct catgatggc gttgtaacgg ccaaaaggac agaggggttg   2040
gagggtcagg ctgtagttgc gaggacaagg gaggagctcc ttgaaactgc cggaaacaag   2100
tggagcatag tgcccttcgc ctccaggatg aaggccaaga tagaggagga agacctaaag   2160
aacgttgccg tggtctgcct cccctgccag gcccagttct tcggccagat gagggacttc   2220
ccactcctgg aaagcgattt cggagagagg ataaagtaca tcgttagtct cttctgcata   2280
ggaacattcg cattcgaggc attcctcaac tacctcagga tgaagcacgg cataatggcc   2340
caggatatca aggacatagt ccttaagggg gacttcctcg agatatacca cggcgattca   2400
gtgctctcac tgccgataaa agaggtttac tcatacctcc aagccggctg tctggtctgt   2460
actgactaca ccggaacctg gagcgacatc tcggccggct tcgtggagag cgagagggga   2520
tggactgtcc tcataacgcg caaccttaag gcagaagagc tcgttaagag cgccgagaag   2580
gacggataca tagagctgcg cgacggctcc cacgtgatgg gagaagtcct caaagcggcc   2640
agggaaaagc ttgcgagagc gcagaagaac atgatgtatc tgctctgatt gataaagaaa   2700
gtgaaaattc tcaagtggca agatgggctc gttcccaccg aggactatat ctgcgtcgag   2760
gagacctttg aaatcttcgc agtacacgaa aaggacgaag agtttctcgc cgaacttcct   2820
gcttcaccca accagctgaa ggaacttgga gccggattcg tcgtgtgcgg aggctatgaa   2880
agaccggagg acatagttga cgtatgggtt gagggcaagg agatttacgt gaagttgaag   2940 gataccccg ccacgggcga gctggttgtg aaacacaccc cctgcggcga cccctacaga   3000
atgaaggagg gcagaattct cagcaggaag ggcgaggaag tcaaaataac ccccggcctc   3060
gtattgaaga tatcctccac gatgacaacg ctggctgaga cgtggagaaa dacagggggc   3120
acccactggg cggccctctt cgatttgaac gccaatgtcg ttgccttcag cgaggacata   3180
ggcaggcaca acgccgtcga taaggtcgta ggatacgccg tcctcaacgg actcgacctt   3240
gaaaggctta tcctggcatc gagcggcagg atgccatacg gcatggtaag aaaggcagtc   3300
aacgcgggca ttccagtagt ggtgacgaaa tcaccgccga cggacaaggg cgtggagctc   3360
gccagggagc acggggtaac cctaataggc ttcgcgaggg aaggcgcctt caacgtgtac   3420
tccggggagc atcgattatt gttctaa                                      3447
```

<210> SEQ ID NO 18
<211> LENGTH: 8730
<212> TYPE: DNA
<213> ORGANISM: Thermococcus onnurineus NA1

<400> SEQUENCE: 18

```
atggaagagc ttttattct ttccttttca attccgctgg ttggaggcct tttactgttc    60
aaactcgacg gtaaaagagc ggattacttc atgctcatca ctgtcatcct tgccacaata   120
ctcaatctcg cgggagttta tgagttctat tcctctggga tgcctactat acacaaaact   180
ctcgtgagct ccacaaccct cggtgaggtc tacggtctct tgatagaccc aatgagtgtg   240
tgcgttggcc tggttgtgat aacagccgga ctgcttttta tgatctatgc aaaagactat   300
```

```
atgagcccgg agaacaaaga gcacccagtc tatgaggata agggtaggtt ttacgcttgg      360
atggtgctct ttatcggagc aacactcgca ttcatttact cctcgtcggt tctccagctg      420
ctgatattct tcgaaattat gagcctcgcc tgttggggtg tagcaggcta ttatggaagt      480
aaaaaggcca aaagggcagc atataaagcg ttgcttgtta ccaactttgg agcggtgata      540
ggtctataca ccgcggtagg tataggaatc acacaccttc acgacctgag catatttgca      600
tattctggcc tcaatgacag ccttaaactc gtcgttttta tcggggtcat gatagctgct      660
tttaccaaga gtgcccagtt tccgctttat tcatggctcc cagatgcaat ggtcgcccca      720
acacctgctt cagccttcct ccacggtgca gcgatggttg agatgggtgt ctacctgctg      780
gccagattca tccagttcat gaatcccata cccaaagaag gattttacgt catggcagcc      840
ctcatcatcg ccactcagat aatctgcatc ctgatgtatc ctctccagaa gagcgcgaag      900
aggctgctcg cctactcaac aatagcagag tctggactga tgtacgtggc ccttgcgacg      960
gcagtcctcg ggttgcaggg gggacttcag gcttcaatgt tccagctatt caaccatgcc     1020
tacatcaaag gtctcgcttt cctgacggct ggaacgttca gctacgccct gggaaccctt     1080
gagatggaca ggataaaggg cctcattaaa tcccctgtgg tcggctacag ctggaccttt     1140
gccctgcttg gtttagctgg cgttccacca ttcggcgtgt tcttcggaaa gctgggaata     1200
ctcagcaatg ccaaggcaat ggaagagagc gtcctcatca ttgccatgtt tgttttactt     1260
ctcctcgact cagcagtgtt cctcatggtg tctctgaaga ggatacacgg catggtcttc     1320
agcgagggcg gagaagaagt cgagattaca ccactgatga aggctgtgat ggttatcctg     1380
ctcgtcctgg ccatgctggc cccgtacata gcgtatccac tgatcgtcaa agtggggtgg     1440
tgaatgttcg acgtaacgct cactctttca ctcgatagaa ctgcagtgtt cttcgtactc     1500
aacgtcgcga tactcggcat agcggcgcta gttgcatcgt tcagatacat gaggatatac     1560
gagttcaaac caaagatacc ctactaccca acgctcgcca tcttcatagt ctcgatgctt     1620
ctcatcccaa tggtccagga ctggctcagt ttcctcttcc tctgggagat aatgactctc     1680
gcctcatact tcctgataat ctacgactgg ccggaggaga gcgtcaagaa ggccggctgg     1740
aagtacttcg tgaccatgca cctcttcgac acatctcccc tcatgctggc agtgactatg     1800
tactacgcct tccatggaac gttcaacttt ggggccataa cggagtacag caatgccata     1860
gtcgctctct ttctcctggg atttgcggcc aaggccggcc tcttcccgct ccacttctgg     1920
ttaccggacg cccacccggc cgcaccgagc ccggtctcag ccttgatgag tggtgccatg     1980
gtcgaactcg gcctctacgg aaccatcagg gttctcaatg ctgtgggatg gagcgtcgca     2040
acctggatag tctatctcat cggcgctatg gcagtgctca gcatgctggc tgccatattc     2100
agctacgccc tccaggacga cgtcaagagg ctccttcgcat ggtccaccat cgacaacatg     2160
ggctggatgt atctgctcat cctggcaggc ctccttggcg tttcaggagt ggagaagggc     2220
gttgactact acgtcgtggc acatggactc gcgaaggcgg cggcgttcat atcaacgggt     2280
gccctcctct acgttttcgg tacgaggagc ctgaagaagg caaaaggtat gatgaacact     2340
gacagcctca ccgcgggact catgatggcc tcaatattcg ccctcgaagg tgttccgccc     2400
ttcaacctct tcatgaacaa gctcaatgtg ataaagactc tcctgacggt cagcccggcc     2460
ctggcatact tcacggccct tgagtgggtg atagcgttca tactgttcct cagagtggtt     2520
cacgcctaca tcctcagcga aggtgaacca gaggccaaga gaaagcttgc tggaagcata     2580
gccctctccg tgatagtcct gctcatcctc tccatggtaa gccagttcgt ctgcgactac     2640
atatgggtga ggtggtgaat ggagggactc tttacgctcg ccgtcatcct gtatttcctc     2700
```

```
tccatacccg cagcgttagc cctcaaaagg agcttcaagg cttcaatcag cattggccac    2760
atactcacgc tctagcctc catagctctg ttagcattta cctttgtgtc aataccagat    2820
atcctcagcg ggaaggccat agaattcaca tatgacttag gagtggccca gattccgttc    2880
cagattgatg ggctctcgct gataatgtgc ttcatcttcg gcgccctcgg acttgcagcg    2940
tcaatatatt ccccgagata catggcaatc tacgagaagt caggcagagg ctggatgtac    3000
ataaccatat attcagtgtt tatgctctcc atgatactca tagtaacaat agccaacatg    3060
ttctggttca ttttcctctg ggaggtcatg acgtttacat cgtacctcct gacgatctgg    3120
gaaagcgaca agaggatgt cagaaaagcc ggctggaagt acttcgtgac catgcacata    3180
gtgagcacac tgccactgat aatcgccctc gccctgctgt atgcagacgt tagctcaatc    3240
gagggactta actttgagag tctagcggcc ttaaaactaa gcccagtatt ctacgccctc    3300
ttcctgatag gctttggaag caagtcaggc gttgtcccgc tgcacttctg gccccggag    3360 gcctatacgg tcgccccgag caacgtctcc gctctaatgg ctggagcact ggagaaggtc    3420
gcggtctatg ccctgataag gactacatgc tttatcatga agccaaacga gactttcgga    3480
tatgcagttg ccctgcttgg aacagtaacc ctgacagttg gaaccctcta cgcgttgaag    3540
cagaccgatg ccaagagact tttggcctac cacagtatcg gccagatagg ctacatctgg    3600
ctcggcatgg gcgttgggat agttttcata gccaggggag atatgtactc agccttcgga    3660
gccatagccc tagcatcaag tctgtaccac ctcgttaacc acacgttctt caagggactg    3720
ctcttcctgt cgacgggctc aatattctac agaacccgca gcaggatct caaccagctg    3780 agaggtctgg ctaaactgat gccctttacg gcgctcttca cattcatagc cgcaatgtca    3840
atagctggaa ctcctccgtt caacggcttt atgagcaagt ggatgattta tcagtcaacg    3900
ttcctctcgg gcaacggcct gatagtgttc tttggagtga tggccctctt cataagcgca    3960
gcaacgctgg cttcattcat caagttctac acaaccgcat ttggaggaga acctactgag    4020
tttacgaagg atgctgagga agttccatcc cctatgctca tcgccaaggg cttcctggct    4080
tcactctgca tcctccttgg actggttcca agcctcatcc tgccgatact gctttcgcca    4140
ggggcagccc tagccggtat agatgtctca ggactgatga acacaaacta ctggcttgtc    4200
acgattaaag ctccgcttat gccgacaggg gcagagagct acttcaaacc gctactcttt    4260
gcgacactct tcggcgtgat cttcctcggc atgtacctgc tcttcccaat ctcaaagaaa    4320
acctacagac cctggaccct cggtgagccc gtggcgatgg agcactacaa gttcaaggcg    4380
ataaactact acgaaccctt cgaggagtac atccaccccgc tctaccacac cggccacgtt    4440
ctcagcgagt tcggatctgc cctgattggc gcagtcgcca atgcgtacgt ctcaacaaca    4500
agggctctcc acagagtatg cgattctata agcaagagtg tggccgggat cggaaaagag    4560
tacgagaaga agtgccccga agtctacctt gacgaatact tccttgcccc actggtcaag    4620
atagtgaggg tctcaggagt gcttctagat gagggattca tgaggccaaa tgcagcgttc    4680
acaatagccc tggtaactct ggcggttata cttgccctga tggtgctgtg aatgacgctc    4740
gaaaaaattg cattcgcggc cctttcactg atgataatca tcctccttcc gccctcctc    4800 gacggaataa gcagaaagat caaggctacc gtccaagaga ggcaggggcc cccgtcttc    4860 cagacctact atgacctctc aagcctgctc tcaatggagc cgatccttcc aacgacaga    4920 ctgggcttcc tcatagctcc ctatgtggcc tttgcttcag cagtctcagc cgccctgctc    4980
ctccccttcg ggaacttcgt cccagtggcc ttcacagggg acatcttcgt cttcctctac    5040
gtgctggcga tattctcgat atcgatgatg atggcaggct tcctcgtgaa caacacctac    5100
```

```
tcaaacgcgg gtgccaacag ggagatgatg ctcatcctca gcgtggagcc gatactggga    5160
atagcgatag gcatactcgc gcttaagacc cactcgctca gcgtgagcgg aattccactc    5220
aacctcagcc tcacaccctc cgttgtcctc gctttcatct tcctcgccta cgccgtctat    5280
actgagtgcg ccttcatacc cttcgacata gccgaggccg aaacggagat acttgagggt    5340
ccactcgtcg agtacagcgg gaagctgctt ggaatcttca agtgggccat gctgataaag    5400
cgcgtagccc tgatatggct gttcgcgagc ttcatagtca ttccagtcat gaagggttc     5460 gtcgacatca cgacgcccta cggtggtgca gtaacgctcg cggcacagct ggtactcctg    5520
gtggtcttct acgtcatgtc ggccatcata gagtcaacga cggcccgtat gaaggtaatc    5580
caggccatca ggcagaacac ggtgatattc cttgcgggaa tagtcgcgct ggtgatagct    5640
tccctgggat ggtgaatgtc tgaagttatc aagtttaacg aggctctgaa aaagaagcgc    5700
gtacacaggg gagatgaaaa agccaaagta acgcgggagt acttggatga gattatcgag    5760
aagttcgggg agaagataag ggacgtcaag caggccgctt acaaccagtg gattataacc    5820
gtcgagaggg aagaccttcc ggagatagtc ctctacttcc tcaaccaccc ggagtggaag    5880
gagacccagc tctcatcgat ggtggccacc gacgagaggc ccctaaacgg caagttcagc    5940
atcacctact ggctcagcgt taacggaaag gcgggtgact tctatctcgg cgtcagggct    6000
tacctgccgg aggacgaccc gaggttcacc tcgatagcgg ccaagcacag gggcgcgaac    6060
tggtacgaga gggaagccat ggagatgctc ggcctcactg ccgaaggcca ccccgacccg    6120
aggcggctcg tccttccgga cgactggccg tcctgcgtct acccgctcag gaaggacttc    6180
cactactcga acagcccgcc gggggagaag ttctacccct acaaggaacc gaagaaggac    6240
gagatagtcg tccccctacgg accgtatcat gtggcccttg aagaggcagc acacttcagg    6300
ctctatgtta agggagaaac cataacagac gttgactatc gcggcttcta cgcccacagg    6360
ggcatagaga agatatccga gggaaggcta acctacgacc aggtctgctt catagcggag    6420
agaatatgtg gaatctgcgg ctgcacacac tccacagcct actgccaggc ggttgagaac    6480
gccggaggta tagaggttcc cgagagagcc gagtacatca ggacgatagt cctcgagata    6540
gagagactcc acagccacct gctcaacttt ggaaatagtct cccacctcgt tggctacgac    6600
tacggcttca tgaaagcctg gaggataagg gagcacgtga tgtggctcgc ggaaaggcta    6660
acgggcaaca gaaagaccta cggaatgctc cttgtcggcg gcgttaggag agaccttctg    6720
gagtacagaa aatccctgat agaagacgtc ctcaagaaga taaagaccga gttcagtgag    6780
ctcgtcgatg aggcaatctc aacgagcacc ttcgtgaagc gccttgaagg cgttggggtt    6840
ctgccctaca aggtcgccaa ggagtgggac gttgatggac cccttggcag gggctccgga    6900
agggacttcg acgtgagaag ggaccacccg tacgcgcct acaagtacct cgacttcaag     6960
gtcccagtct acaaggaggg tgacgttctg gcaagggccc tcgtcagaat agaggaagtt    7020
ttcgagagca tctggataat agagcaggcc ctcgaccaga tgcccggagg agacattctg    7080
gcggagtaca aggagatacc cccgtactcg gaagcgatag gcatgactga ggcaccgagg    7140
ggcgagaaca ttcactacgt catgaccggc gagaacaaca aggtctacag gtacagggcc    7200
agggcggcaa cctacaacaa cctgccggct gttcccgaca tgatgcgcgg ctacaccata    7260
gccgacgccc cgtcatagt ggcgagcata gaccctgct actcctgtac ggagagagtt      7320
caggtagtcg acgtcgaaag cgggaaggtt agggttctca gcgagacgga gttcaacaag    7380
ctctccataa aggcctcaag gagggtctga atggccgtga cgctgaagta ccccttcgtg    7440
aagcttgaag cccctccgga gtacagagga attccacaga tagacgcgac cctctgcata    7500
```

-continued

| | |
|---|---|
| ggctgcggtg cctgcgttaa cgcctgtccg ccagatgcac tcctcaggat agacgactac | 7560 |
| aacagaggag ttagagaaat tgtcctcgat gtgggaaggt gcatccgctg tgctcgctgt | 7620 |
| gaggaggtct gtcccaccgg agcgatcaag ctcacgaacc tcttcgaggc cgcttcgccc | 7680 |
| gacaggatgg accacgtgga ggttgttagg ctcaggctcg tgaaatgcaa aaactgcggc | 7740 |
| aggtacgccg acttcactga gaggcaggtg agaaaggccc tccagattct ccccgaggag | 7800 |
| atcatcgaaa gggaagctct ggaagagaag gtctggatct gcagggactg caggaggaaa | 7860 |
| gggacagttg atggaaccat agaagccagc aaggaggtgg ttctatgaat gagcggaaag | 7920 |
| ccgaagctcc gctccatatg gtcttccac ctcaacaccg gctcgtgcaa cggctgtgac | 7980 |
| atcgagataa tcgacgtgct cacaccgttc tacgacgtcg agcgctttgg aatcaagcta | 8040 |
| gttggctcgc cgagacacgc tcatgcactc ctcgtctcgg gtccgctcac gagacaggcc | 8100 |
| tactacggcg ccaaagagac cataaaggcg atgcctccgg agccaagggt aatagtcgcc | 8160 |
| atcggaacgt gcacctgtag cggagggata ttctacaacg gctatccagt ctacagaagg | 8220 |
| cccgagagcg gtagggaggg aagcgagtat ccacggaggg gaggtatagc ggagctcatc | 8280 |
| gctgacttga gggacgaggg cgagaaggtc ggtccggtca tctacatccc cggctgtcca | 8340 |
| ccgagaccgg aggagataat ctacggcata gcacagctcg tgggactcgt cgagaagaag | 8400 |
| ctcagctatc aggagtacag cgacgagctg gttcccttca agctcccaga ggggccgctg | 8460 |
| gaggagcgca tcaggctgac ccttatggag aggctcaggc acctcgtggg atacctcgac | 8520 |
| agggaaaaga tcctcgagga tttcatgggg ctcgttaaag aggccgagaa gagcgagaat | 8580 |
| cccagggagg agctggccag gctcgtcaag gactacgccg ccaaatgcgg ggacgttaga | 8640 |
| ctgggcttct gtatgatgct tctcgaaaga gagtactgga gggtcaaaga tgccctggat | 8700 |
| gctggtaaag agttcgtata ttgggtttaa | 8730 |

<210> SEQ ID NO 19
<211> LENGTH: 4179
<212> TYPE: DNA
<213> ORGANISM: Thermococcus onnurineus NA1

<400> SEQUENCE: 19

| | |
|---|---|
| atgtttggct actgggacgc tctttacttt gtctttatct ttattatcgg cctcatcata | 60 |
| gcatggatgt tgaacgaatg ggccaagaag tctggaatgg gtacgagaga agctggtgat | 120 |
| ggcacgaaag tcttcatcag tggtgaggac ccggacaagg taatcccgg cttcgagcat | 180 |
| tacgaaggtt actacactgg caagaacgtc atgtgggtc tcacatacgc cctcaaaagg | 240 |
| ttcttcgccc tcctcaggaa cgagcacaca ggtctgctca ccgattacgt aagctacctg | 300 |
| ctcataacga cggctttcgt gctcggagtg atactgattt ggggtgaat gagcatcaag | 360 |
| gttcccgctg accagaatag aacaaacgga accacgagtg agcgcgagat gctggagaag | 420 |
| agaatagccc agttgtgccg cttcatagga agatcaccct gggtatttca cgtaaacagt | 480 |
| ggaagctgca acggctgtga catcgaaatc atagccgccc tgaccccgcg ctatgatgcc | 540 |
| gagcgctttg gcgtcaagct cgtgggaagc cccaggcacg ctgatgttct cttagtaaca | 600 |
| gggccagtca cagaccagag ccttgaaagg gtcaagcttg tctacgagca gacaccagac | 660 |
| ccgaagatag tcatagcagt gggatcgtgc cccactggcg gtagcgtgtt ctatgagagc | 720 |
| ccattcacca atgcaccgct gagcaacatc attccggttg acgtctacgt gccaggctgt | 780 |
| ccaccaaggc ccgaggccat actctacggc gtcgttttgg ccccttgaaaa gctggctaaa | 840 |
| atcctgaaag gcgaagttcc ggagggtgaa gagtgaatgg ctgatgataa cagaatcatg | 900 |

```
gagaatgttg ataatgttag agaaccaacc aaggaagata ctgtcgctga gaccataaag    960
agccgtttcc ccaatgctca cgtggagata cgggagaaca agtggggaag aaagcgcgtc   1020
tgggtgatcg ttccacgaga agactacaaa gcgctcatga agttcctcct tgaactcgac   1080
ccagaggccc actattcgat aggaatagag caggactacg gggaagagat aggctatatg   1140
agccacatcc tgctgcacta cgacaatgct ccagcagtct cactgctcgt tgatgttaga   1200
gtacccaaag acgatccagt aattcccgat atcagcgaca tcttcccgat agcactccag   1260
tacgaaaggg aagccgctga gatgatgggc atagtcttcg aaggtatccc cgacagtaga   1320
aggcttttcc ttccggacga cttcccagag ggtatctacc cgctcagact cgacgaaaaa   1380
ggcataccag aagagattgt caagaacgcc ggacacccgt actacctgaa gggggggagat   1440
aaatgaatga ccaagaaggt cgagtactgg ataaagatac cgttcggccc aattcatccc   1500
ggcttagagg aacctgagaa gttcatactt acgctcgatg gcgaaaggat agtcaacgtt   1560
gatgttaagc ttggctacaa tctacgtggc ctgcagtgga tagcatacag agaaaattac   1620
gtccagataa tgtacctcgc ggagaggata tgtggtatct gttcgttctc ccacaaccac   1680
acctacacca gagccgttga ggaagcggcc ggaatagaag tgccagagag ggctgagtac   1740
atccgtgcca taataggcga gctcgagagg gttcactccc acctgcttaa ccttggtgtc   1800
ctcggccacg acataggcta cgacacggtc cttcacctca catggctggc acgcgagagg   1860
gtcatggatg ttcttgaagc catctcaggg aaccgcgtga actactcgat ggtaaccata   1920
ggcggtgtga aagagacat cgatgaaaaa gggaagcggc tcattcttga tatgataaag   1980
tactacagga gcataatgcc tcagatagaa gaggttttcc tccacgaccc aaccatagaa   2040
gcccgtttga gggactgtgc ggtgataagc aagcgcgtcg cccttgagca gggtgcagtg   2100
ggaccgactg ccagagcttc cggtctaaag gtcgatgcca ggtggagtga gaggcttggt   2160
gtttaccctg acctaggagt taagccagtg atgccacagg acgttacggg agaaaaaccg   2220
cacggtgatg tattcgacag ggcagccgta agaataggag aaatatacca gagcctcgac   2280
atgctcgaac acgcactaga ccagatgcca gagggtaaga taaagacatt cccaaaggac   2340
aacatcttgg ttgccaagct caagattatg gttgacggag agggaatcgg aaggtacgag   2400
gctccacgtg gcgagctggt acactatgtt cgcggaaaga aaggctccga taaaccgctc   2460
cgctggaaac caagggagcc aactttcccg aacctcttcg cagttgccaa gggtgtgaca   2520
ggtgatcagg tggcagactt cgtgctggca gtggcctcga tagatccgtg cctgagctgt   2580
acagacaggg ttgccgtagt acaggatgga aagaagagaa ttcttactga aaccgacctg   2640
ctgagactct caataaagaa gacacgcgag ataaaccccg aagttaaagg cgacccaaca   2700
ccggtcggct tcggctgctc gaggtgaatg gacgtaatgg cgaacatcat ttatccggta   2760
gcaggtttaa taggccttta cgctttcgtc tcactggcat cgctcgtctg ggaaggtata   2820
gacagaaagc tcgtcgcaag gatgcagaga agggtaggac cgccgcttct ccagcccctc   2880
tatgacttct tcaagctagc gagcaaggaa acaataatcc ccaacacggc taactttatg   2940
tttagagccg cacctgtact cgccctggca acggccatag cactcctcgc ttacacccccg   3000
atgggctttg ctccactact cgcgagcaag ggagacgtca tcgtttttcat atatctcctc   3060
accctcattg gcttcttcaa gatactcggt ggcataagct caggaagccc ctacgcaaag   3120
ataggagctg caagggaagc agcaataatg gtttccagag agcctgccat gatgctggcc   3180
ctattcgcta taatatggcg tcttggaaaa ctcggagtca acaagccatt cagcatggag   3240
gtcttctacc agtacaacat ttgggaaata ggtaccccgc tcagccttat aggtgccgta   3300
```

-continued
atcctccttt acgtcttcgt catttggctg gcaagtgaaa tagaagtcgg atatttcaac 3360
atacccgatg cagaggagga gatagccgag ggactgctcg ccgagtacag cgggcgctac 3420
ctggccctgt taaagctcac gaaggcactg aaaacttaca tagcagcatc gctcgtcgta 3480
gcaatattct tcccctgggg aatagcagat tacttcaacc tcaccggact tccagcaaac 3540
gtcgtaaacc tgctcttcca tacactcaag gtattcatac tgctctttgc tgtgcagagt 3600
gtcttcaggg ccactacagg cagactcaaa ataacgcagg cggttgactt cctctggaag 3660
aacgtcttct tagcttcgct catcggcaca ctccttatcg ccatggaggt gataatgtga 3720
gtgaggctct ccccactcat ccccaccgtg ctcagaaaca tgttcaaaaa gcctgccacc 3780
aacctctttc ctgcgactga accagtgccg gttccagata acttcagggg ccagctgaag 3840
tacaacgtgg acaagtgtgt cggctgcagg atgtgcgtca cagtctgtcc agccggcgtc 3900
ttcgtcttcc tacctgagat aaggaaggtc gctctgtgga ccgctagatg tgtctactgc 3960
tcgcagtgtg ttgacgtttg tccgaccgca gccctccaga tgagcgatga gttcctgctg 4020
gcaagctaca acaactacga cgacaagttc atcccgctca agcccgaaaa ggttgaagag 4080
ataaagaaga aactggagga gcaaaagaaa gcgaaggcag ctgcagctgc caagaaagcc 4140
atggagaaaa aggaagcagg gaaagaggcc aaaaagtga 4179

<210> SEQ ID NO 20
<211> LENGTH: 2568
<212> TYPE: DNA
<213> ORGANISM: Thermococcus onnurineus NA1

<400> SEQUENCE: 20
atgggtatgg cagaaaagcg catatcagtg gtgtgtccgt ggtgttccgt tggttgtaga 60
ttttacatag taaacgtcaa tggctaccca aagaagatcg agttcgacta cgaccacgac 120
atcaggaacc acggcaagct ctgtccaaag ggtgtcgcag ccttccagca tctcaggcat 180
ccagacaggc ttaaaaagcc ccttaagagg gttggcgaga ggggtgaagg caagttcaag 240
gaaataagct gggaagaggc tattaaggaa atcgcacaga agctcagtga aatcaaggag 300
aagtatggtt cggaggctct tgcttttctc ggaagtgaaa ggtgctccat agaggagaac 360
tacgttcttc agaagctggc aagggctttg ggaaccaaca acattgaata tgtgtgtagg 420
atgtgtcagt caacggctgt tgcaggtaag gggatggttc ttggacaccc cggtctgacg 480
aaccccttcg aggacattct taaggccaaa gttatcgtcc tttggggata caatccagcc 540
gcaactaatc cggtcttctt cggccagtac attgagaagg caattctcga caacaacgcc 600
accctcattg tcgttgaccc aagaaaaacg aagactgcca agtacgcaga catacacctg 660
cagccatatc ccggaaccga ccttgccatt gcgttggcta tgctcaacgt cataatcacc 720
gaggagctct acgataagga cttcgtggcg gagcgcgcgg agggccttga ggagctcgcc 780
aagaccgtcg aaaagtacac tccagaatgg gctgagaagg tcagcggcgt tcctgccgag 840
ctcataagga aggccgcaat cacctttgca acggctggaa ctgccgccct gctgacgaac 900
gagggagtga accagcacgc caacggaacg aggactgtta tggctatcac tgagatgatg 960
gttctctgcg gctacttcgg aaaggagggc gtcatgtctg gagctatacc cggtgcccac 1020
aacggtatgg gcgctggtct aatgggtatt ggaccacacg aactgccagg aagattcccg 1080
ctccacgccg aggagcacaa gaggagaatt gaggaggcat ggggcttcaa gatcccagag 1140
aagcctggaa tcacttacgt tgaaatgatt gatgcaatcc ttgagggcaa gctcaaggcc 1200
ctctacgtca tgggaaccaa ccctgccaag gcccttccga acctcaagaa ggctgaggag 1260

| | | | | |
|---|---|---|---|---|
| gcctttaaga | acatcgagtt | cctcgtcgtc | caggatatct | tccttactga gaccgcgaaa | 1320 |
| tacgccgaca | tagtccttcc | agcggctgca | tggtttgaga | aggacggaac cgccataagc | 1380 |
| ttcgagagaa | gggttcagag | gagctttaag | gctgctgacg | caccgggaga ggccaagcct | 1440 |
| gactgggaaa | tccttgttat | gctcgctaag | gagctcggct | ttggagagta cttcaactac | 1500 |
| tctgatgcag | acgacatcct | gagagaaata | aacagaatca | ttccgcccct gctggcgcg | 1560 |
| acacccgaga | ggctcaagaa | gaacctcaaa | ggctgtatga | taccctgccc agacgagaac | 1620 |
| actgaggttc | cgaggctctt | tgtccagggc | ttcctcacgc | caaacggaaa ggcccagctt | 1680 |
| attcctgtgg | agtataaaga | gcctggagaa | gtccccgatg | aggagtaccc gttctggctc | 1740 |
| accaactaca | ggttcgttgg | ccacttccac | accggaacca | tgagccacag gagcaagagc | 1800 |
| ctgagcaaga | ggtggccaga | ggagtacatt | gagatcaacg | agaacgacgc gaagaggctc | 1860 |
| ggcataaagg | acggcgacct | cgtgagagtc | gagaccagga | gggcagcgct ggttctcagg | 1920 |
| gccaaggtta | caccgcacat | cagggagggc | gtcgttgccg | cgccgtggca ctgggacttc | 1980 |
| aactacctga | ccacggacgt | cctcgacgaa | tacgccaaga | tgccggagtt gaagacggcc | 2040 |
| gcgtgtagga | tctccaaggt | tgaggggtga | atgagcaaaa | agatatttat cgattttaag | 2100 |
| cgctgcattg | cctgtaaggc | ctgtgaagtc | gcctgtgaaa | tggagcacgg ggaagcgagg | 2160 |
| attagggttt | ttgagttccc | cgatctgacc | agcgtcgcct | tcaactgccg ccactgtgaa | 2220 |
| aaggctccat | gtatggaagt | gtgtccagtt | aacgcgctct | ccaaggacga tgatggcgca | 2280 |
| gtcgttctcg | atcccctcaa | gtgtatcggc | tgtctcatgt | gcggtctggc ctgtccattc | 2340 |
| ggcattccaa | agatagacga | gtacaacaag | ataatggaca | agtgcgacct ctgtgcccac | 2400 |
| aggagagccg | aaggaaagct | tcctgcctgt | gtctcagcgt | gcccaactga ggccctcaag | 2460 |
| tacggcgaca | taaacgatgt | cctctgggcc | agagaaggaa | agatagtcgc cgagcttaag | 2520 |
| gacatcggcg | acaggaccaa | cgtcctcgag | gcctacctca | tcagatga | 2568 |

<210> SEQ ID NO 21
<211> LENGTH: 1893
<212> TYPE: DNA
<213> ORGANISM: Thermococcus onnurineus NA1

<400> SEQUENCE: 21

| | | | | | |
|---|---|---|---|---|---|
| atggccggaa | agaaggttcc | ctcaaagcaa | gtctccataa | ctccaggtgt tggaaagctt | 60 |
| attgagaaag | ccgaggagga | tggggtcaag | actgcctggc | acagattttt ggagcagcag | 120 |
| cctcagtgtg | gattcggtct | cttaggtgtc | tgctgtaaga | actgtacaat gggaccatgt | 180 |
| agaatcgatc | cgtttggggt | tggcccaact | aagggagttt | gtggtgcgga tgcagataca | 240 |
| atagtagcaa | ggaacattgt | aagaatgata | gcggctggta | ctgccggtca cagcgatcac | 300 |
| tcaagagatg | tagtccatgt | attcaagggc | attgctgaag | gaaagttcaa ggactataaa | 360 |
| ctaacagatg | ttgaaaagct | caaagagctg | gctaagattc | tgggtgtcga acagagggc | 420 |
| aagagcgaaa | atgaaattgc | attggaagtc | gcccacattc | ttgagatgga gttcggaaaa | 480 |
| caggatgagg | agccagtaag | attacttgca | gcaacagcac | caagaagag gattaaggtc | 540 |
| tgggagaagc | taggagtctt | accaagagcc | atcgacaggg | agatatgtct cagtatgcac | 600 |
| agaacccaca | taggctgtga | tgcagaccct | gcaagcttc | tactgcatgg tgtgaggact | 660 |
| gccctggccg | acggctggtg | cggctcaatg | atggccactt | atctgagcga cattctcttt | 720 |
| ggaacaccaa | agccgataaa | gtcgctggc | aacctgggag | tcttgaagga agacatggtc | 780 |
| aacataatcg | ttcacggcca | caacccgatt | ctctccatga | aaatagcaga gattgcccag | 840 |

```
agtgaagaga tgcagaagct tgcagagcag tacggagcaa agggaattaa cgttgctgga    900
atgtgctgta ccggaaacga agttctctca agaatgggag ttcaggtcgc tggaaacttc    960
ctaatgcaag agctggcgat tataactggt gcagttgagg ccgtgatagt tgactaccag   1020
tgcctaatgc cctcattagt tgatgtcgct tcatgttacc acactaagat aataactact   1080
gagccaaagg ctcgcattcc gggagcaata cacgtcgaat ttgaacctga gaaagcggac   1140
gagatcgcca agagatcat caagattgca attgagaact ataagaacag agttccggca   1200
aaagtctaca ttccagagca caagatggaa ttggttgctg gatttagtgt cgaggcaata   1260
cttgaagccc ttggtggaac actggagccc tcataaaag ccctccagga cggaacaata   1320
aagggaatcg tcggaatcgt tggatgtaac aatccaaggg tcaagcagaa ctacggtcac   1380
gtcaccttgg ccaaggagct catcaagagg gacatcctgg ttgttggaac tggttgctgg   1440
ggaattgctg cagcaatgca tggattacta acccccgaag cagctgaaat ggccggtcca   1500
gggctgaagg cagtatgcga agcgctcgga attccaccat gcctgcacat gggaagctgt   1560
gttgactgtt cgagaatcct gctggtcttg agtgcccttg ccaatgctct gaatgttgac   1620
atttcagact tgccagttgc tggctctgct ccagaatgga tgagcgagaa ggcagtggca   1680
ataggaacct acttcgttgc aagcggcgtc ttcacgcact gggagttat cccaccagtc    1740 cttgaagcc agaaggttac caaactcctt acgatgaca tcgaggatct ccttggaggg    1800
aagttctacg ttgagacaga tccagtgaaa gcggcagaaa caatatacaa cgtgataatt   1860
gagaagagga aaaaacttgg atggcccatc taa                                 1893

<210> SEQ ID NO 22
<211> LENGTH: 2637
<212> TYPE: DNA
<213> ORGANISM: Thermococcus onnurineus NA1

<400> SEQUENCE: 22
atgagtgaaa ggctcgtccc cgtggtctgc ccctactgtg gtgtagggtg caggctatac     60
atcaggagtg ttgatggcta tcccgtaggc atagaatacg ccaaggacat ccccaacatc    120
tcaaacgaac tcggaaagct ctgccctaaa ggcaacgccg tcgttgagta cctcctcgca    180
aaggacaggc tcaagagacc cctcaaggcc aaggaacagg gcaagttcgt tgagataagc    240
tggagcgagg caataaagga ggttgccgag aggctcaagg cttatgccaa ggacgacccg    300
aaccagctca tgttcttcgg ctctgcgaga acattcaacg agcccaacta cctcgtccag    360
aagctggcca ggatgctcgg caccaacaac gttgatcact gtgcaaggct ctgtcatgca    420
ccgaccgtca cgggtctcaa ggctgttttc ggtgccggcg caatgaccaa cacctacaag    480
gacattgaag aggcaaacgt catcttcatt atcggccaca actacgctga cccaccccg    540 gttggcttcc gctacgtcct taaggccaag gagaggggcg ctaaggtcat agtcgctgac    600
ccgaggttca ccaggacggc ctggttcgcc gacatattcc tacagcacta cccgggaagc    660
gacattgcgc tgataaacgg tctcatccac gtcatcatca aggagcggct ctacgacgag    720
aagttcgtga gggagagatg cgttggcttc gatgaagttg tggcagccgt cgagaagttc    780
acacccgagt tcgtcgagaa ggtaaccggt gtcccggcgg aactcatcat tgaagctgca    840
agaaccttcg cgaccgcagg aaagggtgtc ataacctggg ccatgggtct aacccagcac    900
acccacggaa ctgaaaacgt caagctcctt ggaacgctcg cggccatttg cggttatcag    960
ggcaaagaag gtgccggctg ttccccaatg cgcggtcaga acaacgttca gggagcatgt   1020
gacatggcag ccctgccgaa cgtcttccca ggctatcagg ccgtcactga tcctgaaaag   1080
```

```
aggaagttct ttgaggagtt ctggggtgtt gagctgagcg gcgaagttgg actgacaact    1140
gtggaggctg cctacgcggc cgacaagggc aaggtaaagg cctactatgt catgggtgag    1200
aacccagtca taagcgaggc caacgccaac cacgtgatgc acaccctcga gaagctcgag    1260
ttcatggtcg tccaggatat cgtcccgacc ccaactatgg agtatgcaga tatagttctg    1320
ccggccgcgg ccatgctcga gaacgagggt tctctgacca atacagagag gcgcgtgcag    1380
tggagcttcc aggcggtaaa accaccggga gaagcaaggc ccgactggtg gattcttagc    1440
gaggtcggta aggccatcgg ttttgacaag accggatccg gtggattcgt ctacaatgat    1500
gcagccgacg ttctcaggga aatcaacgcc tgtactccgc agtatcgcgg tataactcca    1560
gagaggctca aggagaacct tgcaggactc cactggccgt gcccaagcga ggaccatcca    1620
ggaacgaggg tcctctacaa ggagaagttc ctcactccca gcggaaaggc caacctcgcg    1680
gccgttccgg agtacaaggg accagtcgaa atgccggacg aagagtatcc gttcctcctt    1740
acgacccaca gatacgtcgg aatgtaccac accgcaacca tgaccatgag gagctgcgca    1800
ctcaagaagc gctggccaga acccctcgcc gagatacacc cggatgacgc agtgaagctc    1860
ggaataaaga gtggagactg ggttaaggtc gtcacaagga gaggagcata tccgattaag    1920
gcaaaggtca cccgggctgt caagaagggc gtaatagctg tcccgtggca ctggggagca    1980
aacgtcctca ccaacgatgc cctcgacccg gtagcaaaga taccggaaac caaagcctgt    2040
gcctgtaatg tcgccaagat cacagaagaa gaggccagga agctcatgga gaaactccca    2100
ccactcatac ccaagattga ggtcgttagg gggtgaatgg ctagaaagac cgtctttatt    2160
gacttttcaa agtgcatcga gtgccgcgcc tgtgaggtag cttgcgagcg cgaacacagt    2220
ggaatgtcat tcatcagcgt cttttgagtgg caggaaatgg ccgctatggc cctcaactgc    2280
cgccactgtg agaaggctcc ctgtgttgag gtctgtccaa ccaacgccct ctaccgcgac    2340
aaggatggag cagtcctgct cgctccacag aagtgtatcg gctgtctcat gtgcggcata    2400
gtctgtccct ttggaatacc cgagctcgat ctcatcaaca agataatggg caaatgtgac    2460
ctctgcgccc acaggagagc cgaaggaaag cttccagcct gtgttgagac ctgtccaaca    2520
gatgctctca tctacggcga cttcaacgag atagtcaaga agagaaggga gaagtttacg    2580
gagaaaacca tagaactcgc caaaactgca gagcgcatcc cgctgacggg ggtgtga      2637
```

<210> SEQ ID NO 23
<211> LENGTH: 24
<212> TYPE: DNA
<213> ORGANISM: Artificial Sequence
<220> FEATURE:
<223> OTHER INFORMATION: CODH/F primer

<400> SEQUENCE: 23
ggaccatgta gaatcgayccc gtty                                          24

<210> SEQ ID NO 24
<211> LENGTH: 18
<212> TYPE: DNA
<213> ORGANISM: Artificial Sequence
<220> FEATURE:
<223> OTHER INFORMATION: CODH/R primer

<400> SEQUENCE: 24 ttcrttttccg gtacagca                                                 18

<210> SEQ ID NO 25
<211> LENGTH: 21
<212> TYPE: DNA

```
<213> ORGANISM: Artificial Sequence
<220> FEATURE:
<223> OTHER INFORMATION: Hsp60/F

<400> SEQUENCE: 25
atggcacagc ttagtggaca g                                                  21

<210> SEQ ID NO 26
<211> LENGTH: 22
<212> TYPE: DNA
<213> ORGANISM: Artificial Sequence
<220> FEATURE:
<223> OTHER INFORMATION: Hsp60/R

<400> SEQUENCE: 26
caaggatttc ctgggctttc tc                                                 22

<210> SEQ ID NO 27
<211> LENGTH: 22
<212> TYPE: DNA
<213> ORGANISM: Artificial Sequence
<220> FEATURE:
<223> OTHER INFORMATION: mbh/F primer

<400> SEQUENCE: 27
cacgacatag gctacgacac gg                                                 22

<210> SEQ ID NO 28
<211> LENGTH: 22
<212> TYPE: DNA
<213> ORGANISM: Artificial Sequence
<220> FEATURE:
<223> OTHER INFORMATION: mbh/R primer

<400> SEQUENCE: 28
ctggcttaac tcctaggtca gg                                                 22

<210> SEQ ID NO 29
<211> LENGTH: 22
<212> TYPE: DNA
<213> ORGANISM: Artificial Sequence
<220> FEATURE:
<223> OTHER INFORMATION: mbx/F primer

<400> SEQUENCE: 29
gcgattcggt atgataccgg ac                                                 22

<210> SEQ ID NO 30
<211> LENGTH: 22
<212> TYPE: DNA
<213> ORGANISM: Artificial Sequence
<220> FEATURE:
<223> OTHER INFORMATION: mbx/R primer

<400> SEQUENCE: 30
ccatccttcg ccgaagagct cg                                                 22

<210> SEQ ID NO 31
<211> LENGTH: 23
<212> TYPE: DNA
<213> ORGANISM: Artificial Sequence
<220> FEATURE:
<223> OTHER INFORMATION: frh/F primer

<400> SEQUENCE: 31
gtaagctcga cgagtacgac gtg                                                23
```

<210> SEQ ID NO 32
<211> LENGTH: 23
<212> TYPE: DNA
<213> ORGANISM: Artificial Sequence
<220> FEATURE:
<223> OTHER INFORMATION: frh/R primer

<400> SEQUENCE: 32
gcaccacaac ctatgcagag gcc                                            23

<210> SEQ ID NO 33
<211> LENGTH: 22
<212> TYPE: DNA
<213> ORGANISM: Artificial Sequence
<220> FEATURE:
<223> OTHER INFORMATION: sulf1/F

<400> SEQUENCE: 33
gcagtacgag gaagtcgagg gg                                             22

<210> SEQ ID NO 34
<211> LENGTH: 22
<212> TYPE: DNA
<213> ORGANISM: Artificial Sequence
<220> FEATURE:
<223> OTHER INFORMATION: sulf1/R primer

<400> SEQUENCE: 34
gagggcctcg tcgataaggt cg                                             22

<210> SEQ ID NO 35
<211> LENGTH: 23
<212> TYPE: DNA
<213> ORGANISM: Artificial Sequence
<220> FEATURE:
<223> OTHER INFORMATION: mch/F primer

<400> SEQUENCE: 35
ctaccggacg attggccaga agg                                            23

<210> SEQ ID NO 36
<211> LENGTH: 23
<212> TYPE: DNA
<213> ORGANISM: Artificial Sequence
<220> FEATURE:
<223> OTHER INFORMATION: mch/R primer

<400> SEQUENCE: 36
ccttatatac tgtgctctct ccg                                            23

<210> SEQ ID NO 37
<211> LENGTH: 22
<212> TYPE: DNA
<213> ORGANISM: Artificial Sequence
<220> FEATURE:
<223> OTHER INFORMATION: mfh1/F

<400> SEQUENCE: 37
gcgaccggta cggcaacctt cg                                             22

<210> SEQ ID NO 38
<211> LENGTH: 22
<212> TYPE: DNA
<213> ORGANISM: Artificial Sequence
<220> FEATURE:
<223> OTHER INFORMATION: mfh1/R primer -continued

```
<400> SEQUENCE: 38
cttgtcagtc atgacgtagt gg                                               22

<210> SEQ ID NO 39
<211> LENGTH: 23
<212> TYPE: DNA
<213> ORGANISM: Artificial Sequence
<220> FEATURE:
<223> OTHER INFORMATION: mfh2/F

<400> SEQUENCE: 39
gacccgaggt tcacctcgat agc                                              23

<210> SEQ ID NO 40
<211> LENGTH: 23
<212> TYPE: DNA
<213> ORGANISM: Artificial Sequence
<220> FEATURE:
<223> OTHER INFORMATION: mfh2/R

<400> SEQUENCE: 40
gcagacctgg tcgtaggtta gcc                                              23

<210> SEQ ID NO 41
<211> LENGTH: 32
<212> TYPE: DNA
<213> ORGANISM: Artificial Sequence
<220> FEATURE:
<223> OTHER INFORMATION: primer

<400> SEQUENCE: 41
cgttgtcttt gcccttgggg cagggatata tc                                    32

<210> SEQ ID NO 42
<211> LENGTH: 33
<212> TYPE: DNA
<213> ORGANISM: Artificial Sequence
<220> FEATURE:
<223> OTHER INFORMATION: primer

<400> SEQUENCE: 42
ggcaattgct tggactgccg aaaagccaat ggc                                   33

<210> SEQ ID NO 43
<211> LENGTH: 33
<212> TYPE: DNA
<213> ORGANISM: Artificial Sequence
<220> FEATURE:
<223> OTHER INFORMATION: primer

<400> SEQUENCE: 43
gaagaaatcg cagagggcgc ctatgactat cag                                   33

<210> SEQ ID NO 44
<211> LENGTH: 32
<212> TYPE: DNA
<213> ORGANISM: Artificial Sequence
<220> FEATURE:
<223> OTHER INFORMATION: primer

<400> SEQUENCE: 44
gctcctcgct tactcaagcg ttggacaaat gg                                    32

<210> SEQ ID NO 45
<211> LENGTH: 33
<212> TYPE: DNA
```

```
<213> ORGANISM: Artificial Sequence
<220> FEATURE:
<223> OTHER INFORMATION: primer

<400> SEQUENCE: 45
ggactgctct tcctgtcgac gggctcaata ttc                              33

<210> SEQ ID NO 46
<211> LENGTH: 32
<212> TYPE: DNA
<213> ORGANISM: Artificial Sequence
<220> FEATURE:
<223> OTHER INFORMATION: primer

<400> SEQUENCE: 46
ggacgcactt aaagtcggcg tagccctttg cc                               32

<210> SEQ ID NO 47
<211> LENGTH: 32
<212> TYPE: DNA
<213> ORGANISM: Artificial Sequence
<220> FEATURE:
<223> OTHER INFORMATION: primer

<400> SEQUENCE: 47
aatttaccac cccaccactc ccaaaatcca ac                               32

<210> SEQ ID NO 48
<211> LENGTH: 30
<212> TYPE: DNA
<213> ORGANISM: Artificial Sequence
<220> FEATURE:
<223> OTHER INFORMATION: primer

<400> SEQUENCE: 48
aatggggagg ctgaaactac tgggcaaggc                                  30

<210> SEQ ID NO 49
<211> LENGTH: 29
<212> TYPE: DNA
<213> ORGANISM: Artificial Sequence
<220> FEATURE:
<223> OTHER INFORMATION: primer

<400> SEQUENCE: 49
tggcccaggc gatttccttc accgacagg                                   29

<210> SEQ ID NO 50
<211> LENGTH: 31
<212> TYPE: DNA
<213> ORGANISM: Artificial Sequence
<220> FEATURE:
<223> OTHER INFORMATION: primer

<400> SEQUENCE: 50
aattcaccac cccaccagcg ctattatcag g                                31

<210> SEQ ID NO 51
<211> LENGTH: 32
<212> TYPE: DNA
<213> ORGANISM: Artificial Sequence
<220> FEATURE:
<223> OTHER INFORMATION: primer

<400> SEQUENCE: 51
gagcaccacc tcaccatccc agggaagcta tc                               32
```

```
<210> SEQ ID NO 52
<211> LENGTH: 32
<212> TYPE: DNA
<213> ORGANISM: Artificial Sequence
<220> FEATURE:
<223> OTHER INFORMATION: primer

<400> SEQUENCE: 52
gatggccgtg acgctgaagt accccttcgt ga                               32

<210> SEQ ID NO 53
<211> LENGTH: 25
<212> TYPE: DNA
<213> ORGANISM: Artificial Sequence
<220> FEATURE:
<223> OTHER INFORMATION: primer

<400> SEQUENCE: 53
gaacggtagt tttcgacaaa agacg                                       25

<210> SEQ ID NO 54
<211> LENGTH: 25
<212> TYPE: DNA
<213> ORGANISM: Artificial Sequence
<220> FEATURE:
<223> OTHER INFORMATION: primer

<400> SEQUENCE: 54
gctcaccagc caaaaccgca ccagc                                       25

<210> SEQ ID NO 55
<211> LENGTH: 29
<212> TYPE: DNA
<213> ORGANISM: Artificial Sequence
<220> FEATURE:
<223> OTHER INFORMATION: primer

<400> SEQUENCE: 55
gcaatgtacc acatattcaa ctgcgatac                                   29

<210> SEQ ID NO 56
<211> LENGTH: 29
<212> TYPE: DNA
<213> ORGANISM: Artificial Sequence
<220> FEATURE:
<223> OTHER INFORMATION: primer

<400> SEQUENCE: 56
ccgataccga gtttgaatgg aggaatctc                                   29

<210> SEQ ID NO 57
<211> LENGTH: 25
<212> TYPE: DNA
<213> ORGANISM: Artificial Sequence
<220> FEATURE:
<223> OTHER INFORMATION: primer

<400> SEQUENCE: 57
tcaggccacc cccttgccct tctgt                                       25

<210> SEQ ID NO 58
<211> LENGTH: 25
<212> TYPE: DNA
<213> ORGANISM: Artificial Sequence
<220> FEATURE:
<223> OTHER INFORMATION: primer
```

-continued

```
<400> SEQUENCE: 58
atggagtgca gcgtgtgtgc gggtg                                    25

<210> SEQ ID NO 59
<211> LENGTH: 25
<212> TYPE: DNA
<213> ORGANISM: Artificial Sequence
<220> FEATURE:
<223> OTHER INFORMATION: primer

<400> SEQUENCE: 59
atgtctgaag ttatcaagtt taacg                                    25

<210> SEQ ID NO 60
<211> LENGTH: 25
<212> TYPE: DNA
<213> ORGANISM: Artificial Sequence
<220> FEATURE:
<223> OTHER INFORMATION: primer

<400> SEQUENCE: 60
tgaggccttt atggagagct tgttg                                    25
```

- --

HYDROGENASES ISOLATED FROM *THERMOCOCCUS* SPP., GENES ENCODING THE SAME, AND METHODS FOR PRODUCING HYDROGEN USING MICROORGANISMS HAVING THE GENES

CROSS-REFERENCE TO RELATED APPLICATIONS

This application is the U.S. national stage filing under 35 U.S.C. §371 of international application PCT/KR2009/005060, filed Sep. 7, 2009, which claims benefit of Korean Patent Application 10-2008-0087794, filed Sep. 5, 2008, and Korean Patent Application 10-2008-0087806, filed Sep. 5, 2008.

BACKGROUND OF THE INVENTION

1. Technical Field

The present invention relates to novel hydrogenases isolated from novel strains belonging to the genus *Thermococcus*, genes encoding the same, and methods of producing hydrogen using strains having the genes.

2. Background Art

Hydrogen energy is receiving attention as a next-generation energy source that can substitute for fossil fuels, because its calorific value per unit weight is at least three times higher than that of petroleum oils, while it does not emit substances that can adversely affect the environment, such as carbon dioxide, NOx and SOx.

Conventional processes for producing hydrogen include electrolysis of water, and the thermal-cracking or steam reforming of natural gas or naphtha. However, these production processes have a problem in that they require fossil fuels to provide high-temperature and high-pressure conditions. Also, these methods generate mixed gases containing carbon monoxide, and thus require a difficult process of removing carbon monoxide from the mixed gases.

On the other hand, biological methods of producing hydrogen using microorganisms have advantages in that it is not needed to make high-temperature and high-pressure conditions by introducing separate energy and in that the produced gases contain no carbon monoxide. Such biological hydrogen production methods can be broadly classified into methods utilizing photosynthetic microorganisms and methods utilizing non-photosynthetic microorganisms (mainly anaerobic microorganisms). Examples of the former methods include a method described in Korean Patent Registration No. 10-0680624, entitled "A method of producing hydrogen using the photosynthetic bacteria *Rhodobacter sphaeroides* strain having high hydrogen productivity at high salt concentration.

However, the technology of culturing photosynthetic bacteria at high concentration using light as an energy source is not yet sufficiently developed, and prior photosynthetic bacteria have a shortcoming in that substrate inhibition is severe when a substrate of high partial pressure exists. Also, these bacteria have a problem in that their hydrogen production capacity can be maintained only in the presence of light.

Accordingly, attempts to produce hydrogen using microorganisms that can produce hydrogen using organic carbon have been continuously made, and examples thereof include Korean Patent Registration No. 10-0315663, entitled "*Citrobacter* sp. Y19 and production of hydrogen using the same", and Korean Patent Registration No. 10-0315662, entitled "*Rhodopseduomonas palustris* P4 and production of hydrogen using the same".

The present inventors previously filed a patent application relating to novel proteins isolated from novel hyperthermophilic *Thermococcus onnurineus* NA1 (accession number: KCTC 10859BP) and genes encoding the same on Sep. 5, 2008 (Korean Patent Application No. 10-2008-0087794), and the present invention particularly relates to genes related to hydrogen production among the proteins and genes disclosed in the patent application. The present inventors have carried out experiments on the hydrogen production capacity of the above-described strain and, as a result, have found that the strain produces a large amount of hydrogen even in a high-temperature environment, and have also found novel hydrogenases which are highly expressed, particularly in culture conditions supplemented with carbon monoxide (CO) or formate, thereby completing the present invention.

SUMMARY OF THE INVENTION

It is an object of the present invention to provide hydrogenases isolated from hyperthermophilic *Thermococcus* spp. which can produce hydrogen even in a high-temperature environment, genes encoding the same, and methods of efficiently producing hydrogen using strains having the genes.

To achieve the above object, the present invention provides hydrogenases isolated from the *Thermococcus* spp. strain capable of producing hydrogen in aerobic culture conditions, and genes encoding the same. Also, the present invention provides a method of producing hydrogen by culturing the strain, and a method of producing hydrogen using the genes.

In a first aspect, the present invention provides hydrogenases which are produced by the novel hyperthermophilic strain *Thermococcus onnurineus* NA1 (accession number: KCTC 10859BP). *T. onnurineus* NA1 has eight novel hydrogenase gene clusters, and the amino acid sequences of hydrogenases belonging thereto are shown in SEQ ID NO. 1 to SEQ ID NO: 8.

In a second aspect, the present invention provides genes encoding said amino acid sequences. The genes are preferably, but not limited to, genes of SEQ ID NO. 12 to SEQ ID NO: 19 (the amino acid sequences of SEQ ID NO. 1 to SEQ ID NO: 8 correspond to the genes of SEQ ID NO. 12 to SEQ ID NO: 19, respectively).

In a third aspect, the present invention provides a method of producing hydrogen by culturing *Thermococcus* spp. The method comprises the steps of: 1) preparing a medium in a culture vessel; 2) culturing *Thermococcus* spp. in the culture vessel; 3) extracting hydrogen from the culture vessel. The *Thermococcus* spp. is preferably *Thermococcus onnurineus* NA1 (accession number: KCTC 10859BP).

In addition, the medium may be a medium supplemented with one or more selected from the group consisting of carbon monoxide, formate and starch. The culturing may be carried out at a high temperature of 80° C. in an anaerobic condition.

In a fourth aspect, the present invention provides a dehydrogenase comprising at least one amino acid sequence selected from the group consisting of SEQ ID NO: 9 to SEQ ID NO: 11.

In a fifth aspect, the present invention provides a gene encoding the dehydrogenase. Preferably, the gene has a base sequence selected from SEQ ID NO: 20 to SEQ ID NO: 22 (the amino acids of SEQ ID NOs: 9 to 11 correspond to SEQ ID NOs: 20 to 22, respectively).

In a sixth aspect, the present invention provides a recombinant vector comprising genes that are organized in a CODH-MCH-MNH3 hydrogenase cluster in *T. onnurineus* NA1, wherein the genes are all operably linked. Preferably, the genes include, but are not limited to, genes of SEQ ID NO:

21 (CODH dehydrogenase) and SEQ ID NO: 16 (MCH hydrogenase). In addition, the present invention provides a host cell transformed with the recombinant vector.

Also, the present invention provides a method of producing hydrogen using said transformant, the method comprising the steps of: preparing a medium in a culture vessel; feeding carbon monoxide into a gas phase of the culture vessel; culturing said transformant in the culture vessel; and extracting hydrogen from the culture vessel.

In a seventh aspect, the present invention provides a recombinant vector comprising genes that are organized in a FDH2-MFH2-MNH2 hydrogenase cluster in *T. onnurineus* NA1, wherein the genes are all operably linked. Preferably, the genes include, but are not limited to, genes of SEQ ID NO: 22 (FDH2 dehydrogenase) and SEQ ID NO: 18 (MFH2 hydrogenase). In addition, the present invention provides a host cell transformed with the recombinant vector.

Also, the present invention provides a method of producing hydrogen using said transformant, the method comprising the steps of: preparing a formate-containing medium in a culture vessel; culturing said transformant in the culture vessel; and extracting hydrogen from the culture vessel.

In an eighth aspect, the present invention provides a recombinant vector comprising genes that are organized in a FDH1-MFH1-MNH1 hydrogenase cluster in *T. onnurineus* NA1, wherein the genes are all operably linked. Preferably, the genes include, but are not limited to, genes of SEQ ID NO: 20 (FDH1 dehydrogenase) and SEQ ID NO: 13 (MFH1 hydrogenase). In addition, the present invention provides a host cell transformed with the recombinant vector.

Also, the present invention provides a method of producing hydrogen using said transformant, the method comprising the steps of: preparing a starch-containing medium in a culture vessel; culturing said transformant in the culture vessel; and extracting hydrogen from the culture vessel.

The hydrogen production methods according to the present invention have advantages in that they do not require high-temperature and high-pressure conditions, unlike the prior chemical hydrogen production methods, can generate hydrogen in ambient temperature and atmospheric pressure conditions, and do not generate harmful byproducts. Also, the methods of the present invention have advantages in that they can produce high-purity hydrogen at high efficiency compared to the prior art methods of producing hydrogen using microorganisms and can produce hydrogen even in high-temperature conditions.

Accordingly, the present invention has an economic advantage in that it allows high-temperature carbon monoxide discharged from petroleum purification processes and the like to be used directly for hydrogen production without a separate cooling process after capturing the carbon monoxide. Also, the present invention is useful for air conditioning.

| No. | Gene |
|---|---|
| 1 | Aeropyrum_pernix |
| 2 | Pyrobaculum_aerophilum |
| 3 | Sulfolobus_acidocaldarius_DSM_639 |
| 4 | Sulfolobus_solfataricus |
| 5 | Sulfolobus_tokodaii |
| 6 | Haloarcula_marismortui_ATCC_43049 |
| 7 | Natronomonas_pharaonis |
| 8 | Halobacterium_sp |
| 9 | Haloquadratum_walsbyi |
| 10 | Methanococcoides_burtonii_DSM_6242 |
| 11 | Picrophilus_torridus_DSM_9790 |
| 12 | Trhermoplasma_acidophilum |
| 13 | Thermoplasma_volcanium |
| 14 | Methanosaeta_thermophila_PT |
| 15 | Pyrobaculum_islandicum_DSM_4184 |
| 16 | Thermofilum_pendens_Hrk_5 |
| 17 | Pyrococcus_abyssi |
| 18 | Pyrococcus_furiosus |
| 19 | Pyrococcus_horikoshii |
| 20 | Thermococcus_kodakaraensis_KOD1 |
| 21 | Archaeogiobus_fulgidus |
| 22 | Methanosarcina_barkeri_fusaro |
| 23 | Methanosarcina_mazei |
| 24 | Methanosarcina_acetivorans |
| 25 | Methanospirillum_hungatei_JF-1 |
| 26 | Methanobacterium_thermoautotrophicum |
| 27 | Methanococcus_jannaschii |
| 28 | Methanococcus_maripaludis_S2 |
| 29 | Methanosphaera_stadtmanae |
| 30 | Methanopyrus_kandleri |
| 31 | Nanoarchaeum_equitans |

Figure 4:
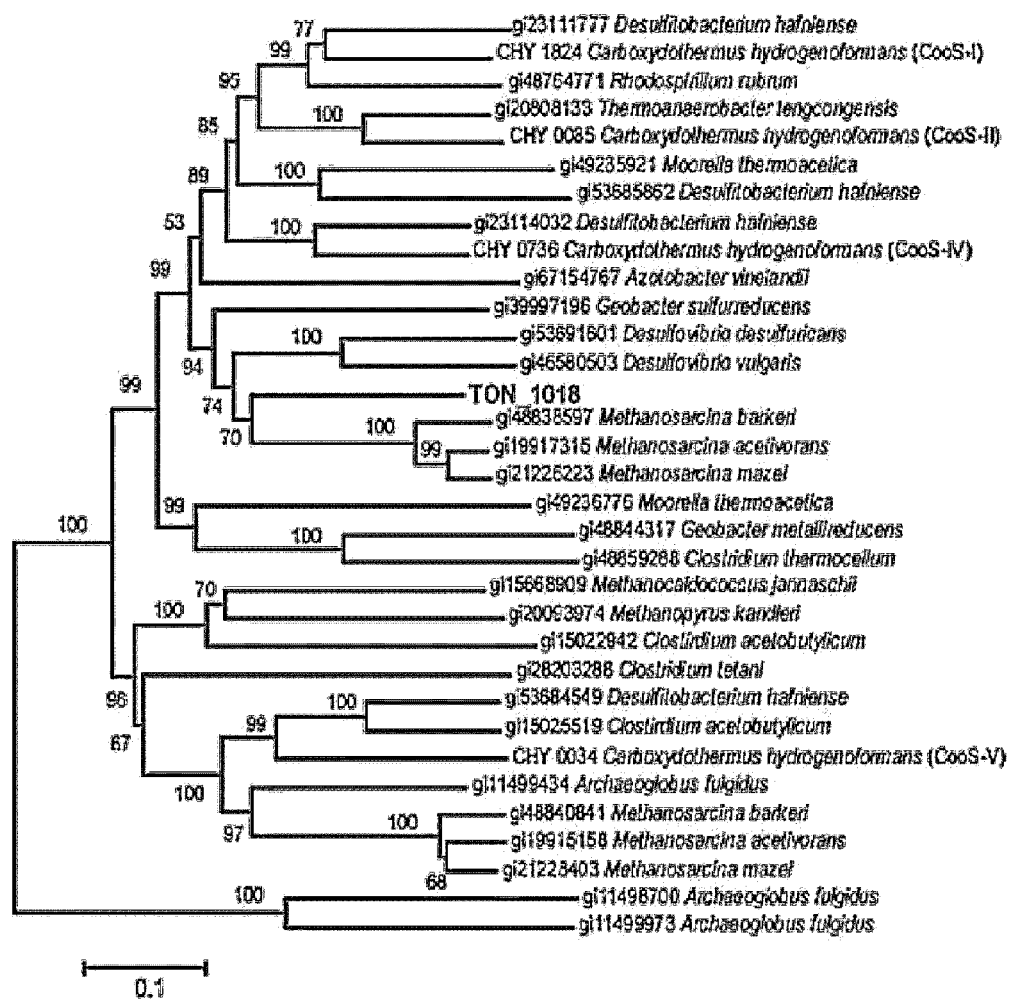
Figure 5:
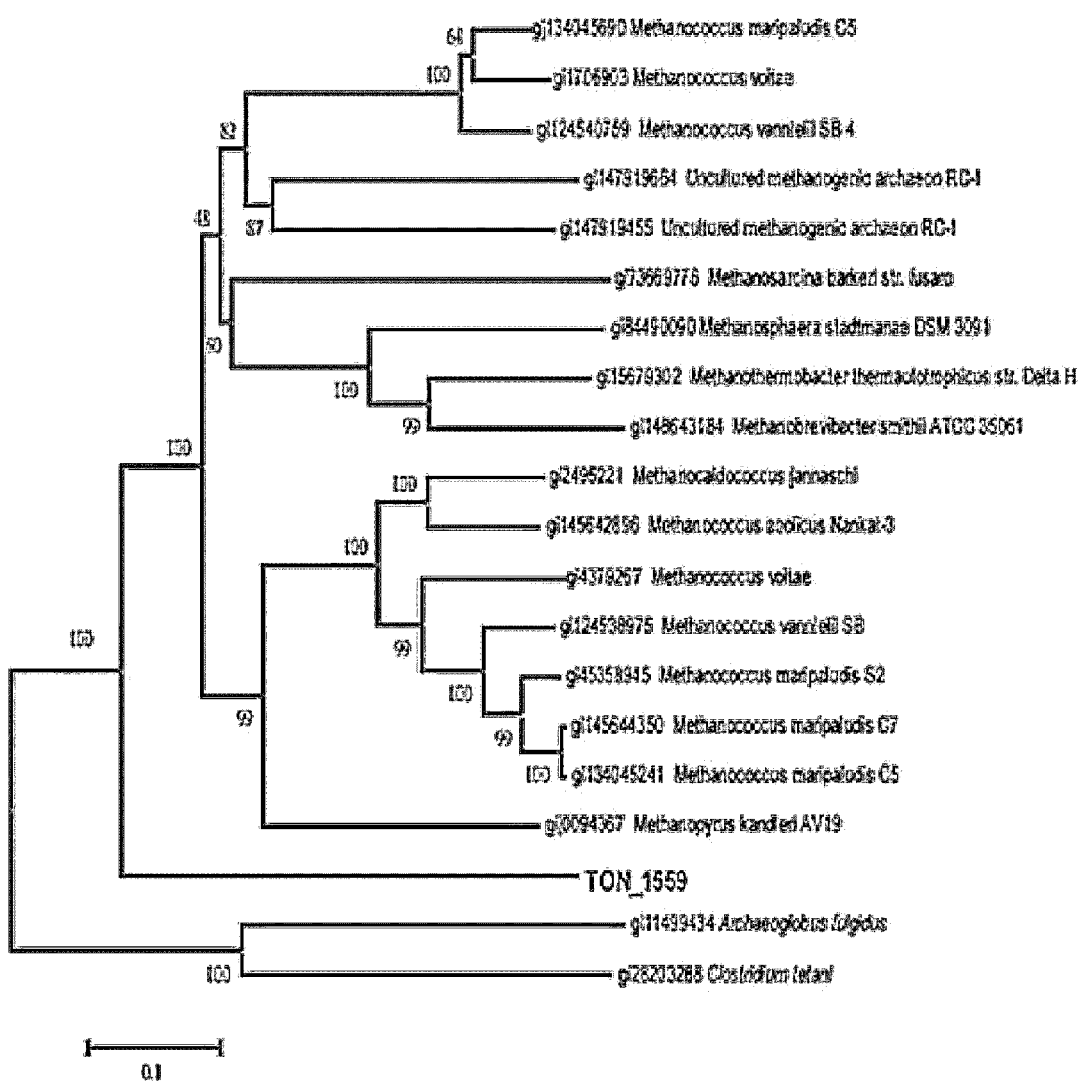

FIGS. 4 and 5 show a comparison of the α subunits of CODH and F420 hydrogenase proteins. FIG. 4 is the phylogenetic tree of CODH, and FIG. 5 is the phylogenetic tree of the α subunit of F420 hydrogenase. Homologues of the proteins on the phylogenetic trees were obtained from the NCBI nr database.

Figure 6:
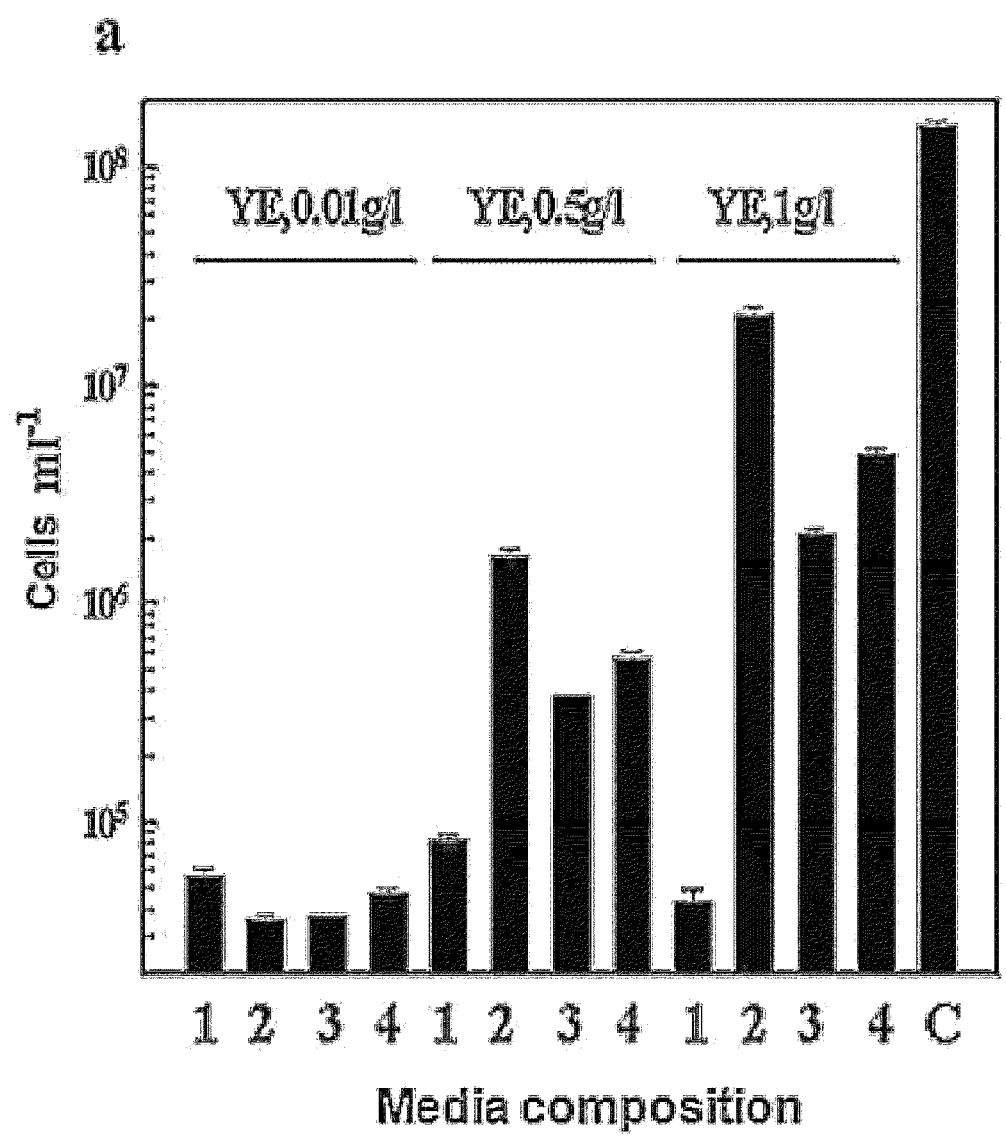
Figure 6:
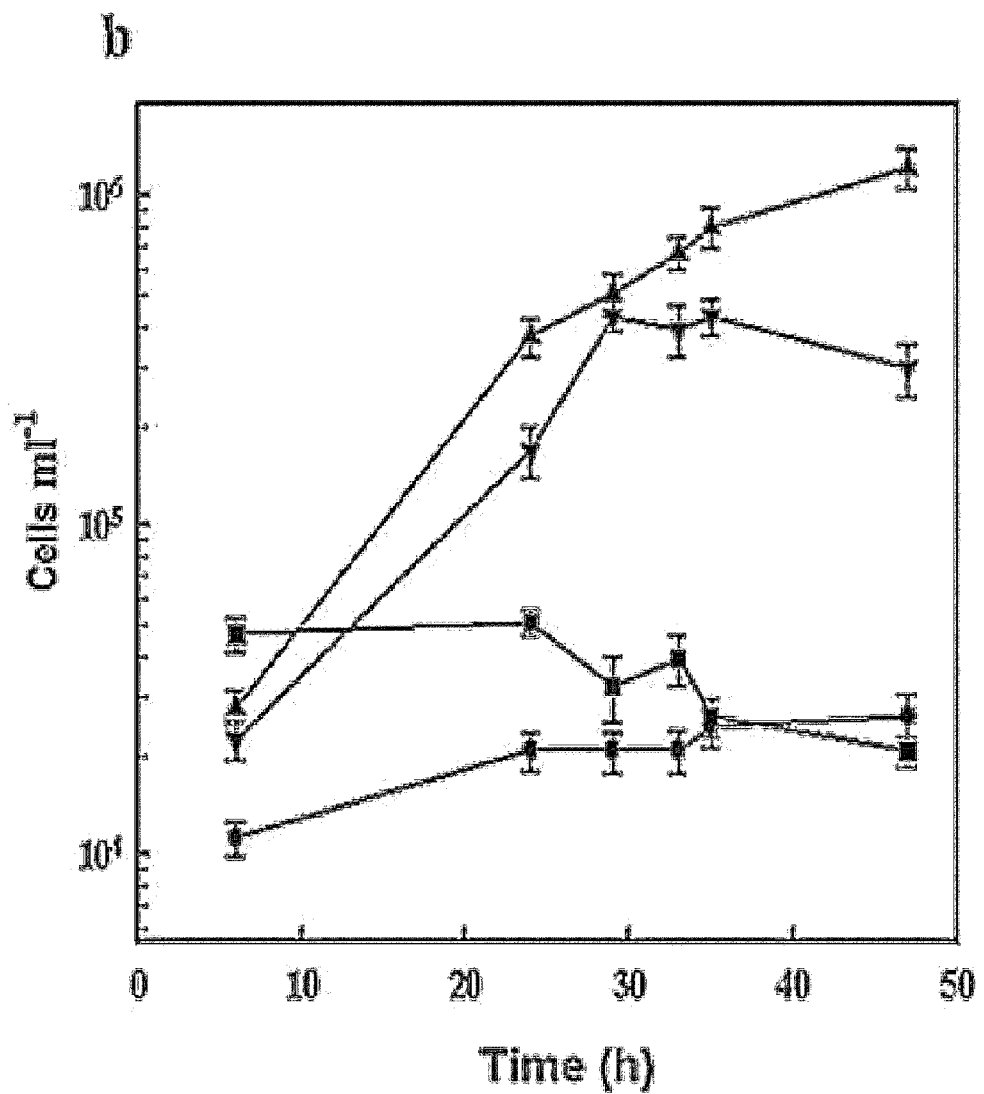
Figure 6:
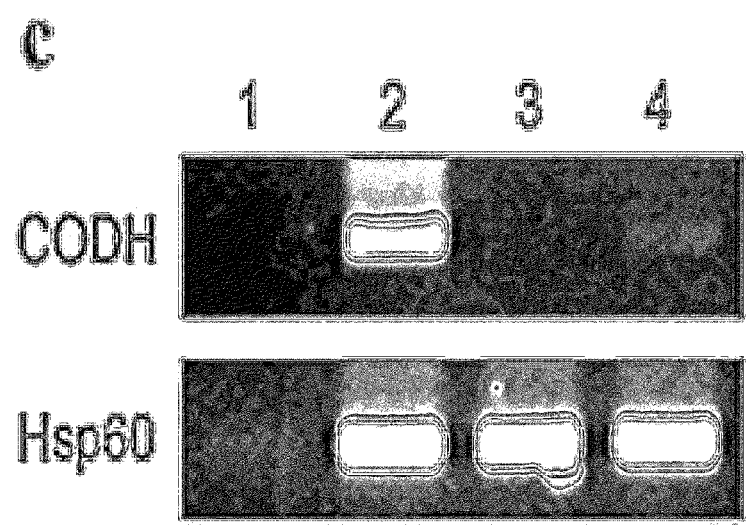

FIG. 6 shows the growth profile of *T. onnurineus* NA1 depending on CO. *T. onnurineus* NA1 was grown in medium 1 supplemented with CO (lane 2; triangles), sulfur (lane 3; squares) or both (lane 4; triangles down). Controls without supplement (lane 1; circles) and culture in YPS medium (C) were included. DAPI-stained cells were directly counted on filters by fluorescence microscopy. a: Effect of medium composition at various concentrations of yeast extract (YE). b: Growth curves of *T. onnurineus* NA1 in medium 1 with other supplements. c: Analysis of the transcription of the CODH gene.

Figure 7:
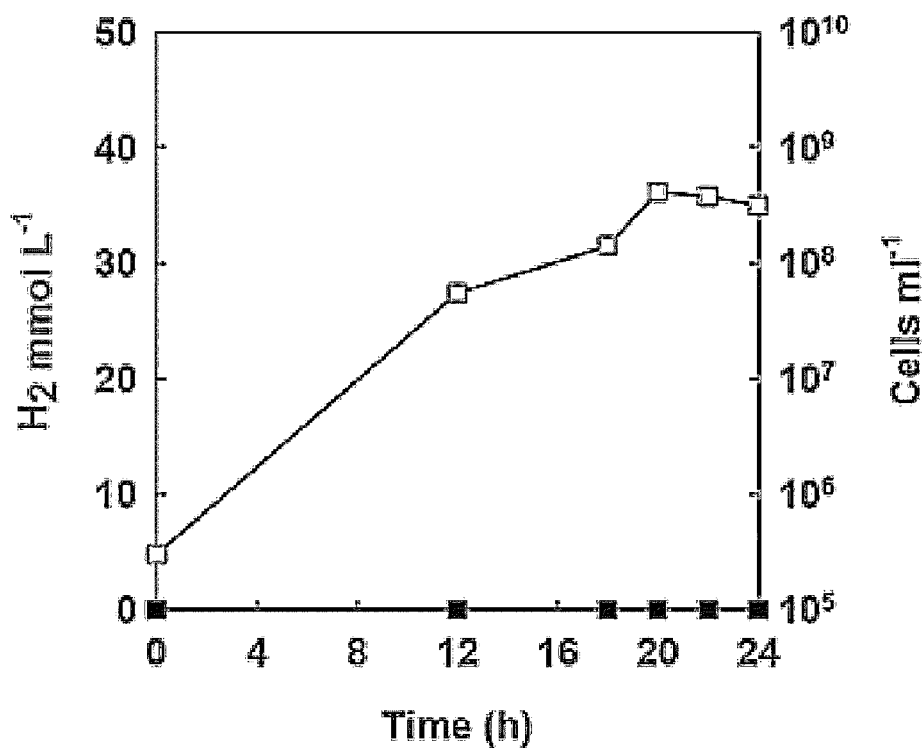
Figure 7:
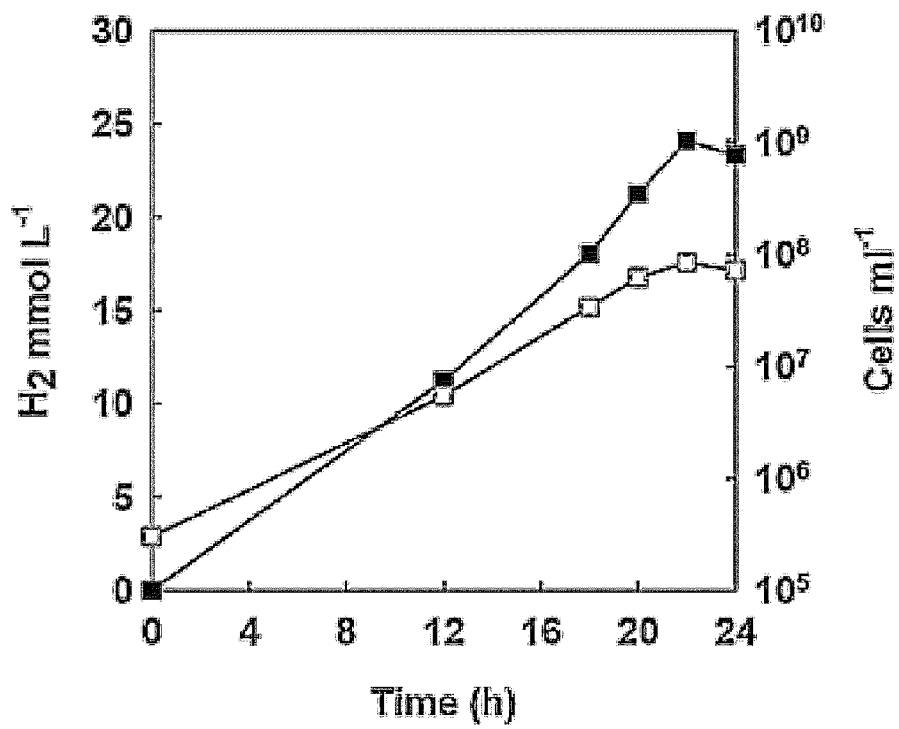

FIG. 7 shows the growth and hydrogen production of *T. onnurineus* NA1 in YPS (A) or CO-containing medium. Open circles: growth; and closed circles: hydrogen production.

Figure 8:
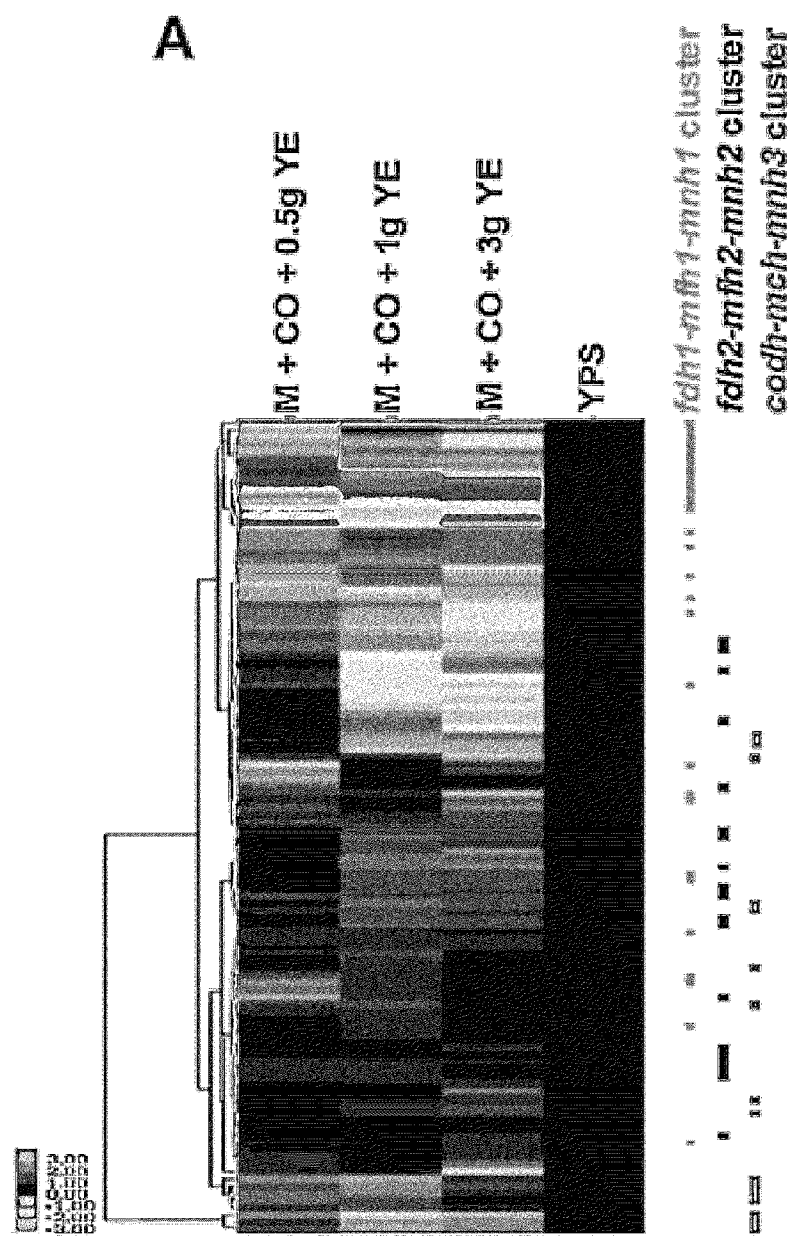
Figure 8:
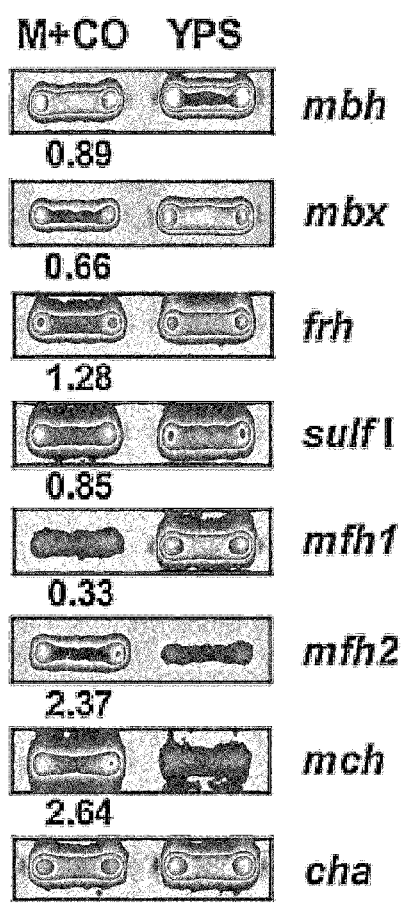

FIG. 8 shows the microarray analysis (A) and RT-PCR analysis (B) of the expression of hydrogenase gene clusters in *T. onnurineus* NA1 in YPS (A) or CO-containing medium (B). FIG. 8(A) shows the microarray analysis of eight hydrogenase gene clusters in *T. onnurineus* NA1. Hierarchical clustering of the mRNA changes in CO was compared with one in an YPS growth condition as a control. Up-regulation and down-regulation were indicated by red and green, respectively. Growth conditions were indicated on top of the clustering picture. At the right side of the clustering picture, ORFs of each of codh-mch-mnh3, fdh1-mfh1-mnh1 or fdh2-mfh2-mnh2 were indicated as bars. YE: yeast extract. FIG. 8(B) shows the results of quantitative RT-PCR analysis in CO or YPS conditions, carried out for each of the large subunits of mbh (TON__1593), mbx (TON 0489), frh (TON__1560), sulf I (TON__0534), mch (TON__1023), mfh2 (TON__1569) and mfh1 (TON__0276) hydrogenases. The chaperonin-encoding gene (cha) was used as a control to normalize expression levels.

Figure 9:
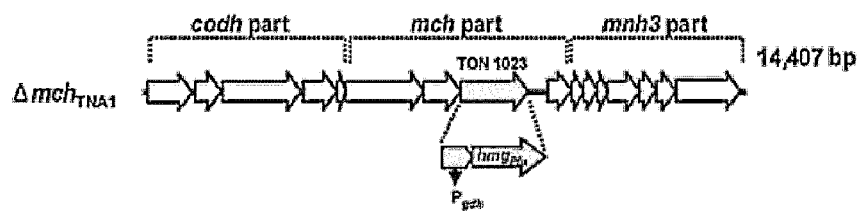
Figure 9:
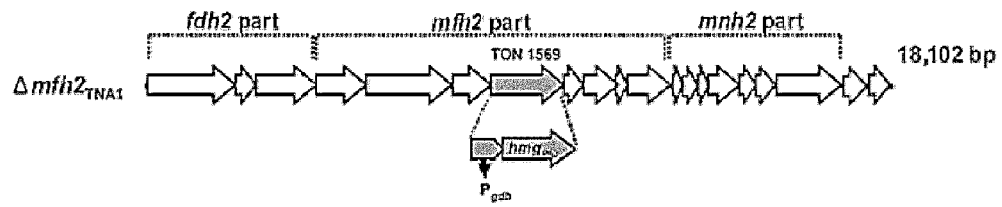
Figure 9:
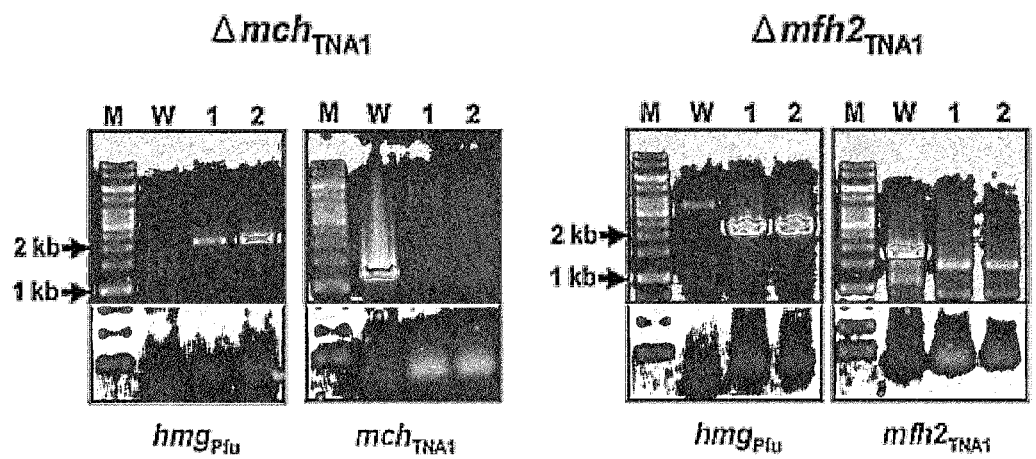

FIG. 9 shows the targeted gene disruption of the large subunit of each of mch (TON__1023) and mfh2 (TON__1569) hydrogenases. FIG. 9(A) shows the gene organization of each of codh-mch-mnh3 and fdh2-mfh2-mnh2 clusters in *T. onnurineus* NA1. $P_{gdh}$: the 5'-upstream promoter region of the glutamate dehydrogenase gene of *T. kodakaraensis* KOD1; and $hmg_{Pfu}$: the 3-hydroxy-methylglutaryl coenzyme A reductase gene of *Pyrococcus furiosus*. FIG. 8(B) shows the identification of gene disruption by PCR. The left panel shows PCR amplification with primers for the overexpression cassette ($P_{gdh}$-$hmg_{Pfu}$) region. The right panel shows PCR amplification with primers for the large subunit of each of $mch_{TNA1}$ and $mfh2_{TNA1}$ hydrogenases. M: size marker (1 kb ladder); W: wild type; lanes 1 and 2: mutant strains.

Figure 10:
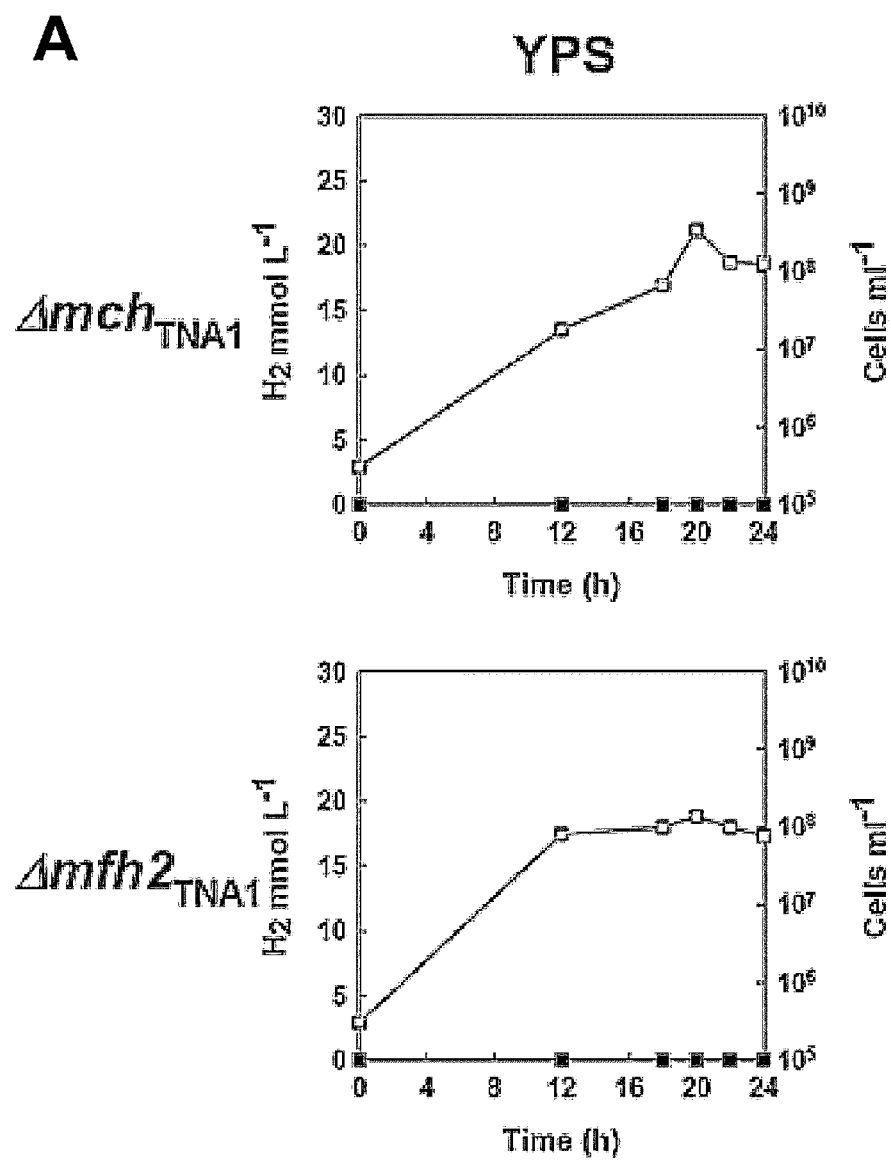
Figure 10:
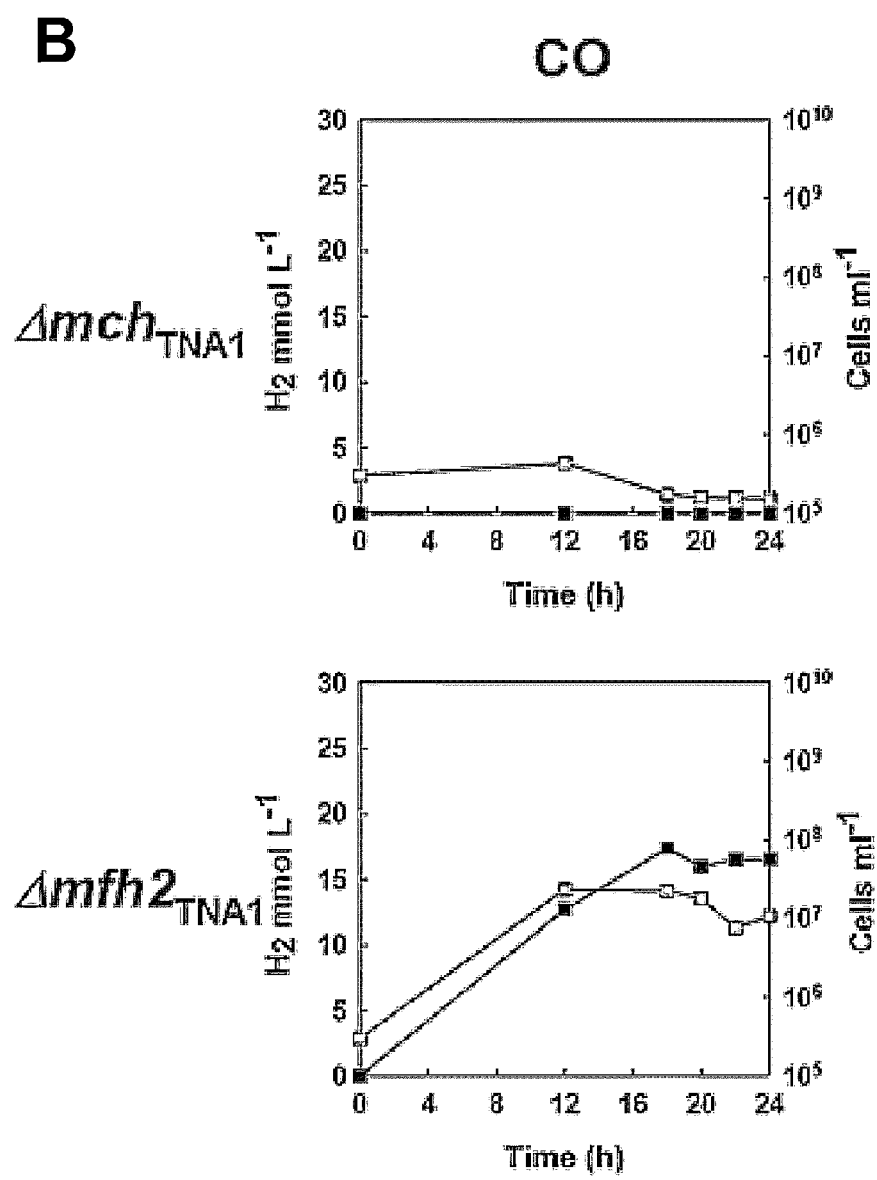

FIG. 10 shows the growth and hydrogen production of a $\Delta mch_{TNA1}$ or $\Delta mfh2_{TNA1}$ mutant strain in YPS or CO-containing medium. Open circles: growth; closed circles: hydrogen production.

DETAILED DESCRIPTION OF THE INVENTION

In a first aspect, the present invention provides hydrogenases which are produced by the novel hyperthermophilic strain *Thermococcus onnurineus* NA1 (accession number: KCTC 10859BP) that produces hydrogen in anaerobic conditions. The strain was isolated from a deep-sea hydrothermal vent area at the PACMANUS field in the East Manus Basin. The isolated strain was deposited in the Korean Collection for Type Cultures (KCTC) at the Korean Research Institute of Bioscience and Biotechnology (KRIBB) on Oct. 7, 2005 and assigned accession number KCTC 10859BP on Oct. 20, 2005. The characteristics and culture methods of the strain are described in Korean Patent Application No. 10-2007-0127255 on which the present invention is based.

*T. onnurineus* NA1 has eight novel hydrogenase gene clusters. The hydrogenases are key enzymes related to the metabolism of molecular hydrogen ($H_2$) and act as catalysts in the following reversible reaction: $2H^+ + 2e^- \Leftrightarrow H_2$. Preferably, the hydrogenases belonging to the above-described clusters provide proteins and functional equivalents thereof comprising one or more amino acid sequences selected from the group consisting of SEQ ID NO: 1 to SEQ ID NO: 8. As used herein, the term "functional equivalent" is intended to include amino acid sequence variants having amino acid substitutions in some or all of the proteins, or amino acid additions or deletions in some of the proteins. The amino acid substitutions are preferably conservative substitutions. Examples of the conservative substitutions of naturally occurring amino acids are as follow: aliphatic amino acids (Gly, Ala, and Pro), hydrophobic amino acids (Ile, Leu, and Val), aromatic amino acids (Phe, Tyr, and Trp), acidic amino acids (Asp, and Glu), basic amino acids (His, Lys, Arg, Gln, and Asn), and sulfur-containing amino acids (Cys, and Met). The deletions of amino acids are preferably located in a region which is not directly involved in the activity of the hydrogenases.

In a second aspect, the present invention provides genes encoding the above-described amino acid sequences. The genes are preferably, but not limited to, genes of SEQ ID NOs: 12 to 19 (the amino acid sequences of SEQ ID NOs: 1 to 8 correspond to the genes of SEQ ID NOs: 12 to 19, respectively).

In a third aspect, the present invention provides a method of producing hydrogen by culturing *Thermococcus* spp. The method comprises the steps of: 1) preparing a medium in a culture vessel; 2) culturing *Thermococcus* spp. in the culture vessel; and 3) extracting hydrogen from the culture vessel. The *Thermococcus* spp. is preferably *Thermococcus onnurineus* NA1 (accession number: KCTC 10859BP).

In addition, the medium may be a medium supplemented with one or more selected from the group consisting of carbon monoxide, formate and starch. Also, the culturing may be carried out at a high temperature of 80° C. in anaerobic conditions.

In a fourth aspect, the present invention provides a dehydrogenase comprising at least one amino acid sequence selected from the group consisting of SEQ ID NO: 9 to SEQ ID NO: 11. The dehydrogenase, Fdh1(SEQ ID NO: 20), Fdh2(SEQ ID NO: 22) and CODH(SEQ ID NO: 21), respectively may be carried out by cluster with hydrogenase MFH1, MFH2 and MCH hydrogenase.

In a fifth aspect, the present invention provides a gene encoding said dehydrogenase. Preferably, the gene is selected from genes of SEQ ID NO: 20 to SEQ ID NO: 22 (the amino acid sequences of SEQ ID NOs: 9 to 11 correspond to the genes of SEQ ID NOs: 20 to 22, respectively).

In a sixth aspect, the present invention provides a recombinant vector comprising genes that are organized in a CODH-MCH-MNH3 hydrogenase cluster in *T. onnurineus* NA1, wherein the genes are all operably linked. Preferably, the genes include, but are not limited to, genes of SEQ ID NO: 21 (CODH dehydrogenase) and SEQ ID NO: 16 (MCH hydrogenase). As used herein, the term "vector" means a nucleic acid molecule that can carry another nucleic acid bound thereto.

As an expression vector which can synthesize a protein encoded by a recombinant gene carried by said vector, a plasmid, cosmid or phage may be used. A preferred vector is a vector that can self-replicate and express a nucleic acid bound thereto.

In addition, the present invention provides a host cell transformed with the recombinant vector. The recombinant vector can be used to transform cells such as prokaryotic, fungal, plant and animal cells so as to prepare transformed cells which can produce hydrogen at high efficiency. As used herein, the term "transformation" means that foreign DNA or RNA is absorbed into cells to change the genotype of the cells. A public announded transformation method along each cell can be used to make the host cell.

Also, the present invention provides a method of producing hydrogen using said transformant, the method comprising the step of: preparing a medium in a culture vessel; feeding carbon monoxide into a gas phase of the culture medium; culturing said transformant in the culture vessel; and extracting hydrogen from the culture vessel.

In a seventh aspect, the present invention provides a recombinant vector comprising genes that are organized in a FDH2-MFH2-MNH2 hydrogenase cluster in *T. onnurineus* NA1, wherein the genes are all operably linked. Preferably, the genes include, but are not limited to, genes of SEQ ID NO: 22 (FDH2 dehydrogenase) and SEQ ID NO: 18 (MFH2 hydrogenase). In addition, the present invention provides a host cell transformed with the recombinant vector.

Particulars regarding the "vector", "transformation" and "host cell" are as described in the above sixth aspect.

Also, the present invention provides a method of producing hydrogen using said transformant, the method comprising the steps of: preparing a formate-containing medium in a culture vessel; culturing said transformant in the culture vessel; and extracting hydrogen from the culture vessel.

In an eighth aspect, the present invention provides a recombinant vector comprising genes that are organized in a FDH1-MFH1-MNH1 hydrogenase cluster in *T. onnurineus* NA1, wherein the genes are all operably linked. Preferably, the genes include, but are not limited to, genes of SEQ ID NO: 20 (FDH1 dehydrogenase) and SEQ ID NO: 13 (MFH1 hydrogenase). In addition, the present invention provides a host cell transformed with the recombinant vector.

Particulars regarding the "vector", "transformation" and "host cell" are as described in the above sixth aspect.

Also, the present invention provides a method of producing hydrogen using said transformant, the method comprising the steps of: preparing a starch-containing medium in a culture vessel; culturing said transformant in the culture vessel; and extracting hydrogen from the culture vessel.

Hereinafter, the present invention will be described in further detail with reference to examples. It is to be understood, however, that these examples are for illustrative purposes only and are not to be construed to limit the scope of the present invention.

EXAMPLE 1

Analysis of Hydrogenase Genes of *Thermococcus onnurineus* NA1 Strain (1) Test Methods
1) Culture Conditions For routine cultivation, cells were grown anaerobically at 80° C. in a yeast extract-peptone-sulfur (YPS) medium (Holden et al. 2001). Physiological tests were performed using modified medium 1 (Sokolova, T. G., C. Jeanthon, N. A Kostrikina, N. A. Chernyh, A. V. Lebedinsky, E. Stackebrandt, and E. A. Bonch-Osmolovskaya. 2004. The first evidence of anaerobic CO oxidation coupled with $H_2$ production by a hyperthermophilic archaeon isolated from a deep-sea hydrothermal vent. Extremophiles 8:317-323) supplemented with 1 ml of a trace element mixture, 1 ml of vitamin solution (Balch, W. E., G. E. Fox, L. J. Magrum, C. R. Woese, and R. S. Wolfe. 1979. Methanogens: reevaluation of a unique biological group. Microbio 1. Rev. 43:260-296), NaCl (30 g g/l), and yeast extract (0.5 g/l). The pH was adjusted to 8.0 using NaOH. The anaerobically prepared medium was dispensed into 25-ml serum bottles, and the gas phase (15 ml) was charged with $N_2/CO_2$ (80:20; 1 bar) or 100% CO. When the cells were cultured with formate or starch, 10 g/L of sodium formate (Sigma) or 5 g/L of soluble starch (Sigma) was added to the medium before autoclaving. All the cultures for physiological tests were all carried out at 80° C. for 2 days.

2) Gene Sequencing

The genome sequence of *T. onnurineus* NA1 was determined by whole-genome shotgun sequencing and pyrosequencing. For capillary sequencing, a 2-kb to 3-kb insert library (11,028 clones), 40-kb insert library (1,870 clones), and 35-kb insert library (288 clones) were constructed and sequenced using an ABI 3730XL sequencer (Applied Biosystems, CA). For pyrosequencing, 581,990 fragments of DNA were sequenced using a GS-20 sequencer (454 Life Sciences). The contigs generated by both sequencers were combined, and closure of the sequencing gap was performed by clone walking and PCR sequencing. ORFs and RNA genes were predicted through a combination of Glimmer 3.0 (University of Maryland), GSFinder and RBSFinder, followed by a manual ORF fitting process. After all the ORFs had been determined, further analysis of the protein sequence was performed by BLASTP searches against the nonredundant protein sequences of the National Center for Biotechnology Information (NCBI), Kyoto Encyclopedia of Genes and Genomes (KEGG), and COG (clusters of orthologous groups of proteins) databases (Tatusova, R. L., D. A. Natale, I. V. Garkavtsev, T. A. Tatusova, U. T. Shankavaram, B. S. Rao, B. Kiryutin, M. Y. Galperin, N. D. Fedorova, and E. V. Koonin. 2001. The COG database: new developments in phylogenetic classification of proteins from complete genomes. Nucleic Acids Res. 29:22-28). tRNAScan-SE was used for the tRNA predictions (Lowe, T. M., and S. R. Eddy. 1997. tRNAscan-SE: a program for improved detection of transfer RNA genes in genomic sequence. Nucleic Acids Res. 25:955-964).

3) Protein Analysis

*T. onnurineus* NA1 cells were suspended in 100 mM Tris-HCl buffer (pH 6.8) containing 4% sodium dodecyl sulfate (SDS) and 4 mM EDTA and boiled for 10 min, followed by centrifugation at 22,000 g for 20 min. The cell lysate was separated using 12% sodium dodecyl sulfate-polyacrylamide gel electrophoresis (SDS-PAGE), and 30 fractions were obtained based on molecular size. They were then in-gel digested using trypsin (Promega, USA) (Kim, Y. H., K. Cho, S. H. Yun, J. Y. Kim, K. H. Kwon, J. S. Yoo, and S. I. Kim. 2006. Analysis of aromatic catabolic pathways in *Pseudomonas putida* KT 2440 by combined proteomic approach: 2-DE/MS and cleavable ICAT analysis. Proteomics 6:1301-1318), and the tryptic digests were dissolved in 0.5% trifluoroacetic acid solution to be analyzed by mass spectrometry (Thermo Finnigan LTQ IT). The identities of peptides were determined using the Sequest program (Thermo Finnigan, San Jose, Calif.).

4) Total RNA Isolation and RT-PCR Analysis

A 50-ml culture of *T. onnurineus* NA1 was grown to mid-exponential growth phase in modified medium 1 supplemented with various concentrations of yeast extract under the gas phase of $N_2/CO_2$ (80:20, 1 bar) or 100% CO. Cells were harvested by centrifugation at 6,000×g for 30 min. The pellet was resuspended in 50 µl of 50 mM Tris-HCl buffer (pH 7.5) supplemented with 500 µl of Trizol reagent (Invitrogen, Carlsbad, Calif.). The cells were lysed by freezing and thawing, and then the samples were extracted with 200 µl of chloroform. The aqueous phase containing total RNA was further processed by ethanol precipitation and then resuspended in distilled water. RNA concentration and integrity were determined by measuring the absorbance at 260 and 280 nm, as well as by 0.8% agarose gel analysis. Reverse transcription and PCR amplification were carried out using SuperScript™ II reverse transcriptase (Invitrogen) according to the manufacturer's instructions. The following two sets of primers were used for amplification of CODH (carbon monoxide dehydrogenase) and Hsp60 (chaperonin) as controls:

```
CODH gene
                                    (SEQ ID NO: 23)
(forward, 5'-GGACCATGTAGAATCGAYCCGTTY-3'
and
                                    (SEQ ID NO: 24))
reverse, 5'-TTCRTTTCCGGTACAGCA-3';
and Hsp60 gene
                                    (SEQ ID NO: 25)
(forward, 5'-ATGGCACAGCTTAGTGGACAG-3'
and
                                    (SEQ ID NO: 26))
reverse, 5'-CAAGGATTTCCTGGGCTTTCTC-3'.
```

5) Computer Analysis

The homology search of amino acid sequences was performed using the BLAST program against the non-redundant protein database of the NCBI. A motif search for proteins having the L1 signal (C[GS][ILV]C[AGNS]xxH, wherein x indicates any amino acid) of the group 4 hydrogenase was performed using the ProteinFinder program (Ensoltek, Korea) against the non-redundant protein database of the NCBI. Multiple sequence alignment for proteins was performed using the ClustalW program (Thompson, J. D., Higgins, D. G. and Gibson, T. J. (1994) CLUSTAL W: improving the sensitivity of progressive multiple sequence alignment through sequence weighting, position-specific gap penalties and weight matrix choice. Nucleic Acids Res. 22, 4673-4680), and a phylogenetic tree was constructed using Molecular Evolutionary Genetics Analysis (Mega 4.1) software (Tamura, K., Dudley, J., Nei, M. and Kumar, S. (2007) MEGA4: Molecular Evolutionary Genetics Analysis (MEGA) software version 4.0. Mol. Biol. Evol. 24, 1596-1599). The phylogenetic tree of 16S rRNA sequences was made using pre-aligned sequences derived from the Ribosomal database site (http://rdp.cme.msu.edu/index.jsp).

6) Generation of Signature Logos

Logo representations are used to visualize the information content associated with each position of a given motif shared by related sequences. In the graphical representation, the overall height of each position is correlated to the conservation at that position (expressed in bits), whereas the relative sizes of the symbols within a position indicate their relative frequencies. Logo analyses were performed at the Berkeley Structural Genomics Center (http://weblogo.berkeley.edu/).

(2) Analysis Result

1) General Features of *T. onnurineus* NA1 Gene

Figure 1:
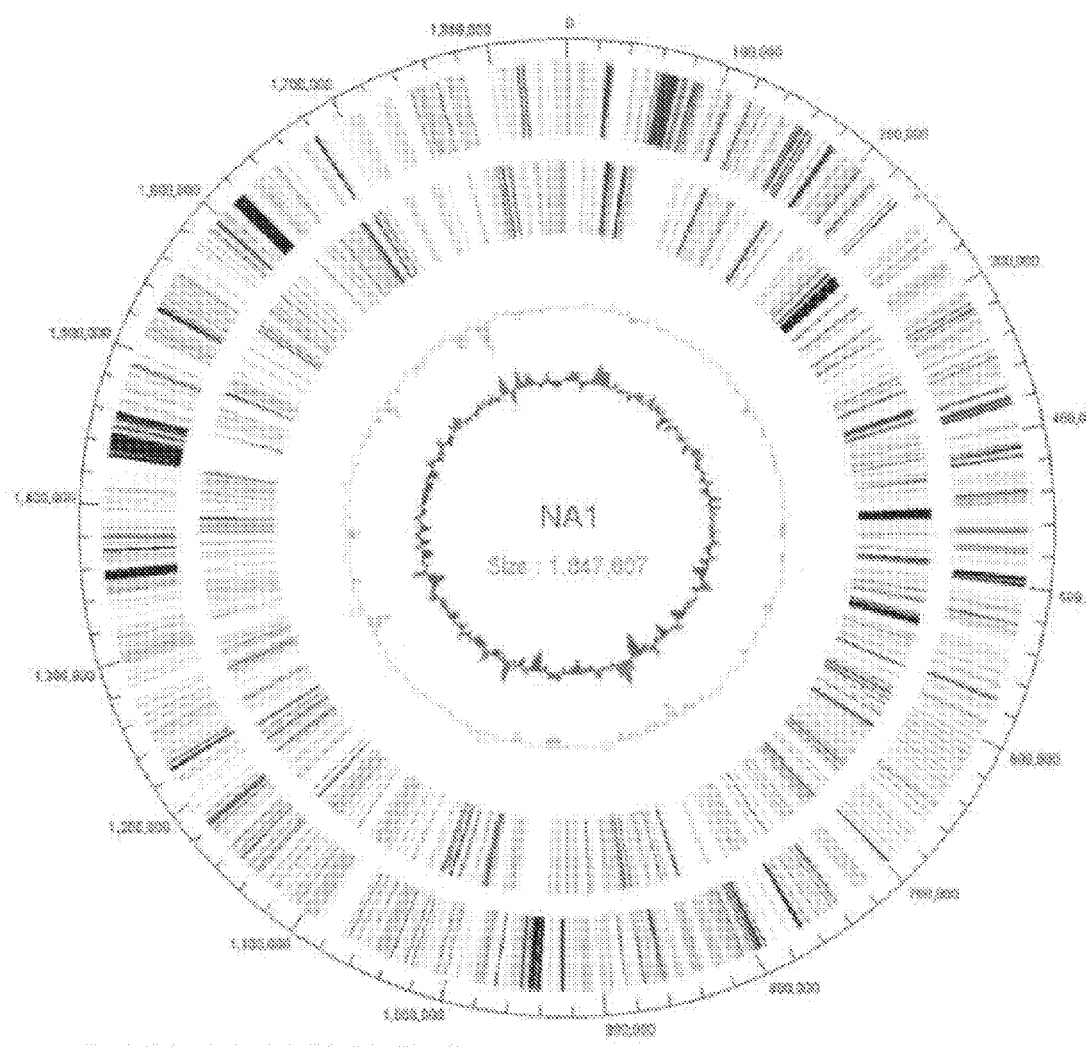
FIG. 1A and FIG. 1B present a Venn diagram showing the shared and unique portions of the proteome of four *Thermococcales* strains, *T. onnurineus* NA1 (NA1), *T. kodakaraensis*, *P. furiosus*, and *P. abyssi*. The protein sets for the strains were obtained from the RefSeq collection in NCBI.

To provide some insight into factors that contributed to the apparent successful competition of *Thermococcus* spp. in hydrothermal vent fields, the genome sequence of *T. onnurineus* NA1 was determined by combining random whole-genome shotgun sequencing with pyrosequencing. As a result, it was revealed that *T. onnurineus* NA1 has a single circular chromosome (1,847,607 bp) without any exochromosomal elements, and a total of 1,976 coding DNA sequences (CDSs) were identified (Table 1 and FIG. 1). Of these, 1,104 CDSs (55.8%) were annotatable by homology and domain searches, but the function of the residual 872 CDSs could not be predicted from the primary structure. When protein similarity was searched on a genome-wide scale, 82.7% of the *T. onnurineus* NA1, proteins showed similarity to those of other members of the *Thermococcales*.

TABLE 1

General features of the *T. onnurineus* NA1 genome and *T. kodakaraensis* KOD1 and *Pyrococcus* strains

|  | NA1 | KOD1 | P. abyssi | P. horikoshii | P. furiosus |
|---|---|---|---|---|---|
| Genome size (bp) | 1,847,607 | 2,088,737 | 1,765,118 | 1,738,505 | 1,908,256 |
| Protein-coding regions | 90.1% | 92.1% | 91.1% | 91.2% | 92.5% |
| GC content | 51.0% | 52.0% | 44.7% | 41.9% | 40.8% |
| CDSs[a] | 1976 | 2306 | 1784 | 2064 | 2065 |
| tRNAs | 46 | 46 | 46 | 46 | 46 |
| rRNAs | 5S(x2), 7S, 16S, 32S | 5S(x2), 7S, 16S, 32S | 5S(x2), 7S, 16S, 32S | 5S(x2), 7S, 16S, 32S | 5S(x2), 7S, 16S, 32S |

[a]The protein sets for the strains were obtained from the RefSeq collection in NCBI.

2) Hydrogenase Clusters

An extraordinary proportion of hydrogenases and related proteins was detected in the *T. onnurineus* NA1 genome (5.5%), reflecting enhanced conservation or recycling of reducing potentials in association with oxidoreductases, including CO dehydrogenase and formate dehydrogenases.

Hydrogenases can be divided into the following three major groups based on their catalytic metal center: [NiFe]-hydrogenases, [FeFe]-hydsrogenases, and [Fe]-hydrogenases. Based on the unique functional center conserved in each of the hydrogenase groups, it is considered that all hydrogenases in *T. onnurineus* NA1, except for one hydrogenase, belong to [NiFe]-hydrogenases. According to the hydrogenase classification system of Vignais et al., the [NiFe]-hydrogenases in *T. onnurineus* NA1 belong to group 3 (one F420-reducing hydrogenase and two NADP-reducing hydrogenases) or group 4 (four membrane-associated hydrogenases) (Silva, P. J., van den Ban, E. C., Wassink, H., Haaker, H., de Castro, B., Robb, F. T. and Hagen, W. R. (2000) Enzymes of hydrogen metabolism in Pyrococcus furiosus. Eur. J. Biochem. 267, 6541-6551). The hydrogenases belonging to group 4 were termed "energy-converting hydrogenases" (Ech) and are widespread among bacteria and archaea.

To understand the molecular basis of hydrogenase metabolism, hydrogenase gene clusters were comparatively analyzed. The hydrogenases were phylogenetically analyzed and, as a result, the group 4 hydrogenases could be divided into two subgroups, 4a and 4b, and a pair of motif patterns common to all the sequences of subgroup 4b could be found.

Figure 2:
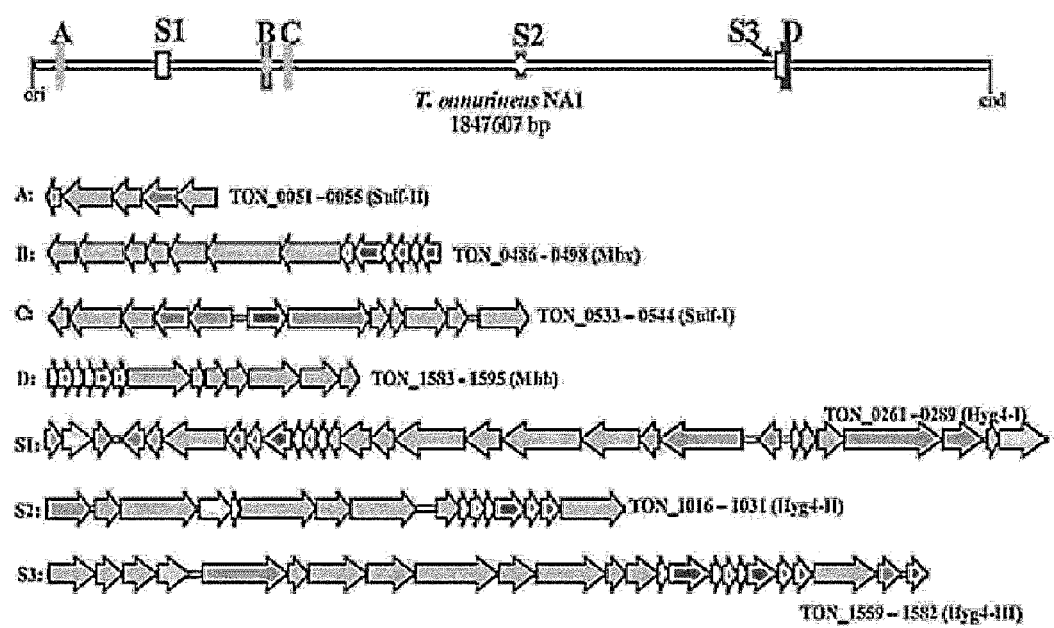
FIG. 2A is a representative map of eight hydrogenase gene clusters in *T. onnurineus* NA1. A, B, C, and D: membrane-bound hydrogenases and cytoplasmic NiFe-hydrogenases. S1, S2, and S3: *T. onnurineus* NA1. Genes were colored according to COG functional categories. TON_0051-0055 represents SEQ ID NOs: 1 to 5; TON_0486-0498 represents SEQ ID NOs: 35 to 47; TON_0533-0544 represents SEQ ID NOs: 48 to 59; TON_1583-1595 represents SEQ ID NOs: 100 to 112; TON_0261-0289 represents SEQ ID NOs: 6 to 34; TON_1016-1031 represents SEQ ID NOs: 60 to 75; and TON_1559-1582 represents SEQ ID NOs: 76 to 99.
FIG. 2B shows the gene organization of three hydrogenase gene clusters (fdh1-mfh1-mnh1, fdh2-mfh2-mnh2 and codh-mch-mnh) having a 3-module gene cluster on the genome of *T. onnurineus* NA1. Genes belonging to the same subclusters were indicated by the same color.
Figure 2:
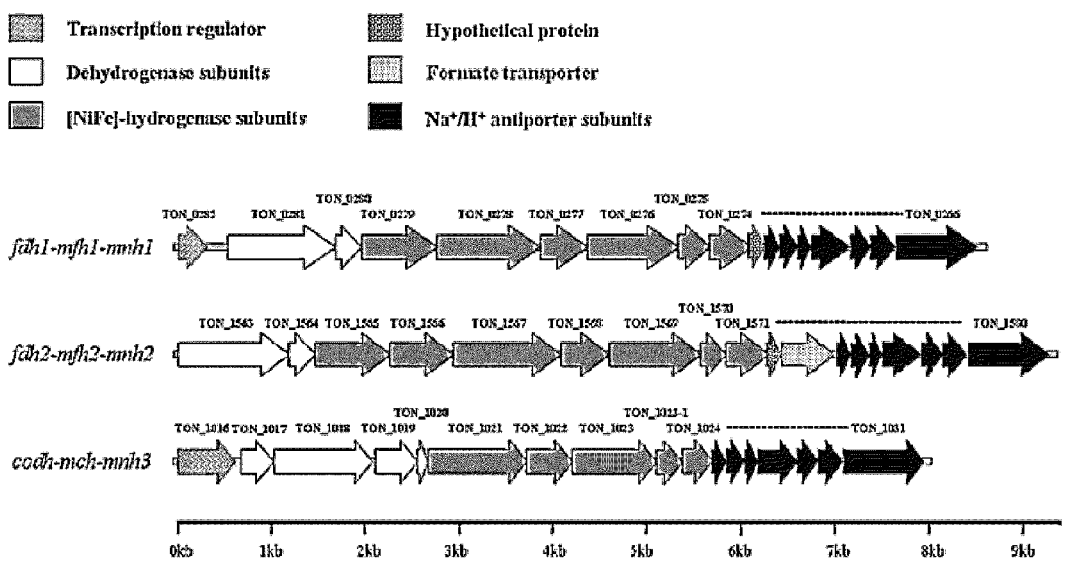
Figure 3:
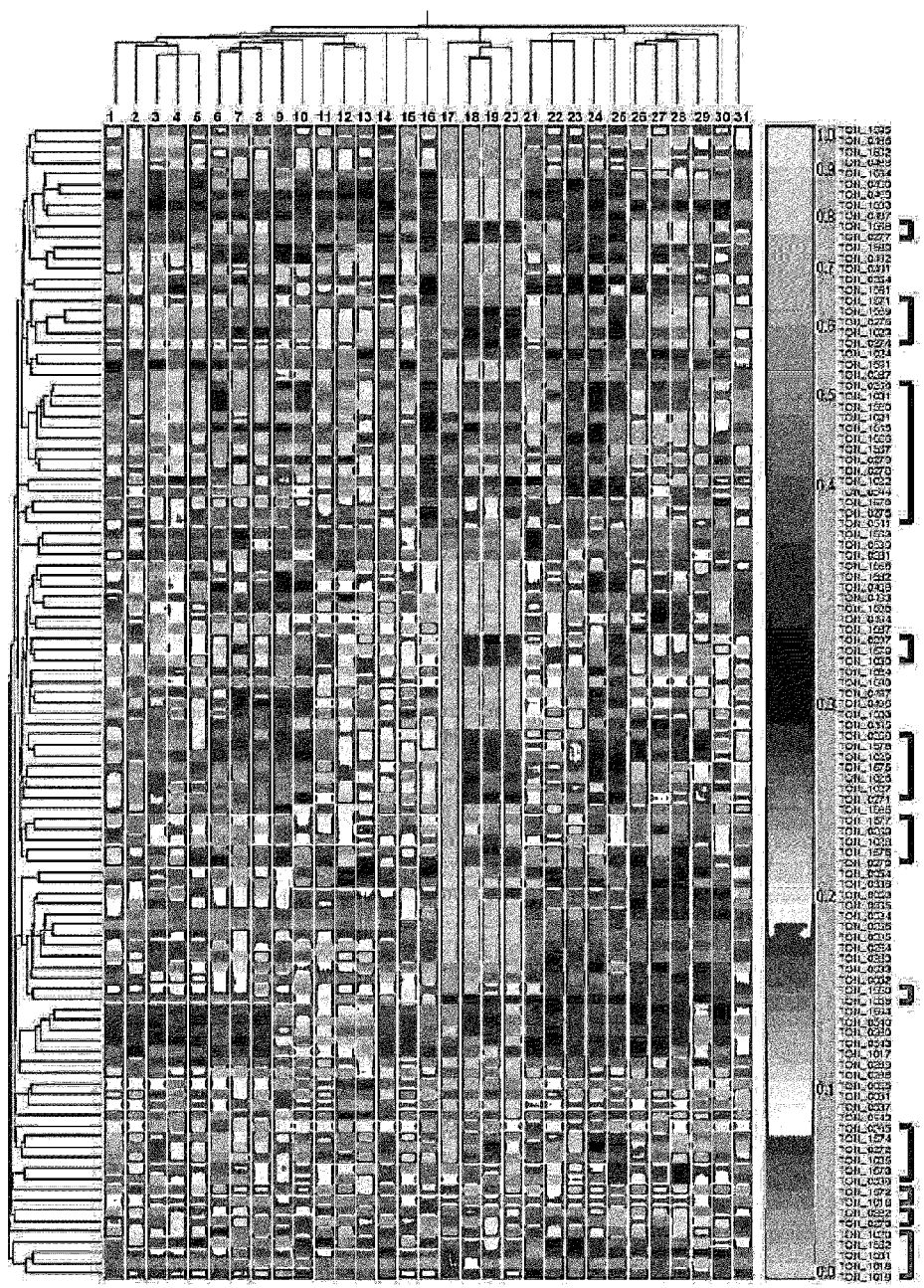
FIG. 3 shows the distribution and conservation patterns of hydrogenase gene clusters in 31 archaeal genomes. Blue brackets (the first bracket, the third bracket, the fifth bracket from the bottom) encompass CDSs showing low similarities (<25%) to any CDSs from 31 archaeal genomes. The black brackets indicate CDSs similar to hydrogenase 4 from *P. abyssi*. The 31 archaeal genes are as follows.

As shown in FIG. 2, three additional hydrogenase clusters (FDH1-MFH1-MNH1 (Hyg4-I, S1:TON_0279-0274, MFH1: SEQ ID NO: 2), CODH-MCH-MNH3 (Hyg4-II, S2:TON_1021-1024, MCH: SEQ ID NO: 5) and FDH2-MFH2-MNH2 (Hyg4-III, S3:TON_1565-1571, MFH2: SEQ ID NO: 7)) and Frh (TON_1559-1562, SEQ ID NO: 6) were found in the *T. onnurineus* NA1 genome along with the two membrane-bound hydrogenases (Mbh (TON_1590-1595, SEQ ID NO: 8) and Mbx (TON_0489-0486, SEQ ID NO: 3)) and two cytoplasmic NiFe-hydrogenases (Sulf-I (TON_0533-0544, SEQ ID NO: 4) and Sulf-II (TON_0051-0055, SEQ ID NO: 1) reported in *Pyrococcus* spp. and *T. kodakaraensis* KOD1. Gene cluster analysis of hydrogenases with CDSs from 31 archaeal genomes clearly showed that FDH1-MFH1-MNH1 (Hyg4-I), CODH-MCH-MNH3 (Hyg4-II) and FDH2-MFH2-MNH2 (Hyg4-III) were unique in primary sequence, showing low similarities to hydrogenase 4 components from *P. abyssi* and *R. rubrum* (FIG. 3). Similarly to the additional hydrogenases, the FDH2-MFH2-MNH2 (Hyg4-III) cluster (TON_1559-1582, SEQ ID NOs: to 99) included the α/β/γ subunits of F420 hydrogenase (TON_1559-1561, SEQ ID NOs: 76 to 78) in the genome. The subunits of F420 hydrogenase had unique primary sequences, showing similarities to the coenzyme F420-reducing hydrogenase (YP_001097176) from *Methanococcus maripaludis* (33%) and coenzyme F420-reducing hydrogenase (NP 987940) from *M. maripaludis* S2 (33%) (FIG. 3 and FIG. 5). No F420-hydrogenase homologues from the *Thermococcales* have been reported.

3) Construction of 3-Module Gene Clusters

It was found that each of the three Ech hydrogenases (MFH1, MFH2, and MCH) belonging the group 4 of [NiFe]-hydrogenases was a portion of large 17- or 18-gene clusters (fdh1-mfh1-mnh1, fdh2-mfh2-mnh2 and codh-mch-mnh3) consisting of TON_266-TON_282, TON_1563-TON_1580 and TON_1016-TON_1031 ORFs (open reading frames) (FIG. 2B). The ORFs in the clusters can be divided into three subclusters. The first part encodes oxidoreductase such as formate dehydrogenases (Fdh1 (SEQ ID NO: 9) or Fdh2 (SEQ ID NO: 11)) or carbon monoxide dehydrogenase (Codh (SEQ ID NO: 10)). The second part encodes multimeric membrane-bound hydrogenases MFH2 or MCH having 5-7 subunits. The last part encodes cation/proton antiporters such as $Na^+/H^+$ antiporter. Such 3-module gene clusters have not yet been reported.

EXAMPLE 2

Analysis of Gas Composition (1) Analysis Method

Hydrogen gas was measured using a gas chromatograph HP 5890 series II (Hewlett Packard) equipped with an HP-PLOT Molesieve column (Agilent) and a TCD detector. Argon was used as a carrier gas. To quantify hydrogen gas, a gas calibration standard (Supleco) containing 1% (w/w) of each of components (CO, $CO_2$, $H_2$, $CH_4$ and $O_2$) in nitrogen was used.

(2) Production of Hydrogen Using Various Substances

In order to examine whether a number of hydrogenases cause *T. onnurineus* NA1 to efficiently produce hydrogen in various environments, hydrogen production rate was analyzed using various energy sources (Table 2). As a result, the NA1 strain could produce hydrogen using starch, CO and formate even under sulfur-free conditions. Particularly, CO and formate were very good energy sources for efficiently producing hydrogen.

TABLE 2

Comparison of hydrogen production of *T. onnurineus* NA1 under various conditions

| Medium | Hydrogen production (mmol/L) |
| --- | --- |
| M + CO | 30.7 |
| M + Formate | 49.7 |
| M + Starch | 15.6 |

M: modified medium 1

The hydrogen productivity of the NA1 strain in batch culture is similar to those obtained in the continuous culture of *T. kodakaraensis* KOD1 and *Pyrococcus furiosus*. Hyperthermophilic archaea have various advantages in that they show a specific production rate higher than the hydrogen production by mesophilic bacterial fermentation or photobacteria in spite of their low volumetric productivity and produce high-purity hydrogen. The high hydrogen production rates described herein can be much improved through the optimization of culture conditions and treatment processes and metabolic engineering.

EXAMPLE 3

CO-Dependent $H_2$ Production b *Thermococcus onnurineus* NA1: Identification of CO-Responsive Hydrogenases (1) CODH Gene Cluster and Carboxydotrophic Growth As described above, it was found that *T. onnurineus* NA1 possessed a unique gene cluster (CODH-MCH-MNH3) that was comprised of a putative transcriptional regulator (TON_1016), a CODH accessory protein (CooC, TON_1019), a CODH catalytic subunit (CooS, TON_1018), and an electron transfer protein (CooF, TON_1017), along with a hydrogenase (mch, TON_1021-1024, SEQ ID NO: 5) (FIG. 2B). CooS (TON_1018), a central enzyme in microbial carbon monoxide (CO) metabolism, showed significant similarities with CODHs from CO-oxidizing methanogenic archaea such as CODH (AAM06652) from *Methanosarcina acetivorans* C2A (60%) and CODH (AAM29817) from *Methanosarcina mazei* Go1 (59%) (FIGS. 3 and 4). It seemed a monofunctional CODH (Bonam, D., L. Lehman, G. P. Roberts, and P. W. Ludden., 1989, Regulation of carbon monoxide dehydrogenase and hydrogenase in *Rhodospirillum rubrum*: effects of CO and oxygen on synthesis and activity. J. Bacteriol. 171:3102-3107; and Wu, M. Q. Ren, A. S. Durkin, S. C. Daugherty, L. M Brinkac, R. J. Dodson, R. Madupu, S. A. Sullivan, J. F. Kolonay, W. C. Nelson, L. J. Tallon, K. M. Jones, L. E. Ulrich, J. M. Gonzalez, I. B. Zhulin, F. T. Robb, and J. A. Eisen. 2005, Life in hot carbon monoxide: the complete genome sequence of *Carboxydothermus hydrogenoformans* Z-2901. PLoS Genet. 1:e65), lacking the acetyl coenzyme A synthesis/cleavage activity of the bifunctional CODH/acetyl coenzyme A synthetase enzyme. According to Fox et al. (Fox, J. D., R. L. Kerby, G. P. Roberts, and P. W. Ludden, 1996, Characterization of the CO-induced, CO-tolerant hydrogenase from *Rhodospirillum rubrum* and the gene encoding the large subunit of the enzyme. J. Bacteriol. 178: 1515-1524), the monofunctional CODH/hydrogenase complex from *Rhodospirillum rubrum* participated in CO-driven proton respiration, whereby energy is conserved in the form of a proton gradient generated across the cell membrane. In this sense, to address the issue that the CODH cluster could play a similar role in energy conservation by oxidizing CO, the present inventors tested whether *T. onnurineus* NA1 could utilize CO. As a result, it was found that the strain, indeed, was able to grow better in medium 1 under a CO atmosphere, in both the absence and the presence of sulfur, than in the basal medium (FIGS. 6a and b), even though the growth yield was still lower than that in the YPS medium (FIG. 6a). The growth under CO atmosphere was associated with the transcription of the CooS gene, indicating that the gene could be induced by the presence of CO (FIG. 6c). It is noteworthy that the addition of sulfur decreased the transcriptional level of the CooS gene. These results support the hypothesis that *T. onnurineus* NA1 generates energy from CO. Hereinafter, specific test methods and results for verifying the hypothesis will be described.

(2) Test Methods

1) Culture Conditions

*T. onnurineus* NA1 was anaerobically cultured in a yeast extract-peptone-sulfur (YPS) medium at 80° C. To examine the growth characteristics of a mutant strain, modified medium 1 supplemented with 30.0 g/L of NaCl was used as a basal medium (Uffen, R. L., 1976, Anaerobic growth of a *Rhodopseudomonas* species in the dark with carbon monoxide as sole carbon and energy substrate. Proc. Natl. Acad. Sci. USA 73:3298-3302). The medium was autoclaved, and then 1.0 ml/L of vitamin solution (Balch, W. E., G. E. Fox, L. J. Magrum, C. R. Woese, and R. S. Wolfe. 1979. Methanogens: reevaluation of a unique biological group. Microbiol. Rev. 43:260-296) and 0.5 g/L of yeast extract were added to modified medium 1 in an aerobic chamber. The pH was adjusted to 8.0 by adding 1N NaOH to the basal medium. 30 ml of the prepared medium was dispensed into 150-ml serum bottles, and the gas phase (120 ml) was changed to 100% CO ($10^5$ Pa). All the cultures for physiological tests were carried out at 80° C. in anaerobic conditions for 24 hours, and the tests were carried out in duplicate.

2) RNA Extraction and Microarray Design

Cultures were centrifuged at 4° C. at 3,500×g for 10 min, and the total RNA was extracted from the cultures with TRIZOL reagent according to the manufacturer's protocol (Invitrogen, Carlsbad, Calif.). The total RNA samples were quantitatively and qualitatively analyzed by a NanoDrop spectrophotometer (ND-1000, Thermo Scientific) and electrophoresis. The micrtoarray used in this experiment was a Roche NimbleGen microarray. Briefly, a total of 31,994 unique 60-mer oligonucleotides were designed and synthesized in situ using photo-deprotection chemistry. Each unique oligonucleotide was repeated twice on the array (a total of ~72,000 features).

3) cDNA Synthesis and Hybridization Conditions

A microarray test was carried out according to the manufacturer's protocol. Each total RNA sample (5 μg) was labeled with Cy5-dCTP (Amersharm, Piscataway, N.J.) by a reverse transcription reaction using reverse transcriptase, SuperScript II (Invitrogen, Carlsbad, Calif.). Then, the labeled cDNA mixture was concentrated using ethanol precipitation. 30 μg of the concentrated Cy5-labeled cDNAs were suspended in a hybridization solution (GenoCheck, Korea). The labeled cDNAs were located on the microarray, and then covered by a MAUI Mixer X4 hybridization chamber (BioMicro Systems, Salt Lake City, Utah). The slides were hybridized using MAUI 12-bay systems (BioMicro Systems, Salt Lake City, Utah) at 42° C. for 12 hours. The hybridized slides were washed at room temperature in 2×SSC, 0.1% SDS for 2 min, 1×SSC for 3 min, and then 0.2×SSC for 2 min. The slides were centrifuged at 1,000×g for 20 sec, followed by drying.

4) Slide Scanning, Normalization, and Data Analysis

Arrays were scanned using a GenePix 4000B scanner (Molecular Devices Corporation, Union City, Calif.), and the data were extracted using NimbleScan 2.4 software. Array normalization was performed using a median polish and quantile normalization method (Amaratunga, D., and J. Cabrera. 2001. Statistical analysis of viral microchip data. J. Am. Stat. Assoc. 96:1161-1170). Normalized expression values for the individual probes were used to obtain expression values for a given ORF using the RMA (robust multi-array average) method previously described by Irizarry et al. (Karl, D. M. 1995. The microbiology of deep-sea hydrothermal vents. CRC Press, Boca Raton, Fla.). Finally, n-fold change ratios (R) were calculated using the RMA-processed expression values (RMA calls) obtained for a particular gene in a sample. Data analysis was performed using GeneSpring GX 7.3.1 (Agilent Technologies, CA). Fold change filters included the requirement that the genes be present in at least 200% of controls for up-regulated genes and lower than 50% of controls for down-regulated genes. The data were clustered into groups of genes that behave similarly in experiments using GeneSpring GX 7.3.1 (Agilent technologies, CA). An algorithm based on the Euclidean distance and average linkage was used to separate the gene of similar patterns.

5) Quantitative RT-PCR

Gene specific primers were designed from the genome sequence of *T. onnurineus* NA1 (Genbank accession number CP000855). The primer sequences are shown in Table 3 below.

cDNAs were synthesized from 350 ng of total RNA using reverse transcriptase, SuperScrip II (Invitrogen, Carlsbad, Calif.), according to the manufacturer's protocol. PCR reactions were performed with rTaq (Takara) DNA polymerase using a T1 thermocycler (Biometra). The reactions were performed in 50 μl of a mixture containing first-strand reaction cDNA, 10 pmol primers, 250 μM dNTPs and manufacturer's buffer. Also, the PCR amplification reactions were performed in the following conditions: denaturation of 2 min for 94° C.; and then 25 cycles of denaturation (30 sec at 94° C.), annealing (30 sec at 56° C.) and extension (1 min at 72° C.). The PCR products were analyzed by 0.8% agarose gel electrophoresis. The expression level was measured using GelPro32.EXE v4.6 (Media Cybernetics, Inc.). A Chaperonin-encoding gene, named "cha", was used as a control to normalize expression levels.

TABLE 3

Oligonucleotides used in this Example

| Gene name | Sense (5'→3') | Anti-sense (5'→3') |
|---|---|---|
| Primers used in RT-PCR | | |
| mbh | Cacgacataggctacgacacgg (SEQ ID NO: 27) | Ctggcttaactcctaggtcagg (SEQ ID NO: 28) |
| mbx | Gcgattcggtatgataccggac (SEQ ID NO: 29) | Ccatccttcgccgaagagctcg (SEQ ID NO: 30) |

TABLE 3-continued

Oligonucleotides used in this Example

| Gene name | Sense (5'→3') | Anti-sense (5'→3') |
|---|---|---|
| frh | Gtaagctcgacgagtacgacgtg (SEQ ID NO: 31) | Gcaccacaacctatgcagaggcc (SEQ ID NO: 32) |
| sulfI | Gcagtacgaggaagtcgaggg (SEQ ID NO: 33) | Gagggcctcgtcgataaggtcg (SEQ ID NO: 34) |
| mch | Ctaccggacgattggccagaagg (SEQ ID NO: 35) | Ccttatatactgtgctctctccg (SEQ ID NO: 36) |
| mfh1 | Gcgaccggtacggcaaccttcg (SEQ ID NO: 37) | Cttgtcagtcatgacgtagtgg (SEQ ID NO: 38) |
| mfh2 | Gacccgaggttcacctegatagc (SEQ ID NO: 39) | Gcagacctggtcgtaggttagcc (SEQ ID NO: 40) |

Primers used in gene disruption

| | | |
|---|---|---|
| Flk-mch | cgttgtctttgcccttggggcagggatatatc (SEQ ID NO: 41) | ggcaattgcttggactgccgaaaagccaatggc (SEQ ID NO 42) |
| Flk-mfh1 | gaagaaatcgcagagggcgcctatgactatcag (SEQ ID NO: 43) | gctcctcgcttactcaagcgttggacaaatgg (SEQ ID NO: 44) |
| Flk-mfh2 | ggactgctcttcctgtcgacgggctcaatattc (SEQ ID NO: 45) | ggacgcacttaaagtcggcgtagccctttgcc (SEQ ID NO: 46) |
| Ivs-mch | aatttaccaccccaccactcccaaaatccaac (SEQ ID NO: 47) | aatggggaggctgaaactactgggcaaggc (SEQ ID NO: 48) |
| Ivs-mfh1 | tggcccaggcgatttccttcaccgacagg (SEQ ID NO: 49) | aattcaccaccccaccagcgctattatcagg (SEQ ID NO: 50) |
| Ivs_mfh2 | gagcaccacctcaccatcccagggaagctatc (SEQ ID NO: 51) | gatggccgtgacgctgaagtaccccttcgtga (SEQ ID NO: 52) |

Primers used in identification of gene disruption

| | | |
|---|---|---|
| $P_{gdh}$-hmg$_{Pfu}$ | gaacggtagttttcgacaaaagacg (SEQ ID NO: 53) | gctcaccagccaaaaccgcaccagc (SEQ ID NO: 54) |
| mch$_{TNA1}$ | gcaatgtaccacatattcaactgcgatac (SEQ ID NO: 55) | ccgataccgagtttgaatggaggaatctc (SEQ ID NO: 56) |
| mfh1$_{TNA1}$ | tcaggccacccccttgcccttctgt (SEQ ID NO: 57) | atggagtgcagcgtgtgtgcgggtg (SEQ ID NO: 58) |
| mfh2$_{TNA1}$ | atgtctgaagttatcaagtttaacg (SEQ ID NO: 59) | tgaggcctttatggagagcttgttg (SEQ ID NO: 60) |

6) Targeted Gene Disruption

To analyze the function of hydrogenases in vivo of *T. onnurineus*, insertional inactivation mutants of the large subunit of mch or mfh2 hydrogenase were constructed using a gene disruption system used for the hyperthermophilic archaeon *T. kodakaraensis* KOD1 (Sapra, R., K. Bagramyan, and M. W. W. Adams, 2003, A simple energy-conserving system: Proton reduction coupled to proton translocation. Proc. Natl. Acad. Sci. USA 100:7545-7550). Specifically, DNA fragments comprising the flanking region of the large subunits ((TON_023 and TON_1569) of each of mch and mfh2 hydrogenases were amplified from the genomic DNA of *T. onnurineus* NA1 using primer sets (Table 3) for Flk-mch or Flk-mfh2. Each of the amplified fragments was ligated into pUC118 digested with HincII. Next, a template (Flk-mch_pUC118 or Flk-mfh2_pUC118 recombinant plasmid) was subjected to inverse PCR using a set of primers (Ivs-mch or Ivs-mfh2) (Table 3), and then ligated into a $P_{gdh}$-hmg$_{Pfu}$ cassette (Sapra, R., K. Bagramyan, and M. W. W. Adams. 2003. A simple energy-conserving system: Proton reduction coupled to proton translocation. Proc. Natl. Acad. Sci. USA 100:7545-7550). The ligated product was transformed into *Escherichia coli* DH5α cells. Recombinant plasmids (mch:: $P_{gdh}$-hmg$_{Pfu}$ and mfh2::$P_{gdh}$-hmg$_{Pfu}$) were prepared with the plasmid mini kit (Qiagen, Hilden, Germany). Finally, the plasmids were transformed into *T. onnurineus* NA1 using a slight modification of the method of Sato et al. (Sato, T., T. Fukui, H. Atomi, and T. Imanaka. 2003. Targeted gene disruption by homologous recombination in the hyperthermophilic archaeon *Thermococcus kodakaraensis* KOD1. J. Bacteriol. 185:210-220., Sato, T., T. Fukui, H. Atomi, and T. Imanaka. 2005. Improved and versatile transformation system allowing multiple genetic manipulations of the hyperthermophilic archaeon *Thermococcus kodakaraensis*. Appl. Environ. Microbiol. 71:3889-3899). The transformants were screened in ASW-YT-S medium in the presence of 10 μM simvastatin (Matsumi, R., K. Manabe, T. Fukui, H. Atomi, and T. Imanaka. 2007. Disruption of a sugar transporter gene cluster in a hyperthermophilic archaeon using a host-marker system based on antibiotic resistance. J. Bacteriol. 189:2683-2691), and the candidate groups thought that the target gene was deleted therefrom could be confirmed by examining whether the $P_{gdh}$-hmg$_{Pfu}$ cassette was present in the target region.

7) Kinetics on Growth and Hydrogen Production

Growth was observed directly by the eye. Samples were diluted in sterile water containing sea salt (30.0 g/L), formalin (2.5%) and 4'-6'-diamidino-2-phenylindole (0.01%) (Sato, T., T. Fukui, H. Atomi, and T. Imanaka. 2005. Improved and versatile transformation system allowing multiple genetic manipulations of the hyperthermophilic archaeon *Thermococcus kodakaraensis*. Appl. Environ. Microbiol. 71:3889-3899). The diluted samples were filtered through a black polycarbonate filter (pore size: 0.2 μm; Whatman), and then analyzed by an optical phase contrast microscope (Zeiss Axioplan). Hydrogen gas was measured using a gas chromatograph HP 5890 series II (Hewlett Packard) equipped with a HP-PLOT Molesieve column (Agilent) and a TCD detector. Argon was used as a gas carrier. The oven temperature was 40° C. 10 μl of a gas sample for analysis was taken with a gas-tight syringe through a butyl rubber plug. The measurement of the detected hydrogen gas was calculated by comparing the peak area with a calibration curve obtained by regression analysis using a standard gas containing 40% hydrogen in nitrogen.

(3) Test Results

1) In Silico Analysis of *T. onnurineus* NA1 Hydrogenase

The previous genomic analysis of *T. onnurineus* NA1 showed the presence of eight hydrogenase gene clusters (Porter, K. G. and Y. S. Feig. 1980. The use of DAPI for identifying and counting microflora. Limnol. Oceanogr. 25:943-948), which include five membrane-bound [NiFe]-hydrogenases (Mbh, TON_1583-1595; Mbx, TON_0486-0498; Mfh1, TON_0273-0278; Mfh2, TON_1566-1573; and Mch, TON_1021-1024), and three cytoplasmic [NiFe]-hydrogenases (Fru, TON_1559-1562; Sulf I, TON_0533-0544; and Sulf II, TON_0051-0055). Through the comparative analysis of hydrogenase gene clusters and the Thermococcales strains whose genome sequencing has been completed, it could be seen that clusters homology to Mfh1, Mfh2 and Mch clusters were very rare and were found in *Thermococcales* strains whose genome sequences have recently been determined, such as *T. barophilus* MP (Mfh1 and Mch homologues), *Thermococcus* sp. AM4 (Mfh1 and Mch homologues) (Unfinished sequence, GenBank accession number ABXN00000000), and *T. gammatolerans* (Mfh1 and Mfh2 homologues) (GenBank accession number CP001398). The sequencing of fdh1-mdh1-mnh1 (termed "Hyg4-I" in the paper of Lee, H. S., S. G. Kang, S. S. Bae, J. K. Lim, Y. Cho, Y. J. Kim, J. H. Jeon, S.-S. Cha, K. K. Kwon, H.-T. Kim, C.-J. Park, H.-W. Lee, S. I. Kim, J. Chun, R. R. Colwell, S.-J. Kim, and J.-H. Lee. 2008. The complete genome sequence of *Thermococcus onnurineus* NA1 reveals a mixed heterotrophic and carboxydotrophic metabolism. J. Bacteriol. 190:7491-7499), fdh2-mfh2-mnh2 (termed "Hyg4-III") and codh-mch-mnh3 (termed "Hyg4-II") clusters in *T. onnurineus* NA1 showed that each of the clusters included oxidoreductases such as formate dehydrogenase (FDH) and CO dehydrogenase (Codh). Particularly, carboxydotrophic metabolism resulting from growth in a CO-containing atmosphere suggests the functional role of Codh-Mch-Mnh3 that provides energy in hydrogen production pathways by oxidizing CO.

2) Expression of Hydrogenase Genes Under CO-driven Growth Conditions

A test for determining whether *T. onnurineus* NA1 can produce hydrogen while growing in a CO-containing atmosphere was carried out. As shown in FIG. 7, in the YPS medium, hydrogen production could not be detected, but in medium 1 supplemented with CO, the total hydrogen gas and the cell number increased with an increase in culture time.

In order to examine which of hydrogenases are involved in hydrogen production during carboxydotrophic growth, the expression levels of hydrogenase genes in a CO-containing growth condition or a complex medium (YPS) were analyzed. As shown in Tables 4 and 5 and FIG. 8A, the expression levels of some ORFs (10 of 16 ORFs) in the codh-mch-mnh3 cluster were up-regulated at least two-fold in the CO-containing growth condition compared to the YPS. In addition, the expression levels of several ORFs (TON_1563, and TON_1569-1571) in the fdh2-mfh2-mnh2 cluster were also up-regulated in a CO-containing growth condition containing 1 g of yeast extract. The expression levels of ORFs in the codh-mch-mnh3 cluster varied depending on the amount of yeast extract, suggesting that the yeast extract has a correlation with the inhibition or activation of catabolism in CO-driven metabolism (Tables 4 and 5). On the other hand, the expression of other hydrogenase gene clusters did not greatly change, whereas the expression of the genes (20 genes of 29 ORFs) in the fdh1-mfh1-mnh1 cluster was down-regulated. Quantitative RT-PCR data for the large subunit of each of hydrogenases were also consistent with the microarray data. The expression of the large subunits (TON_1023 and TON_1569) of mch and mfh2 hydrogenases was increased at least two-fold (FIG. 8B), whereas the expression of the large subunit (TON_0276) of mfh1 hydrogenase was inhibited and the expression of other large subunits (mbh, mbx, frh, and sulfI) was maintained constant in both conditions. Such results suggest that the codh-mch-mnh3 or fdh2-mfh2-mnh2 clusters can be derived by CO and involved in hydrogen production processes associated with carboxydotrophic metabolism.

TABLE 4

Expression levels of ORFs of each of hydrogenase gene clusters in CO-containing growth condition compared to those in YPS medium

| Gene cluster and ORFs | Annotation | M + CO + 0.5 g YE/YPS | M + CO + 1 g YE/YPS | M + CO + 3 g YE/YPS |
|---|---|---|---|---|
| sulfII hydrogenase cluster | | | | |
| TON_0051 | hypothetical protein | 1.273306 | 3.1454 | 2.569546 |
| TON_0052 | hydrogenase subunit alpha | 1.085002 | 0.652365 | 0.550585 |
| TON_0053 | Sulfhydrogenase II, delta chain | 0.896129 | 1.898148 | 1.337585 |
| TON_0054 | hydrogenase subunit gamma | 0.606088 | 0.517724 | 0.630549 |
| TON_0055 | sulfhydrogenase II, beta chain | 0.84527 | 1.44889 | 1.452254 |
| fdh1-mfh1-mnh1 cluster | | | | |
| TON_0261 | hypA hydrogenase expression/formation protein | 0.658409 | 0.78969 | 0.746964 |
| TON_0262 | ATPase involved in chromosome partitioning, ParA/MinD family, Mrp homolo | 0.640277 | 0.776389 | 0.619674 |
| TON_0263 | hydrogenase maturation protease HycI | 0.775719 | 1.531337 | 1.090123 |
| TON_0264 | molybdopterin-guanine dinucleotide biosynthesis protein A | 0.538102 | 0.957335 | 0.826924 |
| TON_0265 | Nucleotidyltransferase, putative | 0.421398 | 0.554433 | 0.503557 |
| TON_0266 | component F or formate hydrogen lyase | 0.38336 | 0.338185 | 0.333459 |
| TON_0267 | Putative integral membrane protein, DUF68 family | 0.296945 | 1.215972 | 0.838087 |
| TON_0268 | Putative integral membrane protein, DUF67 family | 0.648077 | 0.424896 | 0.386235 |
| TON_0269 | Multisubunit Na+/H+ antiporter, putative MnhB subunit | 0.591411 | 0.571996 | 0.600235 |
| TON_0270 | hypothetical protein | 0.827927 | 0.85379 | 0.581906 |
| TON_0271 | Na+/H+ antiporter subunit | 0.410417 | 0.328062 | 0.51901 |

TABLE 4-continued

Expression levels of ORFs of each of hydrogenase gene clusters in CO-containing growth condition compared to those in YPS medium

| Gene cluster and ORFs | Annotation | M + CO + 0.5 g YE/YPS | M + CO + 1 g YE/YPS | M + CO + 3 g YE/YPS |
|---|---|---|---|---|
| TON_0272 | $Na^+/H^+$ antiporter MnhF subunit, putative | 0.194663 | 0.411647 | 0.331549 |
| TON_0273 | hypothetical protein | 0.269222 | 0.652722 | 0.482705 |
| TON_0274 | component I or formate hydrogen lyase | 0.385799 | 0.627629 | 0.614487 |
| TON_0275 | formate hydrogen lyase subunit 6 | 0.313283 | 0.621333 | 0.511819 |
| TON_0276 | component G or formate hydrogen lyase | 0.275138 | 0.724228 | 0.692331 |
| TON_0277 | component C or formate hydrogen lyase | 0.460646 | 0.357836 | 0.387126 |
| TON_0278 | component B or formate hydrogen lyase | 0.720779 | 0.623875 | 0.510273 |
| TON_0279 | NADH ubiquinone oxidoreductase | 0.80929 | 0.515429 | 0.54289 |
| TON_0280 | oxidoreductase iron-sulfur protein | 0.3913 | 0.690322 | 0.647104 |
| TON_0281 | fdhA formate dehydrogenase, alpha subunit | 0.584576 | 0.446401 | 0.44946 |
| TON_0282 | putative transcriptional regulator | 1.340444 | 1.195043 | 0.883294 |
| TON_0283 | hypC hydrogenase expression/formation protein | 1.007318 | 1.853137 | 2.021914 |
| TON_0284 | 367aa long hypothetical hydrogenase expression/formation protein hypD | 1.036497 | 1.385466 | 1.182663 |
| TON_0285 | hypD hydrogenase expression/formation protein | 0.904687 | 1.066448 | 0.758981 |
| TON_0286 | hydrogenase maturation protein HypF | 0.685606 | 0.778307 | 0.719973 |
| TON_0287 | hydrogenase expression/formation protein HypE | 0.851301 | 1.399569 | 1.257059 |
| TON_0288 | hypothetical protein | 1.004008 | 1.964442 | 2.27641 |
| TON_0289 | cysteine desulfurase | 0.666768 | 1.534991 | 1.148004 |
| mbx hydrogenase cluster | | | | |
| TON_0486 | 4Fe—4S cluster-binding subunit | 0.821271 | 0.718277 | 0.504388 |
| TON_0487 | nuoD NADH dehydrogenase I, subunit D | 0.606823 | 0.730138 | 0.517528 |
| TON_0488 | NADH dehydrogenase subunit | 0.703506 | 0.618352 | 0.49939 |
| TON_0489 | nuoB NADH dehydrogenase I, subunit B | 0.797159 | 0.618863 | 0.547462 |
| TON_0490 | NADH dehydrogenase subunit | 0.372425 | 0.469467 | 0.278163 |
| TON_0491 | 617aa long hypothetical protein | 0.459201 | 0.532164 | 0.388201 |
| TON_0492 | MbxH subunit | 0.862715 | 0.484349 | 0.423606 |
| TON_0493 | Multisubunit Na+/H+ antiporter, putative | 0.70216 | 1.591408 | 1.138149 |
| TON_0494 | Multisubunit $Na^+/H^+$ antiporter, putative MnhB subunit | 0.765286 | 0.716126 | 1.711304 |
| TON_0495 | MbxD subunit | 0.658086 | 0.817339 | 0.749402 |
| TON_0496 | MbxC subunit | 0.609819 | 1.200655 | 0.995067 |
| TON_0497 | MbxB subunit | 0.860304 | 0.889029 | 0.810902 |
| TON_0498 | Multisubunit $Na^+/H^+$ antiporter, putative | 0.675578 | 0.564247 | 0.483617 |
| sulfI hydrogenase cluster | | | | |
| TON_0533 | hydrogenase-specific maturation endopeptidase | 0.977803 | 0.516234 | 0.73084 |
| TON_0534 | cytosolic NiFe-hydrogenase, alpha subunit | 1.283309 | 1.334781 | 1.071667 |
| TON_0535 | cytosolic NiFe-hydrogenase, delta subunit | 0.652099 | 1.080516 | 0.800955 |
| TON_0536 | hydrogenase (gamma subunit) | 1.100959 | 1.192121 | 0.759086 |
| TON_0537 | Sulfhydrogenase beta subunit | 1.025726 | 1.458113 | 1.160718 |
| TON_0538 | probable formate transporter | 0.989789 | 1.113613 | 0.960108 |
| TON_0539 | probable formate dehydrogenase, alpha subunit | 1.158997 | 1.791123 | 1.314525 |
| TON_0540 | oxidoreductase iron-sulfur protein | 0.987581 | 1.525167 | 0.82483 |
| TON_0541 | 4Fe—4S cluster-binding protein | 1.112648 | 1.320761 | 0.855465 |
| TON_0542 | glutamate synthase beta chain-related oxidoreductase | 0.842213 | 1.602828 | 0.936949 |
| TON_0543 | 4Fe—4S cluster-binding protein | 0.9185 | 1.257283 | 1.019564 |
| TON_0544 | alcohol dehydrogenase | 0.87473 | 0.419323 | 0.605934 |
| codh-mch-mnh-3 cluster | | | | |
| TON_1016 | putative transcriptional regulator, ModE family | 1.18798 | 0.634394 | 0.731218 |
| TON_1017 | 4Fe—4S ferredoxin, iron-sulfur binding domain | 1.713085 | 4.46107 | 3.621394 |
| TON_1018 | carbon-monoxide dehydrogenase, catalytic subunit | 1.474238 | 2.204944 | 1.785437 |
| TON_1019 | putative ATP-binding protein | 0.824732 | 2.016924 | 0.974466 |
| TON_1020 | hypothetical protein | 3.375546 | 9.366047 | 5.425704 |
| TON_1021 | component B or format hydrogen lyase | 1.112538 | 1.711122 | 1.250867 |
| TON_1022 | respiratory-chain NADH dehydrogenase, subunit 1 | 0.877363 | 1.428883 | 0.57715 |
| TON_1023 | component G or format hydrogen lyase | 1.927395 | 6.118015 | 4.270288 |
| TON_1024 | NADH dehydrogenase (ubiquinone), 20 kDa subunit | 1.816315 | 3.578841 | 2.009973 |
| TON_1025 | $Na^+/H^+$ antiporter MnhF subunit, putative | 2.443938 | 3.389037 | 1.333503 |
| TON_1026 | $Na^+/H^+$ antiporter subunit | 1.337719 | 0.605839 | 0.623499 |
| TON_1027 | hypothetical protein | 0.991048 | 1.43866 | 0.778446 |
| TON_1028 | Multisubunit $Na^+/H^+$ antiporter, MnhB subunit | 1.019583 | 1.203407 | 0.836452 |
| TON_1029 | Putative integral membrane protein, DUF67 family | 2.648286 | 2.171138 | 1.123898 |
| TON_1030 | Putative integral membrane protein, DUF68 family | 3.779798 | 4.956998 | 1.592196 |
| TON_1031 | component F or format hydrogen lyase | 1.030507 | 2.778588 | 1.982091 |
| frh ($F_{420}$ reducing hydrogenase) hydrogenase cluster | | | | |
| TON_1559 | coenzyme F420 hydrogenase alpha subunit | 0.695408 | 0.64447 | 0.726535 |
| TON_1560 | Coenzyme F420 hydrogenase gamma subunit | 0.56769 | 0.715513 | 0.635236 |

TABLE 4-continued

Expression levels of ORFs of each of hydrogenase gene clusters in CO-containing growth condition compared to those in YPS medium

| Gene cluster and ORFs | Annotation | M + CO + 0.5 g YE/YPS | M + CO + 1 g YE/YPS | M + CO + 3 g YE/YPS |
|---|---|---|---|---|
| TON_1561 | 4Fe—4S ferredoxin, iron-sulfur binding Nitrite/sulfite reductase | 0.824149 | 0.834127 | 0.807754 |
| TON_1562 | Formate dehydrogenase, subunit FdhD | 0.908701 | 1.54082 | 1.468288 |
| Fdh2-mfh2-mnh2 cluster | | | | |
| TON_1563 | Probable formate dehydrogenase, alpha subunit | 1.008259 | 3.037865 | 3.330042 |
| TON_1564 | 4Fe—4S cluster-binding protein | 1.178705 | 1.221574 | 1.445098 |
| TON_1565 | NADH ubiquinone oxidoreductase | 0.811937 | 1.787894 | 2.088693 |
| TON_1566 | NADH dehydrogenase (quinone) | 1.011779 | 0.736029 | 0.787627 |
| TON_1567 | component B or formate hydrogen lyase | 1.091992 | 1.057076 | 1.184573 |
| TON_1568 | component C or formate hydrogen lyase | 1.471267 | 1.365925 | 1.382301 |
| TON_1569 | component G or formate hydrogen lyase | 1.204795 | 2.281342 | 1.780033 |
| TON_1570 | formate hydrogen lyase subunit 6 | 1.257649 | 2.427962 | 1.99559 |
| TON_1571 | component I or formate hydrogen lyase | 1.030626 | 2.15871 | 1.806722 |
| TON_1572 | hypothetical protein | 0.844948 | 0.504955 | 0.692272 |
| TON_1573 | pobable formate transporter | 1.451628 | 1.459657 | 1.158131 |
| TON_1574 | $Na^+/H^+$ antiporter MnhF subunit, putative | 1.53015 | 1.602287 | 1.244315 |
| TON_1575 | $Na^+/H^+$ antiporter subunit | 0.752784 | 0.646406 | 0.578467 |
| TON_1576 | hypothetical protein | 1.168966 | 0.564328 | 0.60819 |
| TON_1577 | Multisubunit $Na^+/H^+$ antiporter MnhB subunit | 0.726511 | 0.655031 | 0.556386 |
| TON_1578 | Putative integral membrane protein, DUF67 family | 0.989286 | 1.061599 | 0.900044 |
| TON_1579 | Putative integral membrane protein, DUF68 family | 0.903028 | 0.812346 | 0.816319 |
| TON_1580 | component F or formate hydrogen lyase | 1.015786 | 0.756283 | 0.529199 |
| TON_1581 | molybdopterin-guanine dinucleotide biosynthesis protein A | 0.61468 | 1.708744 | 1.243367 |
| TON_1582 | hypothetical protein | 0.753301 | 0.998059 | 0.952751 |
| mbh hydrogenase cluster | | | | |
| TON_1583 | MbhB subunit | 1.038442 | 0.519366 | 0.533773 |
| TON_1584 | MbhC subunit | 0.947559 | 0.514932 | 0.5099 |
| TON_1585 | MbhD subunit | 0.774604 | 1.015909 | 0.670497 |
| TON_1586 | MbhE subunit | 1.101069 | 0.811262 | 0.659266 |
| TON_1587 | MbhF subunit | 1.129566 | 0.811366 | 0.872572 |
| TON_1588 | MbhG subunit | 1.027148 | 0.563686 | 0.510924 |
| TON_1589 | MbhH subunit | 1.362042 | 0.948034 | 0.71984 |
| TON_1590 | MbhI subunit | 1.334732 | 1.227655 | 0.904813 |
| TON_1591 | NiFe-hydrogenase small subunit | 1.627315 | 1.158127 | 0.856929 |
| TON_1592 | NiFe-hydrogenase large subunit 1 | 0.940698 | 1.573248 | 0.956935 |
| TON_1593 | NiFe-hydrogenase large subunit 2 | 1.609483 | 2.286207 | 1.354849 |
| TON_1594 | MbhM subunit | 0.982323 | 0.742211 | 0.458623 |
| TON_1595 | 4Fe—4S cluster-binding subunit | 1.589684 | 1.280298 | 0.491906 |

M, medium 1; CO, carbon monoxide; YE, yeast extract.

TABLE 5

Hierarchical clustering of 112 ORFs including hydrogenase clusters from *T. onnurineus* NA1

| Gene cluster | ORFs | Annotation | M + CO + 0.5 g YE/YPS | M + CO + 1 g YE/YPS | M + CO + 3 g YE/YPS |
|---|---|---|---|---|---|
| fdh1-mfh1-mnh1 | TON_0272 | $Na^+/H^+$ antiporter MnhF subunit, putative | 0.194663 | 0.411647 | 0.331549 |
| fdh1-mfh1-mnh1 | TON_0267 | Putative integral membrane protein, DUF68 family | 0.296945 | 1.215972 | 0.838087 |
| fdh1-mfh1-mnh1 | TON_0273 | hypothetical protein | 0.269222 | 0.652722 | 0.482705 |
| fdh1-mfh1-mnh1 | TON_0275 | formate hydrogen lyase subunit 6 | 0.313283 | 0.621333 | 0.511819 |
| fdh1-mfh1-mnh1 | TON_0276 | component G or formate hydrogen lyase | 0.275138 | 0.724228 | 0.692331 |
| fdh1-mfh1-mnh1 | TON_0274 | component I or formate hydrogen lyase | 0.385799 | 0.627629 | 0.614487 |
| fdh1-mfh1-mnh1 | TON_0280 | oxidoreductase iron-sulfur protein | 0.3913 | 0.690322 | 0.647104 |
| fdh1-mfh1-mnh1 | TON_0271 | $Na^+/H^+$ antiporter subunit | 0.410417 | 0.328062 | 0.51901 |
| fdh1-mfh1-mnh1 | TON_0266 | component F or formate hydrogen lyase | 0.38336 | 0.338185 | 0.333459 |
| fdh1-mfh1-mnh1 | TON_0277 | component C or formate hydrogen lyase | 0.460646 | 0.357836 | 0.387126 |
| fdh1-mfh1-mnh1 | TON_0268 | Putative integral membrane protein, DUF67 family | 0.648077 | 0.424896 | 0.386235 |
| fdh1-mfh1-mnh1 | TON_0281 | fdhA formate dehydrogenase, alpha subunit | 0.584576 | 0.446401 | 0.44946 |
| fdh1-mfh1-mnh1 | TON_0265 | Nucleotidyltransferase, putative | 0.421398 | 0.554433 | 0.503557 |
| mbx | TON_0491 | 617aa long hypothetical protein | 0.459201 | 0.532164 | 0.388201 |
| mbx | TON_0490 | NADH dehydrogenase subunit | 0.372425 | 0.469467 | 0.278163 |
| fdh1-mfh1-mnh1 | TON_0261 | hypA hydrogenase expression/formation protein | 0.658409 | 0.78969 | 0.746964 |
| mbx | TON_0495 | MbxD subunit | 0.658086 | 0.817339 | 0.749402 |
| fdh1-mfh1-mnh1 | TON_0286 | hydrogenase maturation protein HypF | 0.685606 | 0.778307 | 0.719973 |
| mbx | TON_0494 | Multisubunit Na+/H+ antiporter, putative MnhB subunit | 0.765286 | 0.716126 | 0.711304 |
| frh | TON_1559 | coenzyme F420 hydrogenase alpha subunit | 0.695408 | 0.64447 | 0.726535 |

TABLE 5-continued

Hierarchical clustering of 112 ORFs including hydrogenase clusters from *T. onnurineus* NA1

| Gene cluster | ORFs | Annotation | M + CO + 0.5 g YE/YPS | M + CO + 1 g YE/YPS | M + CO + 3 g YE/YPS |
|---|---|---|---|---|---|
| mbx | TON_0487 | nuoD NADH dehydrogenase I, subunit D | 0.606823 | 0.730138 | 0.517528 |
| fdh1-mfh1-mnh1 | TON_0262 | ATPase involved in chromosome partitioning, Mrp homolo | 0.640277 | 0.776389 | 0.619674 |
| frh | TON_1560 | Coenzyme F420 hydrogenase gamma subunit | 0.56769 | 0.715513 | 0.635236 |
| sufII | TON_0054 | hydrogenase gamma | 0.606088 | 0.517724 | 0.630549 |
| fdh1-mfh1-mnh1 | TON_0269 | Multisubunit Na+/H+ antiporter, putative MnhB subunit | 0.591411 | 0.571996 | 0.600235 |
| mbx | TON_0486 | 4Fe—4S cluster-binding subunit | 0.821271 | 0.718277 | 0.504388 |
| fdh1-mfh1-mnh1 | TON_0278 | component B or formate hydrogen lyase | 0.720779 | 0.623875 | 0.510273 |
| mbx | TON_0488 | NADH dehydrogenase subunit | 0.703506 | 0.618352 | 0.49939 |
| mbx | TON_0498 | Multisubunit Na$^+$/H$^+$ antiporter, putative | 0.675578 | 0.564247 | 0.483617 |
| mbx | TON_0489 | nuoB NADH dehydrogenase I, subunit B | 0.797159 | 0.618863 | 0.547462 |
| fdh2-mfh2-mnh2 | TON_1575 | Na$^+$/H$^+$ antiporter subunit | 0.752784 | 0.646406 | 0.578467 |
| fdh2-mfh2-mnh2 | TON_1577 | Multisubunit Na$^+$/H$^+$ antiporter MnhB subunit | 0.726511 | 0.655031 | 0.556386 |
| sulfI | TON_0544 | alcohol dehydrogenase | 0.87473 | 0.419323 | 0.605934 |
| sulfI | TON_0533 | hydrogenase-specific maturation endopeptidase | 0.977803 | 0.516234 | 0.73084 |
| fdh2-mfh2-mnh2 | TON_1572 | hypothetical protein | 0.844948 | 0.504955 | 0.692272 |
| mbx | TON_0492 | MbxH subunit | 0.862715 | 0.484349 | 0.423606 |
| fdh1-mfh1-mnh1 | TON_0279 | NADH ubiquinone oxidoreductase | 0.80929 | 0.515429 | 0.54289 |
| mbh | TON_1584 | MbhC subunit | 0.947559 | 0.514932 | 0.5099 |
| mbh | TON_1583 | MbhB subunit | 1.038442 | 0.519366 | 0.533773 |
| mbh | TON_1588 | MbhG subunit | 1.027148 | 0.563686 | 0.510924 |
| sufII | TON_0052 | hydrogenase subunit alpha | 1.085002 | 0.652365 | 0.550585 |
| fdh2-mfh2-mnh2 | TON_1580 | component F or formate hydrogen lyase | 1.015786 | 0.756283 | 0.529199 |
| mbh | TON_1594 | MbhM subunit | 0.982323 | 0.742211 | 0.458623 |
| codh-mch-mnh3 | TON_1016 | putative transcriptional regulator, ModE family | 1.187798 | 0.634394 | 0.731218 |
| codh-mch-mnh3 | TON_1026 | Na$^+$/H$^+$ antiporter subunit | 1.337719 | 0.605839 | 0.623499 |
| fdh2-mfh2-mnh2 | TON_1576 | hypothetical protein | 1.168966 | 0.564328 | 0.60819 |
| codh-mch-mnh3 | TON_1022 | respiratory-chain NADH dehydrogenase, subunit 1 | 0.877363 | 1.428883 | 0.57715 |
| fdh1-mfh1-mnh1 | TON_0264 | molybdopterin-guanine dinucleotide biosynthesis protein A | 0.538102 | 0.957335 | 0.826924 |
| sulfI | TON_0535 | cytosolic NiFe-hydrogenase, delta subunit | 0.652099 | 1.080516 | 0.800955 |
| mbx | TON_0496 | MbxC subunit | 0.609819 | 1.200655 | 0.995067 |
| fdh2-mfh2-mnh2 | TON_1582 | hypothetical protein | 0.753301 | 0.998059 | 0.952751 |
| fdh1-mfh1-mnh1 | TON_0270 | hypothetical protein | 0.827927 | 0.85379 | 0.581906 |
| fdh1-mfh1-mnh1 | TON_0285 | hypD hydrogenase expression/formation protein | 0.904687 | 1.066448 | 0.758981 |
| mbh | TON_1585 | MbhD subunit | 0.774604 | 1.015909 | 0.670497 |
| mbx | TON_0497 | MbxB subunit | 0.860304 | 0.889029 | 0.810902 |
| frh | TON_1561 | 4Fe—4S ferredoxin, iron-sulfur binding Nitrite/sulfite reductase | 0.824149 | 0.834127 | 0.807754 |
| fdh2-mfh2-mnh2 | TON_1579 | Putative integral membrane protein, DUF68 family | 0.903028 | 0.812346 | 0.816319 |
| fdh2-mfh2-mnh2 | TON_1566 | NADH dehydrogenase (quinone) | 1.011779 | 0.736029 | 0.787627 |
| mbh | TON_1587 | MbhF subunit | 1.129566 | 0.811366 | 0.872572 |
| mbh | TON_1586 | MbhE subunit | 1.101069 | 0.811262 | 0.659266 |
| sufII | TON_0051 | hypothetical protein | 1.273306 | 3.1454 | 2.569546 |
| fdh2-mfh2-mnh2 | TON_1563 | Probable formate dehydrogenase, alpha subunit | 1.008259 | 3.037865 | 3.330042 |
| fdh1-mfh1-mnh1 | TON_0283 | hypC hydrogenase expression/formation protein | 1.007318 | 1.853137 | 2.021914 |
| fdh1-mfh1-mnh1 | TON_0288 | hypothetical protein | 1.004008 | 1.964442 | 2.27641 |
| fdh2-mfh2-mnh2 | TON_1571 | component I or formate hydrogen lyase | 1.030636 | 2.15871 | 1.806722 |
| fdh2-mfh2-mnh2 | TON_1565 | NADH ubiquinone oxidoreductase | 0.811937 | 1.787894 | 2.088693 |
| codh-mch-mnh3 | TON_1031 | component F or format hydrogen lyase | 1.030507 | 2.788568 | 1.982091 |
| codh-mch-mnh3 | TON_1018 | carbon-monoxide dehydrogenase, catalytic subunit | 1.474238 | 2.204855 | 1.785437 |
| fdh2-mfh2-mnh2 | TON_1569 | component G or formate hydrogen lyase | 1.204795 | 2.281342 | 1.760033 |
| fdh2-mfh2-mnh2 | TON_1570 | formate hydrogen lyase subunit 6 | 1.257649 | 2.427962 | 1.99559 |
| fdh1-mfh1-mnh1 | TON_0287 | hydrogenase expression/formation protein HypE | 0.851301 | 1.399569 | 1.257059 |
| sufII | TON_0055 | sulfhydrogenase II, beta chain | 0.84527 | 1.44889 | 1.452254 |
| frh | TON_1562 | Formate dehydrogenase, subunit FdhD | 0.908701 | 1.54082 | 1.468288 |
| sufII | TON_0053 | Sulfhydrogenase II, delta chain | 0.896129 | 1.898148 | 1.337585 |
| sulfI | TON_0539 | probable formate dehydrogenase, alpha subunit | 1.158997 | 1.791123 | 1.314525 |
| codh-mch-mnh3 | TON_1021 | component B or format hydrogen lyase | 1.112538 | 1.711122 | 1.250867 |
| fdh1-mfh1-mnh1 | TON_0263 | hydrogenase maturation protease HycI | 0.775719 | 1.531337 | 1.090123 |
| fdh1-mfh1-mnh1 | TON_0289 | cysteine desulfurase | 0.666768 | 1.534991 | 1.148004 |
| mbx | TON_0493 | Multisubunit Na$^+$/H$^+$ antiporter, putative | 0.70216 | 1.591408 | 1.138149 |
| fdh2-mfh2-mnh2 | TON_1581 | molybdopterin-guanine dinucleotide biosynthesis protein A | 0.61468 | 1.708744 | 1.243367 |
| codh-mch-mnh3 | TON_1019 | putative ATP binding protein | 0.824732 | 2.016924 | 0.974426 |
| sulfI | TON_0542 | glutamate synthase beta chain-related oxidoreductase | 0.842213 | 1.602828 | 0.936949 |
| mbh | TON_1592 | NiFe-hydrogenase large subunit 1 | 0.940698 | 1.573248 | 0.956935 |
| fdh1-mfh1-mnh1 | TON_0284 | 367aa long hypothetical hydrogenase protein hypD | 1.036497 | 1.385466 | 1.182663 |
| sulfI | TON_0537 | Sulfhydrogenase beta subunit | 1.025726 | 1.458115 | 1.160718 |
| sulfI | TON_0534 | cytosolic NiFe-hydrogenase, alpha subunit | 1.283309 | 1.334781 | 1.071667 |
| fdh2-mfh2-mnh2 | TON_1564 | 4Fe—4S cluster-binding protein | 1.178705 | 1.221574 | 1.445098 |
| fdh2-mfh2-mnh2 | TON_1567 | component B or formate hydrogen lyase | 1.091992 | 1.057076 | 1.184573 |
| fdh2-mfh2-mnh2 | TON_1568 | component C or formate hydrogen lyase | 1.471267 | 1.365925 | 1.382301 |
| fdh2-mfh2-mnh2 | TON_1573 | pobable formate transporter | 1.451628 | 1.459657 | 1.158131 |
| fdh2-mfh2-mnh2 | TON_1574 | Na$^+$/H$^+$ antiporter MnhF subunit, putative | 1.53015 | 1.602287 | 1.244315 |
| sulfI | TON_0541 | 4Fe—4S cluster-binding protein | 1.112648 | 1.320761 | 0.855465 |
| sulfI | TON_0536 | hydrogenase (gamma subunit) | 1.100959 | 1.192121 | 0.759086 |
| codh-mch-mnh3 | TON_1028 | Multisubunit Na$^+$/H$^+$ antiporter, MnhB subunit | 1.019583 | 1.203407 | 0.836452 |

TABLE 5-continued

Hierarchical clustering of 112 ORFs including hydrogenase clusters from *T. onnurineus* NA1

| Gene cluster | ORFs | Annotation | M + CO + 0.5 g YE/YPS | M + CO + 1 g YE/YPS | M + CO + 3 g YE/YPS |
|---|---|---|---|---|---|
| sulfI | TON_0540 | oxidoreductase iron-sulfur protein | 0.987581 | 1.525167 | 0.82485 |
| codh-mch-mnh3 | TON_1027 | hypothetical protein | 0.991048 | 1.43866 | 0.778446 |
| sulfI | TON_0543 | 4Fe—4S cluster-binding protein | 0.9185 | 1.257283 | 1.019564 |
| sulfI | TON_0538 | probable formate transporter | 0.989789 | 1.113613 | 0.960108 |
| fdh2-mfh2-mnh2 | TON_1578 | Putative integral membrane protein, DUF67 family | 0.989286 | 1.061599 | 0.900044 |
| fdh1-mfh1-mnh1 | TON_0282 | putative transcriptional regulator | 1.340444 | 1.195043 | 0.883294 |
| mbh | TON_1590 | MbhI subunit | 1.334732 | 1.227655 | 0.904813 |
| mbh | TON_1591 | NiFe-hydrogenase small subunit | 1.627315 | 1.158127 | 0.856929 |
| mbh | TON_1589 | MbhH subunit | 1.362042 | 0.948034 | 0.71984 |
| mbh | TON_1595 | 4Fe—4S cluster-binding subunit | 1.589684 | 1.280298 | 0.491906 |
| codh-mch-mnh3 | TON_1030 | Putative integral membrane protein, DUF68 family | 3.779798 | 4.956998 | 1.592196 |
| codh-mch-mnh3 | TON_1024 | NADH dehydrogenase (ubiquinone), 20 kDa subunit | 1.816315 | 3.578841 | 2.009973 |
| codh-mch-mnh3 | TON_1025 | $Na^+/H^+$ antiporter MnhF subunit, putative | 2.443938 | 3.389037 | 1.333503 |
| codh-mch-mnh3 | TON_1029 | Putative integral membrane protein, DUF67 family | 2.648286 | 2.171138 | 1.123898 |
| mbh | TON_1593 | NiFe-hydrogenase large subunit 2 | 1.609483 | 2.286207 | 1.354849 |
| codh-mch-mnh3 | TON_1020 | hypothetical protein | 3.375546 | 9.366047 | 5.425704 |
| codh-mch-mnh3 | TON_1017 | 4Fe—4S ferredoxin, iron-sulfur binding domain protein | 1.713085 | 4.46107 | 3.621394 |
| codh-mch-mnh3 | TON_1023 | component G or format hydrogen lyase | 1.927395 | 6.118015 | 4.270288 |

3) Gene Disruption and Phenotype Analysis of Disruption Mutants

Transcriptome analysis suggests that the mch hydrpogenase clustered close to codh (FIG. 9A) can play an important role in carboxydotrophic hydrogenogenesis in *T. onnurineus* NA1. However, the up-regulation of the fdh2-mfh2-mnh2 cluster and the high copy number of mRNA of other clusters raise a question about whether codh-mch-mnh3 alone is involved in carboxydotrophic hydrogenogenesis or whether other hydrogenases can become alternative pathways for mch by forming complexes in combination with dehydrogenases or recycling electronic carriers such as $FADH_2$ or NADH. Thus, the present inventors constructed disruption mutants of the large subunit of each of mch and mfh2 hydrogenases (Matsumi, R., K. Manabe, T. Fukui, H. Atomi, and T. Imanaka. 2007. Disruption of a sugar transporter gene cluster in a hyperthermophilic archaeon using a host-marker system based on antibiotic resistance. J. Bacteriol. 189:2683-2691). The method of constructing the disruption mutants are shown in FIG. 9A. The large subunit of the Mch or Mfh2 hydrogenase gene cluster was disrupted by insertional inactivation of the $P_{gdh}$-hmg$_{Pfu}$ cassette by homologous recombination in the targeted region and the resulting overexpression of the hmg-CoA gene. The targeted gene disruption was confirmed by examining the presence of the $P_{gdh}$-hmg$_{Pfu}$ cassette through PCR amplification after screening candidate groups in a YPS medium supplemented with 10 μM simvastatin (FIG. 9B). $P_{gdh}$-hmg$_{Pfu}$ could be amplified in the disruption candidate groups (Δmch$_{TNA1}$ and Δmfh2$_{TNA1}$), whereas the amplification of the large subunits of mch or mfh2 was failed. Such results show that the gene disruption system reported in *T. kodakaraensis* KOD1 (Sapra, R., K. Bagramyan, and M. W. W. Adams. 2003. A simple energy-conserving system: Proton reduction coupled to proton translocation. Proc. Natl. Acad. Sci. USA 100:7545-7550) can also be applied to *T. onnurineues* NA1.

Because the disruption mutants (Δmch$_{TNA1}$ and Δmfh2$_{TNA1}$) could be obtained in the YPS medium, it can be seen that Mch or Mfh2 is not essential for the metabolic consumption of the YPS medium. As can be seen in FIG. 10, the changes in the growth and morphology of the mutant strains Δmch$_{TNA1}$ and Δmfh2$_{TNA1}$ confirm that the genes are not necessarily essential in the YPS medium. In addition, the Δmfh2$_{TNA1}$ strain was able to grow and produce hydrogen in the CO-containing growth condition at a level similar to the wild-type strain (FIGS. 7 and 10). On the other hand, the Δmch$_{TNA1}$ mutant was not able to grow in the CO-containing growth condition and did not produce hydrogen in tis condition (FIG. 10). This indicates that the absence of the large subunit of Mch leads to complete disruption of the carboxydotrophic survival ability of *T. onnurineus* NA1 in the presence of CO. Putting these results together, it appears that, when CO is fed as a substrate, only Mch hydrogenase is involved in growth and hydrogen production.

AVAILABILITY IN INDUSTRY

As described above, the novel hydrogenases of the present invention can produce a large amount of hydrogen by responding specifically to various substrates such as carbon monoxide, formate or starch. According to the hydrogen production methods of the present invention, a large amount of hydrogen can be produced merely by culturing the above-described strain in specific culture conditions. Thus, the methods of the present invention have advantages in that they are more economic and efficient than existing hydrogen production methods and can produce hydrogen even at high temperature.

What is claimed is:

1. An isolated hydrogenase comprising the amino acid sequence of SEQ ID NO: 5.

* * * * *